(12) United States Patent
Pringle et al.

(10) Patent No.: US 7,728,009 B1
(45) Date of Patent: Jun. 1, 2010

(54) THIAZOLE AMIDES, IMIDAZOLE AMIDES AND RELATED ANALOGUES

(75) Inventors: Wallace C. Pringle, Guilford, CT (US); John M. Peterson, Durham, CT (US); Linghong Xie, Guilford, CT (US); Ping Ge, Durham, CT (US); Yang Gao, Madison, CT (US); Joseph W. Ochterski, Middlefield, CT (US); Jiong Lan, Moraga, CA (US)

(73) Assignee: Neurogen Corporation, Branford, CT (US)

( * ) Notice: Subject to any disclaimer, the term of this patent is extended or adjusted under 35 U.S.C. 154(b) by 122 days.

(21) Appl. No.: 11/816,294

(22) PCT Filed: Feb. 16, 2006

(86) PCT No.: PCT/US2006/005562

§ 371 (c)(1),
(2), (4) Date: Aug. 15, 2007

(87) PCT Pub. No.: WO2006/089076

PCT Pub. Date: Aug. 24, 2006

Related U.S. Application Data

(60) Provisional application No. 60/720,500, filed on Sep. 26, 2005, provisional application No. 60/654,558, filed on Feb. 18, 2005.

(51) Int. Cl.
*A61K 31/445* (2006.01)
*C07D 241/36* (2006.01)

(52) U.S. Cl. .................. 514/317; 544/366; 546/268.4; 548/146; 548/215; 548/335.1; 514/252.13; 514/365; 514/374; 514/396

(58) Field of Classification Search ................ 544/366; 546/268.4; 548/146, 215, 335.1; 514/317, 514/252.13, 365, 374, 396
See application file for complete search history.

(56) References Cited

U.S. PATENT DOCUMENTS

| | | | |
|---|---|---|---|
| 2,858,318 A | 10/1958 | Stoll et al. | |
| 3,331,830 A | 7/1967 | Tomcufcik et al. | |
| 3,651,054 A | 3/1972 | Crovetti et al. | |
| 4,123,541 A | 10/1978 | Ohata et al. | |
| 4,260,765 A | 4/1981 | Harrison et al. | |
| 4,804,668 A | 2/1989 | Takase et al. | |
| 6,100,279 A | 8/2000 | Vaccaro et al. | |
| 6,288,230 B1 * | 9/2001 | Chen et al. | 544/295 |
| 6,962,936 B2 | 11/2005 | Hale et al. | |
| 6,995,171 B2 | 2/2006 | Autry et al. | |
| 7,208,497 B2 | 4/2007 | Dorwald et al. | |
| 7,223,782 B2 | 5/2007 | Atkinson et al. | |
| 2002/0004511 A1 | 1/2002 | Luzzio et al. | |
| 2004/0132726 A1 | 7/2004 | Arora et al. | |

FOREIGN PATENT DOCUMENTS

| | | |
|---|---|---|
| JP | 54-030162 | 3/1979 |
| JP | 11-080107 | 3/1999 |
| WO | WO 98/15541 | 4/1998 |
| WO | WO 01/02385 | 1/2001 |
| WO | WO 01/32604 | 5/2001 |
| WO | WO 03/037332 | 5/2003 |
| WO | WO 2004/054973 | 7/2004 |
| WO | WO 2004/073594 | 9/2004 |
| WO | WO 2006/011042 | 2/2006 |
| WO | WO 2006/019833 | 2/2006 |

OTHER PUBLICATIONS

Balestra et al. CAS: 145:124560.*
Selwood et al.,2001, CAS: 134:353175.*
Brown et al., 1982, CAS: 96:104173.*
Mitsubishi et al., 1979, CAS: 91: 91633.*
Harrison et al., 1973, CAS: 78:43468.*
Jansen et al., 1961, CAS: 55:59494.*
Kiss-Szikszai et al., (2001) Arkivoc (III) 40-50.
Vakula et al., (1973) Indian Journal of Chemistry, 11(8):732-34.
Jarvest et al., (1992) J. Heterocyclic Chem., 29(6):1401-03.
Haugwitz et al., (1985) J. Med. Chem., 28(9):1234-41.
Brown et al., (1981) Australian J. Chem., 34(11):2423-29.
Roy et al., (2004) Tetrahedron, 60(10):2301-10.
Haruta et al., (2002) Heterocycles, 58:79-83.
Ibata et al., (1989) Bull. Chemical Soc. Japan 62(2):618-620.
Donohue et al., (2002) J. Combinatorial Chemistry 4(1):23-32.
Witkiewicz et al., (1987) Polish J. Pharmacol. 39(6):715-20.

* cited by examiner

*Primary Examiner*—Rei-tsang Shiao
(74) *Attorney, Agent, or Firm*—Cantor Colburn LLP

(57) ABSTRACT

Thiazole amides, imidazole amides and related analogues of the Formula:

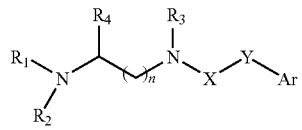

are provided, in which variables are as described herein. Such compounds may be used to modulate ligand binding to histamine H3 receptors in vivo or in vitro, and are particularly useful in the treatment of a variety of central nervous system (CNS) and other disorders in humans, domesticated companion animals and livestock animals. Compounds provided herein may be administered alone or in combination with one or more other CNS agents to potentiate the effects of the other CNS agent(s). Pharmaceutical compositions and methods for treating such disorders are provided, as are methods for using such ligands for detecting histamine H3 receptors (e.g., receptor localization studies).

18 Claims, No Drawings

SEQUENCE LISTING

```
<160> NUMBER OF SEQ ID NOS: 8

<210> SEQ ID NO 1
<211> LENGTH: 21
<212> TYPE: DNA
<213> ORGANISM: homo sapiens

<400> SEQUENCE: 1
tgagcctgcg gggccatgga g                                          21

<210> SEQ ID NO 2
<211> LENGTH: 21
<212> TYPE: DNA
<213> ORGANISM: homo sapiens

<400> SEQUENCE: 2
gaggaggtgc acagcaggta g                                          21

<210> SEQ ID NO 3
<211> LENGTH: 21
<212> TYPE: DNA
<213> ORGANISM: homo sapiens

<400> SEQUENCE: 3
ctacctgctg tgcacctcct c                                          21

<210> SEQ ID NO 4
<211> LENGTH: 22
<212> TYPE: DNA
<213> ORGANISM: homo sapiens

<400> SEQUENCE: 4
gcagtgctct agagagctgt gg                                         22

<210> SEQ ID NO 5
<211> LENGTH: 42
<212> TYPE: DNA
<213> ORGANISM: rattus sp.

<400> SEQUENCE: 5
```

-continued

```
ctctctagag cactgctgga agatgggctg caccgtgagc gc          42
```

<210> SEQ ID NO 6
<211> LENGTH: 24
<212> TYPE: DNA
<213> ORGANISM: Rattus sp.

<400> SEQUENCE: 6

```
tcagaagagg ccacagtcct tcag                              24
```

<210> SEQ ID NO 7
<211> LENGTH: 2403
<212> TYPE: DNA
<213> ORGANISM: Artificial
<220> FEATURE:
<223> OTHER INFORMATION: human/rat chimeric sequence

<400> SEQUENCE: 7

```
atggagcgcg cgccgcccga cgggccgctg aacgcttcgg gggcgctggc gggcgatgcg    60
gcggcggcgg gcggggcgcg cggcttctcg gcagcctgga ccgcggtgct ggccgcgctc   120
atggcgctgc tcatcgtggc cacggtgctg gcaacgcgc tggtcatgct cgccttcgtg   180
gccgactcga gcctccgcac ccagaacaac ttcttcctgc tcaacctcgc catctccgac   240
ttcctcgtcg cgcgccttctg catcccactg tatgtaccct acgtgctgac aggccgctgg   300
accttcggcc ggggcctctg caagctgtgg ctggtagtgg actacctgct gtgcacctcc   360
tctgccttca acatcgtgct catcagctac gaccgcttcc tgtcggtcac ccgagcggtc   420
tcataccggg cccagcaggg tgacacgcgg cgggcagtgc ggaagatgct gctggtgtgg   480
gtgctggcct tcctgctgta cggaccagcc atcctgagct gggagtacct gtccgggggc   540
agctccatcc ccgagggcca ctgctatgcc gagttcttct acaactggta cttcctcatc   600
acggcttcca ccctggagtt ctttacgccc ttcctcagcg tcaccttctt taacctcagc   660
atctacctga acatccagag gcgcacccgc ctccggctgg atggggctcg agaggcagcc   720
ggccccgagc ccctcccga ggcccagccc tcaccacccc caccgcctgg ctgctggggc   780
tgctggagga aggggcacgg ggaggccatg ccgctgcaca ggtatgggt gggtgaggcg   840
gccgtaggcg ctgaggccgg ggaggcgacc ctcgggggtg gcggtggggg cggctccgtg   900
gcttcaccca cctccagctc cggcagctcc tcgagggggca ctgagaggcc gcgctcactc   960
aagaggggct ccaagccgtc ggcgtcctcg gcctcgctgg agaagcgcat gaagatggtg  1020
tcccagagct tcacccagcg cttcggctg tctcgggaca ggaaagtggc caagtcgctg  1080
gccgtcatcg tgagcatctt tgggctctgc tgggccccat acacgctgct gatgatcatc  1140
cgggccgcct gccatggcca ctgcgtccct gactactggt acgaaacctc cttctggctc  1200
ctgtgggcca actcggctgt caaccctgtc ctctaccctc tgtgccacca cagcttccgc  1260
cgggccttca caaagctgct ctgccccag aagctcaaaaa tccagcccca cagctctcta  1320
gagcactgct ggaagatggg ctgcaccgtg agcgccgagg acaaggcggc agccgagcgc  1380
tctaagatga tcgacaagaa cctgcgggag acggcgaga aggcggcacg ggaggtgaag  1440
ttgcttctgt taggtgctgg agaatcaggg aagagcacca tcgtcaagca gatgaagatc  1500
atccacgagg atggctactc agaggaggag tgccggcagt accgtgcggt tgtctacagc  1560
aacaccatcc agtctatcat ggccatcgtc aaagccatgg gcaacctgca gatcgacttt  1620
gctgaccccc agcgtgcgga tgatgccagg cagctgttcg cactgtcctg tgctgccgag  1680
gagcaaggca tgcttccgga agacctgtcg ggcgtcatcc ggaggctctg ggctgaccat  1740
```

-continued

```
ggtgtgcaag cctgctttgg ccgctcacgg gaatatcaac tcaatgactc agccgcttac    1800
tacctgaatg acctggagcg catagcacag agtgactata tccctacaca gcaggatgtg    1860
ctgcggaccc gtgtgaagac cacaggcatc gtcgaaacac acttcacctt caaggactta    1920
cacttcaaga tgtttgatgt gggtggtcag cgatctgagc ggaagaagtg gatccactgc    1980
tttgagggtg tcacggccat catcttctgt gtcgccttga gcgcgtacga cttggtgctg    2040
gctgaggatg aggagatgaa tcgcatgcat gagagcatga agctgtttga tagcatctgc    2100
aataataagt ggttcacaga cacctccatc atcctcttcc tcaacaagaa ggacctgttt    2160
gaagagaaga tcacacagag ccccctgacc atctgtttcc ctgagtacac aggggccaac    2220
aagtatgacg aggcagccag ctacatccag agcaagtttg aggacctgaa taaacgcaaa    2280
gacaccaagg agatctacac gcacttcaca tgcgccaccg acaccaagaa cgtgcagttt    2340
gtgtttgatg ccgtcactga cgtcatcatc aagaacaacc tgaaggactg tggcctcttc    2400
tga                                                                  2403
```

<210> SEQ ID NO 8
<211> LENGTH: 800
<212> TYPE: PRT
<213> ORGANISM: Artificial
<220> FEATURE:
<223> OTHER INFORMATION: human/rat chimeric sequence

<400> SEQUENCE: 8

```
Met Glu Arg Ala Pro Pro Asp Gly Pro Leu Asn Ala Ser Gly Ala Leu
1               5                   10                  15

Ala Gly Asp Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
        35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
        195                 200                 205

Thr Pro Phe Leu Ser Val Thr Phe Phe Asn Leu Ser Ile Tyr Leu Asn
    210                 215                 220

Ile Gln Arg Arg Thr Arg Leu Arg Leu Asp Gly Ala Arg Glu Ala Ala
225                 230                 235                 240
```

-continued

```
Gly Pro Glu Pro Pro Glu Ala Gln Pro Ser Pro Pro Pro Pro
            245                 250                 255

Gly Cys Trp Gly Cys Trp Gln Lys Gly His Gly Glu Ala Met Pro Leu
            260                 265                 270

His Arg Tyr Gly Val Gly Ala Ala Val Gly Ala Glu Ala Gly Glu
            275                 280                 285

Ala Thr Leu Gly Gly Gly Gly Gly Ser Val Ala Ser Pro Thr
    290                 295                 300

Ser Ser Ser Gly Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Phe Thr Gln Arg Phe Arg Leu Ser Arg
                340                 345                 350

Asp Arg Lys Val Ala Lys Ser Leu Ala Val Ile Val Ser Ile Phe Gly
                355                 360                 365

Leu Cys Trp Ala Pro Tyr Thr Leu Leu Met Ile Ile Arg Ala Ala Cys
    370                 375                 380

His Gly His Cys Val Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                405                 410                 415

His Ser Phe Arg Arg Ala Phe Thr Lys Leu Leu Cys Pro Gln Lys Leu
                420                 425                 430

Lys Ile Gln Pro His Ser Ser Leu Glu His Cys Trp Lys Met Gly Cys
            435                 440                 445

Thr Val Ser Ala Glu Asp Lys Ala Ala Ala Glu Arg Ser Lys Met Ile
    450                 455                 460

Asp Lys Asn Leu Arg Glu Asp Gly Glu Lys Ala Ala Arg Glu Val Lys
465                 470                 475                 480

Leu Leu Leu Leu Gly Ala Gly Glu Ser Gly Lys Ser Thr Ile Val Lys
                485                 490                 495

Gln Met Lys Ile Ile His Glu Asp Gly Tyr Ser Glu Glu Cys Arg
            500                 505                 510

Gln Tyr Arg Ala Val Val Tyr Ser Asn Thr Ile Gln Ser Ile Met Ala
    515                 520                 525

Ile Val Lys Ala Met Gly Asn Leu Gln Ile Asp Phe Ala Asp Pro Gln
    530                 535                 540

Arg Ala Asp Asp Ala Arg Gln Leu Phe Ala Leu Ser Cys Ala Ala Glu
545                 550                 555                 560

Glu Gln Gly Met Leu Pro Glu Asp Leu Ser Gly Val Ile Arg Arg Leu
                565                 570                 575

Trp Ala Asp His Gly Val Gln Ala Cys Phe Gly Arg Ser Arg Glu Tyr
            580                 585                 590

Gln Leu Asn Asp Ser Ala Ala Tyr Tyr Leu Asn Asp Leu Glu Arg Ile
            595                 600                 605

Ala Gln Ser Asp Tyr Ile Pro Thr Gln Gln Asp Val Leu Arg Thr Arg
    610                 615                 620

Val Lys Thr Thr Gly Ile Val Glu Thr His Phe Thr Phe Lys Asp Leu
625                 630                 635                 640

His Phe Lys Met Phe Asp Val Gly Gly Gln Arg Ser Glu Arg Lys Lys
                645                 650                 655
```

-continued

```
Trp Ile His Cys Phe Glu Gly Val Thr Ala Ile Ile Phe Cys Val Ala
            660             665             670

Leu Ser Ala Tyr Asp Leu Val Leu Ala Glu Asp Glu Met Asn Arg
        675             680             685

Met His Glu Ser Met Lys Leu Phe Asp Ser Ile Cys Asn Asn Lys Trp
    690             695             700

Phe Thr Asp Thr Ser Ile Ile Leu Phe Leu Asn Lys Lys Asp Leu Phe
705             710             715             720

Glu Glu Lys Ile Thr Gln Ser Pro Leu Thr Ile Cys Phe Pro Glu Tyr
                725             730             735

Thr Gly Ala Asn Lys Tyr Asp Glu Ala Ala Ser Tyr Ile Gln Ser Lys
            740             745             750

Phe Glu Asp Leu Asn Lys Arg Lys Asp Thr Lys Glu Ile Tyr Thr His
        755             760             765

Phe Thr Cys Ala Thr Asp Thr Lys Asn Val Gln Phe Val Phe Asp Ala
770             775             780

Val Thr Asp Val Ile Ile Lys Asn Asn Leu Lys Asp Cys Gly Leu Phe
785             790             795             800
```

THIAZOLE AMIDES, IMIDAZOLE AMIDES AND RELATED ANALOGUES

CROSS-REFERENCE TO RELATED APPLICATIONS

This application is a §371 application of PCT International Application Serial Number PCT/US06/005562, filed Feb. 16, 2006, which PCT application claims priority to U.S. Provisional Application 60/720,500, filed Sep. 26, 2005, and to U.S. Provisional Application 60/654,558, filed Feb. 18, 2005, each of which PCT and Provisional Application is incorporated herein by reference in its entirety.

FIELD OF THE INVENTION

This invention relates generally to thiazole amides, imidazole amides and related analogues, and to the use of such compounds for treating conditions responsive to histamine H3 receptor modulation. The invention further relates to the use of such compounds as probes for the detection and localization of histamine H3 receptors.

DESCRIPTION OF THE SEQUENCE LISTING

SEQ ID NO:1 human H3 receptor 5' fragment forward primer
SEQ ID NO:2 human H3 receptor 5' fragment reverse primer
SEQ ID NO:3 human H3 receptor 3' fragment forward primer
SEQ ID NO:4 human H3 receptor 3' fragment reverse primer
SEQ ID NO:5 rat Gα$_{i2}$ forward primer
SEQ ID NO:6 rat Gα$_{i2}$ reverse primer
SEQ ID NO:7 chimeric human H3 receptor—rat Gα$_{i2}$ cDNA sequence
SEQ ID NO:8 chimeric human H3 receptor—rat Gα$_{i2}$ polypeptide sequence

BACKGROUND OF THE INVENTION

Hormones and neurotransmitters regulate a wide variety of biological functions, often via specific receptor proteins located on the surface of living cells. Many of these receptors carry out intracellular signaling via the activation of coupled guanosine triphosphate-binding proteins (G proteins); such receptors are collectively called G protein-coupled receptors or GPCRs. The important role of GPCRs in the regulation of cell and organ function has attracted attention to these receptors as targets for new pharmaceutical agents.

Histamine is a multifunctional chemical transmitter that signals through specific cell surface GPCRs. To date, four histamine receptor subtypes have been identified: H1, H2, H3 and H4. Histamine H3 receptor is a presynaptic GPCR that is found primarily in the central nervous system, although lower levels are also found in the peripheral nervous system. Genes encoding the H3 receptor have been reported in various organisms, including humans (see Lovenberg et al. (1999) *Molecular Pharmacology* 55:1101-07), and alternative splicing of this gene appears to result in multiple isoforms. The histamine H3 receptor is an auto- and hetero-receptor whose activation leads to a decreased release of neurotransmitters (including histamine, acetylcholine, norepinephrine and glutamate) from neurons in the brain, and is involved in the regulation of processes such as sleep and wakefulness, feeding and memory. In certain systems, the histamine H3 receptor may be constitutively active.

Antagonists of histamine H3 receptor increase synthesis and release of cerebral histamine and other neurotransmitters, inducing an extended wakefulness, an improvement in cognitive processes, a reduction in food intake and a normalization of vestibular reflexes. Such antagonists may find use as therapeutics for central nervous system disorders such as Alzheimer disease, schizophrenia, mood and attention alterations including attention deficit hyperactivity disorder, memory and learning disorders, epilepsy, narcolepsy and cognitive deficits in psychiatric pathologies, as well as in the treatment and prevention of conditions such as obesity, eating disorders, vertigo, motion sickness and allergic rhinitis.

Accordingly, the histamine H3 receptor is an important target for new therapeutics for conditions responsive to H3 receptor modulation. The present invention fulfills this need, and provides further related advantages.

SUMMARY OF THE INVENTION

In certain aspects, the present invention provides thiazole amides, imidazole amides and related analogues of Formula A:

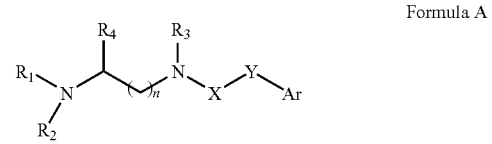

Formula A and pharmaceutically acceptable salts of such compounds.

Within Formula A:

$R_1$ is: (a) $C_1$-$C_8$alkyl, $C_2$-$C_8$alkenyl or ($C_3$-$C_8$cycloalkyl)$C_0$-$C_4$alkyl, each of which is substituted with from 0 to 4 substituents independently chosen from $R_A$; or (b) taken together with $R_2$ or $R_4$ to form a 4- to 8-membered heterocycloalkyl that is substituted with from 0 to 4 substituents independently chosen from $R_A$;

$R_2$ is $C_1$-$C_8$alkyl, $C_2$-$C_8$alkenyl, ($C_3$-$C_8$cycloalkyl)$C_0$-$C_4$alkyl or taken together with $R_1$, $R_3$ or $R_4$ to form a 4- to 8-membered heterocycloalkyl that is substituted with from 0 to 4 substituents independently chosen from $R_A$;

$R_3$ is hydrogen, $C_1$-$C_8$alkyl, $C_2$-$C_8$alkenyl, ($C_3$-$C_8$cycloalkyl)$C_0$-$C_4$alkyl or taken together with $R_2$ or $R_4$ to form a 4- to 8-membered heterocycloalkyl that is substituted with from 0 to 4 substituents independently chosen from $R_A$;

$R_4$ is hydrogen or taken together with $R_1$, $R_2$ or $R_3$ to form an optionally substituted 4- to 8-membered heterocycloalkyl;

n is 1, 2 or 3;

X is substituted carbon (e.g., substituted with one or two groups independently chosen from $C_1$-$C_6$alkyl), $CH_2$ or C=O; in certain embodiments, X is $CH_2$ or C=O;

Y is an optionally substituted, 5-membered, nitrogen-containing heteroaryl; in certain embodiments, Y is

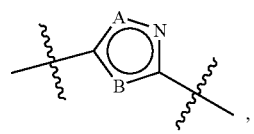

,

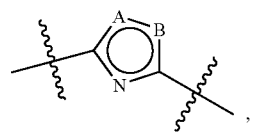

,

-continued

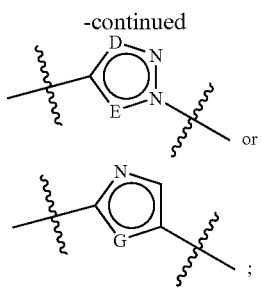

or

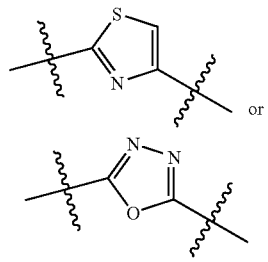

or

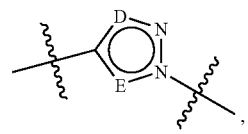

;

A and B are independently $CR_5$, N, $NR_6$, O or S; such that at least one of A and B is not $CR_5$, and no more than one of A and B is chosen from O and S; in certain embodiments, A is $CR_5$, N, $NR_6$ or S and B is $CR_5$, N, $NR_6$, O or S;

D and E are independently $CR_5$ or N;

G is $NR_6$, O or S;

Each $R_5$ is hydrogen, halogen, cyano, or $C_1$-$C_8$alkyl that is substituted with from 0 to 4 substituents independently chosen from hydroxy, halogen, amino, cyano and $C_1$-$C_4$alkoxy;

Each $R_6$ is hydrogen, or $C_1$-$C_8$alkyl that is substituted with from 0 to 4 substituents independently chosen from hydroxy, halogen, amino, cyano and $C_1$-$C_4$alkoxy;

Ar is phenyl, naphthyl, biphenyl or a 5- to 13-membered heteroaryl, each of which is optionally substituted, preferably with from 0 to 4 substituents independently chosen from:

(a) hydroxy, halogen, amino, cyano, nitro, —COOH and aminocarbonyl; and (b) $C_1$-$C_8$alkyl, $C_2$-$C_8$alkenyl, $C_2$-$C_8$alkynyl, $C_3$-$C_8$cycloalkyl, $C_2$-$C_8$alkyl ether, $C_1$-$C_8$alkanoyl, $C_3$-$C_8$alkanone, $C_1$-$C_8$alkoxycarbonyl, $C_2$-$C_8$alkanoyloxy, $C_2$-$C_8$alkanoylamino, $C_1$-$C_8$alkylsulfonyl, $C_1$-$C_8$alkoxy, $C_1$-$C_8$alkylthio, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl)aminosulfonyl, $C_1$-$C_6$alkylsulfonylamino and mono- and di-($C_1$-$C_6$alkyl)amino$C_0$-$C_4$alkyl, each of which is substituted with from 0 to 4 substituents independently chosen from hydroxy, halogen, amino, cyano, $C_1$-$C_4$alkyl and $C_1$-$C_4$alkoxy; and $R_A$ is independently chosen at each occurrence from:

(a) hydroxy, halogen, amino, cyano, nitro, oxo, —COOH, aminosulfonyl and aminocarbonyl; and (b) $C_1$-$C_8$alkyl, $C_3$-$C_8$cycloalkyl, $C_2$-$C_8$alkyl ether, $C_1$-$C_8$alkanoyl, $C_3$-$C_8$alkanone, $C_1$-$C_8$alkylsulfonyl, $C_1$-$C_8$alkoxy, $C_1$-$C_8$alkylthio, $C_1$-$C_8$alkoxycarbonyl, $C_2$-$C_8$alkanoyloxy, $C_2$-$C_8$alkanoylamino, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl)aminosulfonyl, $C_1$-$C_6$alkylsulfonylamino, mono- and di-($C_1$-$C_6$alkyl)amino$C_0$-$C_4$alkyl, and 5- to 7-membered heterocycloalkyl, each of which is substituted with from 0 to 4 substituents independently chosen from hydroxy, halogen, amino, cyano, $C_1$-$C_4$alkyl and $C_1$-$C_4$alkoxy;

such that Y is not if $R_1$ is $C_1$-$C_6$alkyl and Ar is optionally substituted phenyl.

In certain such compounds, if Y is

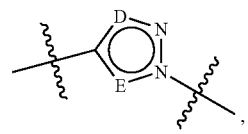

then at least one of $R_2$ and $R_3$ forms a ring.

Certain compounds of Formula A further satisfy Formula I, II, III, IV and/or V, in which (except as noted below) the variables are as described above:

Formula I

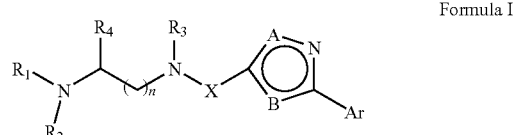

Formula II

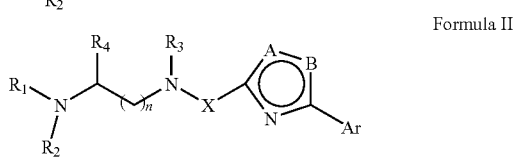

Formula III

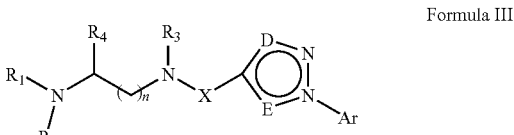

Formula IV

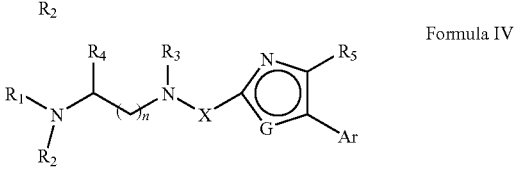

Formula V

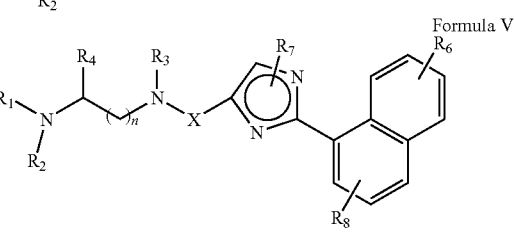

Within Formula V:

$R_7$ represents 0, 1 or 2 substituents independently chosen from hydrogen, halogen, cyano and $C_1$-$C_8$alkyl that is substituted with from 0 to 4 substituents independently chosen from hydroxy, halogen, amino, cyano and $C_1$-$C_4$alkoxy;

Each $R_8$ independently represents 0, 1 or 2 substituents independently chosen from:
(a) hydroxy, halogen, amino, cyano, nitro, —COOH and aminocarbonyl; and
(b) $C_1$-$C_8$alkyl, $C_3$-$C_8$cycloalkyl, $C_2$-$C_8$alkyl ether and $C_1$-$C_8$alkoxy, each of which is substituted with from 0 to 4 substituents independently chosen from hydroxy, halogen, amino, cyano, $C_1$-$C_4$alkyl and $C_1$-$C_4$alkoxy;

In other aspects, the present invention provides compounds of Formula B:

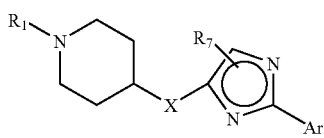

Formula B and pharmaceutically acceptable salts of such compounds.

Within Formula B:

X is optionally substituted carbon (e.g., substituted with one or two groups independently chosen from hydroxy, halogen and $C_1$-$C_6$alkyl); in certain embodiments, X is $CH_2$, CHOH or C=O;

$R_1$ is: (a) $C_1$-$C_8$alkyl or ($C_3$-$C_8$cycloalkyl)$C_0$-$C_4$alkyl, each of which is substituted with from 0 to 4 substituents independently chosen from $R_A$; or (b) taken together with $R_2$ or $R_4$ to form a 4- to 8-membered heterocycloalkyl that is substituted with from 0 to 4 substituents independently chosen from oxo and $R_A$;

$R_7$ represents 0, 1 or 2 substituents independently chosen from hydrogen, halogen, cyano and $C_1$-$C_8$alkyl that is substituted with from 0 to 4 substituents independently chosen from hydroxy, halogen, amino, cyano and $C_1$-$C_4$alkoxy;

Ar is naphthyl or a 9- or 10-membered heteroaryl, each of which is optionally substituted with from 0 to 4 substituents independently chosen from:
(a) hydroxy, halogen, amino, cyano, nitro, —COOH and aminocarbonyl; and
(b) $C_1$-$C_8$alkyl, $C_2$-$C_8$alkenyl, $C_2$-$C_8$alkynyl, $C_3$-$C_8$cycloalkyl, $C_2$-$C_8$alkyl ether, $C_1$-$C_8$alkanoyl, $C_3$-$C_8$alkanone, $C_1$-$C_8$alkoxycarbonyl, $C_2$-$C_8$alkanoyloxy, $C_2$-$C_8$alkanoylamino, $C_1$-$C_8$alkylsulfonyl, $C_1$-$C_8$alkoxy, $C_1$-$C_8$alkylthio, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl)aminosulfonyl, $C_1$-$C_6$alkylsulfonylamino and mono- and di-($C_1$-$C_6$alkyl)amino$C_0$-$C_4$alkyl, each of which is substituted with from 0 to 4 substituents independently chosen from hydroxy, halogen, amino, cyano, $C_1$-$C_4$alkyl and $C_1$-$C_4$alkoxy; and $R_A$ is independently chosen at each occurrence from:
(a) hydroxy, halogen, amino, cyano, nitro, oxo, —COOH, aminosulfonyl and aminocarbonyl; and
(b) $C_1$-$C_8$alkyl, $C_3$-$C_8$cycloalkyl, $C_2$-$C_8$alkyl ether, $C_1$-$C_8$alkanoyl, $C_3$-$C_8$alkanone, $C_1$-$C_8$alkylsulfonyl, $C_1$-$C_8$alkoxycarbonyl, $C_2$-$C_8$alkanoyloxy, $C_2$-$C_8$alkanoylamino, $C_1$-$C_8$alkoxy, $C_1$-$C_8$alkylthio, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl)aminosulfonyl, $C_1$-$C_6$alkylsulfonylamino, and mono- and di-($C_1$-$C_6$alkyl)amino$C_0$-$C_4$alkyl, each of which is substituted with from 0 to 4 substituents independently chosen from hydroxy, halogen, amino, cyano, $C_1$-$C_4$alkyl and $C_1$-$C_4$alkoxy.

Within certain aspects, compounds provided herein are histamine H3 receptor modulators that exhibit a $K_i$ that is no greater than 4 micromolar, 1 micromolar, 500 nanomolar, 100 nanomolar, 50 nanomolar or 10 nanomolar, as determined using an assay for H3 receptor GTP binding.

Within certain aspects, compounds provided herein are labeled with a detectable marker (e.g., radiolabeled or fluorescein conjugated).

The present invention further provides, within other aspects, pharmaceutical compositions comprising at least one compound or pharmaceutically acceptable salt thereof as provided herein in combination with a physiologically acceptable carrier or excipient.

Within further aspects, methods are provided for modulating H3 activity, comprising contacting a cell (e.g., neuronal) expressing H3 receptor with at least one H3 receptor modulator as described herein. Such contact may occur in vivo or in vitro and is generally performed using a concentration of compound that is sufficient to alter H3 receptor GTP binding in vitro (using the assay provided in Example 7, herein).

The present invention further provides methods for treating a condition responsive to H3 receptor modulation in a patient, comprising administering to the patient a therapeutically effective amount of at least one H3 receptor modulator. Such conditions include, for example, attention deficit disorder, attention deficit hyperactivity disorder, schizophrenia, cognitive disorders (including mild cognitive impairment), epilepsy, migraine, narcolepsy, allergic rhinitis, vertigo, motion sickness, memory disorders such as Alzheimer's disease, Parkinson's disease, obesity, an eating disorder and diabetes.

Within further aspects, the present invention provides methods for determining the presence or absence of H3 receptor in a sample, comprising: (a) contacting a sample with a H3 receptor modulator as described herein under conditions that permit binding of the H3 receptor modulator to H3 receptor; and (b) detecting a level of the H3 modulator bound to H3 receptor.

The present invention also provides packaged pharmaceutical preparations, comprising: (a) a pharmaceutical composition as described herein in a container; and (b) instructions for using the composition to treat one or more conditions responsive to H3 receptor modulation, such as the conditions recited herein.

In yet another aspect, the present invention provides methods of preparing the compounds disclosed herein, including the intermediates.

These and other aspects of the present invention will become apparent upon reference to the following detailed description.

DETAILED DESCRIPTION

As noted above, the present invention provides thiazole amides, imidazole amides and related analogues. Such compounds may be used in vitro or in vivo, to modulate H3 receptor activity in a variety of contexts.

TERMINOLOGY

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, X, Ar). Unless otherwise specified, each variable within such a formula is defined independently of any other variable, and any variable that occurs more than one time in a formula is defined independently at each occurrence.

A "pharmaceutically acceptable salt" of a compound recited herein is an acid or base salt or a zwitterion that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC—(CH_2)_n—COOH$ where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred.

It will be apparent that each compound provided herein may, but need not, be formulated as a hydrate, solvate or non-covalent complex. In addition, the various crystal forms and polymorphs are within the scope of the present invention. Also provided herein are prodrugs of the compounds of the recited Formulas. A "prodrug" is a compound that may not fully satisfy the structural requirements of the compounds provided herein, but is modified in vivo, following administration to a patient, to produce a compound a formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

As used herein, the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_4$alkyl" refers to a single covalent bond ($C_0$) or an alkyl group having from 1 to 4 carbon atoms. The term "alkylene" refers to a divalent alkyl group. $C_1$-$C_4$alkylene is an alkylene group having from 1 to 4 carbon atoms. $C_0$-$C_4$alkylene is a single covalent bond or an alkylene group having from 1 to 4 carbon atoms.

"Alkenyl" refers to straight or branched chain alkene groups, which comprise at least one unsaturated carbon-carbon double bond. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. A "($C_3$-$C_8$cycloalkyl)$C_0$-$C_4$alkyl" is a $C_3$-$C_8$cycloalkyl group linked via a single covalent bond or a $C_1$-$C_4$alkylene group.

By "alkoxy," as used herein, is meant an alkyl group as described above attached via an oxygen bridge. Alkoxy groups include $C_1$-$C_8$alkoxy and $C_1$-$C_4$alkoxy groups, which have from 1 to 8 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups. Similarly, "alkylthio" refers to an alkyl group as described above attached via a sulfur bridge.

The term "oxo," as used herein, refers to a keto (C═O) group. An oxo group that is a substituent of a nonaromatic carbon atom results in a conversion of $—CH_2—$ to $—C(═O)—$.

The term "alkanoyl" refers to an acyl group (e.g., —(C═O)-alkyl), in which carbon atoms are in a linear or branched alkyl arrangement and where attachment is through the carbon of the keto group. Alkanoyl groups have the indicated number of carbon atoms, with the carbon of the keto group being included in the numbered carbon atoms. For example a $C_2$alkanoyl group is an acetyl group having the formula —(C═O)$CH_3$. Alkanoyl groups include, for example, $C_2$-$C_8$alkanoyl, $C_2$-$C_6$alkanoyl and $C_2$-$C_4$alkanoyl groups, which have from 2 to 8, from 2 to 6 or from 2 to 4 carbon atoms, respectively. "$C_1$alkanoyl" refers to —(C═O)H, which (along with $C_2$-$C_8$alkanoyl) is encompassed by the term "$C_1$-$C_8$alkanoyl."

An "alkanone" is a ketone group in which carbon atoms are in a linear or branched alkyl arrangement. "$C_3$-$C_8$alkanone," "$C_3$-$C_6$alkanone" and "$C_3$-$C_4$alkanone" refer to an alkanone having from 3 to 8, 6 or 4 carbon atoms, respectively. By way of example, a $C_3$ alkanone group has the structure $—CH_2—(C═O)—CH_3$.

Similarly, "alkyl ether" refers to a linear or branched ether substituent (i.e., an alkyl group that is substituted with an alkoxy group). Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. A $C_2$ alkyl ether has the structure —$CH_2$—O—$CH_3$ The term "alkoxycarbonyl" refers to an alkoxy group attached through a keto (—(C=O)—) bridge (i.e., a group having the general structure —C(=O)—O-alkyl). Alkoxycarbonyl groups include $C_1$-$C_8$, $C_1$-$C_6$ and $C_1$-$C_4$alkoxycarbonyl groups, which have from 1 to 8, 6 or 4 carbon atoms, respectively, in the alkyl portion of the group (i.e., the carbon of the keto bridge is not included in the indicated number of carbon atoms). "$C_1$alkoxycarbony" refers to —C(=O)—O—$CH_3$; $C_3$alkoxycarbonyl indicates —C(=O)—O—$(CH_2)_2CH_3$ or —C(=O)—O—(CH)$(CH_3)_2$.

"Alkanoyloxy," as used herein, refers to an alkanoyl group linked via an oxygen bridge (i.e., a group having the general structure —O—C(=O)-alkyl). Alkanoyloxy groups include $C_2$-$C_8$, $C_2$-$C_6$ and $C_2$-$C_4$alkanoyloxy groups, which have from 2 to 8, 6 or 4 carbon atoms, respectively. For example, "$C_2$alkanoyloxy" refers to —O—C(=O)—$CH_3$.

Similarly, "alkanoylamino," as used herein, refers to an alkanoyl group linked via a nitrogen bridge (i.e., a group having the general structure —N(R)—C(=O)-alkyl), in which R is hydrogen or $C_1$-$C_6$alkyl. Alkanoylamino groups include $C_2$-$C_8$, $C_2$-$C_6$ and $C_2$-$C_4$alkanoylamino groups, which have from 2 to 8, 6 or 4 carbon atoms within the alkanoyl group, respectively.

"Alkylsulfonyl" refers to groups of the formula —($SO_2$)-alkyl, in which the sulfur atom is the point of attachment. Alkylsulfonyl groups include $C_1$-$C_6$alkylsulfonyl and $C_1$-$C_4$alkylsulfonyl groups, which have from 1 to 6 or from 1 to 4 carbon atoms, respectively.

"Alkylsulfonylamino" refers to groups of the formula —N(R)—($SO_2$)-alkyl, in which R is hydrogen or $C_1$-$C_6$alkyl and the nitrogen atom is the point of attachment. Alkylsulfonylamino groups include $C_1$-$C_6$alkylsulfonylamino and $C_1$-$C_4$alkylsulfonylamino groups, which have from 1 to 6 or 1 to 4 carbon atoms, respectively.

"Aminosulfonyl" refers to groups of the formula —($SO_2$)—$NH_2$, in which the sulfur atom is the point of attachment. The term "mono- or di-($C_1$-$C_6$alkyl)aminosulfonyl" refers to groups that satisfy the formula —($SO_2$)—$NR_2$, in which the sulfur atom is the point of attachment, and in which one R is $C_1$-$C_6$alkyl and the other R is hydrogen or an independently chosen $C_1$-$C_0$alkyl.

"Alkylamino" refers to a secondary or tertiary amine having the general structure —NH-alkyl or —N(alkyl)(alkyl), wherein each alkyl may be the same or different. Such groups include, for example, mono- and di-($C_1$-$C_6$alkyl)amino groups, in which each alkyl may be the same or different and may contain from 1 to 6 carbon atoms, as well as mono- and di-($C_1$-$C_4$alkyl)amino groups.

"Alkylaminoalkyl" refers to an alkylamino group linked via an alkylene group (i.e., a group having the general structure -alkyl-NH-alkyl or -alkyl-N(alkyl)(alkyl)) in which each alkyl is selected independently. Such groups include, for example, mono- and di-($C_1$-$C_6$alkyl)amino$C_1$-$C_6$alkyl and mono- and di-($C_1$-$C_6$alkyl)amino$C_1$-$C_4$alkyl, in which each alkyl may be the same or different. "Mono- or di-($C_1$-$C_6$alkyl) amino$C_0$-$C_4$alkyl" refers to a mono- or di-($C_1$-$C_6$alkyl)amino group linked via a direct bond or a $C_1$-$C_4$alkylene group. The following are representative alkylaminoalkyl groups:

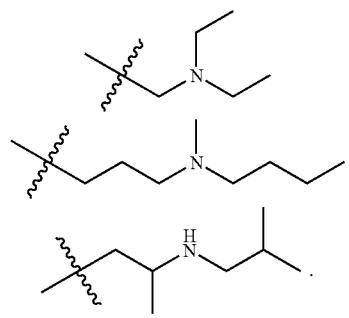

The term "aminocarbonyl" refers to an amide group (i.e., —(C=O)$NH_2$). The term "mono- or di-($C_1$-$C_6$alkyl)aminocarbonyl" refers to groups of the formula —(C=O)—N$(R)_2$, in which the carbonyl is the point of attachment, one R is $C_1$-$C_6$alkyl and the other R is hydrogen or an independently chosen $C_1$-$C_6$alkyl.

The term "halogen" refers to fluorine, chlorine, bromine or iodine.

A "haloalkyl" is an alkyl group that is substituted with 1 or more halogen atoms (e.g., "$C_1$-$C_4$haloalkyl" groups have from 1 to 4 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl. The term "haloalkoxy" refers to a haloalkyl group as defined above attached via an oxygen bridge. "$C_1$-$C_4$haloalkoxy" groups have 1 to 4 carbon atoms.

A dash ("-") that is not between two letters or symbols is used to indicate a point of attachment for a substituent. For example, —$CONH_2$ is attached through the carbon atom.

A "heteroatom," as used herein, is oxygen, sulfur or nitrogen.

A "carbocycle" or "carbocyclic group" comprises at least one ring formed entirely by carbon-carbon bonds (referred to herein as a carbocyclic ring), and does not contain a heterocycle. Certain representative carbocycles are cycloalkyl as described above. Other carbocycles are aryl (i.e., contain at least one aromatic ring).

A "heterocycle" or "heterocyclic group" has from 1 to 3 fused, pendant or spiro rings, at least one of which is a heterocyclic ring (i.e., one or more ring atoms is a heteroatom independently chosen from O, S and N, with the remaining ring atoms being carbon). Additional rings, if present, may be heterocyclic or carbocyclic. Typically, a heterocyclic ring comprises 1, 2, 3 or 4 heteroatoms; within certain embodiments each heterocyclic ring has 1 or 2 heteroatoms per ring. Each heterocyclic ring generally contains from 3 to 8 ring members (rings having from 4 or 5 to 7 ring members are recited in certain embodiments) and heterocycles comprising fused, pendant or spiro rings typically contain from 9 to 14 ring members. Certain heterocycles comprise a sulfur atom as a ring member; in certain embodiments, the sulfur atom is oxidized to SO or $SO_2$. Heterocycles may be optionally substituted with a variety of substituents, as indicated. Unless otherwise specified, a heterocycle may be a heterocycloalkyl group (i.e., each ring is saturated or partially saturated) or a heteroaryl group (i.e., at least one ring within the group is aromatic), and may be linked via any ring atom, provided that a stable compound results. A nitrogen-containing heteroaryl comprises at least one ring nitrogen atom. Additional heteroatoms may, but need not, be present.

Heterocyclic groups include, for example, acridinyl, azepanyl, azocinyl, benzimidazolyl, benzimidazolinyl, benzisothiazolyl, benzisoxazolyl, benzofuranyl, benzothiofuranyl, benzothiophenyl, benzoxazolyl, benzothiazolyl, benzotriazolylcarbazolyl, benztetrazolyl, NH-carbazolyl, carbolinyl, chromanyl, chromenyl, cinnolinyl, decahydroquinolinyl, dihydrofuro[2,3-b]tetrahydrofuran, dihydroisoquinolinyl, dihydrotetrahydrofuranyl, 1,4-dioxa-8-aza-spiro [4.5]dec-8-yl, dithiazinyl, furanyl, furazanyl, imidazolinyl, imidazolidinyl, imidazolyl, indazolyl, indolenyl, indolinyl, indolizinyl, indolyl, isobenzofuranyl, isochromanyl, isoindazolyl, isoindolinyl, isoindolyl, isothiazolyl, isoxazolyl, isoquinolinyl, morpholinyl, naphthyridinyl, octahydroisoquinolinyl, oxadiazolyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, piperidinyl, piperidonyl, pteridinyl, purinyl, pyranyl, pyrazinyl, pyrazolidinyl, pyrazolinyl, pyrazolyl, pyridazinyl, pyridoimidazolyl, pyridooxazolyl, pyridothiazolyl, pyridyl, pyrimidyl, pyrrolidinyl, pyrrolidonyl, pyrrolinyl, pyrrolyl, quinazolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienothiazolyl, thienooxazolyl, thienoimidazolyl, thienyl, thiophenyl, thiomorpholinyl and variants thereof in which the sulfur atom is oxidized, triazinyl, xanthenyl and any of the foregoing that are substituted with from 1 to 4 substituents as described above.

Certain heterocycles are 5- to 10-membered heteroaryl groups, or 5- or 6-membered heteroaryl groups (e.g., pyridyl, pyrimidyl and pyridazinyl), each of which may be substituted as indicated, heterocycles are 9- or 10-membered heteroaryl groups, which may be substituted as indicated. Such groups comprise two fused rings, at least one of which comprises a heteroatom and at least one of which is aromatic; preferably both rings are aromatic. Representative such groups include, for example, quinolinyl, quinazolinyl, isoquinolinyl, pyridoimidazolyl and pyridopyrazinyl. Other heterocycles are 4- to 8-membered heterocycloalkyl groups, which are saturated or partially saturate heterocyclic rings as described above, containing 4, 5, 6, 7 or 8 ring members.

A "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents). Other optionally substituted groups are substituted with at least one substituent (e.g., substituted with from 1 to 2, 3 or 4 independently selected substituents).

Unless otherwise specified, the term "H3 receptor" is used herein to refer to any histamine H3 subtype receptor, including human H3 receptor (see, e.g., U.S. Pat. No. 6,136,559), H3 receptor found in other mammals and chimeric receptors retaining H3 function, including the chimeric H3 receptor provided herein as SEQ ID NO:8.

A "H3 receptor modulator," also referred to herein as a "modulator," is a compound that modulates H3 receptor GTP binding. A H3 receptor modulator may be a H3 receptor agonist or antagonist. A modulator binds with "high affinity" if the $K_i$ at H3 receptor is less than 4 micromolar, preferably less than 1 micromolar, 500 nanomolar, 100 nanomolar, 50 nanomolar or 10 nanomolar. A representative assay for evaluating an effect on H3 receptor GTP binding is provided in Example 7, herein.

A modulator is considered an "antagonist" if it detectably inhibits H3 receptor agonist-stimulated GTP binding (using, for example, the representative assay provided in Example 7); in general, such an antagonist inhibits such GTP binding with a $IC_{50}$ value of less than 4 micromolar, preferably less than 1 micromolar, 500 nanomolar, 100 nanomolar, 50 nanomolar or 10 nanomolar. H3 receptor antagonists include neutral antagonists and inverse agonists.

An "inverse agonist" of H3 receptor is a compound that reduces the GTP binding activity of H3 receptor below its basal activity level in the absence of added agonist. Inverse agonists of H3 receptor may also inhibit the activity in the presence of agonist. The basal activity of H3 receptor, as well as the reduction in H3 receptor GTP binding activity due to the presence of H3 receptor antagonist, may be determined using the assay of Example 7.

A "neutral antagonist" of H3 receptor is a compound that inhibits the activity of H3 receptor agonist, but does not significantly change the basal activity of the receptor (i.e., within the assay of Example 7 performed in the absence of agonist, H3 receptor activity is reduced by no more than 10%, preferably by no more than 5%, and more preferably by no more than 2%; most preferably, there is no detectable reduction in activity). The basal activity is the level of GTP binding observed in the assay in the absence of added histamine or any other agonist, and in the further absence of any test compound. Neutral antagonists of H3 receptor may, but need not, inhibit the binding of agonist to H3 receptor.

As used herein a "H3 receptor agonist" is a compound that elevates the activity of the receptor above the basal activity level of the receptor. H3 receptor agonist activity may be identified using the representative assay provided in Example 7. In general, such an agonist has an $EC_{50}$ value of less than 4 micromolar, preferably less than 1 micromolar, 500 nanomolar, 100 nanomolar, 50 nanomolar or 10 nanomolar within the assay provided in Example 7. If the GTP binding activity brought about by a test compound attains the same level to that of histamine, it is defined as a full agonist. If the level of GTP binding activity brought about by a test compound is above baseline but below the level attained by histamine, it is defined as a partial agonist. Preferred antagonist compounds provided herein do not elevate GTP binding activity under such conditions more than 10% above baseline, preferably not more than 5% above baseline, and most preferably not more than 2% above baseline.

A "therapeutically effective amount" (or dose) is an amount that, upon administration to a patient, results in a discernible patient benefit (e.g., provides detectable relief from a condition being treated). Such relief may be detected using any appropriate criteria, including alleviation of one or more symptoms characteristic of the condition. A therapeutically effective amount or dose generally results in a concentration of compound in a body fluid (such as blood, plasma, serum, CSF, synovial fluid, lymph, cellular interstitial fluid, tears or urine) that is sufficient to alter H3 receptor GTP binding in vitro.

A "patient" is any individual treated with a compound or pharmaceutically acceptable salt thereof provided herein. Patients include humans, as well as other animals such as companion animals (e.g., dogs and cats) and livestock. Patients may be experiencing one or more symptoms of a condition responsive to H3 receptor modulation, or may be free of such symptom(s) (e.g., treatment may be prophylactic).

Thiazole Amides, Imidazole Amides and Related Analogues

As noted above, the present invention provides thiazole amides, imidazole amides and related analogues of Formula A and pharmaceutically acceptable salts of such compounds. Within certain aspects, such compounds are H3 receptor modulators that may be used in a variety of contexts, including in the therapeutic treatment of human and animal patients as discussed below. H3 receptor modulators may also be used within in vitro assays (e.g., assays for receptor activity), and as probes for detection and localization of H3 receptor.

Within certain embodiments, compounds of Formula A further satisfy Formula I:

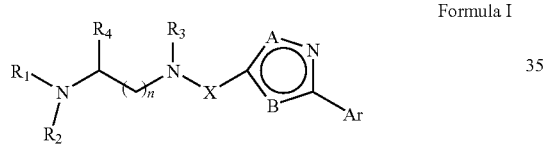

Formula I or are a pharmaceutically acceptable salt thereof, in which variables are as noted above. Within certain embodiments of Formula I, at least one of A and B is not $CR_5$ and A is not N if B is O.

In certain compounds of Formula I, the 5-membered heteroaryl ring designated:

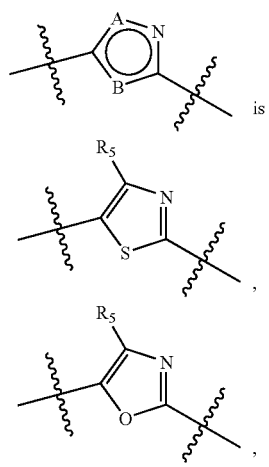

is

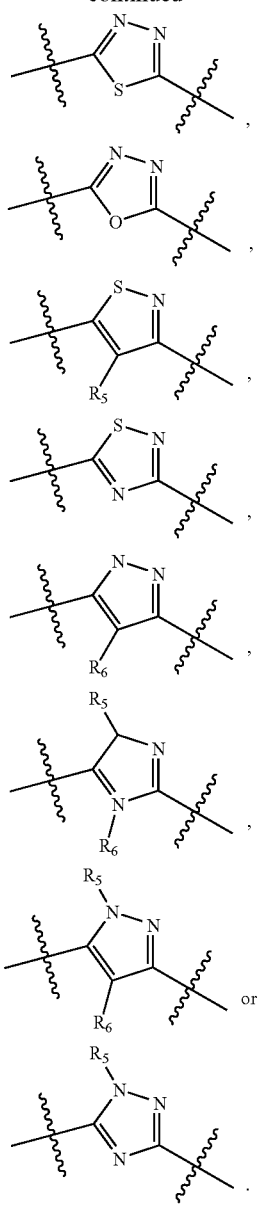

For example, in certain compounds, B is N, $NR_6$, O or S. In other compounds, A is N, $NR_6$ or S (e.g., N or $NR_6$). In certain such compounds, A is N, $NR_6$ or S (e.g., N or $NR_6$) and B is N, $NR_6$, O or S.

Certain compounds of Formula I further satisfy one or more of Formulas Ia-Ii, or are a pharmaceutically acceptable salt of such a compound.

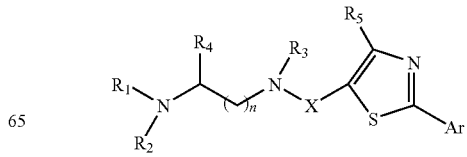

Formula Ia

Formula Ib
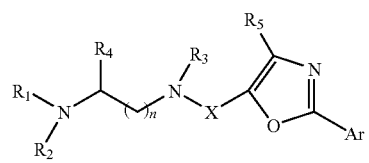

Formula Ic
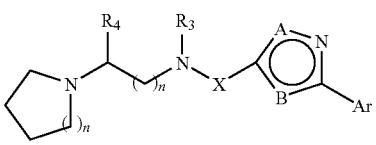

Formula Id
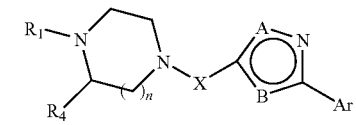

Formula Ie
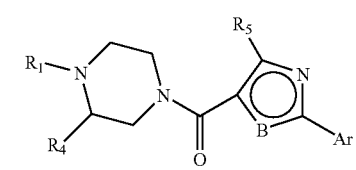

Formula If
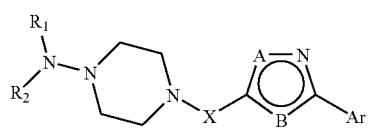

Formula Ig
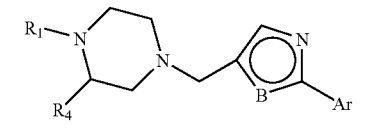

Formula Ih
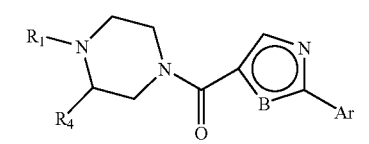

Formula Ii
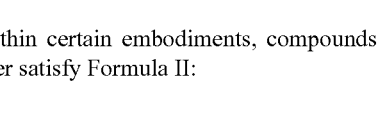

Within certain embodiments, compounds of Formula A further satisfy Formula II:

Formula II
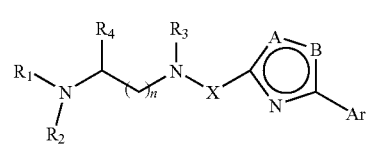

or are a pharmaceutically acceptable salt thereof, in which variables are as noted above.

In certain compounds of Formula II, A is N, $NR_6$ or $CR_5$; in further embodiments, A is $NR_6$ or $CR_5$. Within still further embodiments, the 5-membered heteroaryl ring designated:

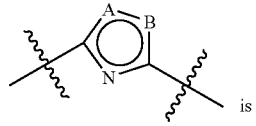

is

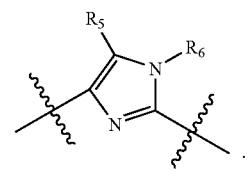

Certain compounds of Formula II further satisfy one or more of Formulas IIa–IIg, or are a pharmaceutically acceptable salt of such a compound.

Formula IIa

Formula IIb

Formula IIc

Formula IId

Formula IIe

Formula IIf

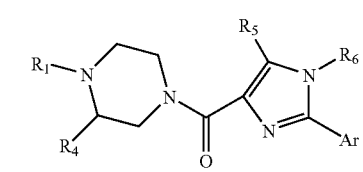

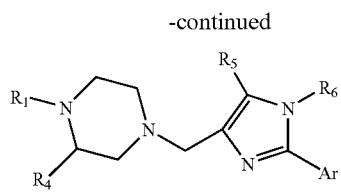

Formula IIg

Within certain embodiments, compounds of Formula A further satisfy Formula III:

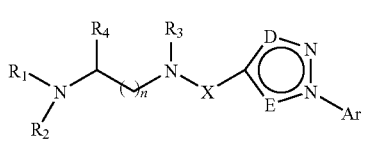

Formula III or are a pharmaceutically acceptable salt thereof, in which variables are as noted above.

In certain compounds of Formula III, the 5-membered heteroaryl ring designated:

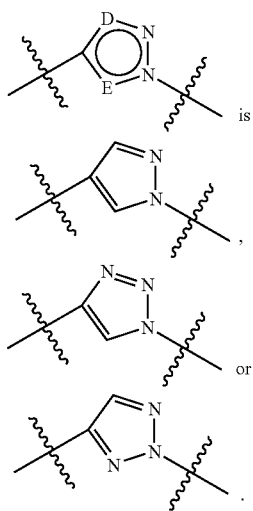

is

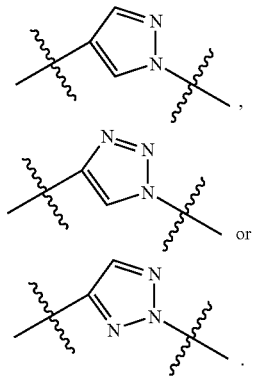

, or

.

For example, in certain compounds, D and E are independently $CR_5$, wherein $R_5$ is hydrogen, cyano or $C_1$-$C_8$alkyl that is substituted with from 0 to 4 substituents independently chosen from hydroxy, halogen, amino and cyano. Within further such compounds, D and E are each CH. Within other compounds, one of D and E is N, and the other of D and E is $CR_5$.

Certain compounds of Formula III further satisfy one or more of Formulas IIIa-IIIg, or are a pharmaceutically acceptable salt of such a compound.

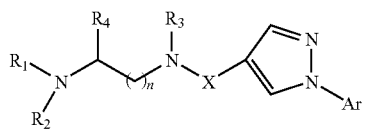

Formula IIIa

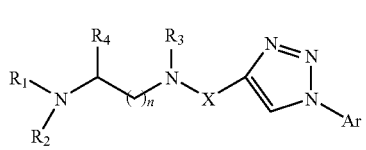

Formula IIIb

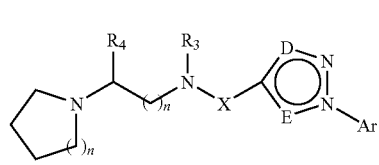

Formula IIIc

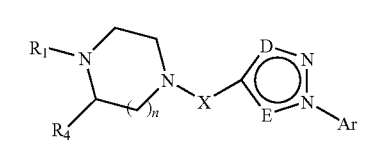

Formula IIId

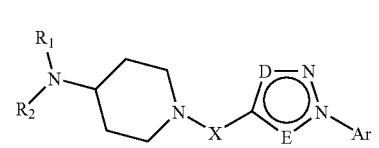

Formula IIIe

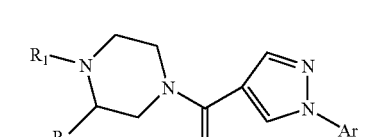

Formula IIIf

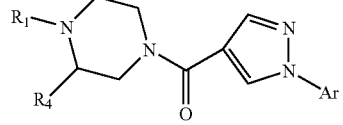

Formula IIIg

Within certain embodiments, compounds of Formula A further satisfy Formula IV:

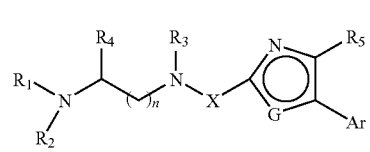

Formula IV or are a pharmaceutically acceptable salt thereof, in which variables are as noted above.

In certain compounds of Formula IV, the 5-membered heteroaryl ring designated:

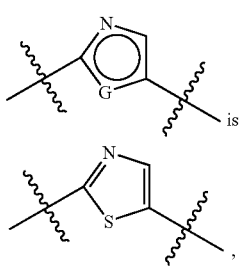

is

,

-continued

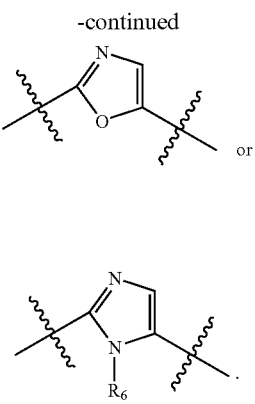

or

In certain compounds, G is O or S.

Certain compounds of Formula IV further satisfy one or more of Formulas IVa-IVh, or are a pharmaceutically acceptable salt of such a compound.

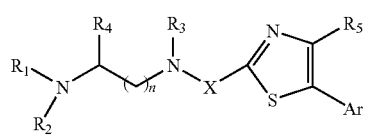
Formula IVa

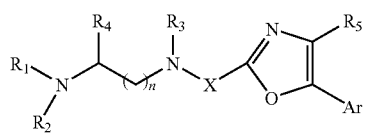
Formula IVb

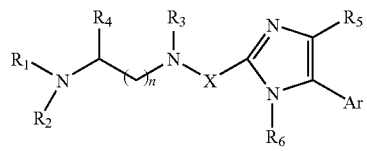
Formula IVc

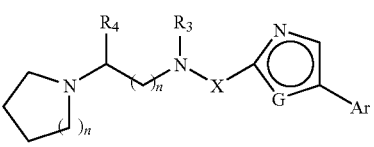
Formula IVd

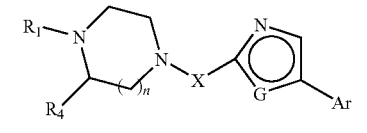
Formula IVe

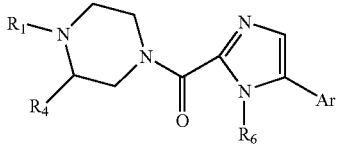
Formula IVf

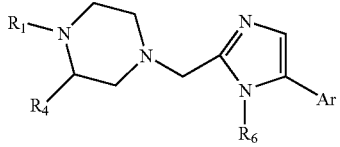
Formula IVg

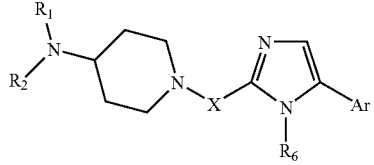
Formula IVh

Within certain embodiments, compounds of Formula A further satisfy Formula V:

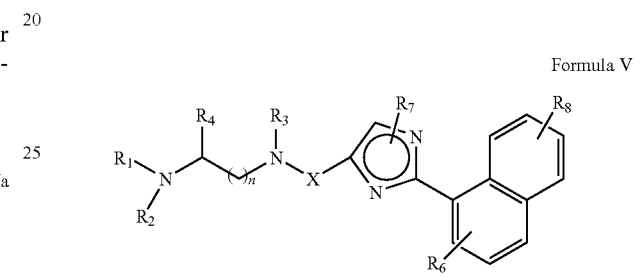
Formula V or are a pharmaceutically acceptable salt thereof, in which:

$R_7$ represents 0, 1 or 2 substituents independently chosen from hydrogen, halogen, cyano and $C_1$-$C_8$alkyl that is substituted with from 0 to 4 substituents independently chosen from hydroxy, halogen, amino, cyano and $C_1$-$C_4$alkoxy;

Each $R_8$ independently represents 0, 1 or 2 substituents independently chosen from:
(a) hydroxy, halogen, amino, cyano, nitro, —COOH and aminocarbonyl; and
(b) $C_1$-$C_8$alkyl, $C_3$-$C_8$cycloalkyl, $C_2$-$C_8$alkyl ether and $C_1$-$C_8$alkoxy, each of which is substituted with from 0 to 4 substituents independently chosen from hydroxy, halogen, amino, cyano, $C_1$-$C_4$alkyl and $C_1$-$C_4$alkoxy; and the remaining variables are as noted above.

Within certain such compounds, $R_8$ represents 0 or 1 substituent independently chosen from halogen, cyano, amino, $C_1$-$C_4$alkyl, $C_1$-$C_4$haloalkyl, $C_1$-$C_4$alkoxy and $C_1$-$C_4$haloalkoxy. Further compounds of Formula V further satisfy Formula Va:

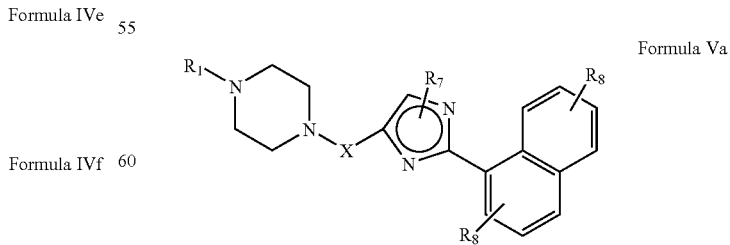
Formula Va or are a pharmaceutically acceptable salt thereof, in which variables are as described for Formula V.

As noted above, the present invention further provides compounds of Formula B

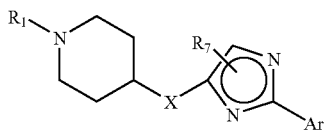

Formula B and the pharmaceutically acceptable salts thereof, in which variables are as described above. Certain such compounds further satisfy the formula:

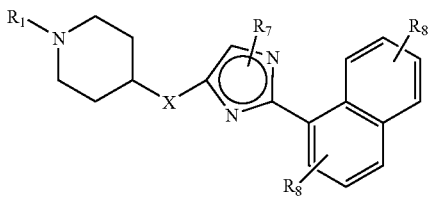

wherein each $R_8$ independently represents 0, 1 or 2 substituents independently chosen from: (a) hydroxy, halogen, amino, cyano, nitro, —COON and aminocarbonyl; and (b) $C_1$-$C_8$alkyl, $C_3$-$C_8$cycloalkyl, $C_2$-$C_8$alkyl ether and $C_1$-$C_8$alkoxy, each of which is substituted with from 0 to 4 substituents independently chosen from hydroxy, halogen, amino, cyano, $C_1$-$C_4$alkyl and $C_1$-$C_4$alkoxy. Within certain such compounds, wherein each $R_8$ independently represents 0 or 1 substituent independently chosen from halogen, cyano, amino, $C_1$-$C_4$alkyl, $C_1$-$C_4$haloalkyl, $C_1$-$C_4$alkoxy and $C_1$-$C_4$haloalkoxy.

Within certain compounds of Formulas A, B, I, II, III, IV or V, or the subformulas thereof, X is CO. Within other compounds, X is $CH_2$. Within further compounds of Formula B, X is CH(OH), CF or $CF_2$.

$R_3$, within certain compounds of Formulas A, B, I, II, III, IV or V, or the subformulas thereof, is hydrogen or $C_1$-$C_8$alkyl.

Within certain compounds of Formulas A, I, II, III or IV, or the subformulas thereof, Ar is phenyl, pyridyl, naphthyl or a 9- or 10-membered heteroaryl, each of which is substituted with form 0 to 3 substituents independently chosen from halogen, cyano, amino, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkanoyl, $C_1$-$C_4$alkoxycarbonyl, $C_2$-$C_4$alkanoyloxy and mono- and di-($C_1$-$C_4$alkyl)amino. In certain such compounds, Ar is naphthyl or a 9- or 10-membered heteroaryl, optionally substituted (e.g., with from 0 to 3 substituents independently chosen from halogen, cyano, amino, $C_1$-$C_4$alkyl, $C_1$-$C_4$haloalkyl, $C_1$-$C_4$alkoxy and $C_1$-$C_4$haloalkoxy. In other compounds, Ar is phenyl or a 6-membered heteroaryl, each of which is preferably substituted at a ring carbon atom that is located ortho to the point of attachment to Y.

Within certain compounds of Formulas A, B, I, II, III, IV or V, or the subformulas thereof, $R_1$ is $C_1$-$C_6$alkyl and $R_4$ is hydrogen.

Within certain compounds of Formulas A, I, II, III, IV or V, or the subformulas thereof, $R_3$ (where present) is hydrogen or $C_1$-$C_8$alkyl.

Representative compounds provided herein include, but are not limited to, those specifically described in Examples 1-3. It will be apparent that the specific compounds recited herein are representative only, and are not intended to limit the scope of the present invention. Further, as noted above, all compounds of the present invention may be present as a free acid or base or as a pharmaceutically acceptable salt.

In certain aspects, compounds provided are H3 receptor modulators, as determined using an assay for H3 receptor GTP binding. References herein to an "assay for H3 receptor GTP binding" are intended to refer to a standard in vitro GTP binding assay such as that provided in Example 7, which may be performed in the presence or absence of added agonist. If performed in the presence of added agonist, the assay is referred to as an "assay for H3 receptor agonist-stimulated GTP binding." Briefly, to assess H3 receptor agonist-stimulated GTP binding, a H3 receptor preparation is incubated with a H3 receptor agonist (e.g., histamine or an analogue thereof such as R-alpha-methylhistamine), labeled (e.g., $^{35}S$) GTP and unlabeled test compound. Within the assays provided herein, the H3 receptor used is preferably mammalian H3 receptor (e.g., human or rat H3 receptor), and more preferably a chimeric human H3 receptor such as a receptor having the sequence provided in SEQ ID NO:8. The receptor may be recombinantly expressed or naturally expressed. The H3 receptor preparation may be, for example, a membrane preparation from cells that recombinantly express H3 receptor. Incubation with an H3 receptor modulator results in a decrease or increase in the amount of label bound to the H3 receptor preparation, relative to the amount of label bound in the absence of the compound. This decrease or increase may be used to determine whether the compound functions as an agonist or antagonist, and to determine the $K_i$ at H3 receptor as described herein.

As noted above, compounds that are H3 receptor antagonists are preferred within certain embodiments. When agonist-contacted cells are contacted with a compound that is a H3 receptor antagonist, the response is generally reduced by at least 20%, preferably at least 50% and more preferably at least 80%, as compared to cells that are contacted with the agonist in the absence of test compound. The $IC_{50}$ for H3 receptor antagonists provided herein is preferably less than 4 micromolar, less than 1 micromolar, less than 500 nM, less than 100 nM, less than 50 nM or less than 10 nM. In certain embodiments, H3 receptor antagonists provided herein exhibit no detectable agonist activity in an in vitro assay of H3 receptor agonism at a concentration of compound equal to the $IC_{50}$. Certain such antagonists exhibit no detectable agonist activity an in vitro assay of H3 receptor agonism at a concentration of compound that is 100-fold higher than the $IC_{50}$.

In certain embodiments, preferred H3 receptor modulators provided herein are non-sedating. In other words, a dose of H3 receptor modulator that is twice the minimum therapeutically effective dose causes only transient (i.e., lasting for no more than ½ the time that the therapeutic effect lasts) or preferably no statistically significant sedation in an animal model assay of sedation (using the method described by Fitzgerald et al. (1988) *Toxicology* 49(2-3):433-9). Preferably, a dose that is from 5 to 100 times the minimum therapeutically effective dose does not produce statistically significant sedation. More preferably, a H3 receptor modulator does not produce sedation at oral doses of less than 140 mg/kg (preferably less than 50 mg/kg, more preferably less than 30 mg/kg).

If desired, H3 receptor modulators provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, and still more preferably less than 1 mg/kg), toxicity (a preferred H3 receptor modulator is nontoxic when a therapeutically effective amount is administered to a subject), side effects (a preferred H3 receptor modulator produces side effects comparable to placebo when a therapeutically effective amount of the compound is administered to a subject), serum protein binding and in vitro and in vivo half-life (a preferred H3 receptor modulator exhibits an in vivo half-life allowing for Q.I.D. dosing, preferably T.I.D. dosing, more preferably B.I.D. dosing, and most preferably once-a-day dosing). In addition, differential penetration of the blood brain barrier may be desirable for certain H3 receptor modulators. Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays or whole serum binding assays. Compound half-life is inversely proportional to the frequency of dosage of a compound. In vitro half-lives of compounds may be predicted from assays of microsomal half-life as described within Example 8, herein.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, or (4) does not cause substantial release of liver enzymes.

As used herein, a compound that does not substantially inhibit cellular ATP production is a compound that satisfies the criteria set forth in Example 9, herein. In other words, cells treated as described in Example 9 with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the $EC_{50}$ or $IC_{50}$ for the compound. In certain preferred embodiments, a dose of 0.01, 0.05, 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound does not cause substantial liver enlargement if daily treatment of laboratory rodents (e.g., mice or rats) for 5-10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05, 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the $EC_{50}$ or $IC_{50}$ for the compound does not elevate serum levels of ALT, LDH or AST in laboratory rodents by more than 100% over matched mock-treated controls. In more highly preferred embodiments, such doses do not elevate such serum levels by more than 75% or 50% over matched controls. Alternatively, a H3 receptor modulator does not promote substantial release of liver enzymes if, in an in vitro hepatocyte assay, concentrations (in culture media or other such solutions that are contacted and incubated with hepatocytes in vitro) that are equal to the $EC_{50}$ or $IC_{50}$ for the compound do not cause detectable release of any such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the $EC_{50}$ or $IC_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the $EC_{50}$ or $IC_{50}$ for the compound.

Certain preferred compounds are not clastogenic (e.g., as determined using a mouse erythrocyte precursor cell micronucleus assay, an Ames micronucleus assay, a spiral micronucleus assay or the like) at a concentration equal the $EC_{50}$ or $IC_{50}$ for the compound. In other embodiments, certain preferred H3 receptor modulators do not induce sister chromatid exchange (e.g., in Chinese hamster ovary cells) at such concentrations.

For detection purposes, as discussed in more detail below, H3 receptor modulators provided herein may be isotopically-labeled or radiolabeled. For example, compounds may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation of Thiazole Amides, Imidazole Amides and Related Analogues

Compounds provided herein may generally be prepared using standard synthetic methods. Starting materials are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein.

Certain definitions used in the following Schemes and elsewhere herein are:

| | |
|---|---|
| Bu | butyl |
| BOP | benzotriazol-1-yl-oxy-tris(dimethylamino)phosphonium hexafluorophosphate |
| $CDCl_3$ | deuterated chloroform |
| δ | chemical shift |
| DCM | dichloromethane |

| | |
|---|---|
| hr | hour(s) |
| Hz | hertz |
| LCMS | liquid chromatography/mass spectrometry |
| MS | mass spectrometry |
| (M + 1) | mass + 1 |
| MeOH | methanol |
| min | minute(s) |
| MOM | methoxymethyl |
| NBS | N-bromosuccinimide |
| NCS | N-chlorosuccinimide |
| n-BuLi | n-butyl lithium (also BuLi) |
| $P(t-Bu)_3HBF_4$ | tri-t-butylphosphonium tetrafluoroborate |
| $Pd_2(dba)_3$ | tris(dibenzylideneacetone)dipalladium(0) |
| $Pd(PPh_3)_4$ | tetrakis(triphenylphosphine)palladium(0) |
| PTLC | preparative thin layer chromatography |
| rt | room temperature |
| TBAF | tetrabutylammonium fluoride |
| TFA | trifluoroacetic acid |
| THF | tetrahydrofuran |
| TLC | thin layer chromatography |
| TMSCl | trimethylsilyl chloride |

Scheme 1

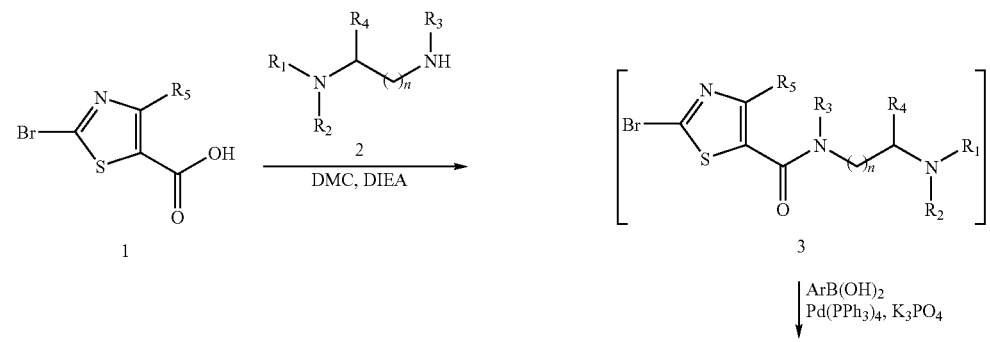

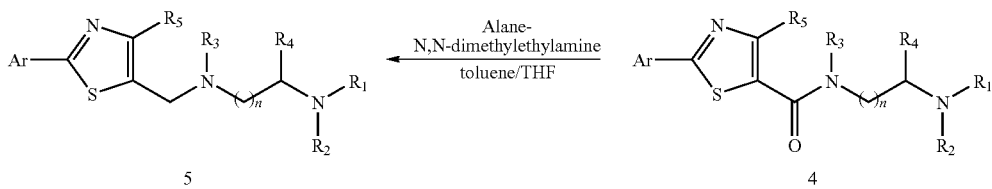

| | |
|---|---|
| DIBAL-H | diisobutylaluminium hydride |
| DMC | 2-chloro-1,3-dimethylimidazolinium chloride |
| DMF | dimethylformamide |
| DIEA | N,N-diisopropylethylamine |
| $Et_3N$ | triethylamine |
| $Et_2O$ | diethyl ether |
| EtOAc | ethyl acetate |
| EtOH | ethanol |
| $^1$H NMR | proton nuclear magnetic resonance |
| HPLC | high pressure liquid chromatography |

Scheme 1 illustrates the synthesis of compounds of Formula 4 and 5. 2-Bromo-thiazol-5-carboxylic acid 1 is reacted with amine 2 in the presence of DMC and DIEA to afford 2-bromo-thiazol-5-carboxamide 3, which without separation is treated with arylboronic acid under Suzuki coupling conditions to give 2-aryl-thiozol-5-carboxamide 4. Reduction of amide 4 with Alane-N,N-dimethylethylamine complex produces compound 5.

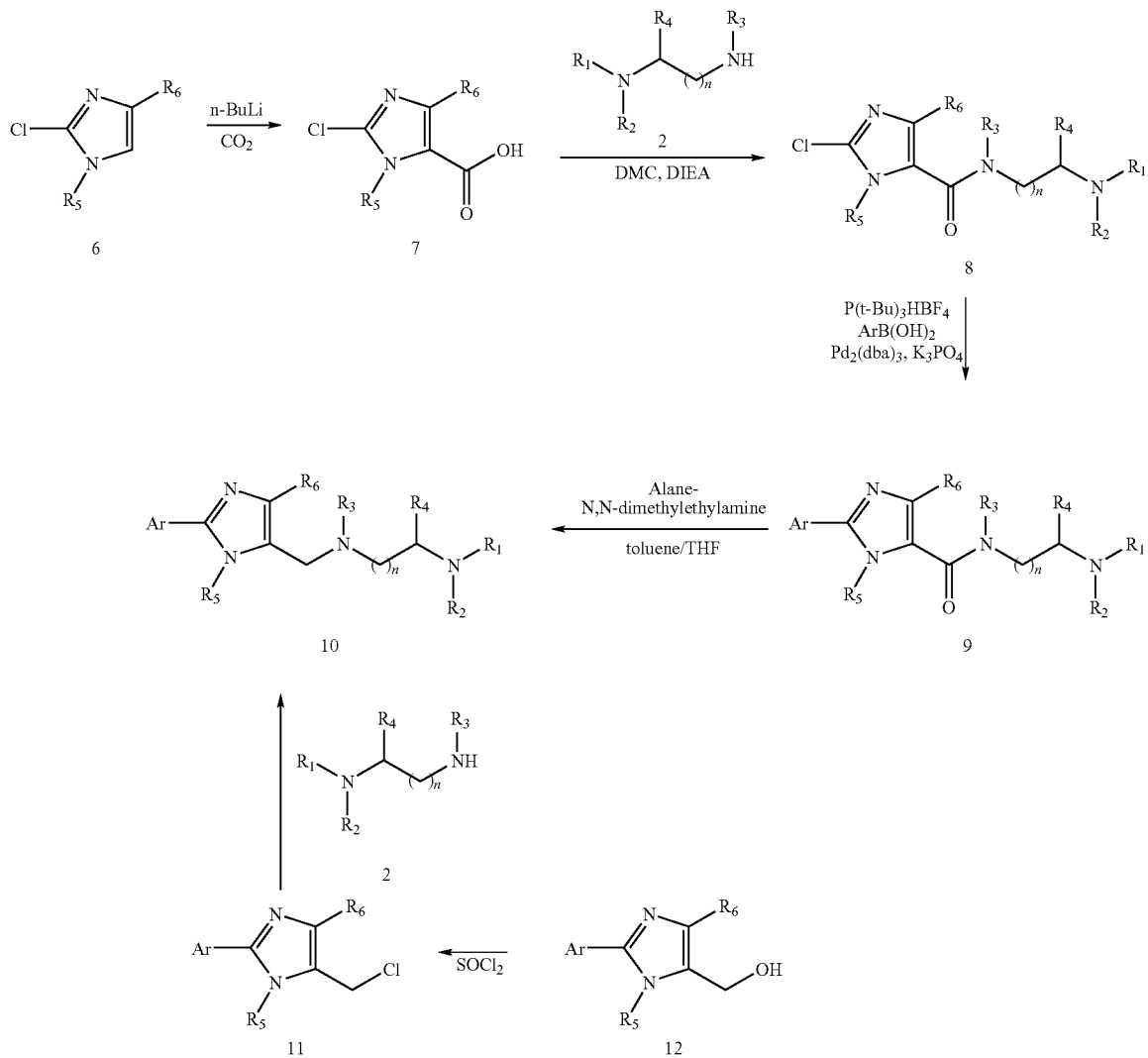

Scheme 2 illustrates the synthesis of compounds 9 and 10. Lithiation of compound 6 with n-BuLi followed by the addition of carbon dioxide affords 2-chloro-imidazole-4-carboxylic acid 7. Reaction of acid 7 with amine 2 in the presence of DMC and DIEA furnishes 2-chloro-imidazole-4-carboxamide 8, which undergoes Suzuki coupling reaction with arylboronic acid to give 2-aryl-imidazole-4-carboxamide 9. Reduction of amide 9 with Alane-N,N-dimethylethylamine complex gives compound 10. Alternatively, compound 10 is prepared from hydroxymethylimidazoles 12 via $SOCl_2$ treatment and subsequent alkylation reaction with amine 2.

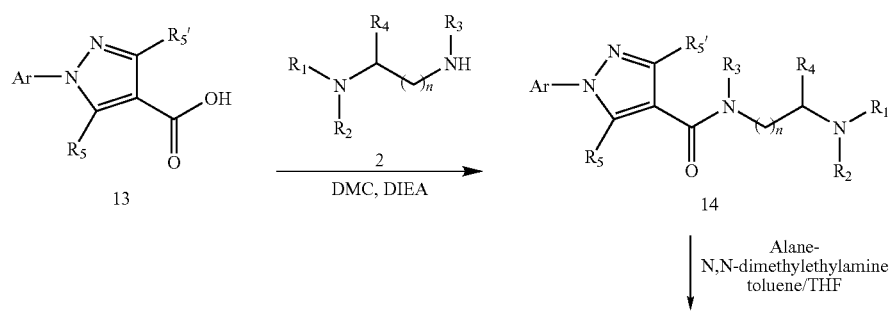

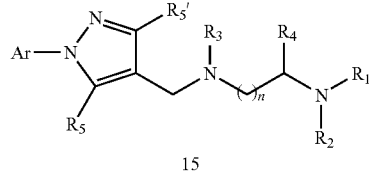
15
Scheme 3 illustrates the synthesis of 1-arylpyrazoles 14 and 15. Similar to the synthesis of thiazoles and imidazoles described in Schemes 1 and 2, reaction of 1-arylpyrazol-4-ylcarboxylic acid 13 with amine 2 gives amide 14, which can be reduced to the corresponding pyrazole 15.
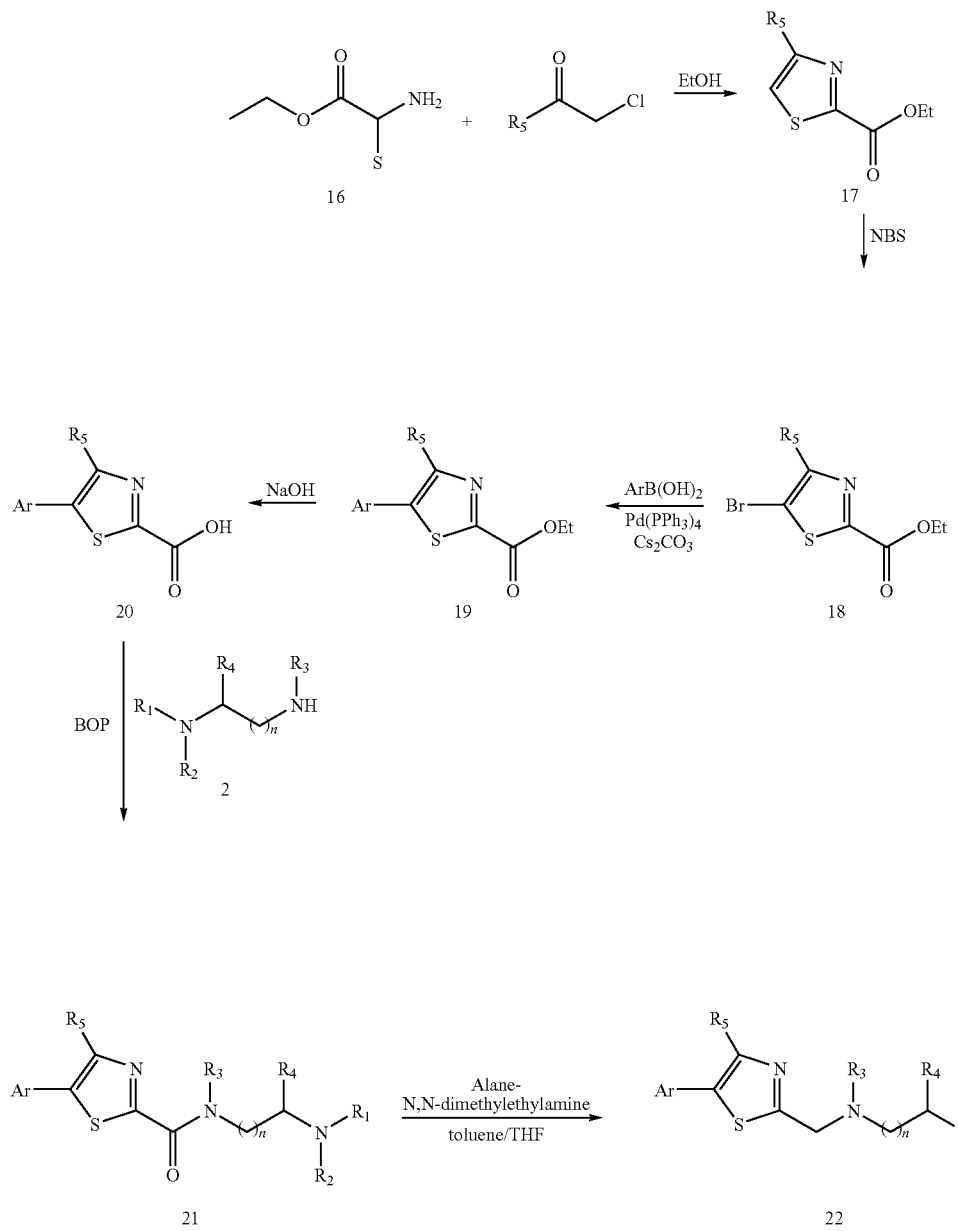

Scheme 4 illustrates the synthesis of 5-arylthiazoles 21 and 22. Reaction of thiooxamate 16 with α-chloroketone gives thiazole-2-carboxylic acid ethyl ester 17. Bromination of 17 with NBS provides 5-bromo-thiozole-2-carboxaylic acid ethyl ester 18. Reaction of 18 with arylboronic acid under Suzuki coupling conditions affords 5-aryl-thiazole-2-carboxylic acid ethyl ester 19, which is hydrolized to the corresponding carboxylic acid 20 in the presence of sodium hydroxide. Reaction of 20 with amine under BOP coupling conditions affords 5-aryl-thiazole-2-carboxamide 21, which can be reduced with Alane-N,N-dimethylethylamine complex to the corresponding thiazole 22.

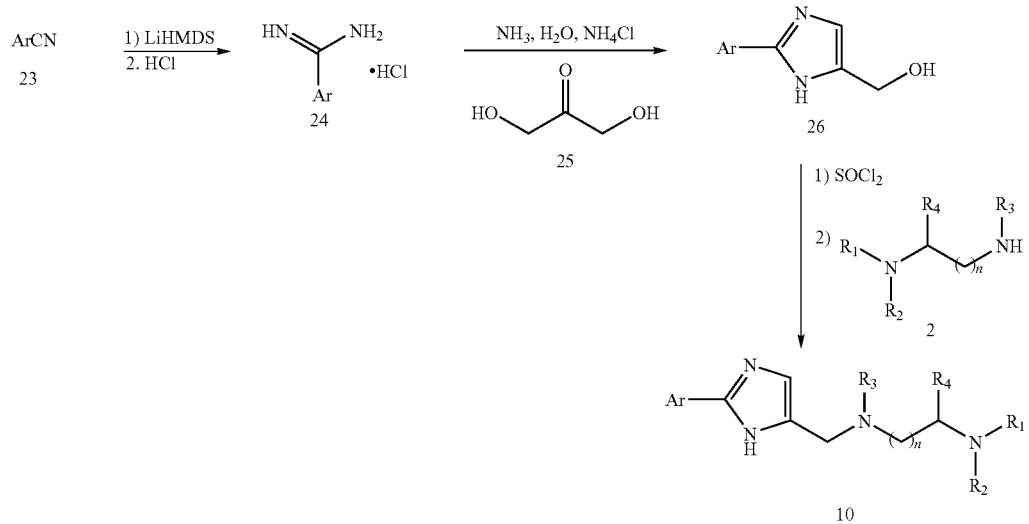

In an alternative procedure, compound 10 (when $R_5=R_6=H$) can be prepared from nitrile 23 as illustrated in Scheme 5. Treatment of nitrile 23 with lithium bis(trimethylsilyl)amide affords imidine 24, which upon reaction with ammonium hydroxide and dihydroxyacetone gives hydroxymethylimidazole 26. Compound 10 is prepared via the reaction of hydroxymethylimidazole 26 with thionyl chloride followed by treatment with amine 2.

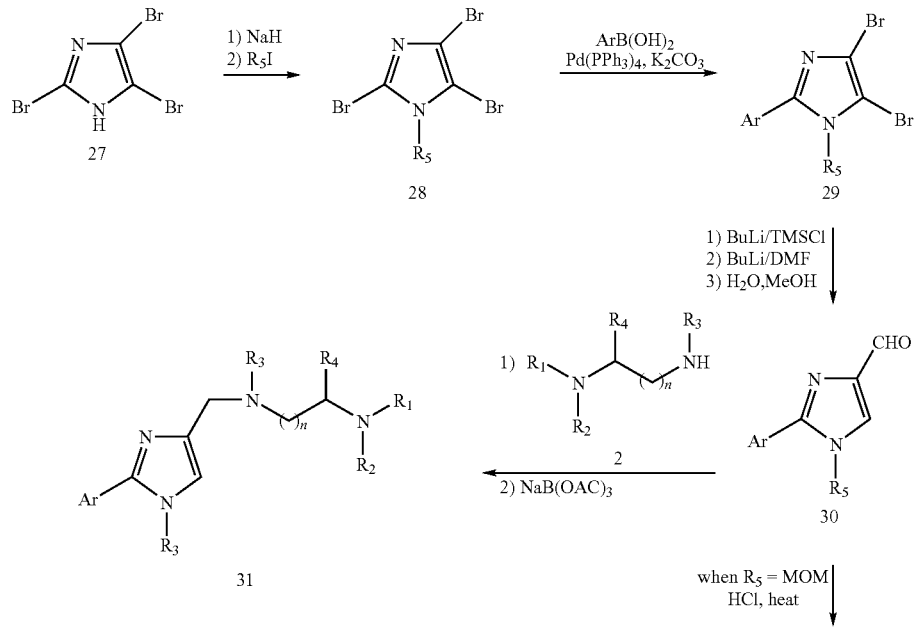

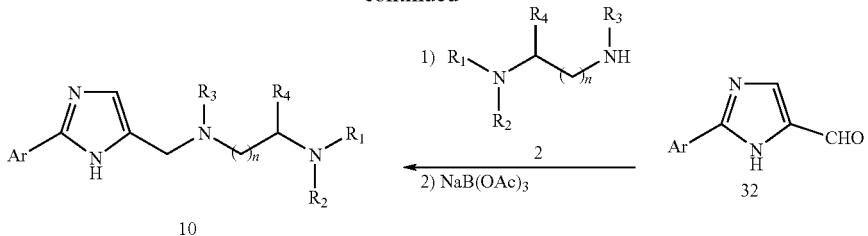

Alternatively, compound 10 (when $R_5=R_6=H$) can be prepared from 2,4,5-tribromoimidazole 27. MOM protection of the NH group of imidazole 27, followed by Suzuki coupling with a boronic acid provides 29. Stepwise lithiation strategy gives aldehyde intermediate 30. Deprotection followed by reductive amination of 30 affords compound 10. Compound 31 (regioisomer of 10 when $R_5 \neq H$) is synthesized via reductive amination of aldehyde 30 (when $R_5$=alkyl) with an appropriate amine 2.

Scheme 7

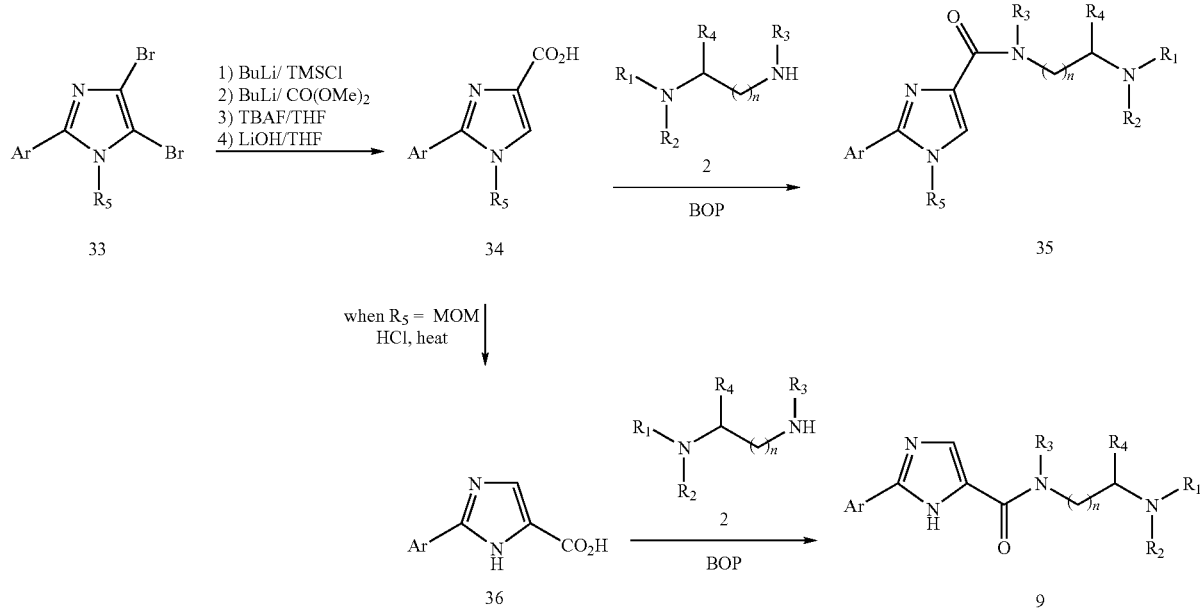

Similarly, as an alternative synthesis, dibromide intermediate 33 (when $R_5$=MOM) can be converted to amide 9 ($R_5=H$) via stepwise lithiation and amidation with amine 2. 4-Amidoimidazole 35 (regioisomer of 9 when $R_5 \neq H$) is synthesized from acid 34 via amidation.

Scheme 8

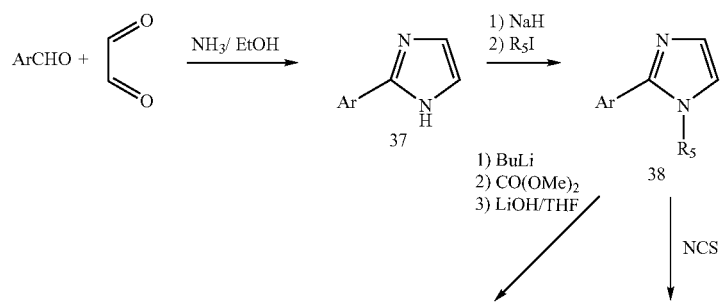

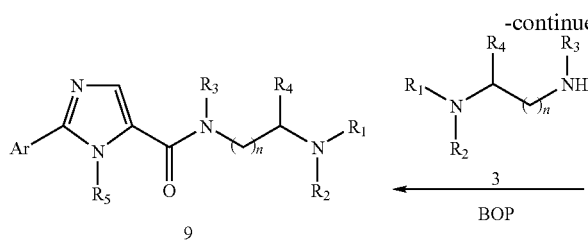
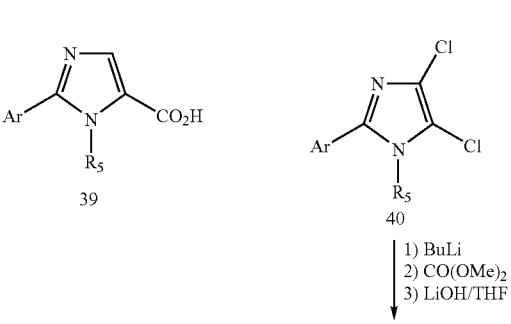
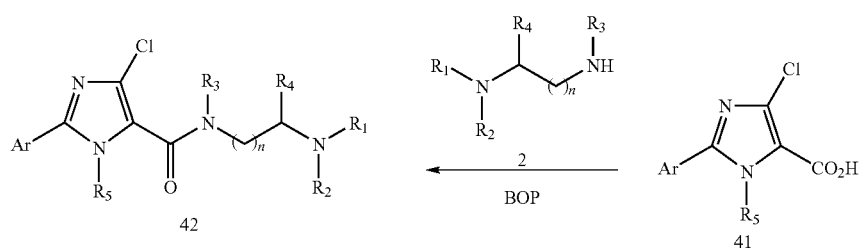

In compounds wherein $R_5$ is an alkyl group, 5-amidoimidazole 9 is convergently prepared from the corresponding acid 39, which is achieved via imidazole formation, alkylation and lithiation starting from an aryl aldehyde and glyoxal. 4-Chloro-5-amidoimidazole 42 is available from the chlorination of imidazole 38, followed by selective chlorine/lithium exchange and amidation as illustrated in Scheme 8.

Scheme 9

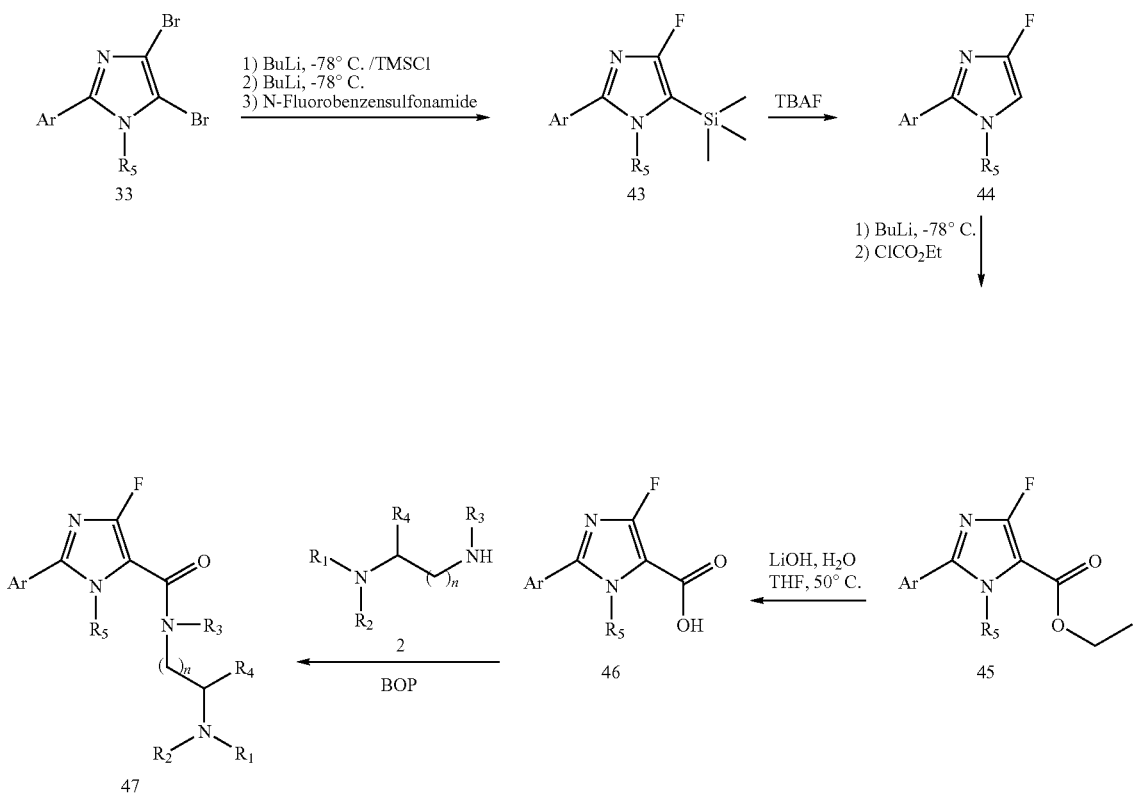

Scheme 9 illustrates the synthesis of 4-fluoro-5-amidoimidazole 47. The 4-fluororine atom is introduced by lithiation of dibromoimidazole 33, followed by reaction with N-fluorobenzenesulfonamide. Anion produced from the lithiation of 44 reacts with chloroformate followed by hydrolysis to give acid 46. Amidation of 46 with amine 2 produces amide 47.
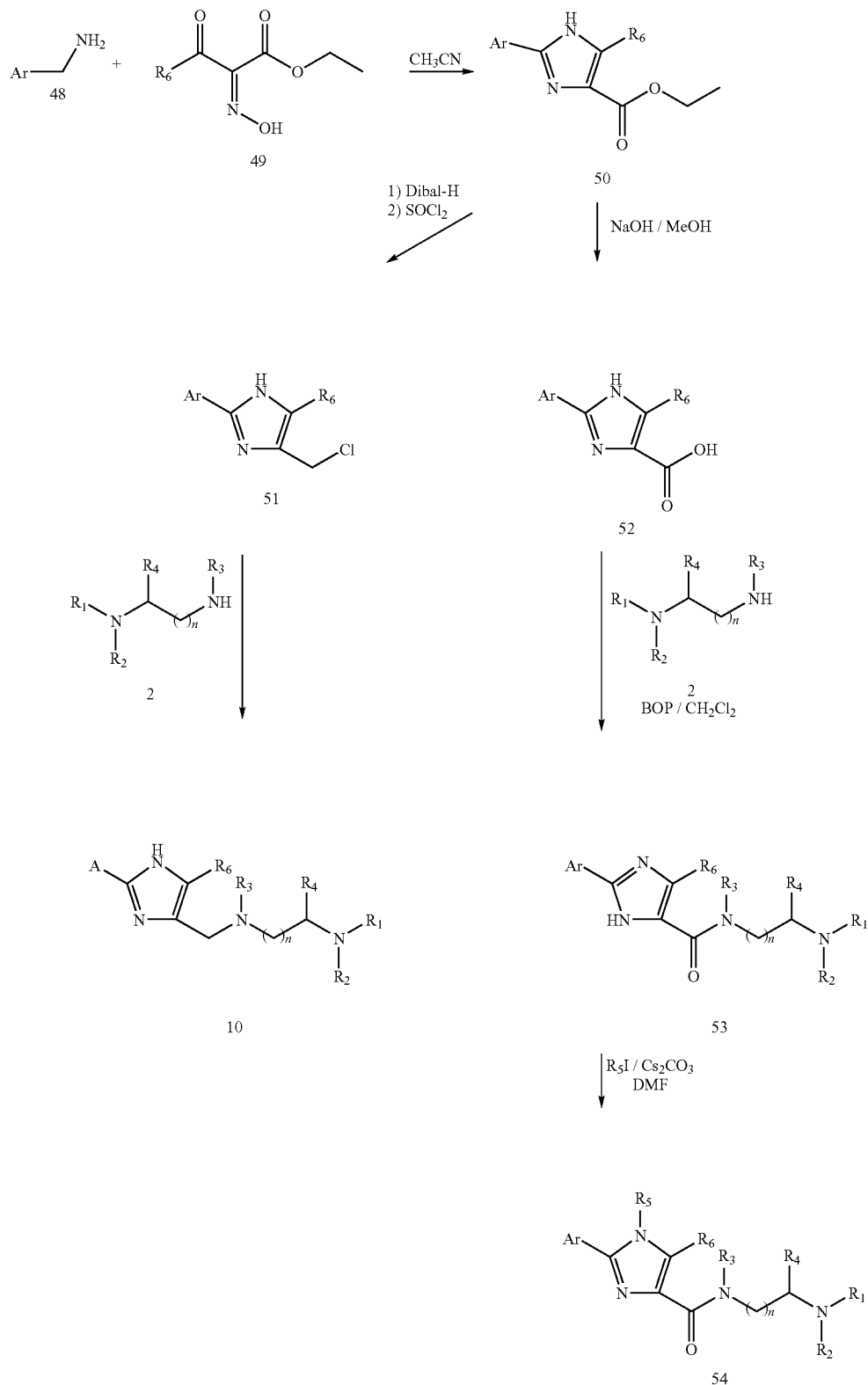

In compounds wherein $R_6$ is an alkyl, imidazoles 10 and 54 are prepared in slightly modified routes, as illustrated in Scheme 10. Arylmethylamine 48 reacts with oxime 49 to produce ester 50. By standard procedures, 50 can be converted to aminomethylimidazole 10 and amidoimidazoles 53 and 54.
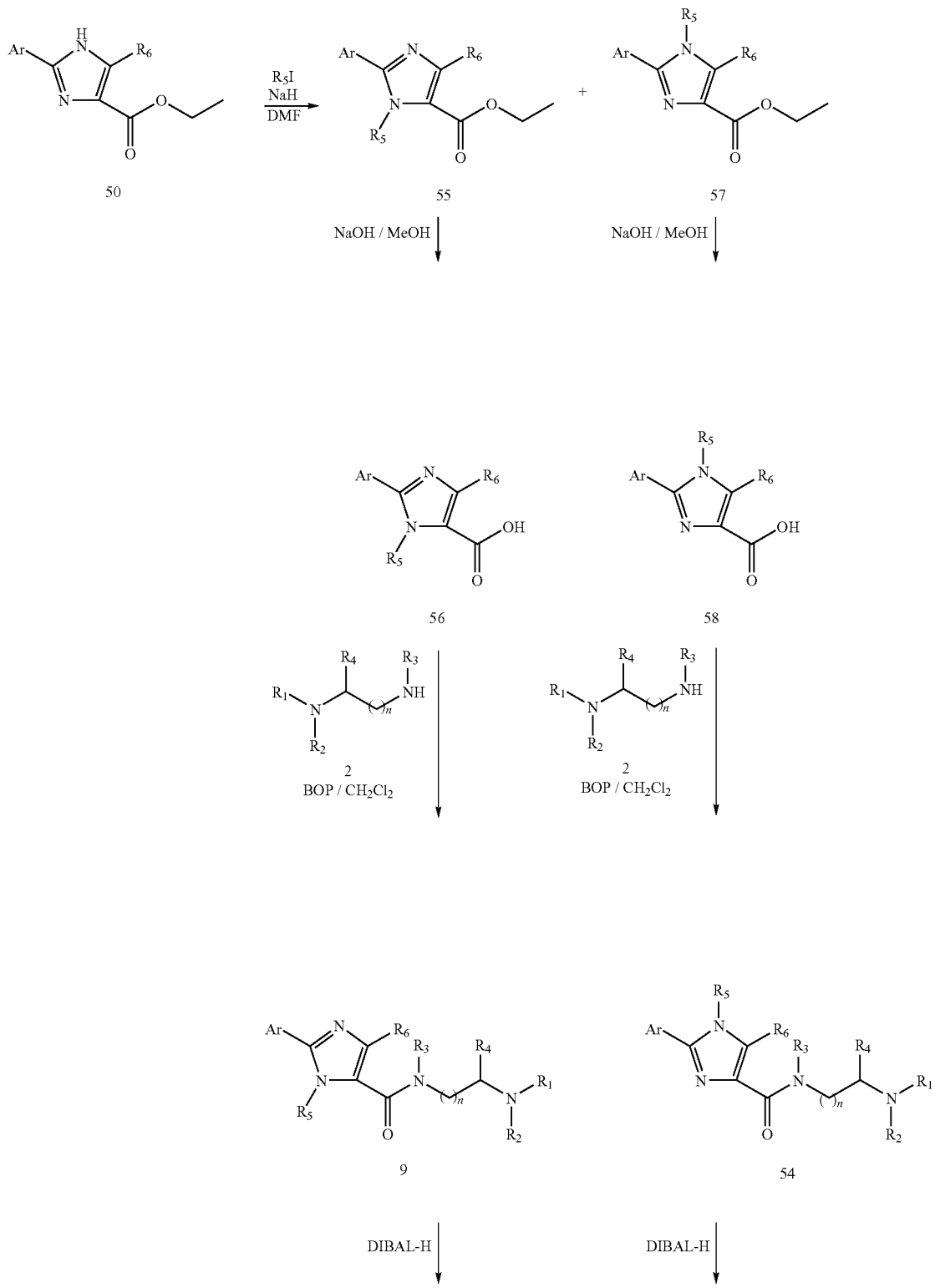

-continued
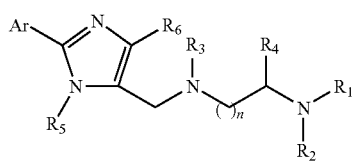
10
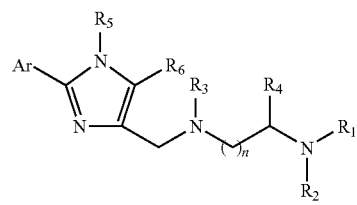
59
Ester intermediate 50 can also be manipulated to provide aminomethylimidazoles 10 and 59, and amidoimidazoles 9 and 54 using routine procedures, as illustrated in Scheme 11.
Scheme 12
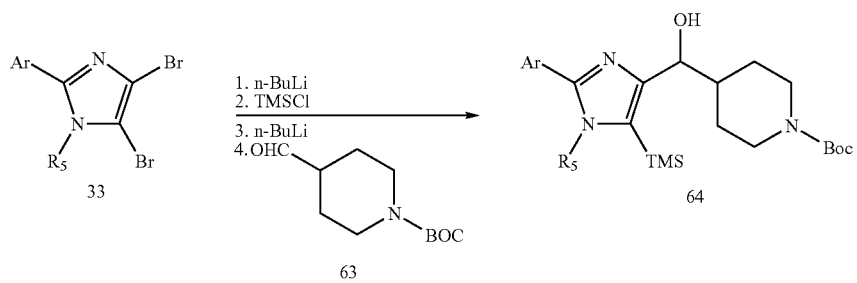
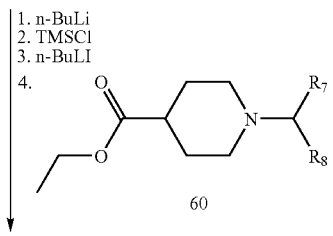
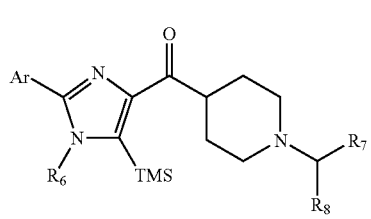
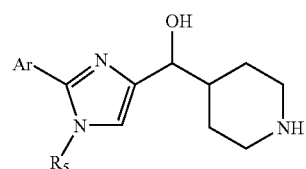
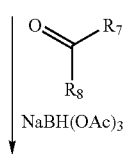

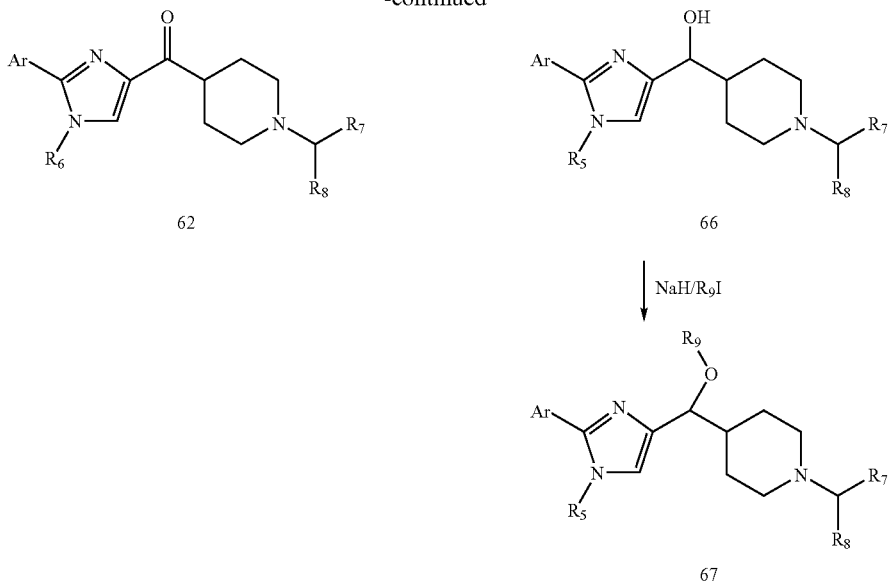

Scheme 12 illustrates the synthesis of alcohol 66, ether 67 and ketone 62. Stepwise halogen/lithium exchange followed by reaction with aldehyde 63 or ester 60 provides alcohol 64 and ketone 61, respectively. Subsequent manipulations as illustrated in Scheme 12 furnish compounds 66, 62 and 67.

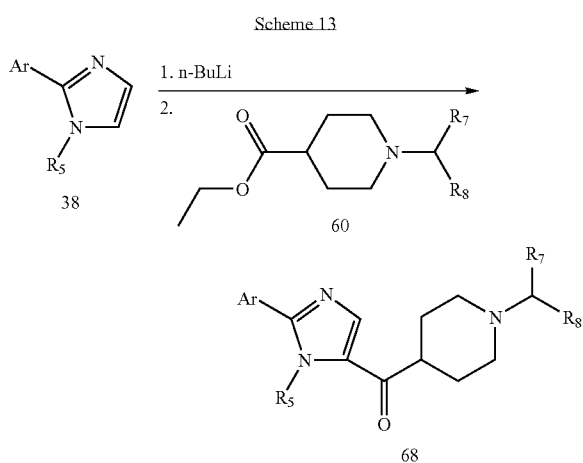

5-Carbonyl analog 68 (regioisomer of 62 when $R_5 \neq H$) is prepared from compound 38 via lithiation and reaction from ester 60 as illustrated in Scheme 13.

In certain embodiments, a compound provided herein may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active folios). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$) or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising one or more compounds provided herein, together with at least one physiologically acceptable carrier or excipient. Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs or cats). In addition, other active ingredients may (but need not) be included in the pharmaceutical compositions provided herein.

Pharmaceutical compositions may be formulated for any appropriate manner of administration, including, for example, inhalation (e.g., nasal or oral), topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents to increase the bulk weight of the material to be tableted (e.g., calcium carbonate, sodium carbonate, lactose, calcium phosphate or sodium phosphate), granulating and disintegrating agents that modify the disintegration rate in the environment of use (e.g., corn starch, starch derivatives, alginic acid and salts of carboxymethylcellulose), binding agents that impart cohesive qualities to the powdered material(s) (e.g., starch, gelatin, acacia and sugars such as sucrose, glucose, dextrose and lactose) and lubricating agents (e.g., magnesium stearate, calcium stearate, stearic acid or talc). Tablets may be formed using standard techniques, including dry granulation, direct compression and wet granulation. The tablets may be uncoated or they may be coated by known techniques.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active material(s) in admixture with one or more suitable excipients, such as suspending agents (e.g., sodium carboxymethylcellulose, methylcellulose, hydroxypropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectable aqueous or oleaginous suspension. The active ingredient(s), depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Pharmaceutical compositions may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Pharmaceutical compositions may be formulated as controlled release formulations (i.e., a formulation such as a capsule, tablet or coated tablet that slows and/or delays release of active ingredient(s) following administration), which may be administered by, for example, oral, rectal or subcutaneous implantation, or by implantation at a target site. In general, a controlled release formulation comprises a matrix and/or coating that delays disintegration and absorption in the gastrointestinal tract (or implantation site) and thereby provides a delayed action or a sustained action over a longer period. One type of controlled-release formulation is a sustained-release formulation, in which at least one active ingredient is continuously released over a period of time at a constant rate. Preferably, the therapeutic agent is released at such a rate that blood (e.g., plasma) concentrations are maintained within the therapeutic range, but below toxic levels, over a period of time that is at least 4 hours, preferably at least 8 hours, and more preferably at least 12 hours.

Controlled release may be achieved by combining the active ingredient(s) with a matrix material that itself alters release rate and/or through the use of a controlled-release coating. The release rate can be varied using methods well known in the art, including (a) varying the thickness or composition of coating, (b) altering the amount or manner of addition of plasticizer in a coating, (c) including additional ingredients, such as release-modifying agents, (d) altering the composition, particle size or particle shape of the matrix, and (e) providing one or more passageways through the coating. The amount of modulator contained within a sustained release formulation depends upon, for example, the method of administration (e.g., the site of implantation), the rate and expected duration of release and the nature of the condition to be treated or prevented.

The matrix material, which itself may or may not serve a controlled-release function, is generally any material that supports the active ingredient(s). For example, a time delay material such as glyceryl monosterate or glyceryl distearate may be employed. Active ingredient(s) may be combined with matrix material prior to formation of the dosage form (e.g., a tablet). Alternatively, or in addition, active ingredient(s) may be coated on the surface of a particle, granule, sphere, microsphere, bead or pellet that comprises the matrix material. Such coating may be achieved by conventional means, such as by dissolving the active ingredient(s) in water or other suitable solvent and spraying. Optionally, additional ingredients are added prior to coating (e.g., to assist binding of the active ingredient(s) to the matrix material or to color the solution). The matrix may then be coated with a barrier agent prior to application of controlled-release coating. Multiple coated matrix units may, if desired, be encapsulated to generate the final dosage form.

In certain embodiments, a controlled release is achieved through the use of a controlled release coating (i.e., a coating that permits release of active ingredient(s) at a controlled rate in aqueous medium). The controlled release coating should be a strong, continuous film that is smooth, capable of supporting pigments and other additives, non-toxic, inert and tack-free. Coatings that regulate release of the modulator include pH-independent coatings, pH-dependent coatings (which may be used to release modulator in the stomach) and enteric coatings (which allow the formulation to pass intact through the stomach and into the small intestine, where the coating dissolves and the contents are absorbed by the body). It will be apparent that multiple coatings may be employed (e.g., to allow release of a portion of the dose in the stomach and a portion further along the gastrointestinal tract). For example, a portion of active ingredient(s) may be coated over an enteric coating, and thereby released in the stomach, while the remainder of active ingredient(s) in the matrix core is protected by the enteric coating and released further down the GI tract. pH dependent coatings include, for example, shellac, cellulose acetate phthalate, polyvinyl acetate phthalate, hydroxypropylmethylcellulose phthalate, methacrylic acid ester copolymers and zein.

In certain embodiments, the coating is a hydrophobic material, preferably used in an amount effective to slow the hydration of the gelling agent following administration. Suitable hydrophobic materials include alkyl celluloses (e.g., ethylcellulose or carboxymethylcellulose), cellulose ethers, cellulose esters, acrylic polymers (e.g., poly(acrylic acid), poly (methacrylic acid), acrylic acid and methacrylic acid copolymers, methyl methacrylate copolymers, ethoxy ethyl methacrylates, cyanoethyl methacrylate, methacrylic acid alkamide copolymer, poly(methyl methacrylate), polyacrylamide, ammonia methacrylate copolymers, aminoalkyl methacrylate copolymer, poly(methacrylic acid anhydride) and glycidyl methacrylate copolymers) and mixtures of the foregoing. Representative aqueous dispersions of ethylcellulose include, for example, AQUACOAT® (FMC Corp., Philadelphia, Pa.) and SURELEASE® (Colorcon, Inc., West Point, Pa.), both of which can be applied to the substrate according to the manufacturer's instructions. Representative acrylic polymers include, for example, the various EUDRAGIT® (Rohm America, Piscataway, N.J.) polymers, which may be used singly or in combination depending on the desired release profile, according to the manufacturer's instructions.

The physical properties of coatings that comprise an aqueous dispersion of a hydrophobic material may be improved by the addition or one or more plasticizers. Suitable plasticizers for alkyl celluloses include, for example, dibutyl sebacate, diethyl phthalate, triethyl citrate, tributyl citrate and triacetin. Suitable plasticizers for acrylic polymers include, for example, citric acid esters such as triethyl citrate and tributyl citrate, dibutyl phthalate, polyethylene glycols, propylene glycol, diethyl phthalate, castor oil and triacetin.

Controlled-release coatings are generally applied using conventional techniques, such as by spraying in the form of an aqueous dispersion. If desired, the coating may comprise pores or channels or to facilitate release of active ingredient. Pores and channels may be generated by well known methods, including the addition of organic or inorganic material that is dissolved, extracted or leached from the coating in the environment of use. Certain such pore-forming materials include hydrophilic polymers, such as hydroxyalkylcelluloses (e.g., hydroxypropylmethylcellulose), cellulose ethers, synthetic water-soluble polymers (e.g., polyvinylpyrrolidone, cross-linked polyvinylpyrrolidone and polyethylene oxide), water-soluble polydextrose, saccharides and polysaccharides and alkali metal salts. Alternatively, or in addition, a controlled release coating may include one or more orifices, which may be formed my methods such as those described in U.S. Pat. Nos. 3,845,770; 4,034,758; 4,077,407; 4,088,864; 4,783,337 and 5,071,607. Controlled-release may also be achieved through the use of transdermal patches, using conventional technology (see, e.g., U.S. Pat. No. 4,668,232).

Further examples of controlled release formulations, and components thereof, may be found, for example, in U.S. Pat. Nos. 5,524,060; 4,572,833; 4,587,117; 4,606,909; 4,610,870; 4,684,516; 4,777,049; 4,994,276; 4,996,058; 5,128,143; 5,202,128; 5,376,384; 5,384,133; 5,445,829; 5,510,119; 5,618,560; 5,643,604; 5,891,474; 5,958,456; 6,039,980; 6,143,353; 6,126,969; 6,156,342; 6,197,347; 6,387,394; 6,399,096; 6,437,000; 6,447,796; 6,475,493; 6,491,950; 6,524,615; 6,838,094; 6,905,709; 6,923,984; 6,923,988; and 6,911,217; each of which is hereby incorporated by reference for its teaching of the preparation of controlled release dosage forms.

In addition to or together with the above modes of administration, a compound provided herein may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Compounds provided herein are generally present within a pharmaceutical composition in a therapeutically effective amount, as described above. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing and procedures that are well known in the art.

Pharmaceutical compositions may be packaged for treating conditions responsive to H3 receptor modulation, including those specifically recited herein (e.g., attention deficit disorder, attention deficit hyperactivity disorder, schizophrenia, a cognitive disorder (such as mild cognitive impairment), epilepsy, migraine, narcolepsy, allergic rhinitis, vertigo, motion sickness, a memory disorder such as Alzheimer's disease, Parkinson's disease, obesity, an eating disorder or diabetes). Packaged pharmaceutical preparations comprise a container holding a therapeutically effective amount of at least one H3 receptor modulator as described herein and instructions (e.g., labeling) indicating that the contained composition is to be used for treating a condition responsive to H3 receptor modulation in the patient.

Methods of Use

H3 receptor modulators provided herein may be used to alter activity and/or activation of H3 receptors in a variety of contexts, both in vitro and in vivo. Within certain aspects, H3 receptor modulators may be used to inhibit or enhance (preferably to inhibit) H3 receptor activity in vitro or in vivo. In general, such methods comprise the step of contacting a H3 receptor with one or more H3 receptor modulators provided herein, in aqueous solution and under conditions otherwise suitable for binding of the modulator(s) to H3 receptor. The H3 receptor modulator(s) are generally present at a concentration that is sufficient to alter H3 receptor GTP binding activity in vitro (using the assay provided in Example 7). The H3 receptor may be present in solution or suspension (e.g., in an isolated membrane or cell preparation), or in a cultured or isolated cell. Within certain embodiments, the H3 receptor is present in a patient (e.g., expressed by a neuronal cell), and the aqueous solution is a body fluid. Preferably, one or more H3 receptor modulators are administered to a patient in an amount such that each H3 receptor modulator is present in at least one body fluid of the patient at a therapeutically effective concentration that is 1 micromolar or less; preferably 500 nanomolar or less; more preferably 100 nanomolar or less, 50 nanomolar or less, 20 nanomolar or less, or 10 nanomolar or less. For example, such compounds may be administered at a dose that is less than 20 mg/kg body weight, preferably less than 5 mg/kg and, in some instances, less than 1 mg/kg. In vivo, modulation of H3 receptor activity may be assessed by detecting an alteration of a symptom (e.g., memory or attention) in a patient being treated with one or more H3 receptor modulators provided herein.

The present invention further provides methods for treating conditions responsive to H3 receptor modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to H3 receptor modulation" if it is characterized by inappropriate activity of H3 receptor, regardless of the amount of H3 receptor ligand present locally, and/or if modulation of H3 receptor activity results in alleviation of the condition or a symptom thereof. Such conditions may be diagnosed and monitored using criteria that have been established in the art. Patients may include humans, domesticated companion animals and livestock, with dosages as described above.

Conditions that are responsive to H3 receptor modulation include, for example:

Cardiovascular disorders, including atherosclerosis, hypertension, myocardial infarction, coronary heart disease and stroke;

Cancer (e.g., endometrial, breast, prostate and colon cancer, cutaneous carcinoma, medullary thyroid carcinoma and melanoma);

Metabolic disorders including impaired glucose tolerance, dislipidaemia, dyslipidaemia, diabetes (e.g., non-insulin dependent diabetes mellitus);

Immune conditions and disorders including osteoarthritis, allergy (e.g., allergic rhinitis), and inflammation;

Respiratory conditions including nasal congestion, upper airway allergic response, asthma and chronic obstructive pulmonary disease;

Disorders associated with the regulation of sleep and wakefulness, or arousal and vigilance, including narcolepsy, insomnia and jet lag;

Eating disorders (e.g., bulimia, binge eating and anorexia) and obesity;

Digestive system and gastrointestinal disorders including gallbladder disease, ulcer, hyper- and hypo-motility of the gastrointestinal tract and irritable bowel syndrome;

CNS disorders including hyper- and hypo-activity of the central nervous system, migraine, epilepsy, seizures, convulsions, mood disorders, attention deficit disorder, attention deficit hyperactivity disorder, bipolar disorder, depression, manic disorders, obsessive compulsive disorder, schizophrenia, migraine, vertigo, motion sickness, dementia, cognitive deficit (e.g., in psychiatric disorder, such as mild cognitive impairment), learning deficit, memory deficit (e.g., age-related memory dysfunction), multiple sclerosis, Parkinson's disease, Alzheimer's disease and other neurodegenerative disorders, addiction (e.g., resulting from drug abuse), neurogenic inflammation and Tourette's syndrome;

Vestibular dysfunction Meniere's disease, dizziness and motion sickness);
Pain (e.g., inflammatory pain or neuropathic pain) and itch;
Septic shock; and
Glaucoma.

H3 receptor modulators may further be used to enhance a patient's cognitive ability.

In certain embodiments, compounds provided herein are used to treat attention deficit disorder, attention deficit hyperactivity disorder, schizophrenia, a cognitive disorder (such as mild cognitive impairment), epilepsy, migraine, narcolepsy, allergic rhinitis, vertigo, motion sickness, a memory disorder such as Alzheimer's disease, Parkinson's disease, obesity, an eating disorder or diabetes. Treatment regimens may vary depending on the compound used and the particular condition to be treated. However, for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Within other aspects, H3 receptor modulators provided herein may be used within combination therapy for the treatment of conditions that are responsive to H3 receptor modulation, as described above. Within such combination therapy, a H3 receptor modulator is administered to a patient along with a second therapeutic agent that is not a H3 receptor modulator. The H3 receptor modulator and second therapeutic agent may be present in the same pharmaceutical composition, or may be administered separately in either order. It will be apparent that additional therapeutic agents may, but need not, also be administered.

Second therapeutic agents suitable for use in such combination therapy include, for example, antiobesity agents, antidiabetics, antihypertensive agents, antidepressants, antipsychotic agents and anti-inflammatory agents. In certain combinations, the second therapeutic agent is a compound for the treatment of attention deficit disorder or attention deficit hyperactivity disorder, an antipsychotic agent or an anti-obesity agent.

Histamine H1 receptor modulators represent one class of second therapeutic agents. Combination with H1 receptor modulators may be used, for example, in the treatment of Alzheimer's disease, inflammatory diseases and allergic conditions. Representative H1 receptor antagonists include, for example, loratadine (CLARITIN™), desloratadine (CLARINEX™), fexofenadine (ALLEGRA™) and cetirizine (ZYRTEC™). Other H1 receptor antagonists include ebastine, mizolastine, acrivastine, astemizole, azatadine, azelastine, brompheniramine, chlorpheniramine, clemastine, cyproheptadine, dexchlorpheniramine, diphenhydramine, hydroxyzine, levocabastine, promethazine and tripelenamine.

Antiobesity therapeutic agents for use in combination therapy include, for example, leptin, leptin receptor agonists, melanin concentrating hormone (MCH) receptor antagonists, melanocortin receptor 3 (MC3) agonists, melanocortin receptor 4 (MC4) agonists, melanocyte stimulating hormone (MSH) agonists, cocaine and amphetamine regulated transcript (CART) agonists, dipeptidyl aminopeptidase inhibitors, a growth hormone secretagogue, beta-3 adrenergic agonists, 5HT-2 agonists, orexin antagonists, neuropeptide $Y_1$ or $Y_5$ antagonists, tumor necrosis factor (TNF) agonists, galanin antagonists, urocortin agonists, cholecystokinin (CCK) agonists, GLP-1 agonists, serotonin (5HT) agonists, bombesin agonists, CB1 antagonists such as rimonabant, growth hormone, growth factors such as prolactin or placental lactogen, growth hormone releasing compounds, thyrotropin (TRH) agonists, uncoupling protein 2 or 3 (UCP 2 or 3) modulators, dopamine agonists, agents that modify lipid metabolism such as antilipidemic agents (e.g., cholestyramine, colestipol, clofibrate, gemfibrozil, lovastatin, pravastatin, simvastatin, probucol or dextrothyroxine), lipase/amylase inhibitors, peroxisome proliferator-activated receptor (PPAR) modulators, retinoid X receptor (RXR) modulators, TR-beta agonists, agouti-related protein (AGRP) inhibitors, opioid antagonists such as naltrexone, exendin-4, GLP-1, ciliary neurotrophic factor, corticotropin-releasing factor binding protein (CRF BP) antagonists and/or corticotropin-releasing factor (CRF) agonists. Representative such agents include, for example, sibutramine, dexfenfluramine, dextroamphetamine, amphetamine, orlistat, mazindol, phentermine, phendimetrazine, diethylpropion, fluoxetine, bupropion, topiramate and ecopipam.

Antihypertensive therapeutic agents for use in combination therapy include, for example, beta-blockers such as alprenolol, atenolol, timolol, pindolol, propranolol and metoprolol, angiotensin converting enzyme (ACE) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, alpha-blockers such as doxazosin, urapidil, prazosin and terazosin, and angiotensin receptor blockers such as losartan.

CNS-active agents for use in combination therapy include, but are not limited to the following: for anxiety, depression, mood disorders or schizophrenia—serotonin receptor (e.g., 5-$HT_{1A}$) agonists and antagonists, neurokinin receptor antagonists or corticotropin releasing factor receptor ($CRF_1$) antagonists; for sleep disorders—melatonin receptor agonists; and for neurodegenerative disorders—such as Alzheimer's dementia, nicotinic agonists, muscarinic agents, acetylcholinesterase inhibitors and dopamine receptor agonists. For example, such combination therapy may include a selective serotonin reuptake inhibitor (SSRI) or a non-selective serotonin, dopamine and/or norepinephrine reuptake inhibitor. Such agents include, for example, fluoxetine, sertraline, paroxetine, amitriptyline, seroxat and citalopram.

Other therapeutic agents suitable for combination therapy include, for example, agents that modify cholinergic transmission (e.g., 5-$HT_6$ antagonists), M1 muscarinic agonists, M2 muscarinic antagonists and acetylcholinesterase inhibitors.

Suitable doses for H3 receptor modulator within such combination therapy are generally as described above. Doses and methods of administration of other therapeutic agents can be found, for example, in the manufacturer's instructions in the *Physician's Desk Reference*. In certain embodiments, the combination administration of a H3 receptor modulator with the second therapeutic agent results in a reduction of the dosage of the second therapeutic agent required to produce a therapeutic effect (i.e., a decrease in the minimum therapeutically effective amount). Thus, preferably, the dosage of second therapeutic agent in a combination or combination treatment method is less than the maximum dose advised by the manufacturer for administration of the second therapeutic agent without combination administration of a H3 receptor modulator. More preferably this dosage is less than ¾, even more preferably less than ½, and highly preferably, less than ¼ of the maximum dose, while most preferably the dose is less than 10% of the maximum dose advised by the manufacturer for the second therapeutic agent when administered without combination administration of a H3 receptor modulator. It will be apparent that the dosage amount of H3 receptor modulator component(s) of the combination needed to achieve the desired effect may similarly be affected by the dosage amount and potency of the other therapeutic component(s) of the combination.

In certain preferred embodiments, the combination administration of a H3 receptor modulator with other therapeutic agent(s) is accomplished by packaging one or more H3 receptor modulators and one or more other therapeutic agents in the same package, either in separate containers within the package or in the same contained as a mixture of one or more H3 receptor modulators and one or more other therapeutic agents. Preferred mixtures are formulated for oral administration (e.g., as pills, capsules, tablets or the like). In certain embodiments, the package comprises a label bearing indicia indicating that the one or more H3 receptor modulators and one or more other therapeutic agents are to be taken together for the treatment of attention deficit disorder, attention deficit hyperactivity disorder, schizophrenia, a cognitive disorder (such as mild cognitive impairment), epilepsy, migraine, narcolepsy, allergic rhinitis, vertigo, motion sickness, a memory disorder such as Alzheimer's disease, Parkinson's disease, obesity, an eating disorder or diabetes.

Within separate aspects, the present invention provides a variety of non-pharmaceutical in vitro and in vivo uses for the compounds provided herein. For example, such compounds may be labeled and used as probes for the detection and localization of H3 receptor (in samples such as cell preparations or tissue sections, preparations or fractions thereof). In addition, compounds provided herein that comprise a suitable reactive group (such as an aryl carbonyl, nitro or azide group) may be used in photoaffinity labeling studies of receptor binding sites. In addition, compounds provided herein may be used as positive controls in assays for receptor activity, as standards for determining the ability of a candidate agent to bind to H3 receptor, or as radiotracers for positron emission tomography (PET) imaging or for single photon emission computerized tomography (SPECT). Such methods can be used to characterize H3 receptors in living subjects. For example, a H3 receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of H3 receptor in the sample. Detection assays, including receptor autoradiography (receptor mapping) of H3 receptor in cultured cells or tissue samples may be performed as described by Kuhar in sections 8.1.1 to 8.1.9 of Current Protocols in Pharmacology (1998) John Wiley & Sons, New York.

Compounds provided herein may also be used within a variety of well known cell separation methods. For example, modulators may be linked to the interior surface of a tissue culture plate or other support, for use as affinity ligands for immobilizing and thereby isolating, H3 receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

H3 receptor modulators provided herein may further be used within assays for the identification of other agents that bind to H3 receptor. In general, such assays are standard competition binding assays, in which bound, labeled H3 receptor modulator is displaced by a test compound. Briefly, such assays are performed by: (a) contacting H3 receptor with a radiolabeled H3 receptor modulator as described herein, under conditions that permit binding of the H3 receptor modulator to H3 receptor, thereby generating bound, labeled H3 receptor modulator; (b) detecting a signal that corresponds to the amount of bound, labeled H3 receptor modulator in the absence of test agent; (c) contacting the bound, labeled H3 receptor modulator with a test agent; (d) detecting a signal that corresponds to the amount of bound labeled H3 receptor modulator in the presence of test agent; and (e) detecting a decrease in signal detected in step (d), as compared to the signal detected in step (b), and therefrom identifying an agent that binds to H3 receptor.

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

Mass spectroscopy data in this and the following Examples is Electrospray MS, obtained in positive ion mode using a Micromass Time-of-Flight LCT (Micromass, Beverly Mass.), equipped with a Waters 600 pump (Waters Corp., Milford, Mass.), Waters 996 photodiode array detector, Gilson 215 autosampler (Gilson, Inc. Middleton, Wis.), and a Gilson 841 microinjector. MassLynx (Advanced Chemistry Development, Inc; Toronto, Canada) version 4.0 software with OpenLynx processing is used for data collection and analysis. MS conditions are as follows: capillary voltage=3.5 kV; cone voltage=30 V, desolvation and source temperature=350° C. and 120° C., respectively; mass range=181-750 with a scan time of 0.22 seconds and an interscan delay of 0.05 min.

Sample volume of 1 microliter is injected onto a 50×4.6 mm Chromolith SpeedROD RP-18e column (Merck KGaA, Darmstadt, Germany), and eluted using a 2-phase linear gradient at 6 ml/min flow rate. Sample is detected using total absorbance count over the 220-340 nm UV range. The elution conditions are: Mobile Phase A-95/5/0.05 Water/Methanol/TFA; Mobile Phase B-5/95/0.025 Water/Methanol/TFA. The following gradient is used, with an inject to inject cycle of 2.2 min: 0-0.5 minutes 10-100% B, hold at 100% B to 1.2 minutes, return to 10% B at 1.21 minutes.

Example 1

Preparation of Representative Compounds

A. (4-Isopropyl-piperazin-1-yl)-(4-methyl-2-naphthalen-1-yl-thiazol-5-yl)-methanone

COMPOUND 1

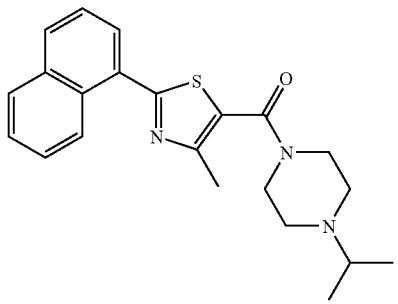

2-Bromo-4-methylthiazol-5-carboxylic acid (0.2 M in toluene with 5% DIEA; 0.100 mL; 0.020 mmol) is added to a reaction vessel followed by N-isopropylpiperizine (0.2 M in toluene; 0.110 mL; 0.022 mmol) and 2-chloro-1,3-dimethylimidazolinium chloride (0.2 M in acetonitrile; 0.110 mL; 0.022 mmol). The reaction mixture is allowed to stand at rt for 2 hr, followed by the addition of potassium phosphate (tribasic, 1.0 M, 0.100 mL; 0.100 mmol), 1-naphthaleneboronic acid (0.2 M in 1,4-dioxane; 0.150 mL, 0.030 mmol), and Pd(PPh$_3$)$_4$ (0.01 M in toluene, 0.050 mL; 0.0005 mmol) under nitrogen. The reaction mixture is heated to 80° C. under nitrogen for 14 hr, and is then treated with saturated NaHCO$_3$ (0.5 mL) and EtOAc (0.3 mL). The organic layer is purified via SCX SPE column to give (4-isopropyl-piperazin-1-A-(4-methyl-2-naphthalen-1-yl-thiazol-5-yl)-methanone. LC-MS (M+1) 380.2.

B. 1-Isopropyl-4-(4-methyl-2-naphthalen-1-yl-thiazol-5-ylmethyl)-piperazine

COMPOUND 2

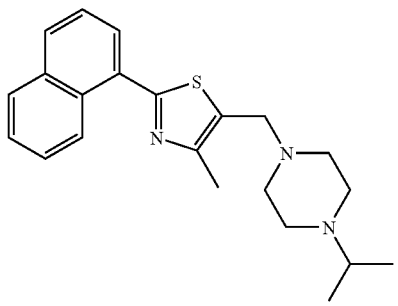

To a solution of (4-isopropyl-piperazin-1-yl)-(4-methyl-2-naphthalen-1-yl-thiazol-5-yl)-methanone (25 mg, 0.066 mmol) in anhydrous THF (2.5 ml) is added a solution of alane-dimethylethylamine complex in toluene (0.5 M, 0.4 ml, 0.2 mmol, 3.0 eq.) dropwise at 0° C. The resulting mixture is stirred at rt overnight. The reaction is quenched with one drop of water, followed by one drop of 10 N sodium hydroxide solution and two more drops of water. The resulting mixture is diluted with EtOAc (10 ml), dried over magnesium sulfate, and concentrated. The residue is purified through PTLC (EtOAc/Et$_3$N, 25:1) to give the desired product. $^1$H NMR (300 MHz, CDCl$_3$) δ 8.78 (1H, dd), 7.89 (2H, m), 7.78 (1H, dd), 7.60~7.45 (3H, m), 3.74 (2H, s), 2.76~2.54 (9H, m, overlapped), 2.51 (3H, s), 1.06 (6H, d); LC-MS (M+1) 366.2.

Example 2

Preparation of Additional Representative Compounds

A. (4-Isopropyl-piperazin-1-yl)-(3-methyl-2-o-tolyl-3H-imidazol-4-yl)-methanone

COMPOUND 3

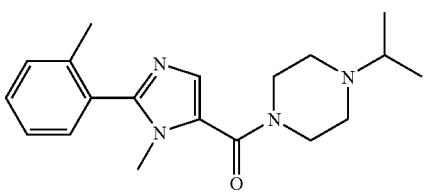

Step 1. Preparation of 2-chloro-3-methyl-3H-imidazole-4-carboxylic acid

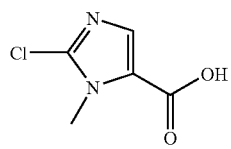

To a solution of 2-chloro-1-methyl-1H-imidazole (4.25 g, 36.5 mmol) in THF (50 mL, anhydrous) under nitrogen at −78° C. is added n-BuLi (19 mL, 2.0 Min cyclohexane, 38 mmol) over 10 min. The reaction mixture is stirred for 1 hr at −78° C. CO$_2$ is then bubbled through the solution. The reaction is kept at −78° C. for 0.25 hr, and is then allowed to warm to rt. The reaction is quenched with ice (25 g, crushed) and is then concentrated to ~½ volume in vacuo. The resulting solution is diluted with Et$_2$O and extracted with NaOH (1 N). The basic aqueous extracts are washed with Et$_2$O and then acidified with HCl (2N) to pH 4 forming a white precipitate. The precipitate is isolated via Buchner filtration and the filter cake is washed with minimal water then suction dried and further dried in vacuo.

Step 2. Preparation of (2-chloro-3-methyl-3H-imidazol-4-yl)-(4-isopropyl-piperazin-1-yl)-methanone

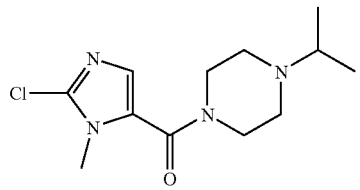

Under nitrogen, 2-chloro-3-methyl-3H-imidazole-4-carboxylic acid (0.161 g, 1.0 mmol) is dissolved in toluene (5 mL, anhydrous) and DIEA (0.26 mL). N-isopropylpiperazine (0.2 M in toluene; 5.5 mL; 1.1 mmol) is added followed by the slow addition of 2-chloro-1,3-dimethylimidazolinium chloride (0.3 M in acetonitrile; 4.0 mL; 1.2 mmol). The reaction mixture is stirred at rt for 2 hr and is then diluted with EtOAc and washed with NaOH (1 N). The aqueous layer is drained and reextracted with EtOAc and the combined organic extracts are extracted twice with HCl (1 N). The combined acidic aqueous extracts are washed with EtOAc then basified with NaOH (2.5 M). The resulting basic aqueous solution is extracted three times with EtOAc and the combined organic extracts are washed with brine, then dried over $Na_2SO_4$, filtered and concentrated in vacuo.

Step 3. Preparation of (4-isopropyl-piperazin-1-yl)-(3-methyl-2-o-tolyl-3H-imidazol-4-yl)-methanone

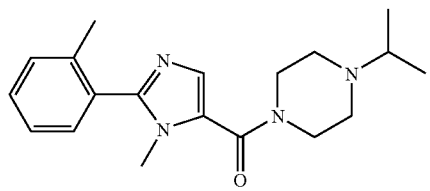

A reaction vessel is charged with $Pd_2(dba)_3$ (0.0183 g, 0.02 mmol), $P(t-Bu)_3HBF_4$ (0.0116 g, 0.04 mmol), $K_3PO_4$ (0.127 g, 0.60 mmol), o-tolylboronic acid (0.0408 g, 0.30 mmol) and (2-chloro-3-methyl-3H-imidazol-4-yl)-(4-isopropyl-piperazin-1-yl)-methanone (0.0542 g, 0.20 mmol). Toluene (2.4 mL, anhydrous) is added and the reactor is flushed and sealed under argon. The reaction is stirred at 100° C. for 16 hr; then at rt water (2 mL) and isopropyl acetate (1 mL) are added. The organic layer is removed and the aqueous layer is reextracted with isopropyl acetate. The combined organic extracts are passed through a plug of celite with EtOAc as the eluent. The filtered solution is concentrated to ~⅓ volume in vacuo and the resulting solution is purified via SCX solid phase extraction. Purification of this crude product via preparative LC-MS gives (4-isopropyl-piperazin-1-yl)-(3-methyl-2-o-tolyl-3H-imidazol-4-yl)-methanone. LC-MS (M+1) 327.3.

B. 1-{[2-(2-fluorophenyl)-1H-imidazol-5-yl]methyl}-4-isopropyl-1,4-diazepane

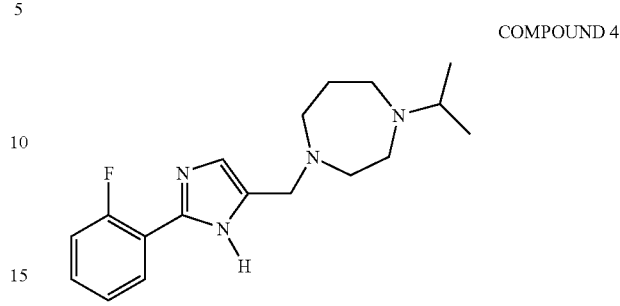

COMPOUND 4

[2-(2-Fluorophenyl)-1H-imidazol-5-yl]methyl alcohol (69 mg, 0.36 mmol, prepared essentially as described in PCT International Publication No. WO 96/16040) is dissolved in $SOCl_2$ (4 mL) and stirred at 65° C. for 1 hr. The reaction mixture is cooled to rt then concentrated in vacuo. The residue is dissolved in toluene, and then re-concentrated. The residue is suspended in $CHCl_3$ (3 mL) at it $Et_3N$ (1 mL) is added, followed by 4-isopropyl-1,4-diazepane (0.8 mL, 0.4 mmol). The reaction mixture is stirred for 90 min at rt, and then the solvent is removed in vacuo. The residue is dissolved in $CH_2Cl_2$ and applied to a PTLC plate then eluted with EtOAc/MeOH/$Et_3N$ (10/2/1). The product is removed from the plate and the silica stirred in EtOAc/MeOH (10/1) then filtered. The filtrate is concentrated to give the title compound. 1H NMR 8.24 (br t, 1H), 7.30-7.21 (m, 2H), 7.13 (dd, 1H), 7.01 (s, 1H), 3.70 (s, 2H), 2.90 (m, 1H), 2.74-2.71 (m, 8H), 1.80 (br s, 2H), 1.06 (d, 3H), 1.02 (d, 3H).

C. 1-[(3,5-dimethyl-1-phenyl-1H-pyrazol-4-yl)carbonyl]-4-isopropylpiperazine

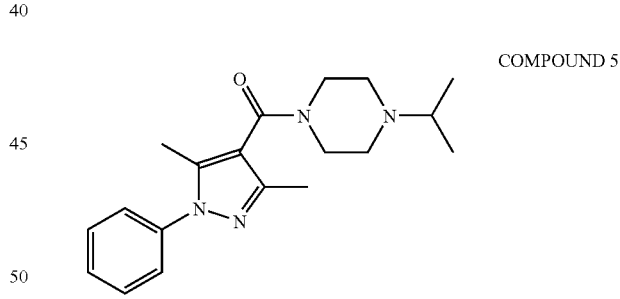

COMPOUND 5

3,5-Dimethyl-1-phenyl-1H-pyrazol-4-yl)carboxylic acid (36 mg, 0.17 mmol) is dissolved in $SOCl_2$ (2 mL) then stirred at 60° C. for 1 hr. The reaction mixture is cooled to rt, and then concentrated in vacuo. The residue is dissolved in toluene (2 mL) then re-concentrated. The residue is dissolved in $CH_2Cl_2$ (1 mL) at rt. 4-Isopropylpiperazine (28 μL, 0.2 mmol) is added, followed by saturated $NaHCO_3$ solution. The mixture is stirred overnight at rt. The reaction mixture is transferred to a separatory funnel and the organic phase removed. The aqueous layer is extracted twice with $CH_2Cl_2$ (1 mL each). The combined organic phase is dried over $MgSO_4$, filtered, and then concentrated. The residue is purified by PTLC eluting with EtOAc. The product is removed from the plate, the silica stirred in EtOAc, then filtered. The filtrate is concentrated to give the title compound. $^1$H NMR ($CDCl_3$) 7.45-7.26 (m, 5H), 3.72 (br s, 2H), 3.56 (br s, 2H), 2.73 (h, 1H), 2.53 (br s, 4H), 2.46 (s, 3H), 2.30 (s, 3H), 1.06 (s, 3H), 1.04 (s, 3H).

D. (4-Isopropyl-piperazin-1-yl)-(4-methyl-5-naphthalene-1-yl-thiazol-2-yl)-methanone

COMPOUND 6

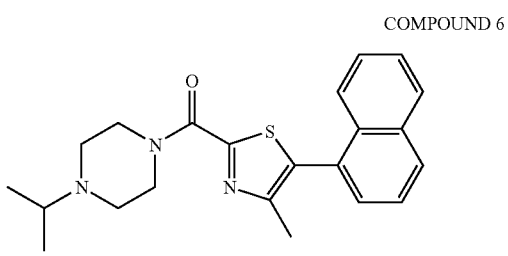

Step 1. Preparation of 4-methyl-thiazole-2-carboxylic acid ethyl ester

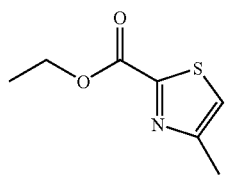

To a solution of ethyl thiooxamate (266 mg, 2.0 mmol) in EtOH (5 ml) is added chloroacetone (116 mg, 2.0 mmol). The reaction mixture is stirred at 80° C. for 2 hr. The solvent is removed and the resulting residue is purified by PTLC to give the title compound.

Step 2. Preparation of 5-bromo-4-methyl-thiazole-2-carboxylic acid ethyl ester

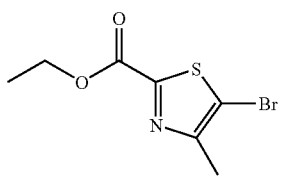

To a solution of 4-methyl-thiazole-2-carboxylic acid ethyl ester (171 mg, 1.0 mmol) in acetonitrile (5 ml) is added NBS (180 mg, 1.0 mmol). The reaction mixture is stirred at rt for 2 hr followed by the addition of a second portion of NBS (180 mg, 1.0 mmol). After stirring at rt for 3 hr, the solvent is removed. The resulting residue is purified by PTLC to give the title compound.

Step 3. Preparation of 4-methyl-5-naphthalen-1-yl-thiazole-2-carboxylic acid ethyl ester

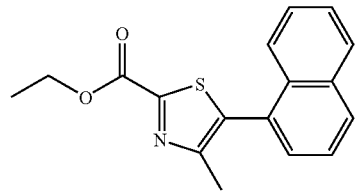

To a solution of 5-bromo-4-methyl-thiazole-2-carboxylic acid ethyl ester (60 mg, 0.24 mmol) in 1,4-dioxane (2 ml) is added 1-naphthaleneboronic acid (50 mg, 0.29 mmol), cesium carbonate (187 mg, 0.58 mmol) and Pd(PPh$_3$)$_4$ (28 mg, 0.024 mmol). The reaction mixture is stirred in a sealed tube at 110° C. overnight. After cooling to rt, the mixture is purified by PTLC to give the title compound.

Step 4. Preparation of 4-methyl-5-naphthalen-1-yl-thiazole-2-carboxylic acid

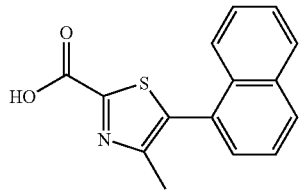

To a solution of 4-methyl-5-naphthalen-1-yl-thiazole-2-carboxylic acid ethyl ester (30 mg, 0.10 mmol) in water (1 ml) and THF (1 ml) is added sodium hydroxide (0.2 mL, 1M, 0.20 mmol). The reaction mixture is stirred at rt for 1 hr, and then extracted with ethyl ether (30 mL). The aqueous layer is acidified to pH<7.0 by phosphate buffer and then extracted with EtOAc (2×50 mL). The combined organic layers are washed with brine, dried over MgSO$_4$, and then concentrated. The crude product is used in the next step without further purification.

Step 5. Preparation of (4-isopropyl-piperazin-1-yl)-(4-methyl-5-naphthalen-1-yl-thiazol-2-yl)-methanone

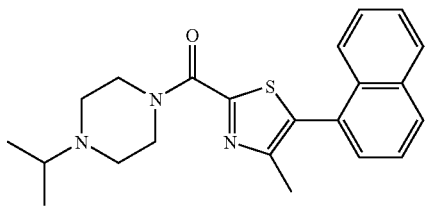

To a solution of 4-methyl-5-naphthalen-1-yl-thiazole-2-carboxylic acid in methylene chloride (2 ml) is added BOP (44 mg, 0.10 mmol), isopropylpiperazine (13 mg, 0.10 mmol) and Et$_3$N (20 mg, 0.20 mmol). The reaction mixture is stirred at rt for 2 hr. Solvent is removed and the resulting mixture is purified by PTLC to give the title compound. LC-MS M+1 380.03. $^1$H NMR δ (CDCl$_3$) 7.90-7.96 (m, 2H), 7.68-7.72 (m, 1H), 7.46-7.56 (m, 4H), 4.51 (brs, 2H), 3.85 (brs, 2H), 2.77 (m, 1H), 2.67 (brs, 4H), 2.25 (s, 3H), 1.10 (d, 6H). LC-MS (M+1) 380.1.

E. 1-Cyclopentyl-4-[2-(4-methyl-naphthalen-1-yl)-3H-imidazol-4-ylmethyl]-piperazine

COMPOUND 7

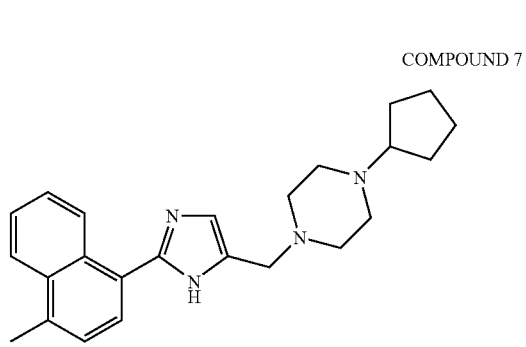

Step 1. Preparation of 4-methyl-naphthalene-1-carboxamidine

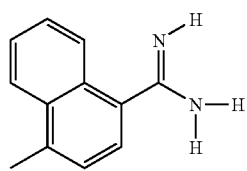

To a solution of 4-methylnaphthonitrile (2.00 g, 12 mmol) in ether (25 ml) cooled to 0° C. is added a solution of lithium bis(trimethylsilyl)amide (1.0 M, 23.9 ml, 23.9 mmol, 2.0 eq.). The resulting mixture is stirred at rt overnight. The reaction mixture is cooled to 0° C., and to the solution is added 6.0N hydrochloric acid (ca. 8.0 ml) dropwise. The resulting mixture is stirred at 0° C. for an additional 30 min. The solid precipitate is collected, washed with ether, dried under high vacuum to give the title amidine as hydrochloric acid salt. LCMS 185 (M+1).

Step 2. Preparation of [2-(4-methyl-naphthalen-1-yl)-3H-imidazol-4-yl]-methanol

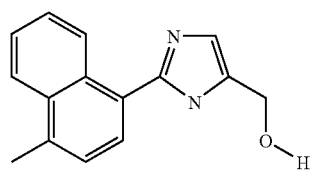

To a suspension of the amidine hydrochloric acid salt obtained in step 1 (1.07 g, 4.85 mmol) in concentrated ammonium hydroxide solution (20 ml) is added ammonium hydrochloride (3.0 g) and dihydroxyacetone dimer (510 mg, 2.91 mmol, 0.6 eq.). The resulting mixture is heated at 80° C. for 2 hr, and then cooled to rt. After the reaction mixture is extracted with DCM, the combined organic layers are dried over sodium sulfate, and solvent removed. The crude product is purified through flash chromatography to give the title compound. LCMS 239 (M+1).

Step 3. Preparation of 1-cyclopentyl-4-[2-(4-methyl-naphthalen-1-yl)-3H-imidazol-4-ylmethyl]-piperazine

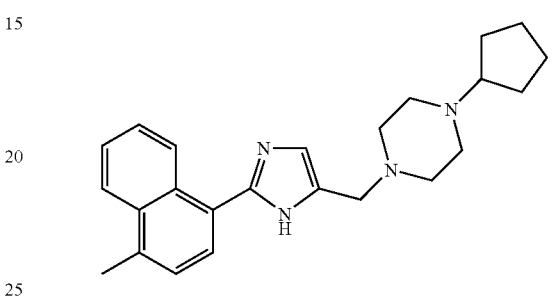

To a solution of [2-(4-methyl-naphthalen-1-yl)-3H-imidazol-4-yl]-methanol (50 mg, 0.21 mmol) in 1,2-dichloroethane (5 ml) at 0° C. is added thionylchloride (5 eq.). The resulting mixture is stirred at 50° C. for 1 hr. Solvent and remaining thionylchloride are evaporated, and the residue is dissolved in acetonitrile (3 ml), followed by the addition of substituted 4-cyclopentylpiperazine (1.0 eq.) and potassium carbonate (2.0 eq.). The resulting mixture is stirred at rt overnight. The reaction is diluted with EtOAc (10 ml), washed with brine, dried, and solvent is removed. The crude product is purified through PTLC to give 1-cyclopentyl-4-[2-(4-methyl-naphthalen-1-yl)-3H-imidazol-4-ylmethyl]-piperazine. LCMS 375 (M$^+$+1).

F. 1-Cyclobutyl-4-(1-ethyl-2-naphthalen-1-yl-1H-imidazol-4-ylmethyl)-piperazine

COMPOUND 8

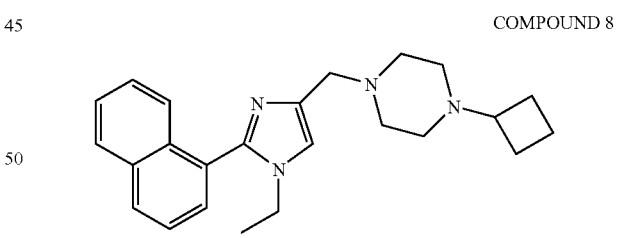

Step 1. Preparation of 2,4,5-tribromo-1-ethyl-1H-imidazole

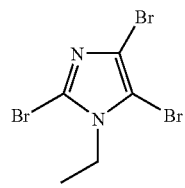

To a suspension of sodium hydride (2.40 g, 60% mineral oil suspension, 60 mmol) in anhydrous DMF (50 ml) is added a solution of 2,4,5-tribromoimidazole (15.09 g, 50 mmol) in DMF (30 ml) at rt. The resulting mixture is stirred at 50° C. for 1 hr, and then cooled to 0° C., followed by the dropwise addition of iodoethane (8.19 g, 52.5 mmol, 1.05 eq.). The mixture is stirred at rt for 1 hr, and then heated to 50° C. for an additional 8 hr. The reaction mixture is cooled to rt, and poured into ice-water (200 ml). The mixture is extracted with EtOAc (100 ml×3). The combined organic layers are washed with water, brine, dried over anhydrous sodium sulfate, filtered, and solvent evaporated at reduced pressure. The crude product is purified by flash chromatography on silica gel to give the title product. LCMS 330 (M+1).

Step 2. Preparation of 4,5-dibromo-1-ethyl-2-naphthalen-1-yl-1H-imidazole

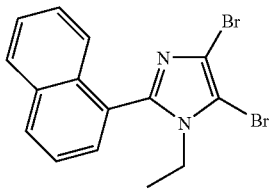

To a solution of 2,4,5-tribromo-1-ethyl-1H-imidazole (13.19 g, 40 mmol) and 1-naphthylphenylboronic acid (6.88 g, 40 mmol, 1.0 eq.) in toluene (100 ml) is added aqueous potassium carbonate solution (2.0 N, 40 ml, 2.0 eq.), followed by the addition of Pd(PPh$_3$)$_4$ (1.154 g, 1 mmol, 0.025 eq.). The resulting mixture is degassed with nitrogen, and then stirred at 90° C. for 16 hr. After cooling to rt, the reaction mixture is diluted with EtOAc (100 ml), washed with water and brine, and dried over sodium sulfate. After the solvent is removed, the crude product is purified through flash chromatography to afford the title product LCMS 380 (M+1).

Step 3. Preparation of 1-ethyl-2-naphthalen-1-yl-1H-imidazole-4-carbaldehyde

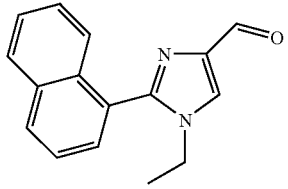

To a solution of 4,5-dibromo-1-ethyl-2-naphthalen-1-yl-1H-imidazole (3.80 g, 10 mmol) in anhydrous THF (60 ml) at −78° C. under nitrogen is added a solution of n-BuLi in hexane (1.6 M, 6.88 ml, 11 mmol, 1.1 eq.) dropwise. The resulting mixture is stirred at −78° C. for 1 hr, followed by dropwise addition of TMSCl (1.188 g, 11 mmol, 1.1 eq.). The resulting solution is stirred at −78° C. After 1 hr, n-BuLi in hexane (1.6 M, 6.88 ml, 11 mmol, 1.1 eq.) is added dropwise. The resulting mixture is stirred at −78° C. for 1 hr followed by the addition of anhydrous DMF (3.65 g, 50 mmol, 5.0 eq.). The resulting solution is stirred at −78° C. for 10 min, and then warmed to rt and stirred for additional 10 min. Water (30 ml) is added to quench the reaction, followed by the addition of MeOH (3 ml). The resulting mixture is stirred at rt for 4 hr. The organic solvent is evaporated under reduced pressure and the residue is extracted with EtOAc (50 ml×3). The combined organic layers are washed with water and brine, and dried over Na$_2$SO$_4$. Concentration and purification through silica gel chromatography (hexanes/EtOAc, from 8:1 to 4:1) affords the title compound. LCMS 251 (M+1).

Step 4. Preparation of 1-cyclobutyl-4-(1-ethyl-2-naphthalen-1-yl-1H-imidazol-4-ylmethyl)-piperazine

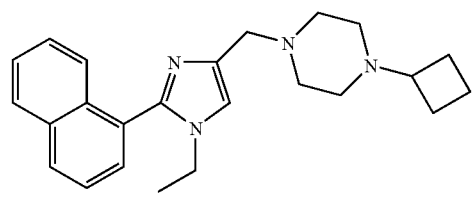

To the solution of 1-ethyl-2-naphthalen-1-yl-1H-imidazole-4-carbaldehyde (50 mg, 0.2 mmol) in 1,2-dichloroethane (2 ml) is added 1-cyclobutylpiperazine bis-trifluoroacetate (73.6 mg, 0.2 mmol, 1.0 eq.). The resulting mixture is stirred at rt for 1 hr. Sodium triacetoxyborohydride (84.8 mg, 0.4 mmol, 2.0 eq.) is added, and the resulting mixture is stirred at rt overnight. Aqueous sodium bicarbonate is added to quench to solution, and the mixture is extracted with DCM. The organic layers and combined and washed with brine, and dried over sodium sulfate. Concentration and purification through PTLC gives the title compound. $^1$H NMR (400 MHz, CDCl$_3$) δ 7.84~7.96 (2H, m, overlapped), 7.61 (1H, d), 7.42~7.54 (4H, m), 7.04 (1H, s), 3.71 (2H, q), 3.67 (2H, s), 2.30~2.85 (9H, m, overlapped), 1.60~2.10 (6H, m), 1.23 (3H, t); LCMS 375 (M+1).

G. 1-Cyclobutyl-4-[2-(2-ethoxy-naphthalen-1-yl)-3H-imidazol-4-ylmethyl]-piperazine

COMPOUND 9

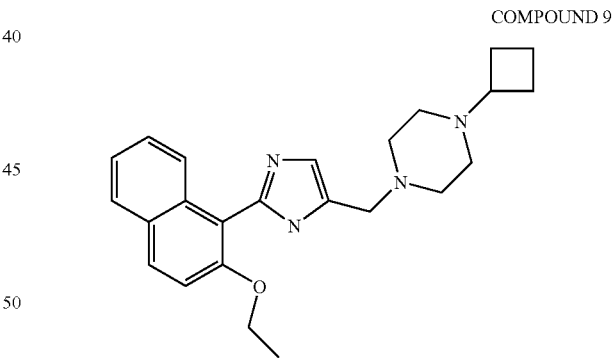

Step 1. Preparation of 2-(2-ethoxy-naphthalen-1-yl)-3H-imidazole-4-carbaldehyde

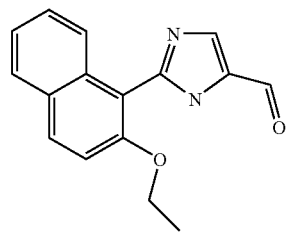

To a solution of 2-(2-ethoxy-naphthalen-1-yl)-3-methoxymethyl-3H-imidazole-4-carbaldehyde (prepared as described for 1-ethyl-2-naphthalen-1-yl-1H-imidazole-4-carbaldehyde illustrated in example 2.F) (2.4 g, 7.4 mmol) in dioxane (30 ml) is added 6.0 N hydrochloric acid (10 ml). The resulting mixture is stirred at 80° C. for 3 hr, and then cooled to rt. Dioxane is evaporated, and the residue is basified with 2.0N sodium hydroxide solution. The solid precipitate is collected, washed with water, dried under vacuum to give the title compound. LCMS 267 (M+1).

Step 2. Preparation of 1-cyclobutyl-4-[2-(2-ethoxy-naphthalen-1-yl)-3H-imidazol-4-ylmethyl]-piperazine

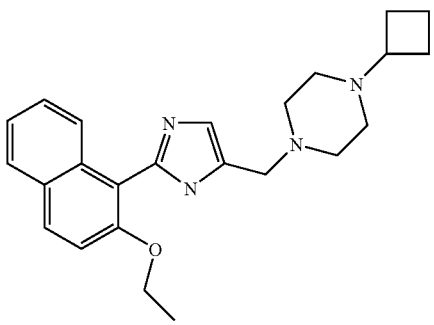

To a solution of 2-(2-ethoxy-naphthalen-1-yl)-3H-imidazole-4-carbaldehyde (53 mg, 0.2 mmol) in 1,2-dichloroethane (2 ml) is added 1-cyclobutylpiperazine bistrifluoroacetate (73.6 mg, 0.2 mmol, 1.0 eq.). The resulting mixture is stirred at rt for 1 hr. Sodium triacetoxyborohydride (84.8 mg, 0.4 mmol, 2.0 eq.) is added, and the resulting mixture is stirred at rt overnight. Aqueous sodium bicarbonate is added to quench to solution, and the mixture is extracted with DCM. The combined organic layers are washed with brine, dried over sodium sulfate, and concentrated. The crude product is purified through PTLC to give the title compound. ¹H NMR (300 MHz, CDCl₃) δ 9.90~10.30 (1H, d, br), 8.90~9.10 (1H, br), 7.83 (1H, d), 7.78 (1H, d), 7.51 (1H, t), 7.38 (1H, t), 7.30 (1H, d), 7.15 (1H, br), 4.21 (2H, t), 3.58~3.78 (2H, d, br), 2.10~2.81 (9H, m), 1.54~2.10 (6H, m), 1.44 (3H, t); LCMS 391 (M+1).

H. (4-Cyclobutyl-piperazin-1-yl)-(1-ethyl-2-naphthalen-1-yl-1H-imidazol-4-yl)-methanone

COMPOUND 10

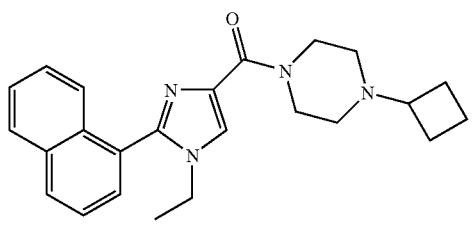

Step 1. Preparation of 1-ethyl-2-naphthalen-1-yl-1H-imidazole-4-carboxylic acid

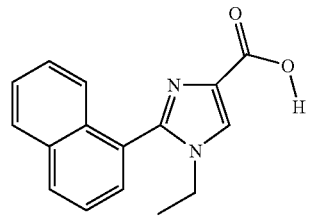

To a solution of 4,5-dibromo-1-ethyl-2-naphthalen-1-yl-1H-imidazole (3.80 g, 10 mmol) in anhydrous THF (60 ml) at −78° C. under nitrogen is added a solution of n-BuLi in hexane (1.6 M, 6.88 ml, 11 mmol, 1.1 eq.) dropwise. The resulting mixture is stirred at −78° C. for 1 hr, after which chlorotrimethylsilane (1.188 g, 11 mmol, 1.1 eq.) is added. The resulting solution is stirred at −78° C. After 1 hour, n-BuLi in hexane (1.6 M, 6.88 ml, 11 mmol, 1.1 eq.) is added dropwise. The resulting mixture is stirred at −78° C. for 1 hr, followed by the addition of diethyl carbonate (3.54 g, 30 mol, 3.0 eq.). The resulting solution is stirred at −78° C. for 30 min, waned to rt slowly, and stirred for an additional 30 min at rt. Water (30 ml) is added to quench the reaction, and THF is evaporated under reduced pressure. The residue is extracted with EtOAc (30 ml×2). The combined organic layers are washed with water and brine, dried over sodium sulfate, and concentrated to give the crude product, which is dissolved in THF (30 ml). To this THF solution is added tetrabutylammonium fluoride (1.1 eq.), and the resulting mixture is stirred at it for 2 hr. The solvent is evaporated under reduced pressure, and the residue is diluted with water (30 ml). The mixture is extracted with EtOAc (30 ml×3), washed with water and brine, dried over Na₂SO₄ and concentrated. Purification through silica gel chromatography (hexanes/EtOAc, from 8:1 to 4:1) affords 1-ethyl-2-naphthalen-1-yl-1H-imidazole-4-carboxylic acid ethyl ester. LCMS 295 (M+1).

1-Ethyl-2-naphthalen-1-yl-1H-imidazole-4-carboxylic acid ethyl ester (2.2 g, 7.48 mmol) is dissolved in THF (20 ml), followed by the addition of aqueous lithium hydroxide solution (2.0 N, 7.5 ml, 2.0 eq.). The mixture is heated at 50° C. overnight. THF is stripped off under reduced pressure, and the residue is diluted with water (10 ml), basified to pH=4~5. The solid precipitate is collected, washed with water and ether, dried under high vacuum to give the title compound. LCMS 267 (M+1).

Step 2. Preparation of (4-cyclobutyl-piperazin-1-yl)-(1-ethyl-2-naphthalen-1-yl-1H-imidazol-4-yl)-methasone

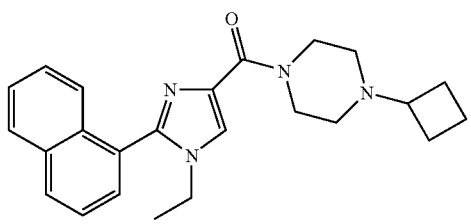

1-Ethyl-2-naphthalen-1-yl-1H-imidazole-4-carboxylic acid (53.2 mg, 0.2 mmol) and 1-cyclobutylpiperazine bistrifluoroacetate (73.6 mg, 0.2 mmol, 1.0 eq.) are dissolved in DCM (2 ml) and to the solution is added Et₃N (4 eq.), followed by the addition of BOP coupling regent (93 mg, 0.22 mmol, 1.1 eq.). The resulting mixture is stirred at rt overnight. DCM is evaporated, and the residue is taken up in EtOAc (6 ml). The solution is washed thoroughly with water (3.0 ml×3) to remove the by-product from BOP, and then washed with brine. The solution is dried over sodium sulfate, and concentrated. The crude product is purified through PTLC to give the title compound. NMR (300 MHz, CDCl₃) δ 7.88~8.02 (2H, m), 7.79 (1H, s), 7.44~7.60 (5H, m), 4.41 (2H, s, br), 3.82 (2H, s, br), 3.74 (2H, q), 2.74 (1H, m), 2.40 (4H, s, br), 1.58~2.60 (6H, m), 1.25 (3H, t); LCMS 389 (M+1).

I. (4-Cyclobutyl-piperazin-1-yl)-(3-ethyl-2-naphthalen-1-yl-3H-Imidazol-4-yl)-methanone

COMPOUND 11

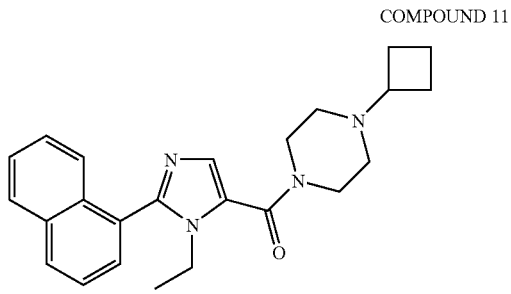

Step 1. Preparation of 1-ethyl-2-naphthalen-1-yl-1H-imidazole

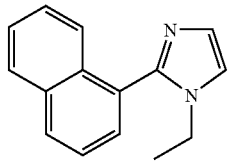

To a solution of 1-naphthaldehyde (46.82 g, 0.3 mol) in EtOH (400 ml) at 0° C. is added a solution of 40% glyoxal in water (70 ml) and concentrated ammonium hydroxide (ca. 20 M, 105 ml). The reaction mixture is stirred at 0° C. for 30 min and then at rt overnight. The reaction mixture is concentrated, and the residual solid precipitate is collected by filtration, and washed with water and ether. The crude product is recrystallized from hexane/EtOAc to give 2-naphthalen-1-yl-1H-imidazole as a pale-yellow solid. LCMS 195 (M+1).

To a suspension of sodium hydride (2.40 g, 60% mineral oil suspension, 60 mmol) in anhydrous DMF (30 ml) is added a solution of 2-naphthalen-1-yl-1H-imidazole (9.70 g, 50 mmol) in DMF (70 ml) at rt. The resulting mixture is stirred at 50° C. for 1 hr, and then cooled to 0° C., after which iodoethane (8.19 g, 52.5 mmol, 1.05 eq.) is added dropwise. The mixture is stirred at rt for 1 hr, and then heated to 50° C. and stirred for an additional 8 hr. The reaction mixture is cooled to rt, and poured into ice-water (500 ml). The mixture is extracted with EtOAc (100 ml×3). The combined organic layers are washed with water and brine, dried over anhydrous sodium sulfate, and solvent is evaporated at reduced pressure. The crude product is purified by flash chromatography on silica gel to give the title compound. LCMS 223 (M+1).

Step 2. Preparation of (4-cyclobutyl-piperazin-1-yl)-(3-ethyl-2-naphthalen-1-yl-3H-imidazol-4-yl)-methanone

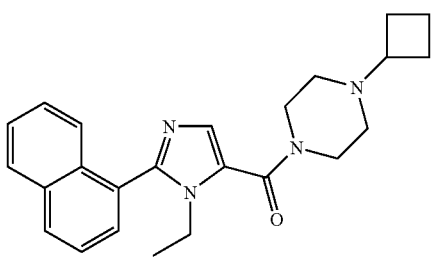

To a solution of 1-ethyl-2-naphthalen-1-yl-1H-imidazole (1.11 g, 5 mmol) in anhydrous THF (30 ml) at −78° C. under nitrogen is added a solution of n-BuLi in hexane (1.6 M, 3.44 ml, 5.5 mmol, 1.1 eq.) dropwise. The resulting mixture is stirred at −78° C. for 1 hr, followed by the addition of diethyl carbonate (1.77 g, 15 mmol, 3.0 eq.). The resulting solution is stirred at −78° C. for 30 min, warmed to rt slowly, and stirred for an additional 30 min at rt. Water (30 ml) is added to quench the reaction, and THF is evaporated under reduced pressure. The residue is extracted with EtOAc (30 ml×2) and the combined organic layers are washed with water and brine, dried over sodium sulfate, and concentrated. The crude product is purified through silica gel chromatography (hexanes/EtOAc, from 8:1 to 4:1) to give 3-ethyl-2-naphthalen-1-yl-3H-imidazole-4-carboxylic acid ethyl ester. LCMS 295 (M+1).

3-Ethyl-2-naphthalen-1-yl-3H-1-imidazole-4-carboxylic acid ethyl ester (690 mg, 2.34 mmol) is dissolved in THF (10 ml), followed by the addition of aqueous lithium hydroxide solution (2.0 N, 2.4 ml, 2.0 eq.). The mixture is heated at 50° C. overnight. THF is stripped off under reduced pressure, and the residue is diluted with water (10 ml), and basified to pH=4~5. The solid precipitate is collected, washed with water and ether, dried under high vacuum to give 3-ethyl-2-naphthalen-1-yl-3H-imidazole-4-carboxylic acid. LCMS 267 (M+1).

3-Ethyl-2-naphthalen-1-yl-3H-imidazole-4-carboxylic acid (105 mg, 0.394 mmol) and 1-cyclobutylpiperazine bistrifluoroacetate (145 mg, 0.394 mmol, 1.0 eq.) are dissolved in DCM (5 ml), and to the solution is added Et₃N (4 eq.), followed by BOP coupling regent (183 mg, 0.433 mmol, 1.1 eq.). The resulting mixture is stirred at rt overnight. DCM is evaporated, and the residue is taken up in EtOAc (1.0 ml). The solution is washed thoroughly with water (3.0 ml×3) to remove the by-product from BOP, and then washed with brine. The solution is dried over sodium sulfate, concentrated and purified through PTLC to give the title compound. ¹H NMR (300 MHz, CDCl₃) δ 7.98 (1H, m), 7.92 (1H, dd), 7.44~7.63 (5H, m), 7.39 (1H, s), 4.05 (2H, q), 3.89 (4H, s, br), 2.80 (1H, m), 2.43 (4H, s, br), 1.50~2.20 (6H, m), 1.09 (3H, t); LCMS 389 (M+1).

J. (5-Chloro-3-ethyl-2-naphthalen-1-yl-3H-imidazol-4-yl)-(4-cyclobutyl-piperazin-1-yl)-methanone

COMPOUND 12

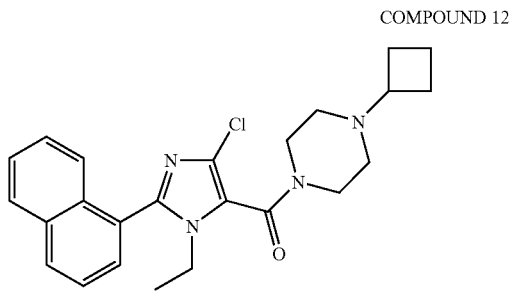

Step 1. Preparation of 4,5-dichloro-1-ethyl-2-naphthalen-1-yl-1H-imidazole

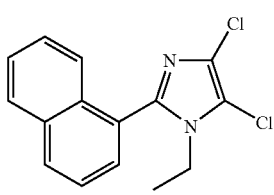

To a solution of 1-ethyl-2-naphthalen-1-yl-1H-imidazole (2.52 g, 11.34 mmol) in acetonitrile (30 ml) is added NCS (3.18 g, 23.81 mmol, 3.1 eq.) in portions. The resulting mixture is heated at 50° C. for 2 hr, and then cooled to rt. The solvent is evaporated, and the residue is dissolved in EtOAc (50 ml), washed with water and brine, dried over sodium sulfate, and concentrated. The crude product is purified through silica gel flash chromatography (hexane/EtOAc, 10:1) to give the title compound. LCMS 291 (M+1).

Step 2. Preparation of 5-chloro-3-ethyl-2-naphthalen-1-yl-3H-imidazole-4-carboxylic acid

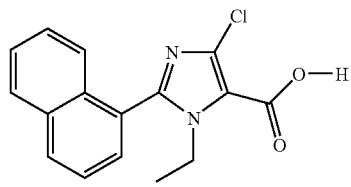

To a solution of 4,5-dichloro-1-ethyl-2-naphthalen-1-yl-1H-imidazole (2.87 g, 9.86 mmol) in anhydrous THF (60 ml) at −78° C. under nitrogen is added a solution of n-BuLi in hexane (1.6 M, 6.78 ml, 10.84 mmol, 1.1 eq.) dropwise. The resulting mixture is stirred at −78° C. for 1 hr, followed by the addition of dimethyl carbonate (2.66 g, 29.6 mmol, 3.0 eq.). The resulting solution is stirred at −78° C. for 30 min, warmed to rt slowly, and stirred for an additional 60 min at rt. Water (30 ml) is added to quench the reaction, and THF is evaporated under reduced pressure. The residue is extracted with EtOAc (30 ml×2) and the combined organic layers are washed with water and brine, dried over sodium sulfate, and concentrated. The crude product is purified through silica gel chromatography (hexanes/EtOAc, from 20:1 to 10:1) to give 5-chloro-3-ethyl-2-naphthalen-1-yl-3H-imidazole-4-carboxylic acid ethyl ester. LCMS 315 (M+1).

5-Chloro-3-ethyl-2-naphthalen-1-yl-3H-imidazole-4-carboxylic acid ethyl ester (62 g, 35 mmol) is dissolved in. THF (10 ml), and aqueous lithium hydroxide solution (2.0 N, 6.35 ml, 2.0 eq.) is added. The mixture is heated at 50° C. overnight. THF is stripped off under reduced pressure, and the residue is diluted with water (10 ml) and basified to pH=4=5. The solid precipitate is collected, washed with water and ether, and dried under high vacuum to give the title compound. LCMS 301 (M+1).

Step 3. Preparation of (5-Chloro-3-ethyl-2-naphthalen-1-yl-3H-imidazol-4-yl)-(4-cyclobutyl-piperazin-1-yl)-methanone

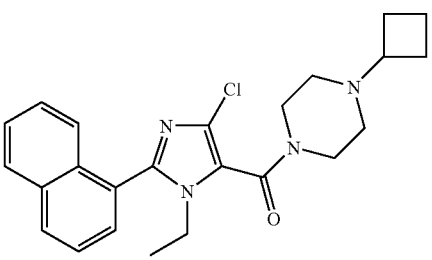

(5-Chloro-3-ethyl-2-naphthalen-1-yl-3H-imidazol-4-yl)-(4-cyclobutyl-piperazin-1-yl)-methanone is prepared from 5-chloro-3-ethyl-2-naphthalen-1-yl-3H-imidazole-4-carboxylic acid and 1-cyclobutylpiperazine bistrifluoroacetate using the amidation method described in Example 2.1. LCMS 423 (M+1).

K. (4-Cyclobutyl-piperazin-1-yl)-(3-ethyl-5-fluoro-2-naphthalen-1-yl-3H-imidazol-4-YL)-methanone

COMPOUND 13

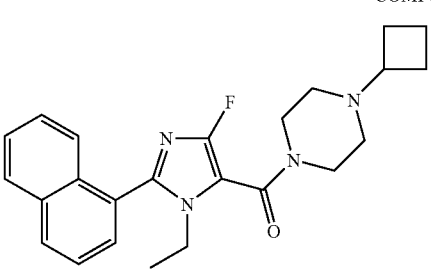

Step 1. Preparation of 1-ethyl-4-fluoro-2-naphthalen-1-yl-1H-imidazole

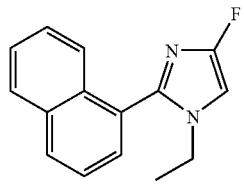

To a solution of 4,5-dibromo-1-ethyl-2-naphthalen-1-yl-1H-imidazole (6.55 g, 17.2 mmol) in anhydrous THF (150 ml) at −78° C. under nitrogen is added a solution of n-BuLi in hexane (1.6 M, 11.8 ml, 19 mmol, 1.1 eq.) dropwise. The resulting mixture is stirred at −78° C. for 1 hr, and TMSCl (2.05 g, 19 mmol, 1.1 eq.) is added. The resulting solution is stirred at −78° C. After 1 hr, n-BuLi in hexane (1.6 M, 11.8 ml, 19 mmol, 1.1 eq.) is added dropwise. The resulting mixture is stirred at −78° C. for 1 hr, and N-fluorobenzenesulfonimide (5.99 g, 19 mmol, 1.1 eq.) is added. The resulting solution is stirred at −78° C. for 2 hr, warmed to rt slowly, and then stirred at rt overnight. Water (50 ml) is added to quench the reaction, and THF is evaporated. The residue is extracted with EtOAc (75 ml×2) and the combined organic layers are washed with water and brine, dried and concentrated to give crude 1-ethyl-4-fluoro-2-naphthalen-1-yl-5-trimethylsilanyl-1H-imidazole as a yellow oil. LCMS 313 (M+1).

Crude 1-ethyl-4-fluoro-2-naphthalen-1-yl-5-trimethylsilanyl-1H-imidazole (5.49 g) is dissolved in THF (75 ml), and to the solution is added tetrabutylammonium fluoride hydrate (5.4 g, 20.6 mmol, 1.2 eq.). The resulting mixture is stirred at rt for 4 hr. The organic solvent is evaporated under reduced pressure, and the residue is dissolved in EtOAc (150 ml), washed with water and brine, and dried over $Na_2SO_4$. Concentration and purification through silica gel chromatography (hexanes/EtOAc, from 8:1 to 4:1) affords 1-ethyl-4-fluoro-2-naphthalen-1-yl-1H-imidazole. LCMS 241 (M+1).

Step 2. Preparation of (4-cyclobutyl-piperazin-1-yl)-(3-ethyl-5-fluoro-2-naphthalen-1-yl-3H-imidazol-4-yl)-methanone

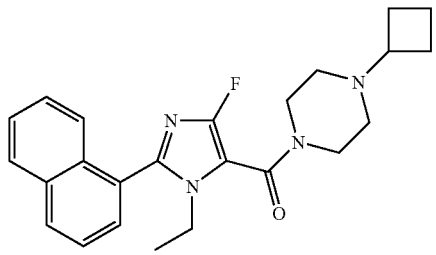

(4-cyclobutyl-piperazin-1-yl)-(3-ethyl-5-fluoro-2-naphthalen-1-yl-3H-imidazol-4-yl)-methanone is prepared from 1-ethyl-4-fluoro-2-naphthalen-1-yl-1H-imidazole as described in Example 2.1 and illustrated in Scheme 9.

L. 1-Cyclopentyl-4-(5-methyl-2-naphthalen-1-yl-3H-imidazol-4-ylmethyl)-piperazine

COMPOUND 14

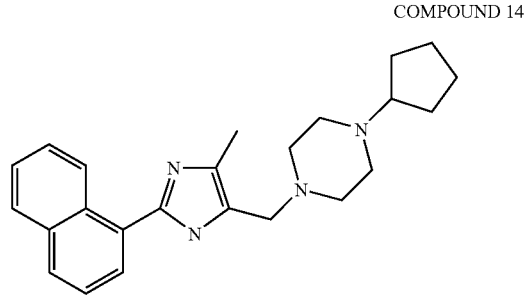

Step 1. Preparation of 5-methyl-2-naphthalen-1-yl-3H-imidazole-4-carboxylic acid ethyl ester

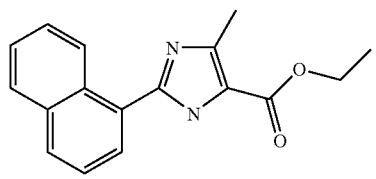

A solution of 2,3-dioxobutyric acid ethyl ester, (Z)-2-oxime (3 g), 1-naphthalenemethylamine (3.26 g) in acetonitrile (45 ml) is refluxed for 10 hr to give a white precipitate. The solid is then collected, washed with acetonitrile and dried to yield 5-methyl-2-naphthalen-1-yl-3H-imidazole-4-carboxylic acid ethyl ester. LCMS 281.3 (M+1).

Step 2. Preparation of 1-cyclopentyl-4-(5-methyl-2-naphthalen-1-yl-3H-imidazol-4-ylmethyl)-piperazine

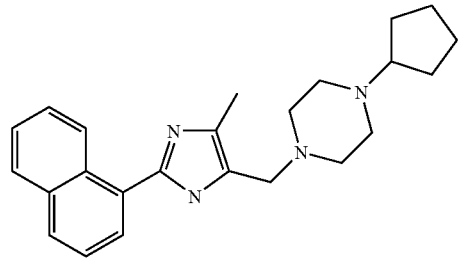

To a solution of 5-methyl-2-naphthalen-1-yl-3H-imidazole-4-carboxylic acid ethyl ester (280 mg) in THF (8 ml) is added DIBAL-H (3.3 ml, 1.5 M in toluene) at 0° C. The resulting solution is stirred at rt for 2 hr, and quenched with brine. The THF layer is separated and then evaporated. The residue is dissolved in EtOAc, washed with water and brine, dried and solvent evaporated to afford (5-methyl-2-naphthalen-1-yl-3H-imidazol-4-yl)-methanol.

(5-Methyl-2-naphthalen-1-yl-3H-imidazol-4-yl)-methanol (40 mg) is treated with $SOCl_2$, followed by N-cyclopentylpiperazine (60 mg) and $Et_3N$ (0.04 ml) in $CH_2Cl_2$ (2 ml).

The crude is purified by column (2% Et₃N, 3% MeOH in EtOAc) to afford the title compound as a white solid. LCMS 375.5 (M+1).

M. (4-Cyclobutyl-piperazin-1-yl)-(3-ethyl-5-methyl-2-naphthalen-1-yl-3H-imidazol-4-yl)-methanone

COMPOUND 15

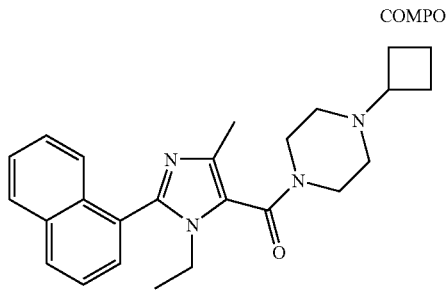

Step 1. Preparation of 3-ethyl-5-methyl-2-naphthalen-1-yl-3H-imidazole-4-carboxylic acid ethyl ester

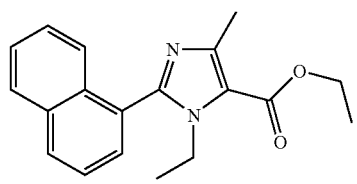

To a solution of 5-methyl-2-naphthalen-1-yl-3H-imidazole-4-carboxylic acid ethyl ester (1.5 g) in DMF (30 ml) is added NaH (320 mg, 60%) at rt. The solution is stirred for 30 min, and EtI (0.6 ml) is added. After 30 min, the mixture is cooled to 0° C. and H₂O is added. The mixture is then extracted with EtOAc. The extracts are combined, dried, evaporated and purified by column (EtOAc:Hexanes 1:1) to give 3-ethyl-5-methyl-2-naphthalen-1-yl-3H-imidazole-4-carboxylic acid ethyl ester [LCMS 309.4 (M+1); δ 4.10 ppm (C$\underline{H}_2$CH₃)] and its regioisomer 1-ethyl-5-methyl-2-naphthalen-1-yl-1H-imidazole-4-carboxylic acid ethyl ester [LCMS 309.4 (M+1); δ 3.72 ppm (C$\underline{H}_2$CH₃)].

Step 2. Preparation of (4-cyclobutyl-piperazin-1-yl)-(3-ethyl-5-methyl-2-naphthalen-1-yl-3H-imidazol-4-yl)-methanone

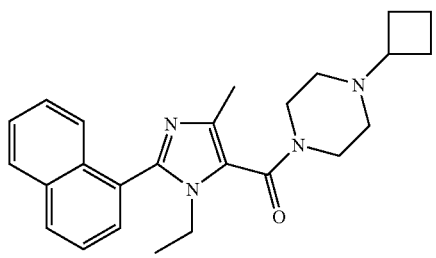

(4-Cyclobutyl-piperazin-1-yl)-(3-ethyl-5-methyl-2-naphthalen-1-yl-3H-imidazol-4-yl)-methanone is prepared from 3-ethyl-5-methyl-2-naphthalen-1-yl-3H-imidazole-4-carboxylic acid ethyl ester via standard hydrolysis and amidation procedures as described above. LCMS 403.64 (M+1).

N. (4-Cyclobutyl-piperazin-1-yl)-(1-ethyl-5-methyl-2-naphthalen-1-yl-1H-imidazol-4-yl)-methanone

COMPOUND 16

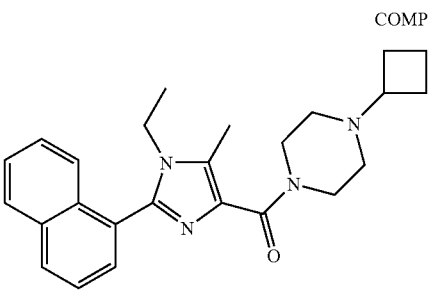

(4-Cyclobutyl-piperazin-1-yl)-(1-ethyl-5-methyl-2-naphthalen-1-yl-1H-imidazol-4-yl)-methanone is prepared from 1-ethyl-5-methyl-2-naphthalen-1-yl-1H-imidazole-4-carboxylic acid ethyl ester (prepared in Example 2.M, step 1) via standard hydrolysis and amidation procedures as described above. LCMS 403.5 (M+1).

O. 1-Cyclobutyl-4-(3-ethyl-5-methyl-2-naphthalen-1-yl-3H-imidazol-4-ylmethyl)-piperazine

COMPOUND 17

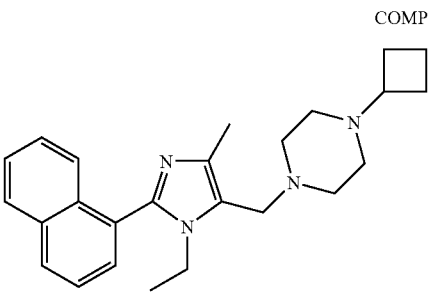

To a solution of (4-cyclobutyl-piperazin-1-yl)-(3-ethyl-5-methyl-2-naphthalen-1-yl-3H-imidazol-4-yl)-methanone (40 mg) in THF (1 ml) is added DIBAL-H (0.25 ml, 1.5 M in toluene) at 0° C. The resulting solution is stirred at rt for 2 hr, and then quenched with brine. The THF layer is separated, evaporated and purified by column (2% Et₃N, 3% MeOH in EtOAc) to afford the title compound. LCMS 389.5 (M+1). NMR (CDCl₃) δ ppm 1.05 (t, 3H), 1.63-2.05 (m, 9H), 2.29 (s, 3H), 2.35-2.56 (m, 5H), 2.74 (m, 1H), 3.52 (s, 2H), 3.82 (q, 2H), 7.42-7.60 (m, 5H), 7.87-7.94 (m, 2H).

P. 1-Cyclobutyl-4-(1-Ethyl-5-methyl-2-naphthalen-1-yl-1H-imidazol-4-ylmethyl)-piperazine

COMPOUND 18

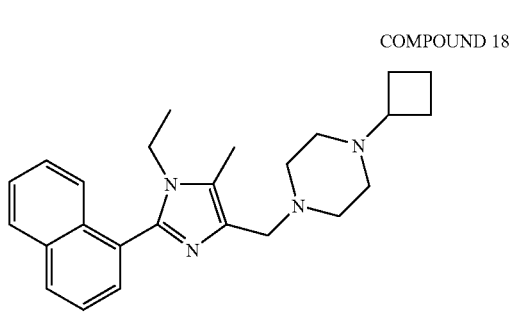

1-Cyclobutyl-4-(1-ethyl-5-methyl-2-naphthalen-1-yl-1H-imidazol-4-ylmethyl)-piperazine is prepared from (4-cyclobutyl-piperazin-1-yl)-(1-ethyl-5-methyl-2-naphthalen-1-yl-1H-imidazol-4-yl)-methanone as described in example 2.O. LCMS 389.5 (M+1). $^1$H NMR (CDCl$_3$) δ ppm 1.05 (t, 3H), 1.65-2.05 (m, 9H), 2.33 (s, 3H), 2.35-2.75 (m, 6H), 3.64 (s, 2H), 3.69 (q, 2H), 7.41-7.54 (m, 4H), 7.58-7.62 (m, 1H), 7.86-7.93 (m, 2H).

Q. (1-Cyclobutyl-piperidin-4-yl)-(1-ethyl-2-naphthalen-1-yl-1H-imidazol-4-yl)-methanone

COMPOUND 19

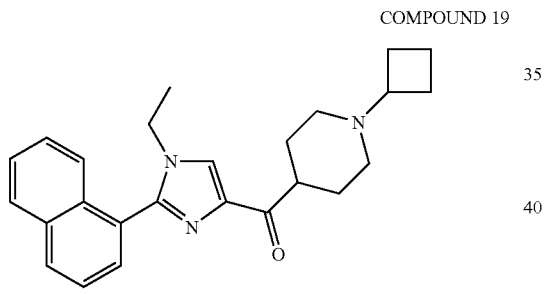

To a solution of 1H-4,5-dibromo-1-ethyl-2-(1-naphthyl)imidazole (380 mg) in THF (6 ml) is added dropwise n-BuLi (0.7 ml, 1.6 M in hexanes) at –78° C. After 30 min stirring, TMSCl (0.14 ml) is added at –78° C. and the mixture is stirred for another 30 min. n-BuLi (0.7 ml, 1.6 M in hexanes) is added dropwise at –78° C. and the mixture is stirred for 30 min, after which a solution of ethyl N-cyclobutyl isonipecotate (265 mg) in THF (1 ml) is added. The resulting mixture is stirred for 2 hr, warmed to rt and stirred overnight. The mixture is quenched and extracted with EtOAc. The combined extracts are concentrated to give (1-cyclobutyl-piperidin-4-yl)-(1-ethyl-2-naphthalen-1-yl-5-trimethylsilanyl-1H-imidazol-4-yl)-methanone as an oil, which is dissolved in THF (10 ml). The THF solution is treated with TBAF (285 mg) at rt for 30 min, after which THF is removed by evaporation. The residue is taken into EtOAc and washed with water and brine, and dried. The crude product is purified by column (2% Et$_3$N, 3% MeOH in EtOAc) to afford the title compound as a solid. LCMS 388.1 (M+1). $^1$H NMR (CDCl$_3$) δ ppm 1.26 (t, 3H), 1.63-2.05 (m, 12H), 2.68 (m, 1H), 2.91 (m, 2H), 3.53 (m, 1H), 3.75 (q, 2H), 7.46-7.60 (m, 5H), 7.84 (s, 1H), 7.90-8.0 (m, 2H).

R. (1-Cyclobutyl-piperidin-4-yl)-(3-ethyl-2-naphthalen-1-yl-3H-imidazol-4-yl)-methanone

COMPOUND 20

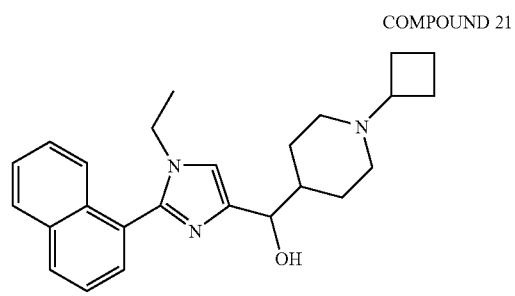

To a solution of 1H-1-ethyl-2-(1-naphthyl)imidazole (130 mg) in THF (4 ml) is added dropwise n-BuLi (0.4 ml, 1.6 M in hexanes) at –78° C. After 40 min stirring, a solution of ethyl N-cyclobutyl isonipecotate (110 mg) in THF (1 ml) is added. The resulting mixture is stirred for 2 hr, then warmed to rt and stirred overnight. The mixture is quenched and extracted with EtOAc. The combined extracts are concentrated and the crude product purified by column (2% Et$_3$N, 3% MeOH in EtOAc) to afford the title compound as a white solid, LCMS 388 (M+1).

S. (1-Cyclobutyl-piperidin-4-yl)-(1-ethyl-2-naphthalen-1-yl-1H-imidazol-4-yl)-methanol

COMPOUND 21

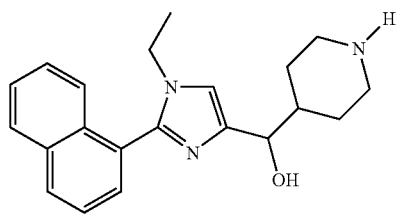

Step 1. Preparation of (1-ethyl-2-naphthalen-1-yl-1H-imidazol-4-yl)-piperidin-4-yl-methanol To a solution of 1H-4,5-dibromo-1-ethyl-2-(1-naphthyl)imidazole (4.0 g) in THF (40 ml) is added dropwise n-BuLi (7.23 ml, 1.6 M in hexanes) at –78° C. After 30 min stirring, TMSCl (1.46 ml) is added at –78° C. and the mixture is stirred for another 30 min. n-BuLi (7.23 ml, 1.6 M in hexanes) is added dropwise at –78° C. and the mixture is stirred for 30 min, after which a solution of 1-Boc-4-piperidinecarboxaldehyde (2.47 g) in THF (10 ml) is added. The resulting mixture is stirred for 2 hr. The mixture is warmed to rt and quenched and extracted with EtOAc. The combined extracts are concentrated to give an oil, which is dissolved in THF (40 ml). The THF solution is then treated with TBAF (3.0 g) at rt for 30 min. THF is removed by evaporation, and the residue is taken into EtOAc and washed with water and brine, dried and purified by column (EtOAc/hexane 1:1) to afford desilylated alcohol as a white foam.

The above desilylated alcohol (1.05 g) is dissolved in CH$_2$Cl$_2$ and TFA (1.25 ml) is added. The resulting solution is stirred at rt overnight, and then solvent evaporated. The residue is dissolved in EtOAc, neutralized with NaOH (10 N), washed with brine, dried and concentrated to give the title compound as a white crystalline solid. LCMS 336.3 (M+1).

Step 2. Preparation of (1-cyclobutyl-piperidin-4-yl)-(1-ethyl-2-naphthalen-1-yl-1H-imidazol-4-yl)-methanol

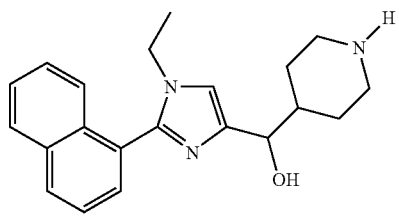

To a solution of (1-ethyl-2-naphthalen-1-yl-1H-imidazol-4-yl)-piperidin-4-yl-methanol (0.53 g) in CH$_2$ClCH$_2$Cl (12 ml) is added cyclobutanone (0.95 ml), followed by NaBH(OAc)$_3$ and acetic acid (0.1 ml). The resulting mixture is stirred at rt overnight, diluted with CH$_2$Cl$_2$, washed with Na$_2$CO$_3$ (1M), H$_2$O and brine, dried and solvent removed. The crude is purified by column (2% Et$_3$N, 3% MeOH in EtOAc) to afford the title compound as a white solid, LCMS 390.1 (M+1).

T. 1-Cyclobutyl-4-[(1-ethyl-2-naphthalen-1-yl-1H-imidazol-4-yl)-methoxy-methyl]-piperidine

COMPOUND 22

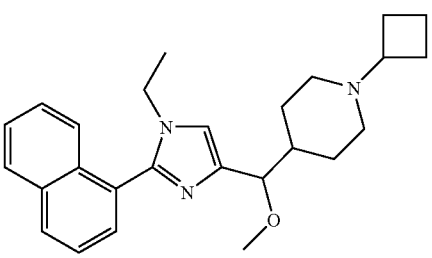

To a solution of (1-cyclobutyl-piperidin-4-yl)-(1-ethyl-2-naphthalen-1-yl-1H-imidazol-4-yl)-methanol (20 mg) in DMF (2 ml) is added NaH (6 mg, 60%), followed by CH$_3$I (15 mg). The resulting mixture is stirred at rt for 30 min, and then diluted with EtOAc, washed with water and brine, dried and solvent removed. The crude product is purified by column (2% Et$_3$N, 3% MeOH in EtOAc) to afford the title compound as an oil. LCMS 404.1 (M+1). $^1$H NMR (CDCl$_3$) δ ppm 1.25 (t, 3H), 1.40-2.05 (m, 11H), 2.60 (m, 1H), 2.90 (m, 2H), 3.36 (s, 3H), 3.75 (q, 214), 4.05 (d, 1H), 7.02 (s, 1H), 7.42-7.60 (m, 5H), 7.86-7.96 (m, 2H).

Example 3

Additional Representative Compounds

Using routine modifications, the starting materials may be varied and additional steps employed to produce other compounds provided herein. Compounds listed in Tables I and II are prepared using such methods. All compounds listed in Table I exhibit a K$_i$ in the assay of Example 7 that is less than 1 micromolar. The calculated molecular weight is provided in the column headed "MW," and the determined molecular weight (presented as M+1) obtained using the method described above is shown in the column headed "MS."

TABLE I

| Compound | | Name | MW | MS |
|---|---|---|---|---|
| 23 | | 1-isopropyl-4-{[2-(1-naphthyl)-1H-imidazol-5-yl]methyl}piperazine | 334.22 | 335.28 |

TABLE I-continued

| | Compound | Name | MW | MS |
|---|---|---|---|---|
| 24 | | 1-isopropyl-4-{[2-(1-naphthyl)-1H-imidazol-5-yl]methyl}-1,4-diazepane | 348.23 | 349.30 |
| 25 | | 1-isopropyl-4-{[2-(2-methoxyphenyl)-1H-imidazol-5-yl]methyl}-1,4-diazepane | 328.23 | 329.30 |
| 26 | | 1-{[2-(2,6-diethylphenyl)-4-phenyl-1,3-thiazol-5-yl]methyl}-4-isopropyl-1,4-diazepane | 447.3 | 448.2 |
| 27 | | 1-{[2-(2,6-diethylphenyl)-4-methyl-1,3-thiazol-5-yl]methyl}-4-isopropylpiperazine | 371.2 | 372.2 |
| 28 | | 1-{[2-(2,6-diethylphenyl)-4-methyl-1,3-thiazol-5-yl]methyl}-4-isopropyl-1,4-diazepane | 385.3 | 386.2 |

TABLE I-continued

| | Compound | Name | MW | MS |
|---|---|---|---|---|
| 29 | (structure) | 1-isopropyl-4-{[2-(2-methylphenyl)-1,3-thiazol-5-yl]methyl}piperazine | 315.2 | 316.1 |
| 30 | (structure) | 1-[(3,5-dimethyl-1-phenyl-1H-pyrazol-4-yl)carbonyl]-4-isopropylpiperazine | 326.21 | 327.2 |
| 31 | (structure) | 1-isopropyl-4-{[1-(4-methoxyphenyl)-3,5-dimethyl-1H-pyrazol-4-yl]carbonyl}piperazine | 356.2 | 357.2 |
| 32 | (structure) | [1-(3-Chloro-phenyl)-3,5-dimethyl-1H-pyrazol-4-yl]-(4-isopropyl-piperazin-1-yl)-methanone | 360.2 | 361.1 |
| 33 | (structure) | 1-isopropyl-4-{[4-methyl-2-(1-naphthyl)-1,3-thiazol-5-yl]carbonyl}piperazine | 379.17 | 380.24 |

TABLE I-continued

| Compound | Name | MW | MS |
|---|---|---|---|
| 34 | 1-isopropyl-4-{[2-(6-isopropyl-2-methoxypyridin-3-yl)-methyl-1,3-thiazol-5-yl]carbonyl}piperazine | 402.21 | 403.21 |
| 35 | 1-isopropyl-4-{[4-methyl-2-(3-methylpyridin-2-yl)-1,3-thiazol-5-yl]carbonyl}piperazine | 344.17 | 345.11 |
| 36 | 8-{5-[(4-isopropylpiperazin-1-yl)carbonyl]-4-methyl-1,3-thiazol-2-yl}quinoline | 380.17 | 381.11 |
| 37 | 2-{5-[(4-isopropylpiperazin-1-yl)carbonyl]-4-methyl-1,3-thiazol-2-yl}benzonitrile | 354.15 | 355.11 |
| 38 | 1-isopropyl-1-{[4-methyl-2-(1-naphthyl)-1,3-thiazol-5-yl]carbonyl}-1,4-diazepane | 393.19 | 394.15 |

TABLE I-continued

| | Compound | Name | MW | MS |
|---|---|---|---|---|
| 39 | | 1-isopropyl-4[(4-methyl-2-phenyl-1,3-thiazol-5-yl)carbonyl]-1,4-diazepane | 343.17 | 344.14 |
| 40 | | 1-isopropyl-4-{[2-(1-naphthyl)-1,3-thiazol-5-yl]carbonyl}-1,4-diazepane | 379.20 | 380.10 |
| 41 | | 1-isopropyl-4-[(4-methyl-2-piperidin-1-yl-1,3-thiazol-5-yl)carbonyl]piperazine | 336.20 | 337.20 |
| 42 | | 1-isopropyl-4-[(4-methyl-2-pyridin-2-yl-1,3-thiazol-5-yl)carbonyl]-1,4-diazepane | 344.20 | 345.20 |
| 43 | | 1-isopropyl-4-{[2-(2-methyloxypyridin-3-yl)-4-methyl-1,3-thiazol-5-yl]carbonyl}-1,4-diazepane | 374.20 | 375.20 |
| 44 | | 3-{5-[(4-isopropyl-1,4-diazepan-1-yl)carbonyl]-4-methyl-1,3-thiazol-2-yl}pyridin-2(1H)-one | | |

TABLE I-continued

| | Compound | Name | MW | MS |
|---|---|---|---|---|
| 45 | | 4-methyl-N-[2-(1-methylpyrrolidin-2-yl)ethyl]-2-(2-naphthyl)-1,3-thiazole-5-carboxamide | 379.17 | 380.21 |
| 46 | | 2-(2-fluoro-4-methylphenyl)-4-methyl-N-[2-(1-methylpyrrolidin-2-yl)ethyl]-1,3-thiazole-5-carboxamide | 361.16 | 362.20 |
| 47 | | 2-(3-fluoro-4-methylphenyl)-4-methyl-N-[2-(1-methylpyrrolidin-2-yl)ethyl]-1,3-thiazole-5-carboxamide | 361.16 | 362.21 |
| 48 | | 2-(4-chlorophenyl)-4-methyl-N-(4-pyrrolidin-1-ylbutyl)-1,3-thiazole-5-carboxamide | 377.13 | 378.17 |

TABLE I-continued

| | Compound | Name | MW | MS |
|---|---|---|---|---|
| 49 | | 2-(3-fluorophenyl)-4-methyl-N-(4-pyrrolidin-1-ylbutyl)-1,3-thiazole-5-carboxamide | 361.16 | 362.21 |
| 50 | | 4-methyl-2-(2-naphthyl)-N-(4-pyrrolidin-1-ylbutyl)-1,3-thiazole-5-carboxamide | 393.19 | 394.22 |
| 51 | | 2-(3-fluoro-4-methylphenyl)-4-methyl-N-(4-pyrrolidin-1-ylbutyl)-1,3-thiazole-5-carboxamide | 375.18 | 376.21 |

TABLE I-continued

| | Compound | Name | MW | MS |
|---|---|---|---|---|
| 52 | | 1-isopropyl-4-[(4-methyl-2-phenyl-1,3-thiazol-5-yl)carbonyl]piperazine | 329.16 | 330.29 |
| 53 | | 1-cyclopentyl-4-[(4-methyl-2-phenyl-1,3-thiazol-5-yl)carbonyl]piperazine | 355.17 | 356.32 |
| 54 | | 1-butyl-4-[(4-methyl-2-phenyl-1,3-thiazol-5-yl)carbonyl]-1,4-diazepane | 357.19 | 358.33 |
| 55 | | 1-{[2-(3-chlorophenyl)-4-methyl-1,3-thiazol-5-yl]carbonyl}-4-cyclopentylpiperazine | 389.13 | 390.30 |

TABLE I-continued

| | Compound | Name | MW | MS |
|---|---|---|---|---|
| 56 | | 1-butyl-4-{[2-(3-chlorophenyl)-4-methyl-1,3-thiazol-5-yl]carbonyl}-1,4-diazepane | 391.15 | 392.31 |
| 57 | | 1-{[2-(4-chlorophenyl)-4-methyl-1,3-thiazol-5-yl]carbonyl}-4-cyclopentylpiperazine | 389.13 | 390.30 |
| 58 | | 1-butyl-4-{[2-(4-chlorophenyl)-4-methyl-1,3-thiazol-5-yl]carbonyl}-1,4-diazepane | 391.15 | 392.32 |
| 59 | | 1-{[2-(4-fluorophenyl)-4-methyl-1,3-thiazol-5-yl]carbonyl}-4-isopropylpiperazine | 347.15 | 348.30 |

TABLE I-continued
| Compound | | Name | MW | MS |
|---|---|---|---|---|
| 60 | 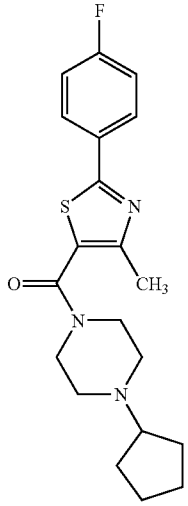 | 1-cyclopentyl-4-{[2-(4-fluorophenyl)-4-methyl-1,3-thiazol-5-yl]carbonyl}piperazine | 373.16 | 374.32 |
| 61 | 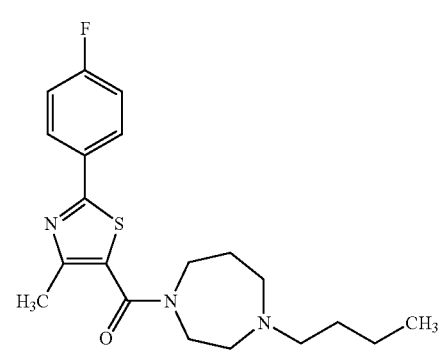 | 1-butyl-4-{[2-(4-fluorophenyl)-4-methyl-1,3-thiazol-5-yl]carbonyl}-1,4-diazepane | 375.18 | 376.34 |
| 62 | 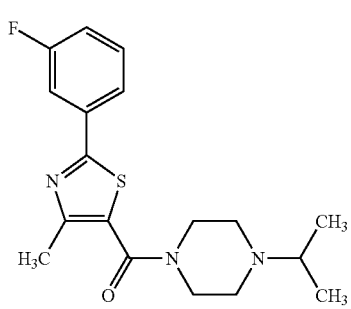 | 1-{[2-(3-fluorophenyl)-4-methyl-1,3-thiazol-5-yl]carbonyl}-4-isopropylpiperazine | 347.15 | 348.30 |

TABLE I-continued

| | Compound | Name | MW | MS |
|---|---|---|---|---|
| 63 | | 1-cyclopentyl-4-{[2-(3-fluorophenyl)-4-methyl-1,3-thiazol-5-yl]carbonyl}piperazine | 373.16 | 374.33 |
| 64 | | 1-butyl-4-{[2-(3-fluorophenyl)-4-methyl-1,3-thiazol-5-yl]carbonyl}-1,4-diazepane | 375.18 | 376.34 |
| 65 | | 1-{[2-(2-fluorophenyl)-4-methyl-1,3-thiazol-5-yl]carbonyl}-4-isopropylpiperazine | 347.15 | 348.30 |
| 66 | | 1-cyclopentyl-4-{[2-(2-fluorophenyl)-4-methyl-1,3-thiazol-5-yl]carbonyl}piperazine | 373.16 | 374.32 |

TABLE I-continued

| | Compound | Name | MW | MS |
|---|---|---|---|---|
| 67 | | 1-butyl-4-{[2-(2-fluorophenyl)-4-methyl-1,3-thiazol-5-yl]carbonyl}-1,4-diazepane | 375.18 | 376.34 |
| 68 | | 1-isopropyl-4-{[4-methyl-2-(2-naphthyl)-1,3-thiazol-5-yl]carbonyl}piperazine | 379.17 | 380.31 |
| 69 | | 1-cyclopentyl-4-{[4-methyl-2-(2-naphthyl)-1,3-thiazol-5-yl]carbonyl}piperazine | 405.19 | 406.32 |
| 70 | | 1-butyl-4-{[4-methyl-2-(2-naphthyl)-1,3-thiazol-5-yl]carbonyl}-1,4-diazepane | 407.20 | 408.37 |

TABLE I-continued
| | Compound | Name | MW | MS |
|---|---|---|---|---|
| 71 | 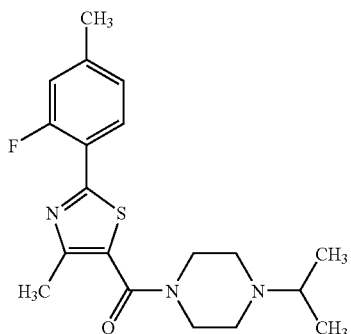 | 1-{[2-(2-fluoro-4-methylphenyl)-4-methyl-1,3-thiazol-5-yl]carbonyl}-4-isopropylpiperazine | 361.16 | 362.31 |
| 72 | 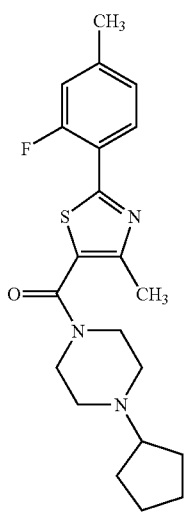 | 1-cyclopentyl-4-{[2-(2-fluoro-4-methylphenyl)-4-methyl-1,3-thiazol-5-yl]carbonyl}piperazine | 387.18 | 388.34 |
| 73 | 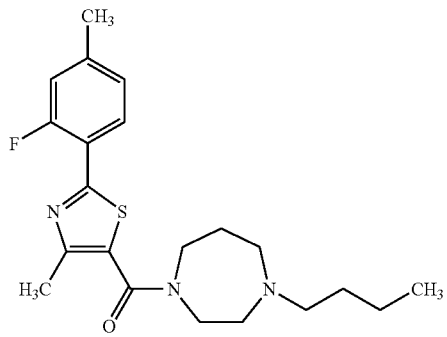 | 1-butyl-4-{[2-(2-fluoro-4-methylphenyl)-4-methyl-1,3-thiazol-5-yl]carbonyl}-1,4-diazepane | | |
| 74 | 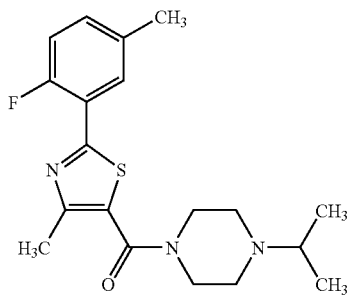 | 1-{[2-(2-fluoro-5-methylphenyl)-4-methyl-1,3-thiazol-5-yl]carbonyl}-4-isopropylpiperazine | 361.16 | 362.32 |

TABLE I-continued

| | Compound | Name | MW | MS |
|---|---|---|---|---|
| 75 | | 1-cyclopentyl-4-{[2-(2-fluoro-5-methylphenyl)-4-methyl-1,3-thiazol-5-yl]carbonyl}piperazine | 378.18 | 388.34 |
| 76 | | 1-butyl-4-{[2-(2-fluoro-5-methylphenyl)-4-methyl-1,3-thiazol-5-yl]carbonyl}-1,4-diazepane | 389.19 | 390.36 |
| 77 | | 1-{[2-(3-fluoro-4-methylphenyl)-4-methyl-1,3-thiazol-5-yl]carbonyl}-4-isopropylpiperazine | 361.16 | 362.32 |

| Compound | Name | MW | MS |
|---|---|---|---|
| 78 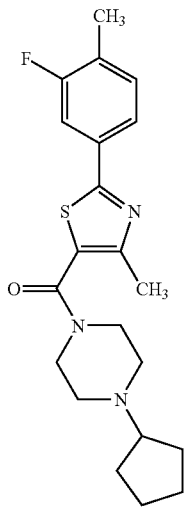 | 1-cyclopentyl-4-{[2-(3-fluoro-4-methylphenyl)-4-methyl-1,3-thiazol-5-yl]carbonyl}piperazine | 387.18 | 388.35 |
| 79 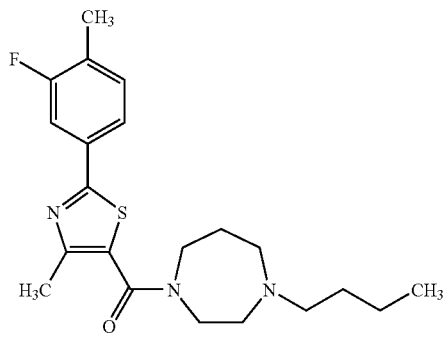 | 1-butyl-4-{[2-(3-fluoro-4-methylphenyl)-4-methyl-1,3-thiazol-5-yl]carbonyl}-1,4-diazepane | 389.19 | 390.36 |
| 80 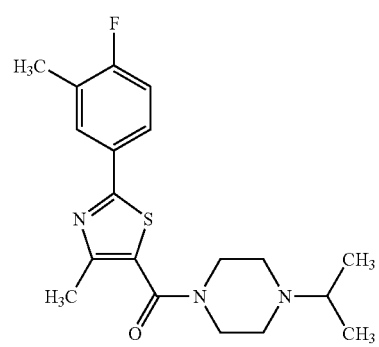 | 1-{[2-(4-fluoro-3-methylphenyl)-4-methyl-1,3-thiazol-5-yl]carbonyl}-4-isopropylpiperazine | 361.16 | 362.32 |

TABLE I-continued
| | Compound | Name | MW | MS |
|---|---|---|---|---|
| 81 | 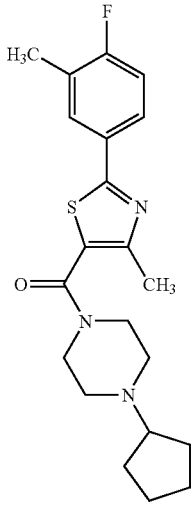 | 1-cyclopentyl-4-{[2-(4-fluoro-3-methylphenyl)-4-methyl-1,3-thiazol-4-yl]carbonyl}piperazine | 387.18 | 388.35 |
| 82 | 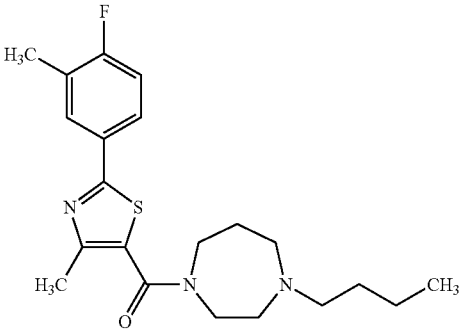 | 1-butyl-4-{[2-(4-fluoro-3-methylphenyl)-4-methyl-1,3-thiazol-5-yl]carbonyl}-1,4-diazepane | 389.19 | 390.36 |
| 83 | 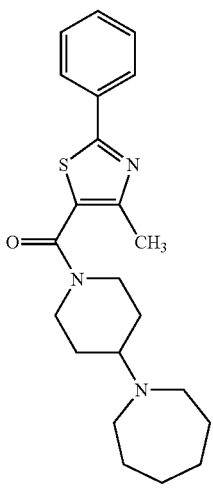 | 1-{1-[(4-methyl-2-phenyl-1,3-thiazol-5-yl)carbonyl]piperidin-4-yl}azepane | 383.20 | 384.36 |

TABLE I-continued

| Compound | | Name | MW | MS |
|---|---|---|---|---|
| 84 | | 1'-[(4-methyl-2-phenyl-1,3-thiazol-5-yl)carbonyl]-1,4'-bipiperidine | 369.19 | 370.35 |
| 85 | | 1-(1-{[2-(3-chlorophenyl)-4-methyl-1,3-thiazol-5-yl]carbonyl}piperidin-4-yl)azepane | 417.16 | 418.34 |
| 86 | | 1'-{[2-(3-chlorophenyl)-4-methyl-1,3-thiazol-5-yl]carbonyl}-1,4'-bipiperidine | 403.15 | 404.32 |

TABLE I-continued
| Compound | | Name | MW | MS |
|---|---|---|---|---|
| 87 | 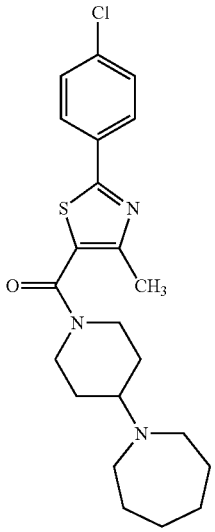 | 1-(1-{[2-(4-chlorophenyl)-4-methyl-1,3-thiazol-5-yl]carbonyl}piperidin-4-yl)azepane | 417.16 | 418.34 |
| 88 | 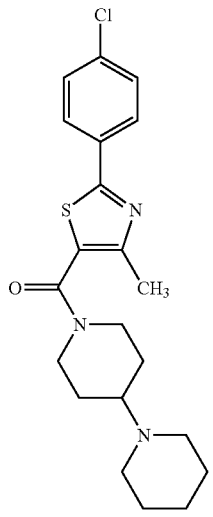 | 1'-{[2-(4-chlorophenyl)-4-methyl-1,3-thiazol-5-yl]carbonyl}-1,4'-bipiperidine | 403.15 | 404.32 |
| 89 | 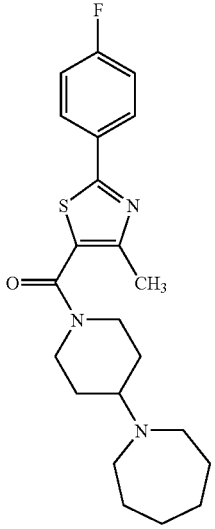 | 1-(1-{[2-(4-fluorophenyl)-4-methyl-1,3-thiazol-5-yl]carbonyl}piperidin-4-yl)azepane | 401.19 | 402.36 |

TABLE I-continued
| Compound | | Name | MW | MS |
|---|---|---|---|---|
| 90 | 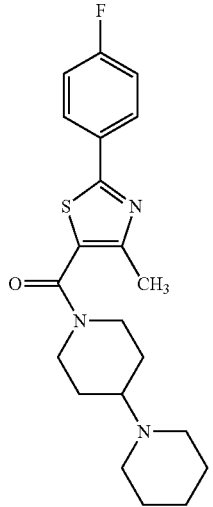 | 1'-{[2-(4-fluorophenyl)-4-methyl-1,3-thiazol-5-yl]carbonyl}-1,4'-bipiperidine | 387.18 | 388.34 |
| 91 | 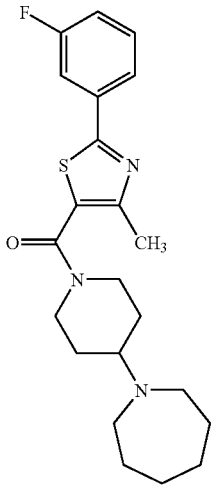 | 1-(1-{[2-(3-fluorophenyl)-4-methyl-1,3-thiazol-5-yl]carbonyl}piperidin-4-yl)azepane | 401.19 | 402.36 |
| 92 |  | 1'-{[2-(3-fluorophenyl)-4-methyl-1,3-thiazol-5-yl]carbonyl}-1,4'-bipiperidine | 387.18 | 388.34 |

TABLE I-continued
| Compound | | Name | MW | MS |
|---|---|---|---|---|
| 93 | 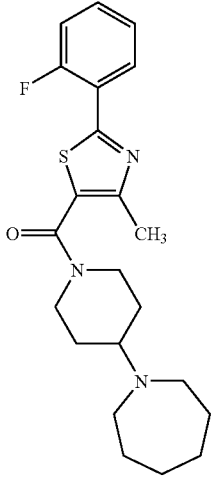 | 1-(1-{[2-(2-fluorophenyl)-4-methyl-1,3-thiazol-5-yl]carbonyl}piperidin-4-yl)azepane | 401.19 | 402.36 |
| 94 | 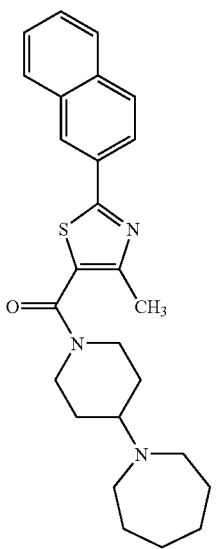 | 1-(1-{[4-methyl-2-(2-naphthyl)-1,3-thiazol-5-yl]carbonyl}piperidin-4-yl)azepane | 433.22 | 434.41 |
| 95 | 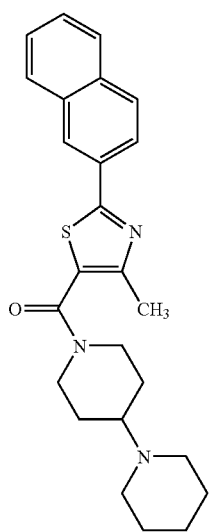 | 1'-{[4-methyl-2-(2-naphthyl)-1,3-thiazol-5-yl]carbonyl}-1,4'-bipiperidine | 419.20 | 420.38 |

TABLE I-continued

| | Compound | Name | MW | MS |
|---|---|---|---|---|
| 96 | (structure) | 1-(1-{[2-(2-fluoro-4-methylphenyl)-4-methyl-1,3-thiazol-5-yl]carbonyl}piperidin-4-yl)azepane | 415.21 | 416.37 |
| 97 | (structure) | 1'-{[2-(2-fluoro-4-methylphenyl)-4-methyl-1,3-thiazol-5-yl]carbonyl}-1,4-bipiperidine | 401.19 | 402.36 |
| 98 | (structure) | 1-(1-{[2-(2-fluoro-5-methylphenyl)-4-methyl-1,3-thiazol-5-yl]carbonyl}piperidin-4-yl)azepane | 415.21 | 416.37 |

TABLE I-continued

| Compound | | Name | MW | MS |
|---|---|---|---|---|
| 99 | [structure] | 1'-{[2-(2-fluoro-5-methylphenyl)-4-methyl-1,3-thiazol-5-yl]carbonyl}-1,4'-bipiperidine | 401.19 | 402.36 |
| 100 | [structure] | 1-(1-{[2-(3-fluoro-4-methylphenyl)-4-methyl-1,3-thiazol-5-yl]carbonyl}piperidin-4-yl)azepane | 415.21 | 416.37 |
| 101 | [structure] | 1'-{[2-(3-fluoro-4-methylphenyl)-4-methyl-1,3-thiazol-5-yl]carbonyl}-1,4'-bipiperidine | 401.19 | 402.36 |

TABLE I-continued
| Compound | | Name | MW | MS |
|---|---|---|---|---|
| 102 | 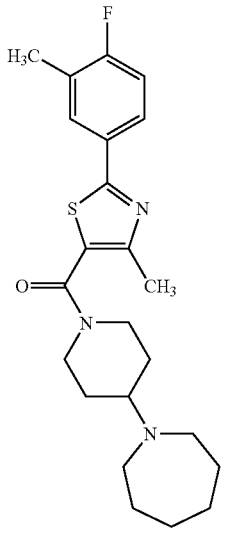 | 1-(1-{[2-(4-fluoro-3-methylphenyl)-4-methyl-1,3-thiazol-5-yl]carbonyl}piperidin-4-yl)azepane | 415.21 | 416.37 |
| 103 | 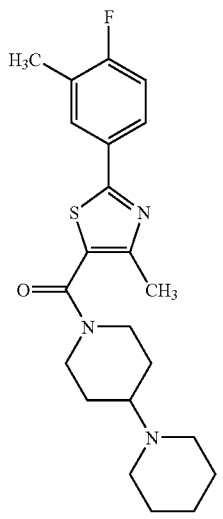 | 1'-{[2-(4-fluoro-3-methylphenyl)-4-methyl-1,3-thiazol-5-yl]carbonyl}-1,4'-bipiperidine | 401.19 | 402.36 |
| 104 | 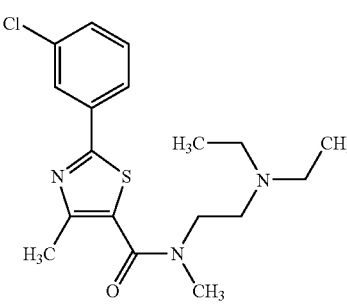 | 2-(3-chlorophenyl)-N-[2-(diethylamino)ethyl]-N,4-dimethyl-1,3-thiazole-5-carboxamide | 365.13 | 366.27 |

TABLE I-continued

| Compound | Name | MW | MS |
|---|---|---|---|
| 105 | N-[2-(diethylamino)ethyl]-N,4-dimethyl-2-(2-naphthyl)-1,3-thiazole-5-carboxamide | 381.19 | 382.32 |
| 106 | N-[2-(diethylamino)ethyl]-2-(2-fluoro-5-methylphenyl)-N,4-dimethyl-1,3-thiazole-5-carboxamide | 363.18 | 364.30 |
| 107 | 2-(3-methoxyphenyl)-4-methyl-N-(2-pyrrolidin-1-ylethyl)-1,3-thiazole-5-carboxamide | 345.15 | 346.26 |
| 108 | 4-methyl-N-(2-pyrrolidin-1-ylethyl)-2-[4-(trifluoromethoxy)phenyl]-1,3-thiazole-5-carboxamide | 399.12 | 400.25 |

TABLE I-continued
| Compound | | Name | MW | MS |
|---|---|---|---|---|
| 109 | 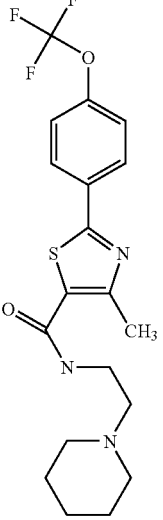 | 4-methyl-N-(2-piperidin-1-ylethyl)-2-[4-(trifluoromethoxy)phenyl]-1,3-thiazole-5-carboxamide | 413.14 | 414.27 |
| 110 | 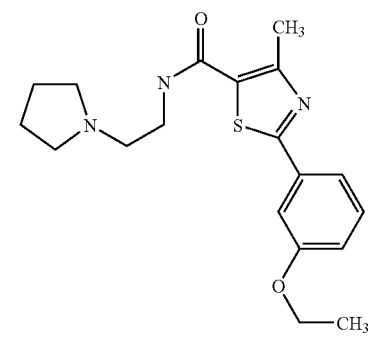 | 2-(3-ethoxypheny)-4-methyl-N-(2-pyrrolidin-1-ylethyl)-1,3-thiazole-5-carboxamide | 359.17 | 360.28 |
| 111 | 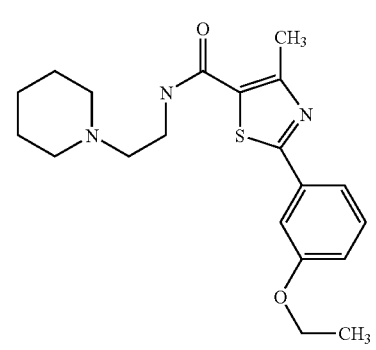 | 2-(3-ethoxypheny)-4-methyl-N-(2-piperidin-1-ylethyl)-1,3-thiazole-5-carboxamide | 373.18 | 374.30 |

TABLE I-continued

| Compound | | Name | MW | MS |
|---|---|---|---|---|
| 112 | | 4-methyl-2-(4-phenoxyphenyl)-N-(2-pyrrolidin-1-ylethyl)-1,3-thiazole-5-carboxamide | 407.17 | 408.29 |
| 113 | | 4-methyl-2-(4-phenoxyphenyl)-N-(2-piperidin-1-ylethyl)-1,3-thiazole-5-carboxamide | 421.18 | 422.31 |
| 114 | | 4-methyl-N-(2-pyrrolidin-1-ylethyl)-2-[3-(trifluoromethoxy)phenyl]-1,3-thiazole-5-carboxamide | 399.12 | 400.24 |

TABLE I-continued

| Compound | | Name | MW | MS |
|---|---|---|---|---|
| 115 | | 4-methyl-N-(2-piperidin-1-ylethyl)-2-[3-(trifluoromethoxy)phenyl]-1,3-thiazole-5-carboxamide | 413.14 | 414.26 |
| 116 | | 4-methyl-2-[3-(methylthio)phenyl]-N-(2-pyrrolidin-1-ylethyl)-1,3-thiazole-5-carboxamide | 361.13 | 362.24 |
| 117 | | 4-methyl-2-[3-(methylthio)phenyl]-N-(2-piperidin-1-ylethyl)-1,3-thiazole-5-carboxamide | 375.14 | 376.26 |
| 118 | | 2-(3-fluoro-4-methoxyphenyl)-4-methyl-N-(2-pyrrolidin-1-ylethyl)-1,3-thiazole-5-carboxamide | 363.14 | 364.25 |

TABLE I-continued

| Compound | | Name | MW | MS |
|---|---|---|---|---|
| 119 | | 2-(2,5-difluoro-4-methoxyphenyl)-4-methyl-N-(2-pyrrolidin-1-ylethyl)-1,3-thiazole-5-carboxamide | 381.13 | 382.24 |
| 120 | | 2-(2,5-difluoro-4-methoxyphenyl)-4-methyl-N-(2-piperidin-1-ylethyl)-1,3-thiazole-5-carboxamide | 395.15 | 396.26 |
| 121 | | 2-(6-methoxy-2-naphthyl)-4-methyl-N-(2-pyrrolidin-1-ylethyl)-1,3-thiazole-5-carboxamide | 395.17 | 396.28 |
| 122 | | 2-(6-methoxy-2-naphthyl)-4-methyl-N-(2-piperidin-1-ylethyl)-1,3-thiazole-5-carboxamide | 409.18 | 410.30 |

TABLE I-continued
| Compound | Name | MW | MS |
|---|---|---|---|
| 123 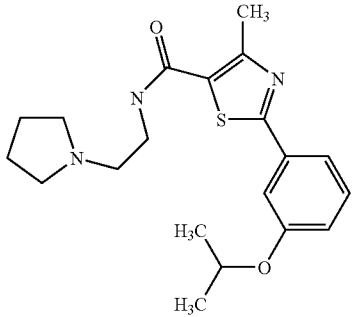 | 2-(3-isopropoxyphenyl)-4-methyl-N-(2-pyrrolidin-1-ylethyl)-1,3-thiazole-5-carboxamide | 373.18 | 374.28 |
| 124 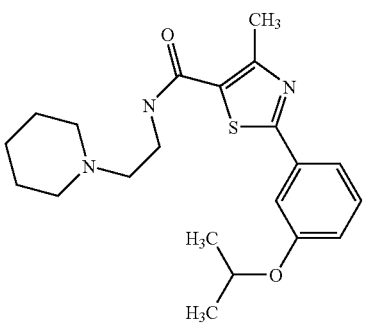 | 2-(3-isopropoxyphenyl)-4-methyl-N-(2-piperidin-1-ylethyl)-1,3-thiazole-5-carboxamide | 387.20 | 388.30 |
| 125 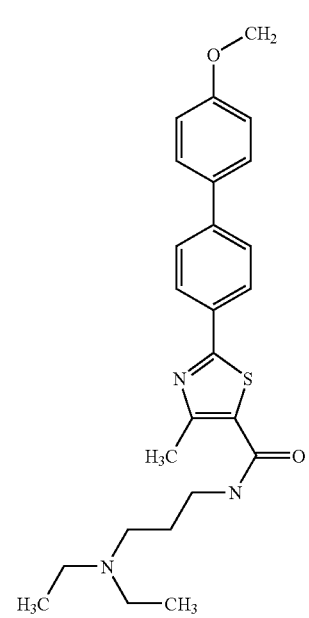 | N-[3-(diethylamino)propyl]-2-(4'-methoxybiphenyl-4-yl)-4-methyl-1,3-thiazole-5-carboxamide | 437.21 | 438.31 |

TABLE I-continued

| Compound | Name | MW | MS |
|---|---|---|---|
| 126 | N-[3-(diethylamino)propyl]-2-(6-methoxy-2-naphthyl)-4-methyl-1,3-thiazole-5-carboxamide | 411.20 | 412.29 |
| 127 | 2-(3-methoxyphenyl)-4-methyl-N-[2-(1-methylpyrrolidin-2-yl)ethyl]-1,3-thiazole-5-carboxamide | 359.17 | 360.25 |
| 128 | 4-methyl-N-[2-(1-methylpyrrolidin-2-yl)ethyl]-2-[4-(trifluoromethoxy)phenyl]-1,3-thiazole-5-carboxamide | 413.14 | 414.22 |
| 129 | 2-(3-ethoxyphenyl)-4-methyl-N-[2-(1-methylpyrrolidin-2-yl)ethyl]-1,3-thiazole-5-carboxamide | 373.18 | 374.26 |

TABLE I-continued

| | Compound | Name | MW | MS |
|---|---|---|---|---|
| 130 | | 4-methyl-N-[2-(1-methylpyrrolidin-2-yl)ethyl]-2-(4-phenoxyphenyl)-1,3-thiazole-5-carboxamide | 421.18 | 422.27 |
| 131 | | 4-methyl-N-[3-(2-methylpiperidin-1-yl)propyl]-2-(4-phenoxyphenyl)-1,3-thiazole-5-carboxamide | 449.21 | 450.30 |
| 132 | | 4-methyl-N-[2-(1-methylpyrrolidin-2-yl)ethyl]-2-[3-(trifluoromethoxy)phenyl]-1,3-thiazole-5-carboxamide | 413.14 | 414.22 |
| 133 | | 4-methyl-N-[2-(1-methylpyrrolidin-2-yl)ethyl]-2-[3-(methylthio)phenyl]-1,3-thiazole-5-carboxamide | 375.14 | 376.23 |

TABLE I-continued

| | Compound | Name | MW | MS |
|---|---|---|---|---|
| 134 | | 4-methyl-N-[3-(2-methylpiperidin-1-yl)propyl]-2-[3-(methylthio)phenyl]-1,3-thiazole-5-carboxamide | 403.18 | 404.26 |
| 135 | | N-[(1-ethylpyrrolidin-2-yl)methyl]-2-(4'-methoxybiphenyl-4-yl)-4-methyl-1,3-thiazole-5-carboxamide | 435.20 | 436.30 |
| 136 | | 2-(4'-methoxybiphenyl-4-yl)-4-methyl-N-[2-(1-methylpyrrolidin-2-yl)ethyl]-1,3-thiazole-5-carboxamide | 435.20 | 436.31 |
| 137 | | 2-(4'-methoxybiphenyl-4-yl)-4-methyl-N-[3-(2-methylpiperidin-1-yl)propyl]-1,3-thiazole-5-carboxamide | 463.23 | 464.33 |

TABLE I-continued

| | Compound | Name | MW | MS |
|---|---|---|---|---|
| 138 | | 2-(3-fluoro-4-methoxyphenyl)-4-methyl-N-[2-(1-methylpyrrolidin-2-yl)ethyl]-1,3-thiazole-5-carboxamide | 377.16 | 378.24 |
| 139 | | 2-(2,5-difluoro-4-methoxyphenyl)-4-methyl-N-[2-(1-methylpyrrolidin-2-yl)ethyl]-1,3-thiazole-5-carboxamide | 395.15 | 396.23 |
| 140 | | N-[(1-ethylpyrrolidin-2-yl)methyl]-2-(6-methoxy-2-naphthyl)-4-methyl-1,3-thiazole-5-carboxamide | 409.18 | 410.28 |
| 141 | | 2-(6-methoxy-2-naphthyl)-4-methyl-N-[2-(1-methylpyrrolidin-2-yl)ethyl]-1,3-thiazole-5-carboxamide | 409.18 | 410.28 |

TABLE I-continued
| Compound | | Name | MW | MS |
|---|---|---|---|---|
| 142 | 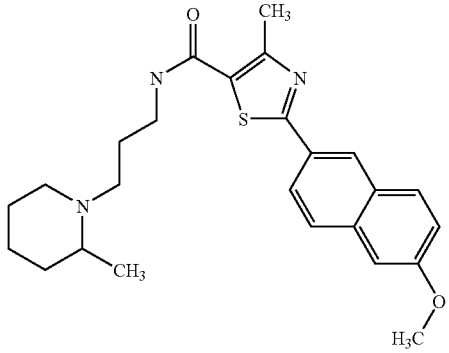 | 2-(6-methoxy-2-naphthyl)-4-methyl-N-[3-(2-methylpiperidin-1-yl)propyl]-1,3-thiazole-5-carboxamide | 437.21 | 438.31 |
| 143 | 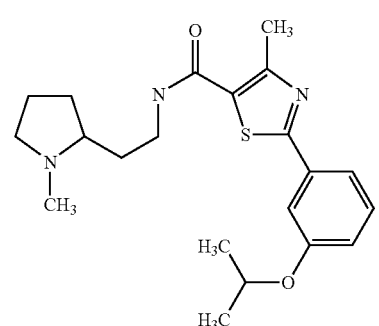 | 2-(3-isopropoxyphenyl)-4-methyl-N-[2-(1-methylpyrrolidin-2-yl)ethyl]-1,3-thiazole-5-carboxamide | 387.20 | 388.28 |
| 144 | 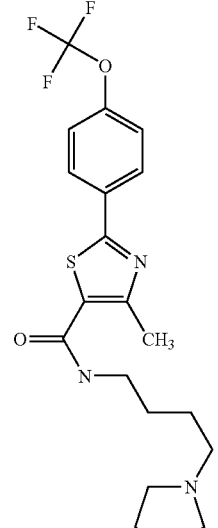 | 4-methyl-N-(4-pyrrolidin-1-ylbutyl)-2-[4-(trifluoromethoxy)phenyl]-1,3-thiazole-5-carboxamide | 427.15 | 428.24 |
| 145 | 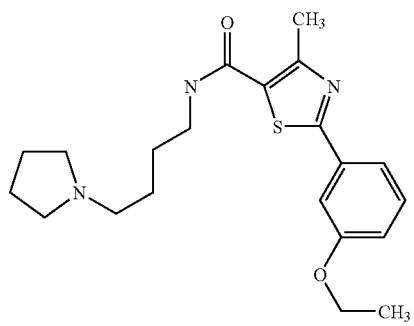 | 2-(3-ethoxyphenyl)-4-methyl-N-(4-pyrrolidin-1-ylbutyl)-1,3-thiazole-5-carboxamide | 387.20 | 388.28 |

TABLE I-continued

| Compound | | Name | MW | MS |
|---|---|---|---|---|
| 146 | | 4-methyl-2-(4-phenoxyphenyl)-N-(4-pyrrolidin-1-ylbutyl)-1,3-thiazole-5-carboxamide | 435.20 | 436.29 |
| 147 | | 4-methyl-N-(4-pyrrolidin-1-ylbutyl)-2-[3-(trifluoromethoxy)phenyl]-1,3-thiazole-5-carboxamide | 427.15 | 428.24 |
| 148 | | 4-methyl-2-[3-(methylthio)phenyl]-N-(4-pyrrolidin-1-ylbutyl)-1,3-thiazole-5-carboxamide | 389.16 | 390.25 |

TABLE I-continued

| Compound | Name | MW | MS |
|---|---|---|---|
| 149 | 2-(4'-methoxybiphenyl-4-yl)-4-methyl-N-(4-pyrrolidin-1-ylbutyl)-1,3-thiazole-5-carboxamide | 449.21 | 450.31 |
| 150 | 2-(3-fluoro-4-methoxyphenyl)-4-methyl-N-(4-pyrrolidin-1-ylbutyl)-1,3-thiazole-5-carboxamide | 391.17 | 392.26 |
| 151 | 2-(2,5-difluoro-4-methoxyphenyl)-4-methyl-N-(4-pyrrolidin-1-ylbutyl)-1,3-thiazole-5-carboxamide | 409.16 | 410.25 |
| 152 | 2-(6-methoxy-2-naphthyl)-4-methyl-N-(4-pyrrolidin-1-ylbutyl)-1,3-thiazole-5-carboxamide | 423.20 | 424.29 |

TABLE I-continued
| Compound | Name | MW | MS |
|---|---|---|---|
| 153 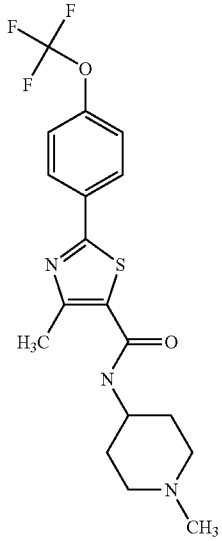 | 4-methyl-N-(1-methylpiperidin-4-yl)-2-[4-(trifluoromethoxy)phenyl]-1,3-thiazole-5-carboxamide | 399.12 | 400.21 |
| 154 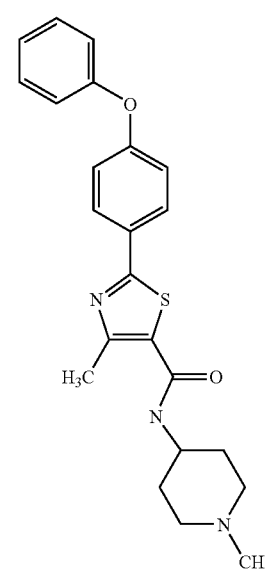 | 4-methyl-N-(1-methylpiperidin-4-yl)-2-(4-phenoxyphenyl)-1,3-thiazole-5-carboxamide | 407.17 | 408.26 |
| 155 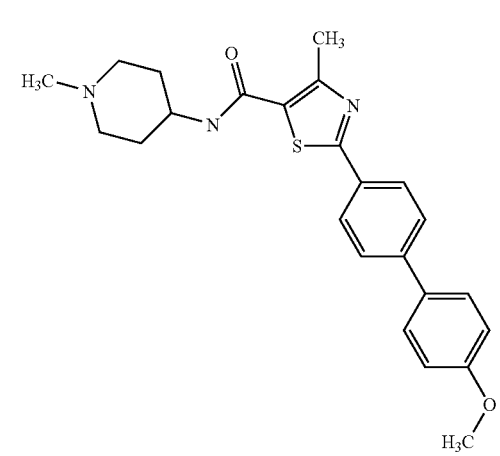 | 2-(4'-methoxybiphenyl-4-yl)-4-methyl-N-(1-methylpiperidin-4-yl)-1,3-thiazole-5-carboxamide | 421.18 | 422.29 |

TABLE I-continued

| Compound | | Name | MW | MS |
|---|---|---|---|---|
| 156 | | 2-(3-fluoro-4-methoxyphenyl)-4-methyl-N-(1-methylpiperidin-4-yl)-1,3-thiazole-5-carboxamide | 363.14 | 364.23 |
| 157 | | 2-(6-methoxy-2-naphthyl)-4-methyl-N-(1-methylpiperidin-4-yl)-1,3-thiazole-5-carboxamide | 395.17 | 396.27 |
| 158 | | 1-isopropyl-4-{[2-(3-methoxyphenyl)-4-methyl-1,3-thiazol-5-yl]carbonyl}piperazine | 359.17 | 360.30 |
| 159 | | 1-cyclopentyl-4-{[2-(3-methoxyphenyl)-4-methyl-1,3-thiazol-5-yl]carbonyl}piperazine | 385.18 | 386.33 |

TABLE I-continued
| | Compound | Name | MW | MS |
|---|---|---|---|---|
| 160 | 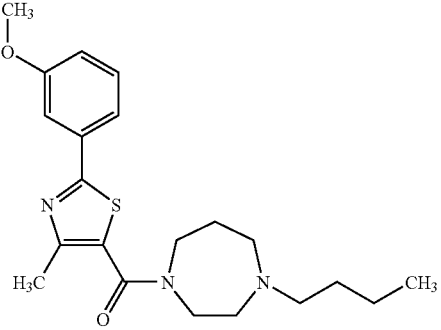 | 1-butyl-4-{[2-(3-methoxyphenyl)-4-methyl-1,3-thiazol-5-yl]carbonyl}-1,4-diazepane | 387.20 | 388.35 |
| 161 | 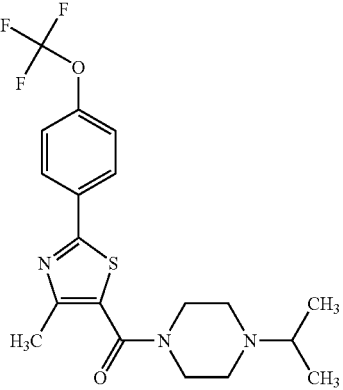 | 1-isopropyl-4-({4-methyl-2-[4-(trifluoromethoxy)phenyl]-1,3-thiazol-5-yl}carbonyl)piperazine | 413.14 | 414.26 |
| 162 | 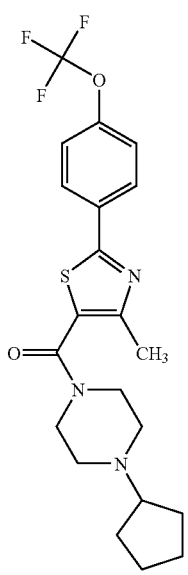 | 1-cyclopentyl-4-({4-methyl-2-[4-(trifluoromethoxy)phenyl]-1,3-thiazol-5-yl}carbonyl)piperazine | 439.15 | 440.30 |

TABLE I-continued

| | Compound | Name | MW | MS |
|---|---|---|---|---|
| 163 | | 1-butyl-4-({4-methyl-2-[4-(trifluoromethoxy)phenyl]-1,3-thiazol-5-yl}carbonyl)-1,4-diazepane | 441.17 | 442.32 |
| 164 | | 1-{[2-(3-ethoxyphenyl)-4-methyl-1,3-thiazol-5-yl]carbonyl}-4-isopropylpiperazine | 373.18 | 374.33 |
| 165 | | 1-cyclopentyl-4-{[2-(3-ethoxyphenyl)-4-methyl-1,3-thiazol-5-yl]carbonyl}piperazine | 399.20 | 400.36 |
| 166 | | 1-butyl-4-{[2-(3-ethoxyphenyl)-4-methyl-1,3-thiazol-5-yl]carbonyl}-1,4-diazepane | 401.21 | 402.36 |

TABLE I-continued

| | Compound | Name | MW | MS |
|---|---|---|---|---|
| 167 | | 1-isopropyl-4-{[4-methyl-2-(4-phenoxyphenyl)-1,3-thiazol-5-yl]carbonyl}piperazine | 421.18 | 422.33 |
| 168 | | 1-cyclopentyl-4-{[4-methyl-2-(4-phenoxyphenyl)-1,3-thiazol-5-yl]carbonyl}piperazine | 447.20 | 448.35 |
| 169 | | 1-butyl-4-{[4-methyl-2-(4-phenoxyphenyl)-1,3-thiazol-5-yl]carbonyl}-1,4-diazepane | 449.21 | 450.35 |

TABLE I-continued

| | Compound | Name | MW | MS |
|---|---|---|---|---|
| 170 | | 1-isopropyl-4-({4-methyl-2-[3-(trifluoromethoxy)phenyl]-1,3-thiazol-5-yl}carbonyl)piperazine | 413.14 | 414.31 |
| 171 | | 1-cyclopentyl-4-({4-methyl-2-[3-(trifluoromethoxy)phenyl]-1,3-thiazol-5-yl}carbonyl)piperazine | 439.15 | 440.32 |
| 172 | | 1-butyl-4-({4-methyl-2-[3-(trifluoromethoxy)phenyl]-1,3-thiazol-5-yl}carbonyl)-1,4-diazepane | 441.17 | 442.33 |
| 173 | | 1-isopropyl-4-({4-methyl-2-[3-(methylthio)phenyl]-1,3-thiazol-5-yl}carbonyl)piperazine | 375.14 | 376.28 |

TABLE I-continued

| | Compound | Name | MW | MS |
|---|---|---|---|---|
| 174 | | 1-cyclopentyl-4-({4-methyl-2-[3-(methylthio)phenyl]-1,3-thiazol-5-yl}carbonyl)piperazine | 401.16 | 420.31 |
| 175 | | 1-butyl-4-({4-methyl-2-[3-(methylthio)phenyl]-1,3-thiazol-5-yl}carbonyl)-1,4-diazepane | 403.18 | 404.32 |
| 176 | | 1-isopropyl-4-{[2-(4'-methoxybiphenyl-4-yl)-4-methyl-1,3-thiazol-5-yl]carbonyl}piperazine | 435.20 | 436.35 |
| 177 | | 1-cyclopentyl-4-{[2-(4'-methoxybiphenyl-4-yl)-4-methyl-1,3-thiazol-5-yl]carbonyl}piperazine | 461.21 | 462.38 |

TABLE I-continued

| | Compound | Name | MW | MS |
|---|---|---|---|---|
| 178 | | 1-butyl-4-{[2-(4'-methoxybiphenyl-4-yl)-4-methyl-1,3-thiazol-5-yl]carbonyl}-1,4-diazepane | 463.23 | 464.39 |
| 179 | | 1-{[2-(3-fluoro-4-methoxyphenyl)-4-methyl-1,3-thiazol-5-yl]carbonyl}-4-isopropylpiperazine | 377.16 | 378.30 |
| 180 | | 1-cyclopentyl-4-{[2-(3-fluoro-4-methoxyphenyl)-4-methyl-1,3-thiazol-5-yl]carbonyl}piperazine | 403.17 | 404.32 |
| 181 | | 1-butyl-4-{[2-(3-fluoro-4-methoxyphenyl)-4-methyl-1,3-thiazol-5-yl]carbonyl}-1,4-diazepane | 405.19 | 406.33 |

TABLE I-continued

| Compound | Name | MW | MS |
|---|---|---|---|
| 182 | 1-{[2-(2,5-difluoro-4-methoxyphenyl)-4-methyl-1,3-thiazol-5-yl]carbonyl}-4-isopropylpiperazine | 395.15 | 396.27 |
| 183 | 1-cyclopentyl-4-{[2-(2,5-difluoro-4-methoxyphenyl)-4-methyl-1,3-thiazol-5-yl]carbonyl}piperazine | 421.16 | 422.30 |
| 184 | 1-butyl-4-{[2-(2,5-difluoro-4-methoxyphenyl)-4-methyl-1,3-thiazol-5-yl]carbonyl}-1,4-diazepane | 423.18 | 424.32 |
| 185 | 1-isopropyl-4-{[2-(6-methoxy-2-naphthyl)-4-methyl-1,3-thiazol-5-yl]carbonyl}piperazine | 409.18 | 410.31 |

TABLE I-continued

| Compound | Name | MW | MS |
|---|---|---|---|
| 186 | 1-cyclopentyl-4-{[2-(6-methoxy-2-naphthyl)-4-methyl-1,3-thiazol-5-yl]carbonyl}piperazine | 435.20 | 426.33 |
| 187 | 1-butyl-4-{[2-(6-methoxy-2-naphthyl)-4-methyl-1,3-thiazol-5-yl]carbonyl}-1,4-diazepane | 437.21 | 438.33 |
| 188 | 1-{[2-(3-isopropoxyphenyl)-4-methyl-1,3-thiazol-5-yl]carbonyl}-4-isopropylpiperazine | 387.20 | 388.32 |
| 189 | 1-cyclopentyl-4-{[2-(3-isopropoxyphenyl)-4-methyl-1,3-thiazol-5-yl]carbonyl}piperazine | 413.21 | 414.35 |

TABLE I-continued

| | Compound | Name | MW | MS |
|---|---|---|---|---|
| 190 | | N,N-diethyl-1-{[2-(4'-methoxybiphenyl-4-yl)-4-methyl-1,3-thiazol-5-yl]carbonyl}piperidin-4-amine | 463.23 | 464.34 |
| 191 | | 1-(1-{[2-(3-methoxyphenyl)-4-methyl-1,3-thiazol-5-yl]carbonyl}piperidin-4-yl)azepane | 413.21 | 414.35 |
| 192 | | 1'-{[2-(3-methoxyphenyl)-4-methyl-1,3-thiazol-5-yl]carbonyl}-1,4'-bipiperidine | 399.20 | 400.32 |

TABLE I-continued
| Compound | | Name | MW | MS |
|---|---|---|---|---|
| 193 | 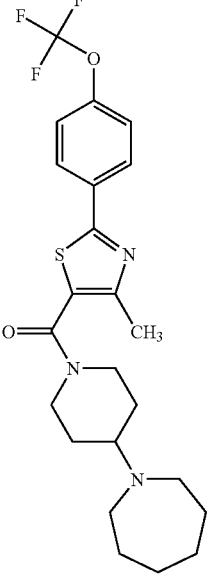 | 1-[1-({4-methyl-2-[4-(trifluoromethoxy)phenyl]-1,3-thiazol-5-yl}carbonyl)piperidin-4-yl]azepane | 467.19 | 468.32 |
| 194 | 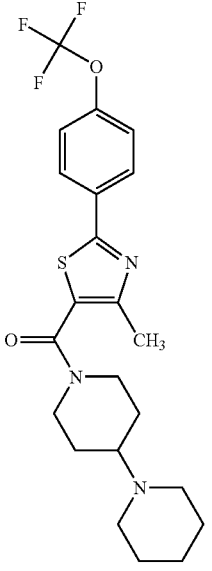 | 1'-({4-methyl-2-[4-(trifluoromethoxy)phenyl]-1,3-thiazol-5-yl}carbonyl)-1,4'-bipiperidine | 453.17 | 454.32 |
| 195 | 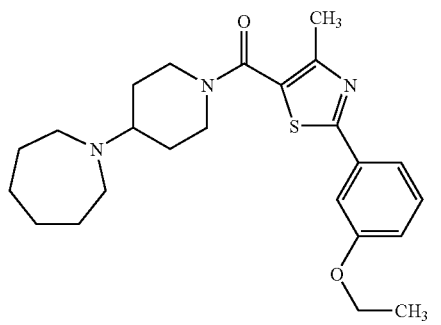 | 1-(1-{[2-(3-ethoxyphenyl)-4-methyl-1,3-thiazol-5-yl]carbonyl}piperidin-4-yl)azepane | 427.23 | 428.37 |

TABLE I-continued

| Compound | Name | MW | MS |
|---|---|---|---|
| 196 | 1'-{[2-(3-ethoxyphenyl)-4-methyl-1,3-thiazol-5-yl]carbonyl}-1,4'-bipiperidine | 413.21 | 414.36 |
| 197 | 1-(1-{[4-methyl-2-(4-phenoxyphenyl)-1,3-thiazol-5-yl]carbonyl}piperidin-4-yl)azepane | 475.23 | 476.36 |
| 198 | 1-{[4-methyl-2-(4-phenoxyphenyl)-1,3-thiazol-5-yl]carbonyl}-4-pyrrolidin-1-ylpiperidine | 447.20 | 448.32 |

TABLE I-continued

| Compound | | Name | MW | MS |
|---|---|---|---|---|
| 199 | | 1'-{[4-methyl-2-(4-phenoxyphenyl)-1,3-thiazol-5-yl]carbonyl}-1,4'-bipiperidine | 461.21 | 462.36 |
| 200 | | 1-{1-({4-methyl-2-[3-(trifluoromethoxy)phenyl]-1,3-thiazol-5-yl}carbonyl)piperidin-4-yl]azepane | 467.19 | 468.38 |

TABLE I-continued

| | Compound | Name | MW | MS |
|---|---|---|---|---|
| 201 | | 1'-({4-methyl-2-[3-(trifluoromethoxy)phenyl]-1,3-thiazol-5-yl}carbonyl)-1,4'-bipiperidine | 453.17 | 454.31 |
| 202 | | 1-[1-({4-methyl-2-[3-(methylthio)phenyl]-1,3-thiazol-5-yl}carbonyl)piperidin-4-yl]azepane | 429.19 | 430.35 |
| 203 | | [1,4']Bipiperidinyl-1'-yl-[4-methyl-2-(3-methylsulfanyl-phenyl)-thiazol-5-yl]-methanone | 415.18 | 416.33 |
| 204 | | 1-(1-{[2-(4'-methoxybiphenyl-4-yl)-4-methyl-1,3-thiazol-5-yl]carbonyl}piperidin-4-yl)azepane | 428.25 | 490.39 |

TABLE I-continued
| Compound | | Name | MW | MS |
|---|---|---|---|---|
| 205 | 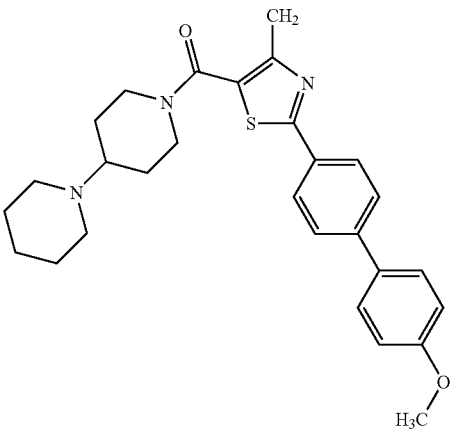 | 1'-{[2-(4'-methoxybiphenyl)-4-yl)-4-methyl-1,3-thiazol-5-yl]carbonyl}-1,4'-bipiperidine | 475.23 | 476.43 |
| 206 | 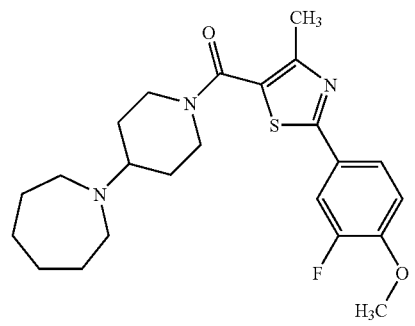 | 1-(1-{[2-(3-fluoro-4-methoxyphenyl)-4-methyl-1,3-thiazol-5-yl]carbonyl}piperidin-4-yl)azepane | 431.20 | 432.33 |
| 207 | 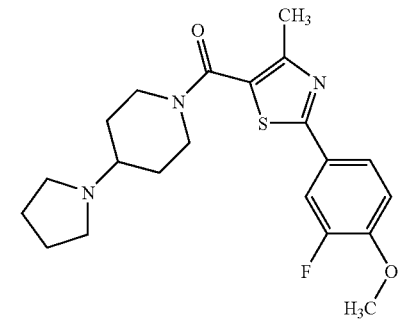 | 1-{[2-(3-fluoro-4-methoxyphenyl)-4-methyl-1,3-thiazol-5-yl]carbonyl}-4-pyrrolidin-1-ylpiperidine | 403.17 | 404.31 |
| 208 | 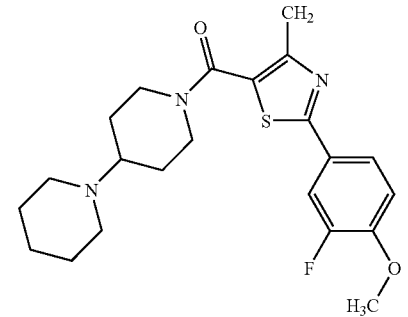 | 1'-{[2-(3-fluoro-4-methoxyphenyl)-4-methyl-1,3-thiazol-5-yl]carbonyl}-1,4'-bipiperidine | 417.19 | 418.33 |

TABLE I-continued

| Compound | Name | MW | MS |
|---|---|---|---|
| 209 | 1-(1-{[2-(2,5-difluoro-4-methoxyphenyl)-4-methyl-1,3-thiazol-5-yl]carbonyl}piperidin-4-yl)azepane | 449.19 | 450.36 |
| 210 | 1'-{[2-(2,5-difluoro-4-methoxyphenyl)-4-methyl-1,3-thiazol-5-yl]carbonyl}-1,4'-bipiperidine | 435.18 | 436.32 |
| 211 | 1-(1-{[2-(6-methoxy-2-naphthyl)-4-methyl-1,3-thiazol-5-yl]carbonyl}piperidin-4-yl)azepane | 463.23 | 464.37 |
| 212 | 1'-{[2-(6-methoxy-2-naphthyl)-4-methyl-1,3-thiazol-5-yl]carbonyl}-1,4'-bipiperidine | 449.21 | 450.35 |

TABLE I-continued

| Compound | | Name | MW | MS |
|---|---|---|---|---|
| 213 | | 1-(1-{[2-(3-isopropoxyphenyl)-4-methyl-1,3-thiazol-5-yl]carbonyl}piperidin-4-yl)azepane | | |
| 214 | | 1'-{[2-(3-isopropoxyphenyl)-4-methyl-1,3-thiazol-5-yl]carbonyl}-1,4'-bipiperidine | 427.23 | 428.42 |
| 215 | | N-[2-(diethylamino)ethyl]-2-(3-methoxyphenyl)-N,4-dimethyl-1,3-thiazole-5-carboxamide | 361.18 | 362.31 |
| 216 | | N-[2-(diethylamino)ethyl]-N,4-dimethyl-2-[4-(trifluoromethoxy)phenyl]-1,3-thiazole-5-carboxamide | 415.15 | 416.29 |

TABLE I-continued

| | Compound | Name | MW | MS |
|---|---|---|---|---|
| 217 | | N-[2-(diethylamino)ethyl]-2-(3-ethoxyphenyl)-N,4-dimethyl-1,3-thiazole-5-carboxamide | 375.20 | 376.32 |
| 218 | | N-[2-(diethylamino)ethyl]-N,4-dimethyl-2-(4-phenoxyphenyl)-1,3-thiazole-5-carboxamide | 423.20 | 424.33 |
| 219 | | N-[2-(diethylamino)ethyl]-N,4-dimethyl-2-[3-(trifluoromethoxy)phenyl]-1,3-thiazole-5-carboxamide | 415.15 | 416.29 |
| 220 | | N-[2-(diethylamino)ethyl]-N,4-dimethyl-2-[3-(methylthio)phenyl]-1,3-thiazole-5-carboxamide | 377.16 | 378.28 |

TABLE I-continued
| Compound | Name | MW | MS |
|---|---|---|---|
| 221 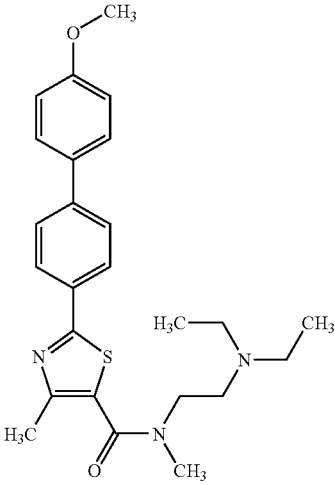 | N-[2-(diethylamino)ethyl]-2-(4'-methoxybiphenyl-4-yl)-N,4-dimethyl-1,3-thiazole-5-carboxamide | 437.21 | 438.35 |
| 222 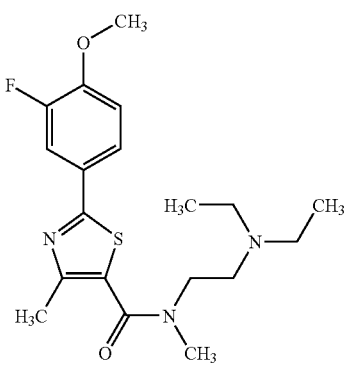 | N-[2-(diethylamino)ethyl]-2-(3-fluoro-4-methoxyphenyl)-N,4-dimethyl-1,3-thiazole-5-carboxamide | 379.17 | 380.30 |
| 223 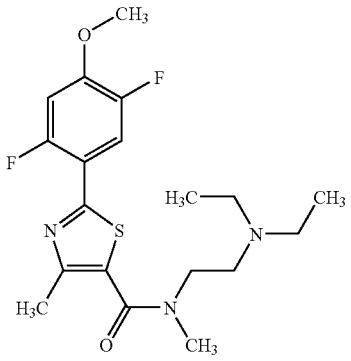 | N-[2-(diethylamino)ethyl]-2-(2,5-difluoro-4-methoxyphenyl)-N,4-dimethyl-1,3-thiazole-5-carboxamide | 397.16 | 398.28 |

TABLE I-continued

| | Compound | Name | MW | MS |
|---|---|---|---|---|
| 224 | | N-[2-(diethylamino)ethyl]-2-(6-methoxy-2-naphthyl)-N,4-dimethyl-1,3-thiazole-5-carboxamide | 411.20 | 412.31 |
| 225 | | N-[2-(diethylamino)ethyl]-2-(3-isopropoxyphenyl)-N,4-dimethyl-1,3-thiazole-5-carboxamide | 389.21 | 390.32 |
| 226 | | 1-isopropyl-4-{[4-methyl-2-(3-methylphenyl)-1,3-thiazol-5-yl]carbonyl}piperazine | 343.17 | 344.31 |
| 227 | | 1-cyclopentyl-4-{[4-methyl-2-(3-methylphenyl)-1,3-thiazol-5-yl]carbonyl}piperazine | 369.19 | 370.33 |

TABLE I-continued

| | Compound | Name | MW | MS |
|---|---|---|---|---|
| 228 | | 1-butyl-4-{[4-methyl-2-(3-methylphenyl)-1,3-thiazol-5-yl]carbonyl}-1,4-diazepane | 371.20 | 372.35 |
| 229 | | 1-isopropyl-4-{[4-methyl-2-(4-methylphenyl)-1,3-thiazol-5-yl]carbonyl}piperazine | 343.17 | 344.31 |
| 230 | | 1-cyclopentyl-4-{[4-methyl-2-(4-methylphenyl)-1,3-thiazol-5-yl]carbonyl}piperazine | 369.19 | 370.33 |
| 231 | | 1-isopropyl-4-{[2-(3-isopropylphenyl)-4-methyl-1,3-thiazol-5-yl]carbonyl}piperazine | 371.20 | 372.35 |

TABLE I-continued

| | Compound | Name | MW | MS |
|---|---|---|---|---|
| 232 | | 1-cyclopentyl-4-{[2-(3-isopropylphenyl)-4-methyl-1,3-thiazol-5-yl]carbonyl}piperazine | 397.22 | 398.37 |
| 233 | | 1-butyl-4-{[2-(3-isopropylphenyl)-4-methyl-1,3-thiazol-5-yl]carbonyl}-1,4-diazepane | 399.23 | 400.39 |
| 234 | | 1-isopropyl-4-{[2-(4-isopropylphenyl)-4-methyl-1,3-thiazol-5-yl]carbonyl}piperazine | 371.20 | 372.35 |
| 235 | | 1-cyclopentyl-4-{[2-(4-isopropylphenyl)-4-methyl-1,3-thiazol-5-yl]carbonyl}piperazine | 397.22 | 398.38 |

TABLE I-continued
| | Compound | Name | MW | MS |
|---|---|---|---|---|
| 236 | 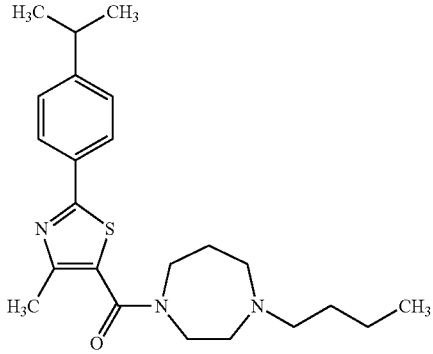 | 1-butyl-4-{[2-(4-isopropylphenyl)-4-methyl-1,3-thiazol-5-yl]carbonyl}-1,4-diazepane | 399.23 | 400.40 |
| 237 | 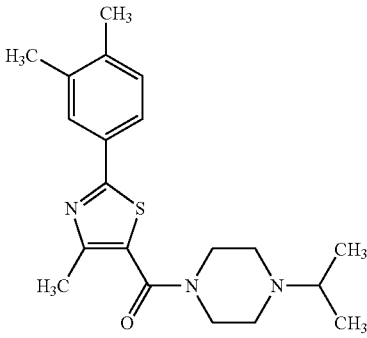 | 1-{[2-(3,4-dimethylphenyl)-4-methyl-1,3-thiazol-5-yl]carbonyl}-4-isopropylpiperazine | 357.19 | 358.33 |
| 238 | 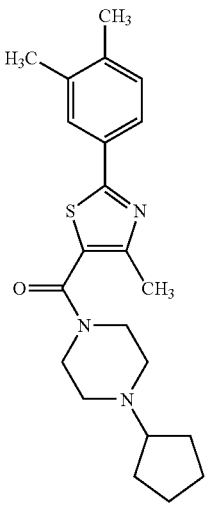 | 1-cyclopentyl-4-{[2-(3,4-dimethylphenyl)-4-methyl-1,3-thiazol-5-yl]carbonyl}piperazine | 383.20 | 384.36 |
| 239 | 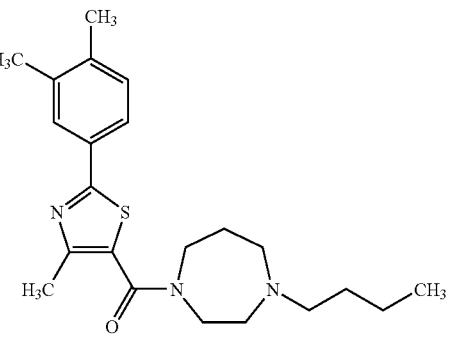 | 1-butyl-4-{[2-(3,4-dimethylphenyl)-4-methyl-1,3-thiazol-5-yl]carbonyl}-1,4-diazepane | 385.22 | 386.38 |

TABLE I-continued
| | Compound | Name | MW | MS |
|---|---|---|---|---|
| 240 | 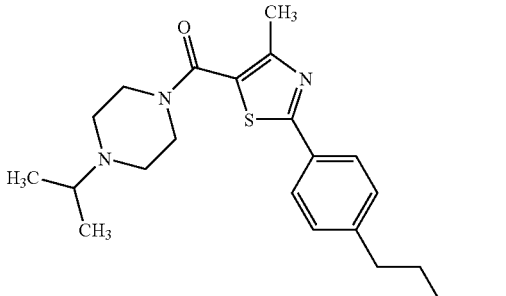 | 1-{[2-(4-butylphenyl)-4-methyl-1,3-thiazol-5-yl]carbonyl}-4-isopropylpiperazine | 385.22 | 386.37 |
| 241 | 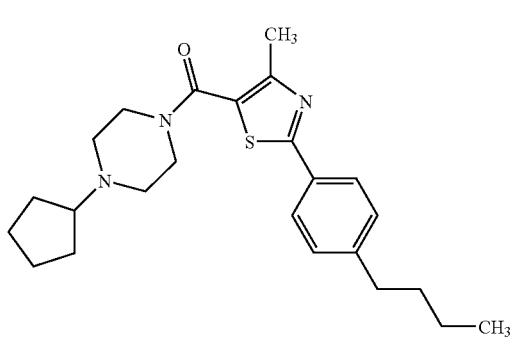 | 1-{[2-(4-butylphenyl)-4-methyl-1,3-thiazol-5-yl]carbonyl}-4-cyclopentylpiperazine | 411.23 | 412.40 |
| 242 | 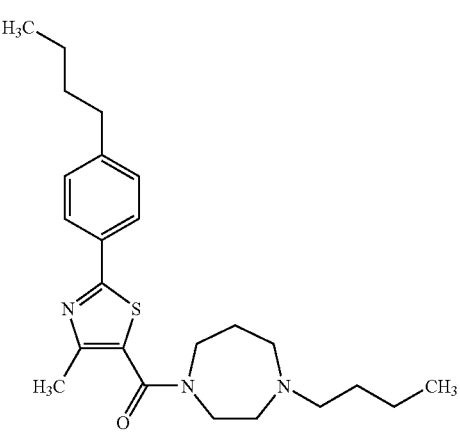 | 1-butyl-4-{[2-(4-butylphenyl)-4-methyl-1,3-thiazol-5-yl]carbonyl}-1,4-diazepane | 413.25 | 414.42 |
| 243 | 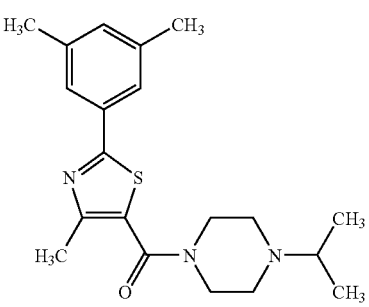 | 1-{[2-(3,5-dimethylphenyl)-4-methyl-1,3-thiazol-5-yl]carbonyl}-4-isopropylpiperazine | 357.19 | 358.34 |

TABLE I-continued

| | Compound | Name | MW | MS |
|---|---|---|---|---|
| 244 | | 1-cyclopentyl-4-{[2-(3,5-dimethylphenyl)-4-methyl-1,3-thiazol-5-yl]carbonyl}piperazine | 383.20 | 384.38 |
| 245 | | 1-butyl-4-{[2-(3,5-dimethylphenyl)-4-methyl-1,3-thiazol-5-yl]carbonyl}-1,4-diazepane | 385.22 | 386.38 |
| 246 | | 1-{[2-(4-ethylphenyl)-4-methyl-1,3-thiazol-5-yl]carbonyl}-4-isopropylpiperazine | 357.19 | 358.35 |
| 247 | | 1-cyclopentyl-4-{[2-(4-ethylphenyl)-4-methyl-1,3-thiazol-5-yl]carbonyl}piperazine | 383.20 | 384.37 |

TABLE I-continued

| | Compound | Name | MW | MS |
|---|---|---|---|---|
| 248 | | 1-isopropyl-4-{[4-methyl-2-(4-propylphenyl)-1,3-thiazol-5-yl]carbonyl}piperazine | 371.20 | 372.37 |
| 249 | | 1-cyclopentyl-4-{[4-methyl-2-(4-propylphenyl)-1,3-thiazol-5-yl]carbonyl}piperazine | 397.22 | 398.38 |
| 250 | | 1-{[2-(3-ethylphenyl)-4-methyl-1,3-thiazol-5-yl]carbonyl}-4-isopropylpiperazine | 357.19 | 358.35 |
| 251 | | 1-cyclopentyl-4-{[2-(3-ethylphenyl)-4-methyl-1,3-thiazol-5-yl]carbonyl}piperazine | 383.20 | 384.37 |
| 252 | | 1-butyl-4-{[2-(3-ethylphenyl)-4-methyl-1,3-thiazol-5-yl]carbonyl}-1,4-diazepane | 385.22 | 386.39 |

| | Compound | Name | MW | MS |
|---|---|---|---|---|
| 253 | 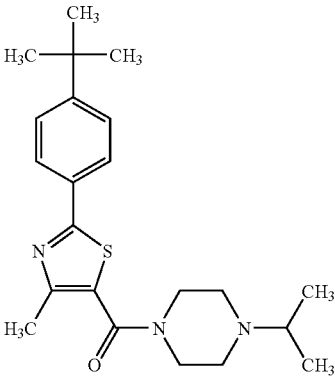 | 1-{[2-(4-tert-butylphenyl)-4-methyl 1,3-thiazol-5-yl]carbonyl}-4-isopropylpiperazine | 385.22 | 386.40 |
| 254 | 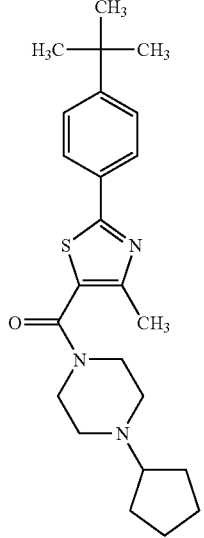 | 1-{[2-(4-tert-butylphenyl)-4-methyl 1,3-thiazol-5-yl]carbonyl}-4-cyclopentylpiperazine | 411.23 | 412.42 |
| 255 | 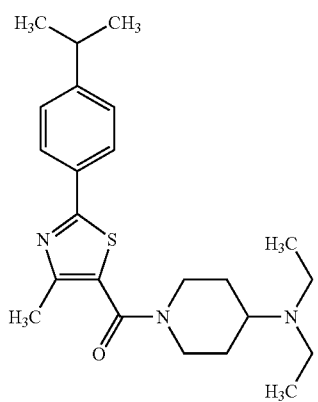 | N,N-diethyl-2-{[2-(4-isopropylphenyl)-4-methyl-1,3-thiazol-5-yl]carbonyl}piperidin-4-amine | 399.23 | 400.34 |

TABLE I-continued

| Compound | | Name | MW | MS |
|---|---|---|---|---|
| 256 | | 1-{[2-(3,4-dimethylphenyl)-4-methyl-1,3-thiazol-5-yl]carbonyl}-N,N-diethylpiperidin-4-amine | 385.22 | 386.07 |
| 257 | | 1-{[2-(3,4-dimethylphenyl)-4-methyl-1,3-thiazol-5-yl]carbonyl}-N,N-diethylpyrrolidin-3-amine | 371.20 | 372.09 |
| 258 | | 1-(1-{[4-methyl-2-(3-methylphenyl)-1,3-thiazol-5-yl]carbonyl}piperidin-4-yl)azepane | 397.22 | 398.34 |
| 259 | | 1'-{[4-methyl-2-(3-methylphenyl)-1,3-thiazol-5-yl]carbonyl}-1,4'-bipiperidine | 383.20 | 384.33 |

TABLE I-continued
| Compound | | Name | MW | MS |
|---|---|---|---|---|
| 260 | 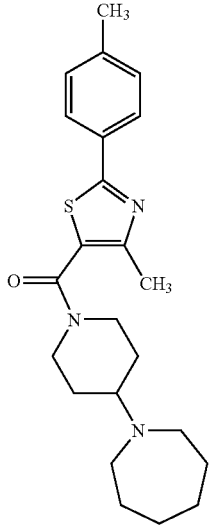 | 1-(1-{[4-methyl-2-(4-methylphenyl)-1,3-thiazol-5-yl]carbonyl}piperidin-4-yl)azepane | 397.22 | 398.35 |
| 261 | 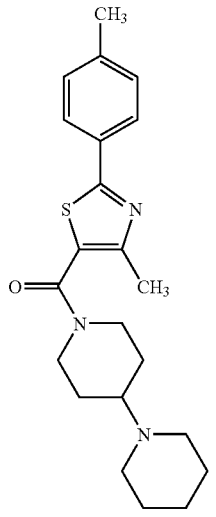 | 1'-{[4-methyl-2-(4-methylphenyl)-1,3-thiazol-5-yl]carbonyl}-1,4'-bipiperidine | 383.20 | 384.33 |
| 262 | 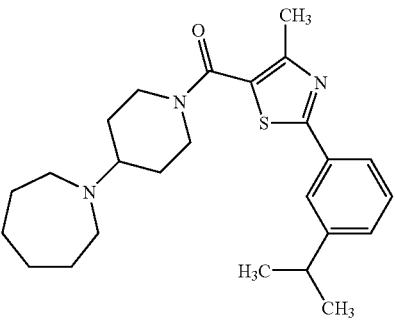 | 1-(1-{[2-(3-isopropylphenyl)-4-methyl-1,3-thiazol-5-yl]carbonyl}piperidin-4-yl)azepane | 425.25 | 426.38 |

TABLE I-continued

| | Compound | Name | MW | MS |
|---|---|---|---|---|
| 263 | | 1'-{[2-(3-isopropylphenyl)-4-methyl-1,3-thiazol-5-yl]carbonyl}-1,4'-bipiperidine | 411.23 | 412.37 |
| 264 | | 1-(1-{[2-(4-isopropylphenyl)-4-methyl-1,3-thiazol-5-yl]carbonyl}piperidin-4-yl)azepane | 425.25 | 426.38 |
| 265 | | 1'-{[2-(4-isopropylphenyl)-4-methyl-1,3-thiazol-5-yl]carbonyl}-1,4'-bipiperidine | 411.23 | 412.37 |
| 266 | | 1-(1-{[2-(3,4-dimethylphenyl)-4-methyl-1,3-thiazol-5-yl]carbonyl}piperidin-4-yl)azepane | 411.23 | 412.37 |

TABLE I-continued
| Compound | | Name | MW | MS |
|---|---|---|---|---|
| 267 | 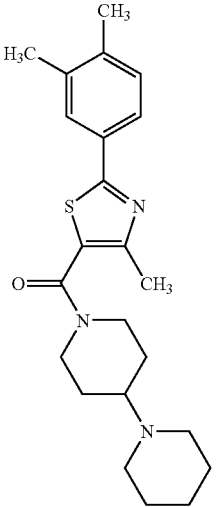 | 1'-{[2-(3,4-dimethylphenyl)-4-methyl-1,3-thiazol-5-yl]carbonyl}-1,4'-bipiperidine | 397.22 | 398.29 |
| 268 | 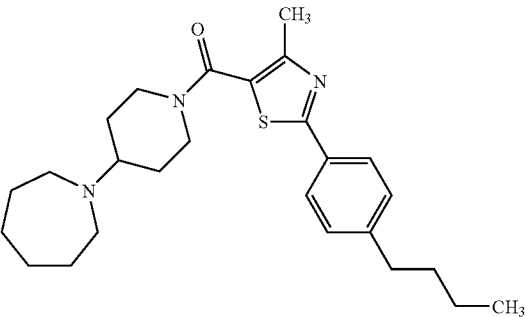 | 1-(1-{[2-(4-butylphenyl)-4-methyl-1,3-thiazol-5-yl]carbonyl}piperidin-4-yl)azepane | 439.27 | 440.41 |
| 269 | 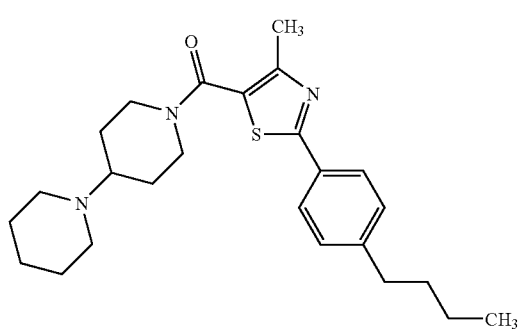 | 1'-{[2-(4-butylphenyl)-4-methyl-1,3-thiazol-5-yl]carbonyl}-1,4'-bipiperidine | 425.25 | 426.39 |

TABLE I-continued
| | Compound | Name | MW | MS |
|---|---|---|---|---|
| 270 | 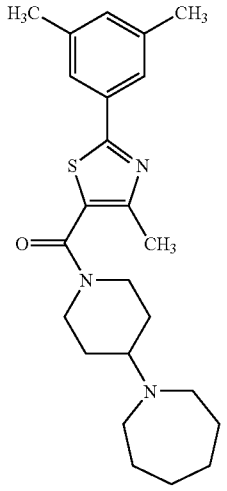 | 1-(1-{[2-(3,5-dimethylphenyl)-4-methyl-1,3-thiazol-5-yl]carbonyl}piperidin-4-yl)azepane | 411.23 | 412.37 |
| 271 | 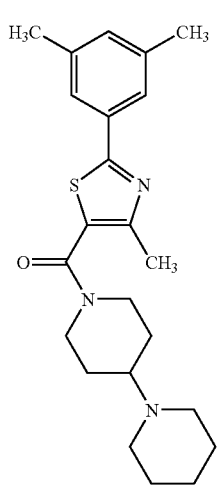 | 1'-{[2-(3,5-dimethylphenyl)-4-methyl-1,3-thiazol-5-yl]carbonyl}-1,4'-bipiperidine | 397.22 | 398.35 |
| 272 | 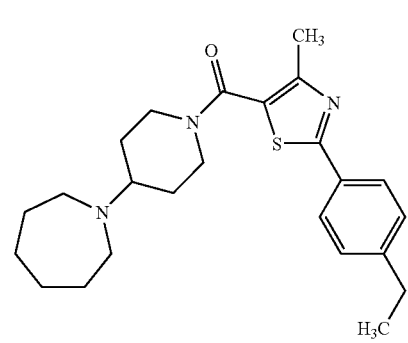 | 1-(1-{[2-(4-ethylphenyl)-4-methyl-1,3-thiazol-5-yl]carbonyl}piperidin-4-yl)azepane | 411.23 | 412.37 |

TABLE I-continued

| | Compound | Name | MW | MS |
|---|---|---|---|---|
| 273 | | 1'-{[2-(4-ethylphenyl)-4-methyl-1,3-thiazol-5-yl]carbonyl}-1,4'-bipiperidine | 397.22 | 398.35 |
| 274 | | 1-(1-{[4-methyl-2-(4-propylphenyl)-1,3-thiazol-5-yl]carbonyl}piperidin-4-yl)azepane | 425.25 | 426.39 |
| 275 | | 1-{[4-methyl-2-(4-propylphenyl)-1,3-thiazol-5-yl]carbonyl}-4-pyrrolidin-ylpiperidine | 397.22 | 398.35 |
| 276 | | 1'-{[4-methyl-2-(4-propylphenyl)-1,3-thiazol-5-yl]carbonyl}-1,4'-bipiperidine | 411.23 | 412.37 |

TABLE I-continued

| | Compound | Name | MW | MS |
|---|---|---|---|---|
| 277 | | 1-(1-{[2-(3-ethylphenyl)-4-methyl-1,3-thiazol-5-yl]carbonyl}piperidin-4-yl)azepane | 411.23 | 412.37 |
| 278 | | 1-{[2-(3-ethylphenyl)-4-methyl-1,3-thiazol-5-yl]carbonyl}-4-pyrrolidin-1-ylpiperidine | 383.20 | 384.33 |
| 279 | | 1'-{[2-(3-ethylphenyl)-4-methyl-1,3-thiazol-5-yl]carbonyl}-1,4'-bipiperidine | 397.22 | 398.35 |
| 280 | | 1-(1-{[2-(4-tert-butylphenyl)-4-methyl-1,3-thiazol-5-yl]carbonyl}piperidin-4-yl)azepane | 439.27 | 440.41 |

TABLE I-continued
| Compound | | Name | MW | MS |
|---|---|---|---|---|
| 281 | 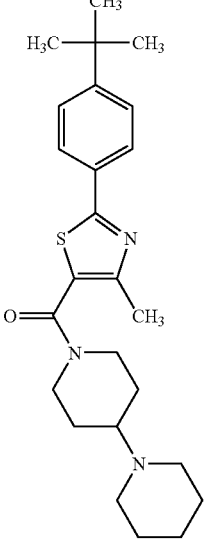 | 1'-{[2-(4-tert-butylphenyl)-4-methyl-1,3-thiazol-5-yl]carbonyl}-1,4'-bipiperidine | 425.25 | 426.39 |
| 282 | 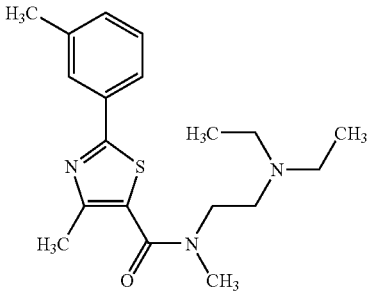 | N-[2-(diethylamino)ethyl]-N,4-dimethyl-2-(3-methylphenyl)-1,3-thiazole-5-carboxamide | 345.19 | 346.26 |
| 283 | 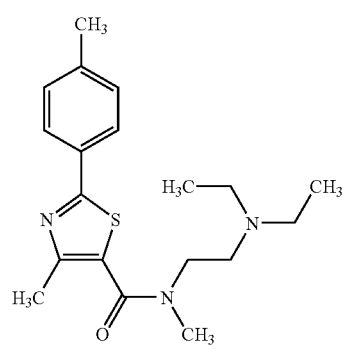 | N-[2-(diethylamino)ethyl]-N,4-dimethyl-1-(4-methylphenyl)-1,3-thiazole-5-carboxamide | 345.19 | 346.26 |
| 284 | 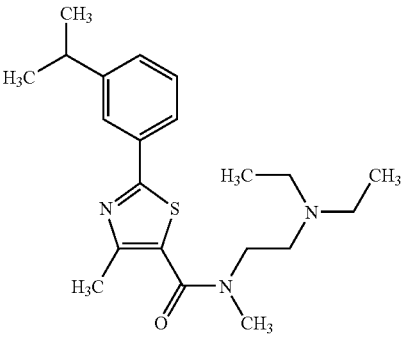 | N-[2-(diethylamino)ethyl]-2-(3-isopropylphenyl)-N,4-dimethyl-1,3-thiazole-5-carboxamide | 373.22 | 374.28 |

TABLE I-continued

| | Compound | Name | MW | MS |
|---|---|---|---|---|
| 285 | | N-[2-(diethylamino)ethyl]-2-(4-isopropylphenyl)-N,4-dimethyl-1,3-thiazole-5-carboxamide | 373.22 | 374.30 |
| 286 | | N-[2-(diethylamino)ethyl]-2-(3,4-dimethylphenyl)-N,4-dimethyl-1,3-thiazole-5-carboxamide | 359.20 | 360.27 |
| 287 | | 2-(4-(butylphenyl)-N-[2-(diethylamino)ethyl]-N,4-dimethyl-1,3-thiazole-5-carboxamide | 387.23 | 388.30 |
| 288 | | N-[2-(diethylamino)ethyl]-2-(3,5-dimethylphenyl)-N,4-dimethyl-1,3-thiazole-5-carboxamide | 359.20 | 360.27 |

TABLE I-continued

| | Compound | Name | MW | MS |
|---|---|---|---|---|
| 289 | | N-[2-(diethylamino)ethyl]-2-(4-ethylphenyl)-N,4-dimethyl-1,3-thiazole-5-carboxamide | 359.20 | 360.26 |
| 290 | | N-[2-(diethylamino)ethyl]-N,4-dimethyl-2-(4-propylphenyl)-1,3-thiazole-5-carboxamide | 373.22 | 374.28 |
| 291 | | N-[2-(diethylamino)ethyl]-2-(3-ethylphenyl)-N,4-dimethyl-1,3-thiazole-5-carboxamide | 359.20 | 360.26 |
| 292 | | 2-(4-tert-butylphenyl)-N-[2-(diethylamino)ethyl]-N,4-dimethyl-1,3-thiazole-5-carboxamide | 387.23 | 388.29 |

TABLE I-continued

| Compound | | Name | MW | MS |
|---|---|---|---|---|
| 293 | | 2-(4-isopropylphenyl)-4-methyl-N-(2-pyrrolidin-1-ylethyl)-1,3-thiazole-5-carboxamide | 357.19 | 358.21 |
| 294 | | 2-(4-isopropylphenyl)-4-methyl-N-[2-(1-methylpyrrolidin-2-yl)ethyl]-1,3-thiazole-5-carboxamide | 371.20 | 372.18 |
| 295 | | 2-(3,4-dimethylphenyl)-4-methyl-N-[2-(1-methylpyrrolidin-2-yl)ethyl]-1,3-thiazole-5-carboxamide | 357.19 | 358.17 |
| 296 | | 2-(4-butylphenyl)-4-methyl-N-[2-(1-methylpyrrolidin-2-yl)ethyl]-1,3-thiazole-5-carboxamide | 385.22 | 386.19 |

TABLE I-continued

| Compound | | Name | MW | MS |
|---|---|---|---|---|
| 297 | | 2-(4-ethylphenyl)-4-methyl-N-[2-(1 methylpyrrolidin-2-yl)ethyl]-1,3-thiazole-5-carboxamide | 357.19 | 358.17 |
| 298 | | 4-methyl-N-[2-(1-methylpyrrolidin-2-yl)ethyl]-2-(4-propylphenyl)-1,3-thiazole-5-carboxamide | 371.20 | 372.18 |
| 299 | | 2-(4-tert-butylphenyl)-4-methyl-N-[2-(1-methylpyrrolidin-2-yl)ethyl]-1,3-thiazole-5-carboxamide | 385.22 | 386.19 |
| 300 | | 2-(4-tert-butylphenyl)-4-methyl-N-(4-pyrrolidin-1-ylbutyl)-1,3-thiazole-5-carboxamide | 399.23 | 400.19 |

TABLE I-continued

| Compound | Name | MW | MS |
|---|---|---|---|
| 301 | 1-(1-{[2-(5-chloro-2-methoxyphenyl)-4-methyl-1,3-thiazol-5-yl]carbonyl}piperidin-4-yl)azepane | 447.17 | 448.30 |
| 302 | 1-(1-{[2-(2,5-dimethoxyphenyl)-4-methyl-1,3-thiazol-5-yl]carbonyl}piperidin-4-yl)azepane | 443.22 | 444.35 |
| 303 | 1'-{[2-(2,5-dimethoxyphenyl)-4-methyl-1,3-thiazol-5-yl]carbonyl}-1,4'-bipiperidine | 429.21 | 430.33 |
| 304 | 1-(1-{[2-(5-fluoro-2-methoxyphenyl)-4-methyl-1,3-thiazol-5-yl]carbonyl}piperidin-4-yl)azepane | 431.20 | 432.33 |
| 305 | 1'-{[2-(5-fluoro-2-methoxyphenyl)-4-methyl-1,3-thiazol-5-yl]carbonyl}-1,4'-bipiperidine | 417.19 | 418.31 |

TABLE I-continued

| Compound | Name | MW | MS |
|---|---|---|---|
| 306 | 1-(1-{[2-(2-methoxy-5-methylphenyl)-4-methyl-1,3-thiazol-5-yl]carbonyl}piperidin-4-yl)azepane | 427.23 | 428.35 |
| 307 | N-[2-(diethylamino)ethyl]-2-(5-isopropyl-2-methoxyphenyl)-N,4-dimethyl-1,3-thiazole-5-carboxamide | 403.23 | 404.33 |
| 308 | N-[2-(diethylamino)ethyl]-2-(2-ethoxyphenyl)-N,4-dimethyl-1,3-thiazole-5-carboxamide | 375.20 | 376.29 |
| 309 | 1-isopropyl-4-{[4-methyl-2-(3,4,5-trimethoxyphenyl)-1,3-thiazol-5-yl]carbonyl}piperazine | 419.19 | 420.17 |
| 310 | 1-cyclopentyl-4-{[4-methyl-2-(3,4,5-trimethoxyphenyl)-1,3-thiazol-5-yl]carbonyl}piperazine | 445.20 | 446.19 |

TABLE I-continued

| | Compound | Name | MW | MS |
|---|---|---|---|---|
| 311 | | 1-butyl-4-{[4-methyl-2-(3,4,5-trimethoxyphenyl)-1,3-thiazol-5-yl]carbonyl}-1,4-diazepane | 447.22 | 448.19 |
| 312 | | 1-isopropyl-4-{[2-(4-methoxyphenyl)-4-methyl-1,3-thiazol-5-yl]carbonyl}piperazine | 359.17 | 360.19 |
| 313 | | 1-cyclopentyl-4-{[2-(4-methoxyphenyl)-4-methyl-1,3-thiazol-5-yl]carbonyl}piperazine | 385.18 | 386.18 |
| 314 | | 1-{[2-(1,3-benzodioxol-5-yl)-4-methyl-1,3-thiazol-5-yl]carbonyl}-4-isopropylpiperazine | 373.15 | 374.14 |

TABLE I-continued

| Compound | | Name | MW | MS |
|---|---|---|---|---|
| 315 | [structure] | 1-{[2-(1,3-benzodioxol-5-yl)-4-methyl-1,3-thiazol-5-yl]carbonyl}-4-cyclopentylpiperazine | 399.16 | 400.15 |
| 316 | [structure] | 1-{[2-(3,4-dimethoxyphenyl)-4-methyl-1,3-thiazol-5-yl]carbonyl}-4-isopropylpiperazine | 398.18 | 390.19 |
| 317 | [structure] | 1-cyclopentyl-4-{[2-(3,4-dimethoxyphenyl)-4-methyl-1,3-thiazol-5-yl]carbonyl}piperazine | 415.19 | 416.20 |
| 318 | [structure] | 1-{[2-(4-ethoxyphenyl)-4-methyl-1,3-thiazol-5-yl]carbonyl}-4-isopropylpiperazine | 373.18 | 374.18 |

TABLE I-continued

| | Compound | Name | MW | MS |
|---|---|---|---|---|
| 319 | | 4-{5-[(4-isopropylpiperazin-1-yl)carbonyl]-4-methyl-1,3-thiazol-2-yl}-N,N-dimethylaniline | 372.20 | 373.20 |
| 320 | | 4-{5-[(4-cyclopentylpiperazin-1-yl)carbonyl]-4-methyl-1,3-thiazol-2-yl}-N,N-dimethylaniline | 398.21 | 399.24 |
| 321 | | 1-{[2-(2,3-dihydro-1,4-benzodioxin-6-yl)-4-methyl-1,3-thiazol-5-yl]carbonyl}-4-isopropylpiperazine | 387.16 | 388.15 |
| 322 | | 1-cyclopentyl-4-{[2-(2,3-dihydro-1,4-benzodioxin-6-yl)-4-methyl-1,3-thiazol-5-yl]carbonyl}piperazine | 413.18 | 414.20 |

TABLE I-continued

| | Compound | Name | MW | MS |
|---|---|---|---|---|
| 323 | | 3-{5-[(4-butyl-1,4-diazepan-1-yl)carbonyl]-4-methyl-1,3-thiazol-2-yl}-N,N-dimethylaniline | 400.23 | 401.24 |
| 324 | | 1-isopropyl-4-{[2-(4-methoxy-3-methylphenyl)-4-methyl-1,3-thiazol-5-yl]carbonyl}piperazine | 373.18 | 374.20 |
| 325 | | 1-cyclopentyl-4-{[2-(4-methoxy-3-methylphenyl)-4-methyl-1,3-thiazol-5-yl]carbonyl}piperazine | 399.20 | 400.22 |
| 326 | | 1-butyl-4-{[2-(4-methoxy-3-methylphenyl)-4-methyl-1,3-thiazol-5-yl]carbonyl}-1,4-diazepane | 401.21 | 402.19 |

TABLE I-continued

| Compound | Name | MW | MS |
|---|---|---|---|
| 327 | 1-isopropyl-4-{[4-methyl-2-(4-propoxyphenyl)-1,3-thiazol-5-yl]carbonyl}piperazine | 387.20 | 388.18 |
| 328 | 1-cyclopentyl-4-{[4-methyl-2-(4-propoxyphenyl)-1,3-thiazol-5-yl]carbonyl}piperazine | 413.21 | 414.20 |
| 329 | 1-isopropyl-4-{[2-(4-methoxy-2-methylphenyl)-4-methyl-1,3-thiazol-5-yl]carbonyl}piperazine | 373.18 | 374.22 |
| 330 | 1-cyclopentyl-4-{[2-(4-methoxy-2-methylphenyl)-4-methyl-1,3-thiazol-5-yl]carbonyl}piperazine | 399.20 | 400.23 |
| 331 | 1-(1-{[4-methyl-2-(3,4,5-trimethoxyphenyl)-1,3-thiazol-5-yl]carbonyl}piperidin-4-yl)azepane | 473.23 | 474.28 |

TABLE I-continued
| Compound | | Name | MW | MS |
|---|---|---|---|---|
| 332 | 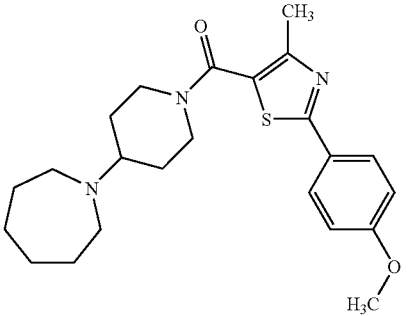 | 1-(1-{[2-(4-methoxyphenyl)-4-methyl-1,3-thiazol-5-yl]carbonyl}piperidin-4-yl)azepane | 413.21 | 414.26 |
| 333 | 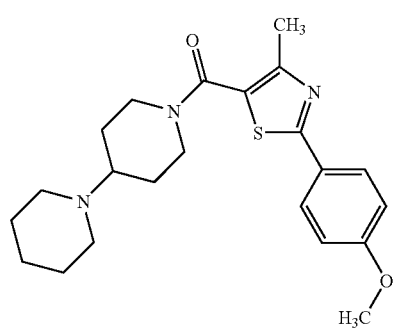 | 1'-{[2-(4-methoxyphenyl)-4-methyl-1,3-thiazol-5-yl]carbonyl}-1,4'-bipiperidine | 399.20 | 400.25 |
| 334 | 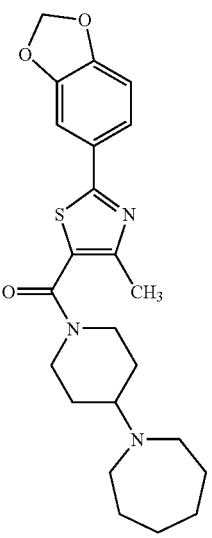 | 1-(1-{[2-(1,3-benzodioxol-5-yl)-4-methyl-1,3-thiazol-5-yl]carbonyl}piperidin-4-yl)azepane | 427.19 | 428.24 |

TABLE I-continued

| Compound | | Name | MW | MS |
|---|---|---|---|---|
| 335 | | 1'-{[2-(1,3-benzodioxol-5-yl)-4-methyl-1,3-thiazol-5-yl]carbonyl}-1,4'-bipiperidine | 413.18 | 414.22 |
| 336 | | 1-(1-{[2-(3,4-dimethoxyphenyl)-4-methyl-1,3-thiazol-5-yl]carbonyl}piperidin-4-yl)azepane | 443.22 | 444.27 |
| 337 | | 1'-{[2-(3,4-dimethoxyphenyl)-4-methyl-1,3-thiazol-5-yl]carbonyl}-1,4'-bipiperidine | 429.21 | 430.27 |
| 338 | | 1-(1-{[2-(4-ethoxyphenyl)-4-methyl-1,3-thiazol-5-yl]carbonyl}piperidin-4-yl)azepane | 427.23 | 428.28 |

TABLE I-continued

| | Compound | Name | MW | MS |
|---|---|---|---|---|
| 339 | | 1'-{[2-(4-ethoxyphenyl)-4-methyl-1,3-thiazol-5-yl]carbonyl}-1,4'-bipiperidine | 413.21 | 414.26 |
| 340 | | 4-{5-[(4-azepan-1-ylpiperidin-1-yl)carbonyl]-4-methyl-1,3-thiazol-2-yl}-N,N-dimethylaniline | 426.25 | 427.33 |
| 341 | | 4-[5-(1,4'-bipiperidin-1'-ylcarbonyl)-4-methyl-1,3-thiazol-2-yl]-N,N-dimethylaniline | 412.23 | 207.19 |
| 342 | | 1-(1-{[2-(2,3-dihydro-1,4-benzodioxin-6-yl)-4-methyl-1,3-thiazol-5-yl]carbonyl}piperidin-4-yl)azepane | 441.21 | 442.26 |

TABLE I-continued

| Compound | Name | MW | MS |
|---|---|---|---|
| 343 | 1'-{[2-(2,3-dihydro-1,4-benzodioxin-6-yl)-4-methyl-1,3-thiazol-5-yl]carbonyl}-1,4'-bipiperidine | 427.19 | 428.24 |
| 344 | 1-(1-{[2-(4-methoxy-3-methylphenyl)-4-methyl-1,3-thiazol-5-yl]carbonyl}piperidin-4-yl)azepane | 427.23 | 428.26 |
| 345 | 1'-{[2-(4-methoxy-3-methylphenyl)-4-methyl-1,3-thiazol-5-yl]carbonyl}-1,4'-bipiperidine | 413.21 | 414.24 |
| 346 | 1'-{[4-methyl-2-(4-propoxyphenyl)-1,3-thiazol-5-yl]carbonyl}-1,4'-bipiperidine | 427.23 | 428.26 |

TABLE I-continued
| Compound | | Name | MW | MS |
|---|---|---|---|---|
| 347 | 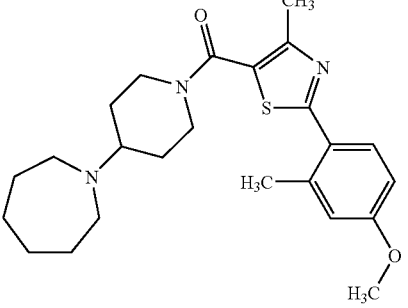 | 1-(1-{[2-(4-methoxy-2-methylphenyl)-4-methyl-1,3-thiazol-5-yl]carbonyl}piperidin-4-yl)azepane | | |
| 348 | 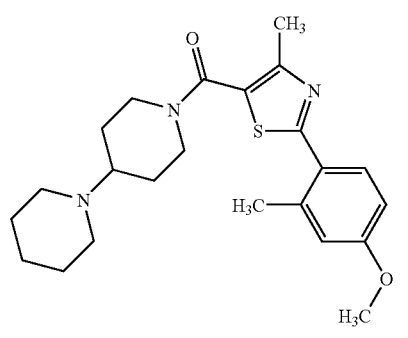 | 1'-{[2-(4-methoxy-2-methylphenyl)-4-methyl-1,3-thiazol-5-yl]carbonyl}-1,4'-bipiperidine | | |
| 349 | 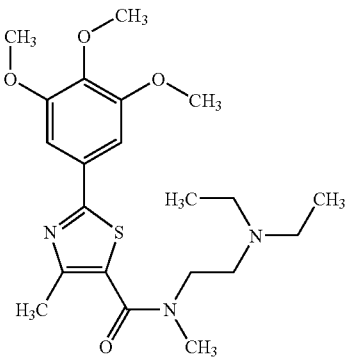 | N-[2-(diethylamino)ethyl]-N,4-dimethyl-2-(3,4,5-trimethoxyphenyl)-1,3-thiazole-5-carboxamide | 421.20 | 422.35 |
| 350 | 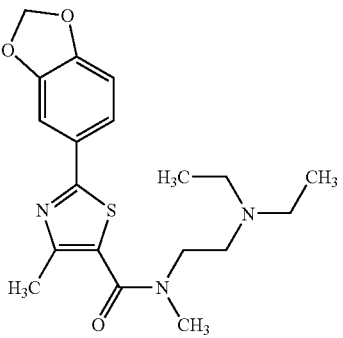 | 2-(1,3-benzodioxol-5-yl)-N-[2-(diethylamino)ethyl]-N,4-dimethyl-1,3-thiazole-5-carboxamide | 375.16 | 376.29 |

TABLE I-continued
| | Compound | Name | MW | MS |
|---|---|---|---|---|
| 351 | 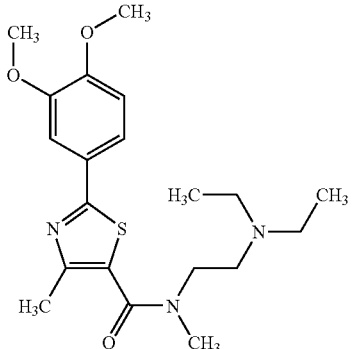 | N-[2-(diethylamino)ethyl]-2-(3,4-dimethoxyphenyl)-N,4-dimethyl-1,3-thiazole-5-carboxamide | 391.19 | 392.33 |
| 352 | 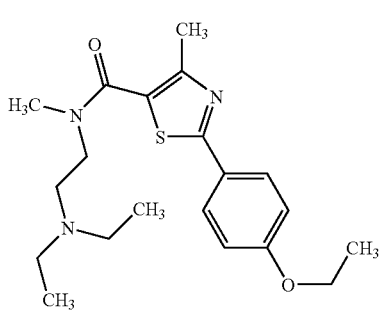 | N-[2-(diethylamino)ethyl]-2-(4-ethoxyphenyl)-N,4-dimethyl-1,3-thiazole-5-carboxamide | 375.20 | 376.33 |
| 353 | 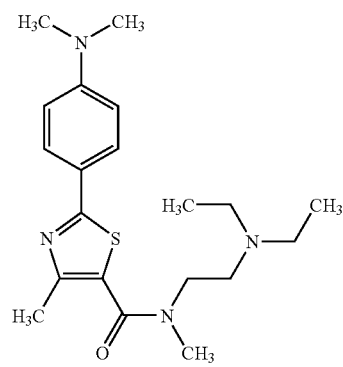 | N-[2-(diethylamino)ethyl]-2-[4-(dimethylamino)phenyl]-N,4-dimethyl-1,3-thiazole-5-carboxamide | 374.21 | 375.35 |
| 354 | 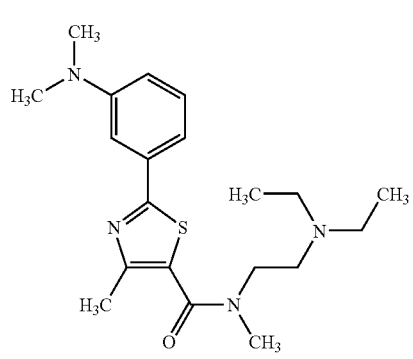 | N-[2-(diethylamino)ethyl]-2-[3-(dimethylamino)phenyl]-N,4-dimethyl-1,3-thiazole-5-carboxamide | 374.21 | 375.35 |

| Compound | Name | MW | MS |
|---|---|---|---|
| 355 | N-[2-(diethylamino)ethyl]-2-(4-methoxy-3-methylphenyl)-N,4-dimethyl-1,3-thiazole-5-carboxamide | 375.20 | 376.33 |
| 356 | N-[2-(diethylamino)ethyl]-N,4-dimethyl-2-(4-propoxyphenyl)-1,3-thiazole-5-carboxamide | 389.21 | 390.35 |
| 357 | N-[2-(diethylamino)ethyl]-2-(4-methoxy-2-methylphenyl)-N,4-dimethyl-1,3-thiazole-5-carboxamide | 375.20 | 376.34 |
| 358 | 2-(3-chloro-4-fluorophenyl)-4-methyl-N-(2-pyrrolidin-1-ylethyl)-1,3-thiazole-5-carboxamide | 367.09 | 368.23 |

TABLE I-continued
| Compound | | Name | MW | MS |
|---|---|---|---|---|
| 359 | 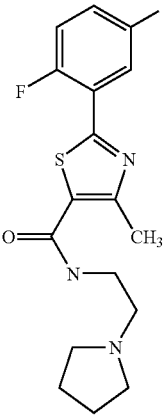 | 2-(2,5-difluorophenyl)-4-methyl-N-(2-pyrrolidin-1-ylethyl)-1,3-thiazole-5-carboxamide | 351.12 | 352.25 |
| 360 | 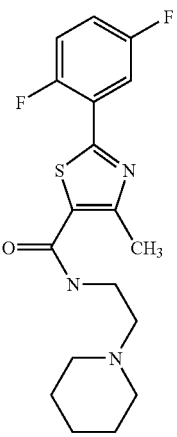 | 2-(2,5-difluorophenyl)-4-methyl-N-(2-piperidin-1-ylethyl)-1,3-thiazole-5-carboxamide | 365.14 | 366.27 |
| 361 | 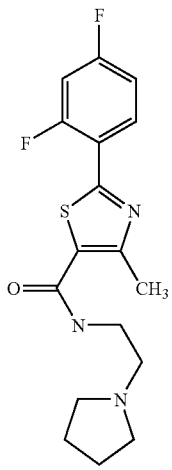 | 2-(2,4-difluorophenyl)-4-methyl-N-(2-pyrrolidin-1-ylethyl)-1,3-thiazole-5-carboxamide | 351.12 | 352.25 |

TABLE I-continued
| Compound | | Name | MW | MS |
|---|---|---|---|---|
| 362 | 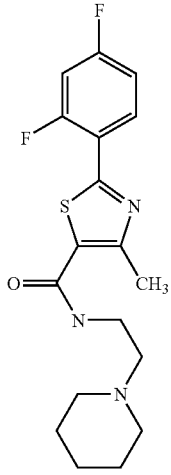 | 2-(2,4-difluorophenyl)-4-methyl-N-(2-piperidin-1-ylethyl)-1,3-thiazole-5-carboxamide | 365.14 | 366.27 |
| 363 | 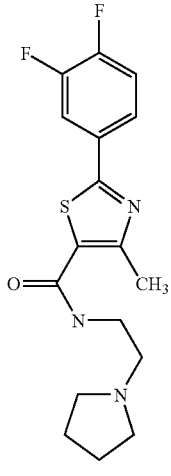 | 2-(3,4-difluorophenyl)-4-methyl-N-(2-pyrrolidin-1-ylethyl)-1,3-thiazole-5-carboxamide | 351.12 | 352.26 |
| 364 | 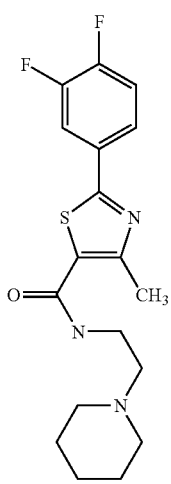 | 2-(3,4-difluorophenyl)-4-methyl-N-(2-piperidin-1-ylethyl)-1,3-thiazole-5-carboxamide | 365.14 | 366.27 |

| | Compound | Name | MW | MS |
|---|---|---|---|---|
| 365 | 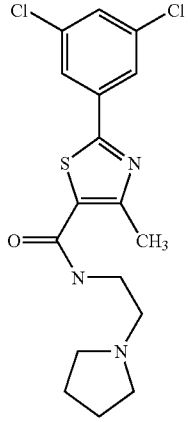 | 2-(3,5-dichlorophenyl)-4-methyl-N-(2-pyrrolidin-1-ylethyl)-1,3-thiazole-5-carboxamide | 383.06 | 384.22 |
| 366 | 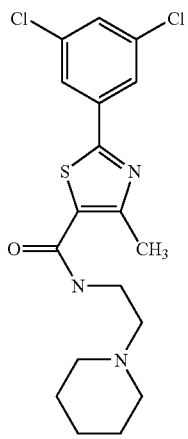 | 2-(3,5-dichlorophenyl)-4-methyl-N-(2-piperidin-1-ylethyl)-1,3-thiazole-5-carboxamide | 397.08 | 398.23 |
| 367 | 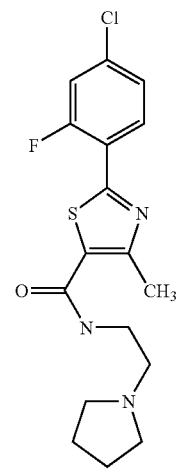 | 2-(4-chloro-2-fluorophenyl)-4-methyl-N-(2-pyrrolidin-1-ylethyl)-1,3-thiazole-5-carboxamide | 367.09 | 368.23 |

TABLE I-continued
| Compound | | Name | MW | MS |
|---|---|---|---|---|
| 368 | 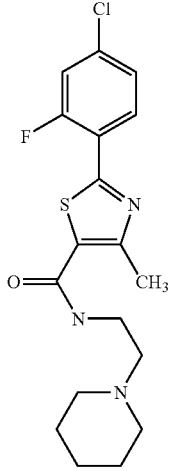 | 2-(4-chloro-2-fluorophenyl)-4-methyl-N-(2-piperidin-1-ylethyl)-1,3-thiazole-5-carboxamide | 381.11 | 382.25 |
| 369 | 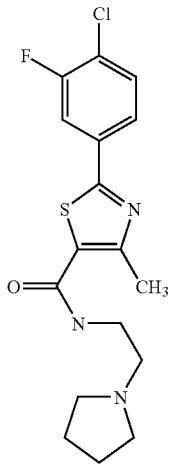 | 2-(4-chloro-3-fluorophenyl)-4-methyl-N-(2-pyrrolidin-1-ylethyl)-1,3-thiazole-5-carboxamide | 367.09 | 368.23 |
| 370 | 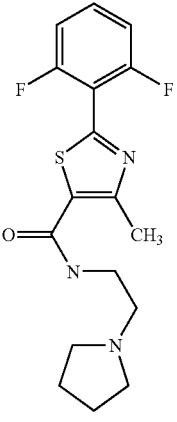 | 2-(2,6-difluorophenyl)-4-methyl-N-(2-pyrrolidin-1-ylethyl)-1,3-thiazole-5-carboxamide | | |

TABLE I-continued
| Compound | Name | MW | MS |
|---|---|---|---|
| 371 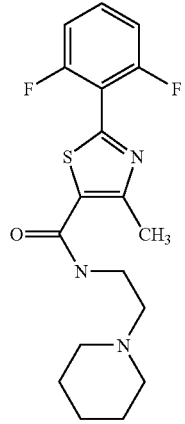 | 2-(2,6-difluorophenyl)-4-methyl-N-(2-piperidin-1-ylethyl)-1,3-thiazole-5-carboxamide | | |
| 372 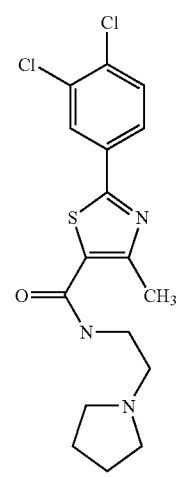 | 2-(3,4-dichlorophenyl)-4-methyl-N-(2-pyrrolidin-1-ylethyl)-1,3-thiazole-5-carboxamide | 383.06 | 384.22 |
| 373 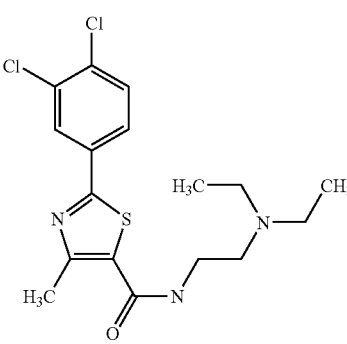 | 2-(3,4-dichlorophenyl)-N-[2-(diethylamino)ethyl]-4-methyl-1,3-thiazole-5-carboxamide | 385.08 | 386.23 |

TABLE I-continued
| Compound | | Name | MW | MS |
|---|---|---|---|---|
| 374 | 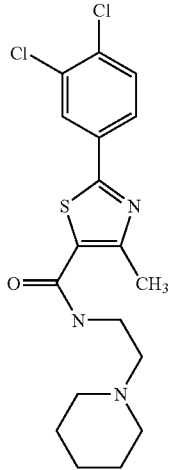 | 2-(3,4-dichlorophenyl)-4-methyl-N-(2-piperidin-1-ylethyl)-1,3-thiazole-5-carboxamide | 397.08 | 398.24 |
| 375 | 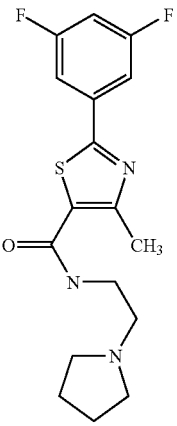 | 2-(3,5-difluorophenyl)-4-methyl-N-(2-pyrrolidin-1-ylethyl)-1,3-thiazole-5-carboxamide | 351.12 | 352.26 |
| 376 | 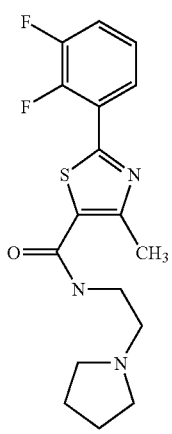 | 2-(2,3-difluorophenyl)-4-methyl-N-(2-pyrrolidin-1-ylethyl)-1,3-thiazole-5-carboxamide | 351.12 | 352.26 |

| Compound | | Name | MW | MS |
|---|---|---|---|---|
| 377 | 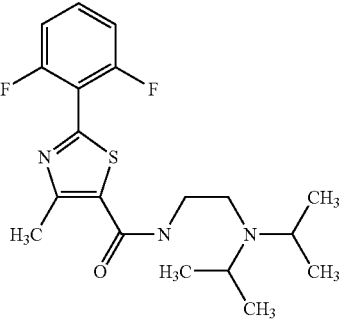 | 2-(2,6-difluorophenyl)-N-[2-(diisopropylamino)ethyl]-4-methyl-1,3-thiazole-5-carboxamide | | |
| 378 | 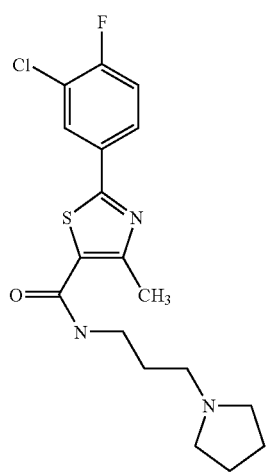 | 2-(3-chloro-4-fluorophenyl)-4-methyl-N-(3-pyrrolidin-1-ylpropyl)-1,3-thiazole-5-carboxamide | 381.11 | 382.26 |
| 379 | 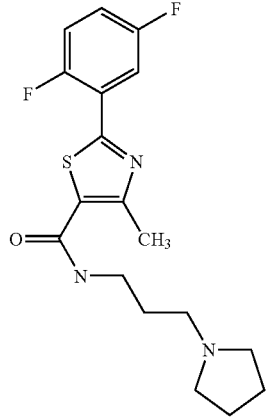 | 2-(2,5-difluorophenyl)-4-methyl-N-(3-pyrrolidin-1-ylpropyl)-1,3-thiazole-5-carboxamide | 365.14 | 366.27 |

TABLE I-continued
| | Compound | Name | MW | MS |
|---|---|---|---|---|
| 380 | 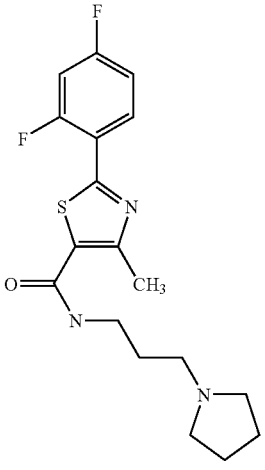 | 2-(2,4-difluorophenyl)-4-methyl-N-(3-pyrrolidin-1-ylpropyl)-1,3-thiazole-5-carboxamide | 365.14 | 366.28 |
| 381 | 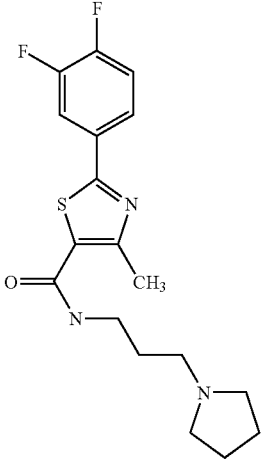 | 2-(3,4-difluorophenyl)-4-methyl-N-(3-pyrrolidin-1-ylpropyl)-1,3-thiazole-5-carboxamide | 365.14 | 366.28 |
| 382 | 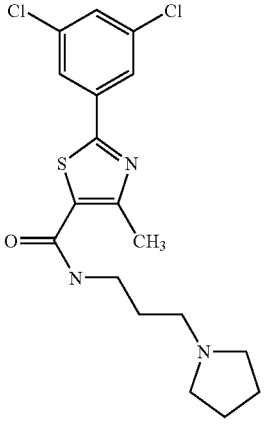 | 2-(3,5-dichlorophenyl)-4-methyl-N-(3-pyrrolidin-1-ylpropyl)-1,3-thiazole-5-carboxamide | 397.08 | 398.24 |

TABLE I-continued

| | Compound | Name | MW | MS |
|---|---|---|---|---|
| 383 | | 2-(4-chloro-3-fluorophenyl)-4-methyl-N-(3-pyrrolidin-1-ylpropyl)-1,3-thiazole-5-carboxamide | 381.11 | 382.25 |
| 384 | | 2-(3-chloro-4-fluorophenyl)-4-methyl-N-[2-(1-methylpyrrolidin-2-yl)ethyl]-1,3-thiazole-5-carboxamide | 381.11 | 382.25 |
| 385 | | 2-(3-chloro-4-fluorophenyl)-4-methyl-N-[3-(2-methylpiperidin-1-yl)propyl]-1,3-thiazole-5-carboxamide | 409.14 | 410.28 |
| 386 | | 2-(2,4-difluorophenyl)-4-methyl-N-[2-(1-methylpyrrolidin-1-yl)ethyl]-1,3-thiazole-5-carboxamide | 365.14 | 366.27 |

TABLE I-continued

| | Compound | Name | MW | MS |
|---|---|---|---|---|
| 387 | | 2-(3,4-difluorophenyl)-4-methyl-N-[2-(1-methylpyrrolidin-1-yl)ethyl]-1,3-thiazole-5-carboxamide | 365.14 | 366.27 |
| 388 | | 2-(4-chloro-2-fluorophenyl)-4-methyl-N-[2-(1-methylpyrrolidin-2-yl)ethyl]-1,3-thiazole-5-carboxamide | 381.11 | 382.24 |
| 389 | | 2-(4-chloro-2-fluorophenyl)-4-methyl-N-[3-(2-methylpiperidin-1-yl)propyl]-1,3-thiazole-5-carboxamide | 409.14 | 410.28 |
| 390 | | 2-(4-chloro-3-fluorophenyl)-4-methyl-N-[2-(1-methylpyrrolidin-2-yl)ethyl]-1,3-thiazole-5-carboxamide | 381.11 | 382.24 |

TABLE I-continued

| Compound | | Name | MW | MS |
|---|---|---|---|---|
| 391 | | 2-(4-chloro-3-fluorophenyl)-4-methyl-N-[3-(2-methylpiperidin-1-yl)propyl]-1,3-thiazole-5-carboxamide | 409.14 | 410.28 |
| 392 | | 2-(2,6-difluorophenyl)-4-methyl-N-[3-(2-methylpiperidin-1-yl)propyl]-1,3-thiazole-5-carboxamide | | |
| 393 | | 2-(3,4-dichlorophenyl)-4-methyl-N-[2-(1-methylpyrrolidin-2-yl)ethyl]-1,3-thiazole-5-carboxamide | 397.08 | 398.22 |
| 394 | | 2-(3,4-dichlorophenyl)-4-methyl-N-[3-(2-methylpiperidin-1-yl)propyl]-1,3-thiazole-5-carboxamide | 425.11 | 426.26 |

TABLE I-continued
| | Compound | Name | MW | MS |
|---|---|---|---|---|
| 395 | 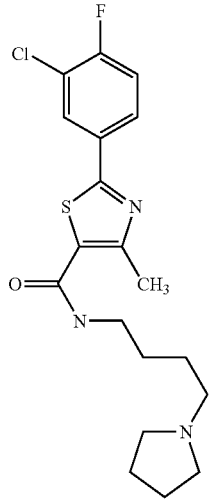 | 2-(3-chloro-4-fluorophenyl)-4-methyl-N-(4-pyrrolidin-1-ylbutyl)-1,3-thiazole-5-carboxamide | 395.12 | 396.25 |
| 396 | 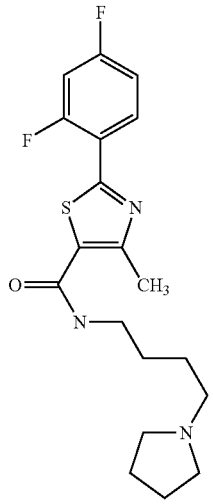 | 2-(2,4-difluorophenyl)-4-methyl-N-(4-pyrrolidin-1-ylbutyl)-1,3-thiazole-5-carboxamide | 379.15 | 380.27 |
| 397 | 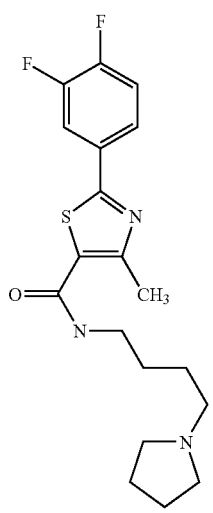 | 2-(3,4-difluorophenyl)-4-methyl-N-(4-pyrrolidin-1-ylbutyl)-1,3-thiazole-5-carboxamide | 379.15 | 380.27 |

TABLE I-continued
| Compound | | Name | MW | MS |
|---|---|---|---|---|
| 398 | 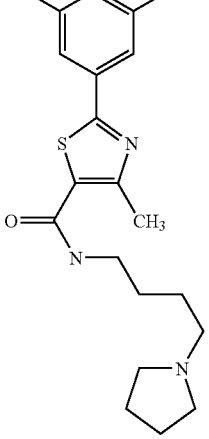 | 2-(3,5-dichlorophenyl)-4-methyl-N-(4-pyrrolidin-1-ylbutyl)-1,3-thiazole-5-carboxamide | 411.09 | 412.23 |
| 399 | 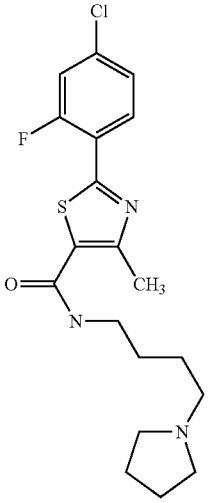 | 2-(4-chloro-2-fluorophenyl)-4-methyl-N-(4-pyrrolidin-1-ylbutyl)-1,3-thiazole-5-carboxamide | 395.12 | 396.26 |
| 400 | 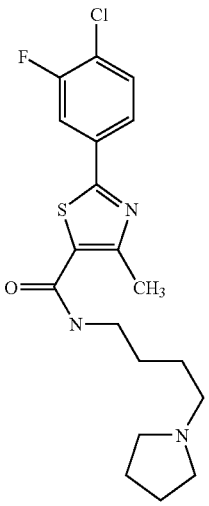 | 2-(4-chloro-3-fluorophenyl)-4-methyl-N-(4-pyrrolidin-1-ylbutyl)-1,3-thiazole-5-carboxamide | 395.12 | 396.26 |

| Compound | | Name | MW | MS |
|---|---|---|---|---|
| 401 | 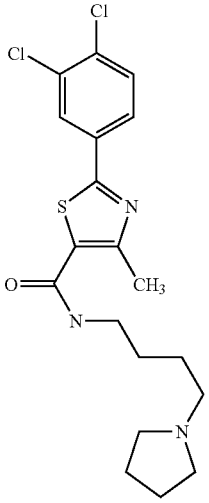 | 2-(3,4-dichlorophenyl)-4-methyl-N-(4-pyrrolidin-1-ylbutyl)-1,3-thiazole-5-carboxamide | 411.09 | 412.23 |
| 402 | 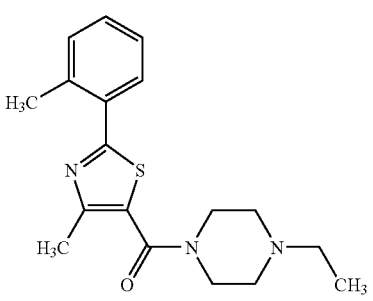 | 1-ethyl-4-{[4-methyl-2-(2-methylphenyl)-1,3-thiazol-5-yl]carbonyl}piperazine | 329.16 | 330.18 |
| 403 | 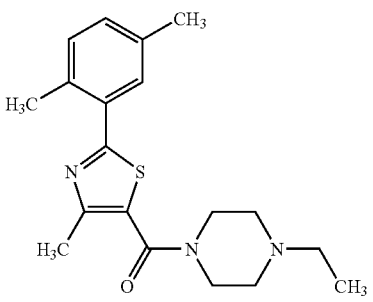 | 1-{[2-(2,5-dimethylphenyl)-4-methyl-1,3-thiazol-5-yl]carbonyl}-4-ethylpiperazine | 343.17 | 344.20 |
| 404 | 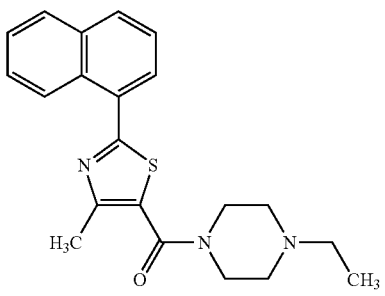 | 1-ethyl-4-{[4-methyl-2-(1-naphthyl)-1,3-thiazol-5-yl]carbonyl}piperazine | 365.16 | 366.19 |

285 286
TABLE I-continued
| Compound | | Name | MW | MS |
|---|---|---|---|---|
| 405 | 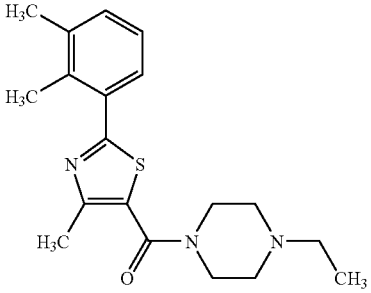 | 1-{[2-(2,3-dimethylphenyl)-4-methyl-1,3-thiazol-5-yl]carbonyl}-4-ethylpiperazine | 343.17 | 344.21 |
| 406 | 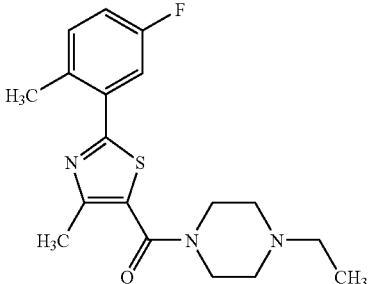 | 1-ethyl-4-{[2-(5-fluoro-2-methylphenyl)-4-methyl-1,3-thiazol-5-yl]carbonyl}piperazine | 347.15 | 348.18 |
| 407 | 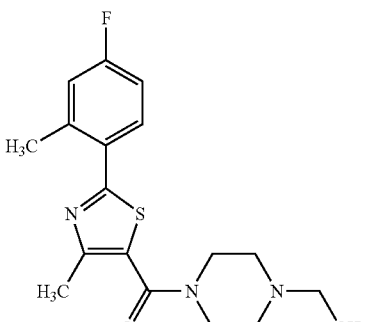 | 1-ethyl-4-{[2-(4-fluoro-2-methylphenyl)-4-methyl-1,3-thiazol-5-yl]carbonyl}piperazine | 347.15 | 348.19 |
| 408 | 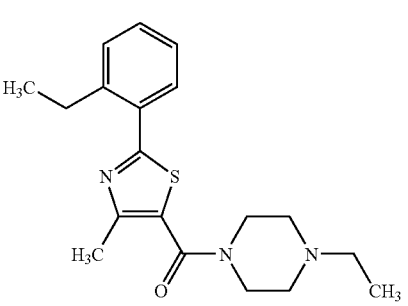 | 1-ethyl-4-{[2-(2-ethylphenyl)-4-methyl-1,3-thiazol-5-yl]carbonyl}piperazine | 343.17 | 344.21 |
| 409 | 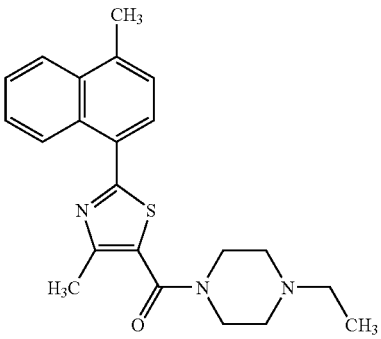 | 1-ethyl-4-{[4-methyl-2-(4-methyl-1-naphthyl)-1,3-thiazol-5-yl]carbonyl}piperazine | 379.17 | 380.23 |

TABLE I-continued
| Compound | | Name | MW | MS |
|---|---|---|---|---|
| 410 | 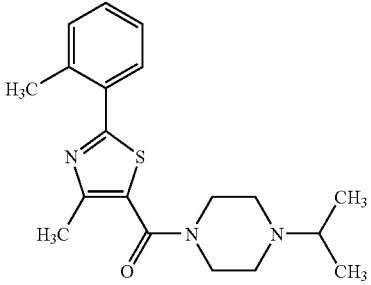 | 1-isopropyl-4-{[4-methyl-2-(2-methyl)-1,3-thiazol-5-yl]carbonyl}piperazine | 343.17 | 344.22 |
| 411 | 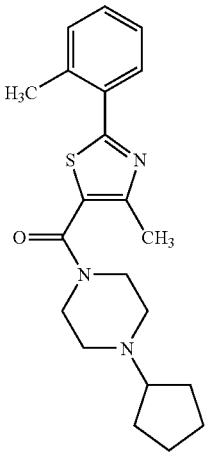 | 1-cyclopentyl-4-{[4-methyl-2-(2-methylphenyl)-1,3-thiazol-5-yl]carbonyl}piperazine | 369.19 | 370.24 |
| 412 | 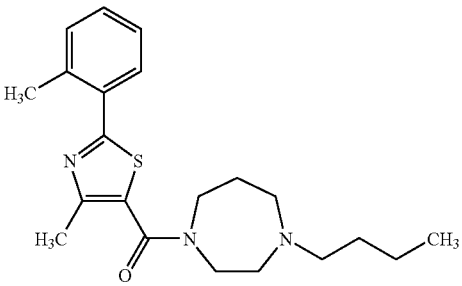 | 1-butyl-4-{[4-methyl-2-(2-methyl)-1,3-thiazol-5-yl]carbonyl}-1,4-diazepane | 371.20 | 372.26 |
| 413 | 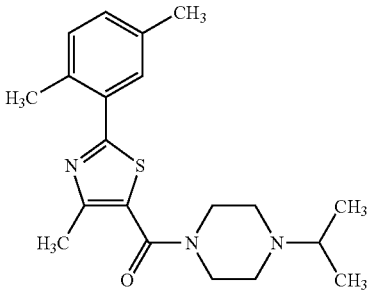 | 1-{[2-(2,5-dimethylphenyl)-4-methyl-1,3-thiazol-5-yl]carbonyl}-4-isopropylpiperazine | 357.19 | 358.24 |

TABLE I-continued

| Compound | | Name | MW | MS |
|---|---|---|---|---|
| 414 | | 1-cyclopentyl-4-{[2-(2,5-dimethylphenyl)-4-methyl-1,3-thiazol-5-yl]carbonyl}piperazine | 383.20 | 384.26 |
| 415 | | 1-butyl-4-{[2-(2,5-dimethylphenyl)-4-methyl-1,3-thiazol-5-yl]carbonyl}-1,4-diazepane | 385.22 | 386.27 |
| 416 | | 1-isopropyl-4-{[4-methyl-2-(1-naphthyl)-1,3-thiazol-5-yl]carbonyl}piperazine | 379.17 | 380.23 |
| 417 | | 1-cyclopentyl-4-{[4-methyl-2-(1-naphthyl)-1,3-thiazol-5-yl]carbonyl}piperazine | 405.19 | 406.25 |

TABLE I-continued
| | Compound | Name | MW | MS |
|---|---|---|---|---|
| 418 | 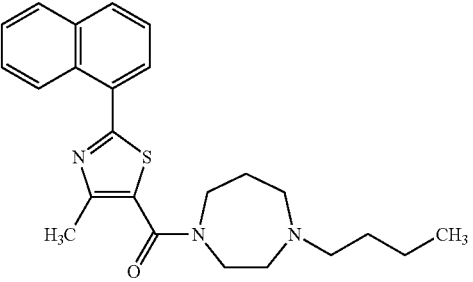 | 1-butyl-4-{[4-methyl-2-(1-naphthyl)-1,3-thiazol-5-yl]carbonyl}-1,4-diazepane | 407.20 | 408.26 |
| 419 | 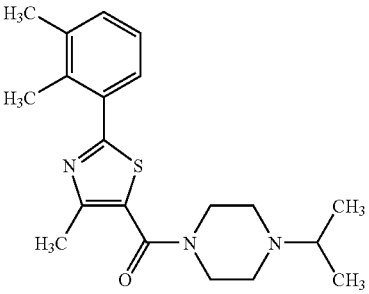 | 1-{[2-(2,3-dimethylphenyl)-4-methyl-1,3-thiazol-5-yl]carbonyl}-4-isopropylpiperazine | 357.19 | 358.24 |
| 420 | 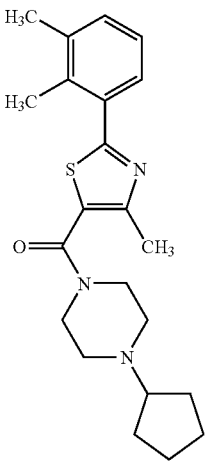 | 1-cyclopentyl-4-{[2-(2,3-dimethylphenyl)-4-methyl-1,3-thiazol-5-yl]carbonyl}piperazine | 383.20 | 384.26 |
| 421 | 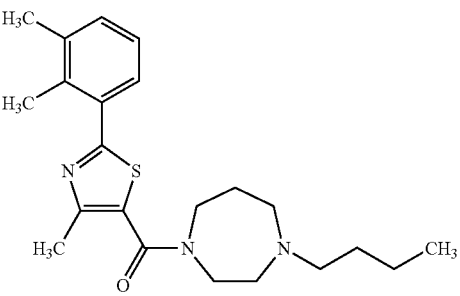 | 1-butyl-4-{[2-(2,3-dimethylphenyl)-4-methyl-1,3-thiazol-5-yl]carbonyl}-1,4-diazepane | 385.22 | 386.27 |

TABLE I-continued

| | Compound | Name | MW | MS |
|---|---|---|---|---|
| 422 | | 1-{[2-(5-fluoro-2-methylphenyl)-4-methyl-1,3-thiazol-5-yl]carbonyl}-4-isopropylpiperazine | 361.16 | 362.22 |
| 423 | | 1-cyclopentyl-4-{[2-(5-fluoro-2-methylphenyl)-4-methyl-1,3-thiazol-5-yl]carbonyl}piperazine | 387.18 | 388.24 |
| 424 | | 1-butyl-4-{[2-(5-fluoro-2-methylphenyl)-4-methyl-1,3-thiazol-5-yl]carbonyl}-1,4-diazepane | 389.19 | 390.26 |
| 425 | | 1-{[2-(4-fluoro-2-methylphenyl)-4-methyl-1,3-thiazol-5-yl]carbonyl}-4-isopropylpiperazine | 361.16 | 362.22 |

TABLE I-continued

| Compound | | Name | MW | MS |
|---|---|---|---|---|
| 426 | | 1-cyclopentyl-4-{[2-(4-fluoro-2-methylphenyl)-4-methyl-1,3-thiazol-5-yl]carbonyl}piperazine | 387.18 | 388.24 |
| 427 | | 1-butyl-4-{[2-(4-fluoro-2-methylphenyl)-4-methyl-1,3-thiazol-5-yl]carbonyl}-1,4-diazepane | 389.19 | 390.25 |
| 428 | | 1-{[2-(2-ethylphenyl)-4-methyl-1,3-thiazol-5-yl]carbonyl}-4-isopropylpiperazine | 357.19 | 358.25 |
| 429 | | 1-cyclopentyl-4-{[2-(2-ethylphenyl)-4-methyl-1,3-thiazol-5-yl]carbonyl}piperazine | 383.20 | 384.27 |

TABLE I-continued

| | Compound | Name | MW | MS |
|---|---|---|---|---|
| 430 | | 1-butyl-4-{[2-(2-ethylphenyl)-4-methyl-1,3-thiazol-5-yl]carbonyl}-1,4-diazepane | 385.22 | 386.28 |
| 431 | | 1-isopropyl-4-{[4-methyl-2-(2,4,5-trimethylphenyl)-1,3-thiazol-5-yl]carbonyl}piperazine | | |
| 432 | | 1-cyclopentyl-4-{[4-methyl-2-(2,4,5-trimethylphenyl)-1,3-thiazol-5-yl]carbonyl}piperazine | | |
| 433 | | 1-isopropyl-4-{[2-(2-methoxy-1-naphthyl)-4-methyl-1,3-thiazol-5-yl]carbonyl}piperazine | 409.18 | 410.25 |

TABLE I-continued

| | Compound | Name | MW | MS |
|---|---|---|---|---|
| 434 | | 1-cyclopentyl-4-{[2-(2-methoxy-1-naphthyl)-4-methyl-1,3-thiazol-5-yl]carbonyl}piperazine | 435.20 | 436.28 |
| 435 | | 1-butyl-4-{[2-(2-methoxy-1-naphthyl)-4-methyl-1,3-thiazol-5-yl]carbonyl}-1,4-diazepane | 437.21 | 438.29 |
| 436 | | 1-{[2-(4-chloro-2-methylphenyl)-4-methyl-1,3-thiazol-5-yl]carbonyl}-4-isopropylpiperazine | 377.13 | 378.21 |
| 437 | | 1-{[2-(4-chloro-2-methylphenyl)-4-methyl-1,3-thiazol-5-yl]carbonyl}-4-cyclopentylpiperazine | 403.15 | 404.23 |

TABLE I-continued

| | Compound | Name | MW | MS |
|---|---|---|---|---|
| 438 | | 1-butyl-4-{[2-(4-chloro-2-methylphenyl)-4-methyl-1,3-thiazol-5-yl]carbonyl}-1,4-diazepane | 405.16 | 406.23 |
| 439 | | 1-isopropyl-4-{[4-methyl-2-(4-methyl-1-naphthyl)-1,3-thiazol-5-yl]carbonyl}piperazine | 393.19 | 394.26 |
| 440 | | 1-cyclopentyl-4-{[4-methyl-2-(4-methyl-)-naphthyl)-1,3-thiazol-5-yl]carbonyl}piperazine | 419.20 | 420.28 |
| 441 | | 1-butyl-4-{[4-methyl-2-(4-methyl-1-naphthyl)-1,3-thiazol-5-yl]carbonyl}-1,4-diazepane | 421.22 | 422.29 |

TABLE I-continued

| | Compound | Name | MW | MS |
|---|---|---|---|---|
| 442 | | N,N-dimethyl-2-(4-{[4-methyl-2-(2,4,5-trimethylphenyl)-1,3-thiazol-5-yl]carbonyl}piperazin-1-yl)ethanamine | 400.23 | 401.30 |
| 443 | | N,N-diethyl-1-{[4-methyl-2-(2-methylphenyl)-1,3-thiazol-5-yl]carbonyl}piperidin-4-amine | 371.20 | 372.27 |
| 444 | | N,N-diethyl-1-{[4-methyl-2-(2-methylphenyl)-1,3-thiazol-5-yl]carbonyl}pyrrolidin-3-amine | 357.19 | 358.25 |
| 445 | | 1-{[2-(2,5-dimethylphenyl)-4-methyl-1,3-thiazol-5-yl]carbonyl}-N,N-diethylpiperidin-4-amine | 385.22 | 386.28 |
| 446 | | 1-{[2-(2,5-dimethylphenyl)-4-methyl-1,3-thiazol-5-yl]carbonyl}-N,N-diethylpyrrolidin-3-amine | 371.20 | 372.27 |

TABLE I-continued

| Compound | Name | MW | MS |
|---|---|---|---|
| 447 | N,N-diethyl-1-{[4-methyl-2-(1-naphthyl)-1,3-thiazol-5-yl]carbonyl}piperidin-4-amine | 407.20 | 408.28 |
| 448 | N,N-dimethyl-1-{[4-methyl-2-(1-naphthyl)-1,3-thiazol-5-yl]carbonyl}pyrrolidin-3-amine | 365.16 | 366.23 |
| 449 | N,N-diethyl-1-{[4-methyl-2-(1-naphthyl)-1,3-thiazol-5-yl]carbonyl}pyrrolidin-3-amine | 393.19 | 394.26 |
| 450 | 1-{[2-(2,3-dimethylphenyl)-4-methyl-1,3-thiazol-5-yl]carbonyl}-N,N-diethylpiperidin-4-amine | 385.22 | 386.28 |
| 451 | 1-{[2-(2,3-dimethylphenyl)-4-methyl-1,3-thiazol-5-yl]carbonyl}-N,N-dimethylpyrrolidin-3-amine | 343.17 | 344.24 |
| 452 | 1-{[2-(2,3-dimethylphenyl)-4-methyl-1,3-thiazol-5-yl]carbonyl}-N,N-diethylpyrrolidin-3-amine | 371.20 | 372.27 |

TABLE I-continued

| | Compound | Name | MW | MS |
|---|---|---|---|---|
| 453 | | N,N-diethyl-1-{[2-(5-fluoro-2-methylphenyl)-4-methyl-1,3-thiazol-5-yl]carbonyl}piperidin-4-amine | 389.19 | 390.26 |
| 454 | | N-N-diethyl-1-{[2-(5-fluoro-2-methylphenyl)-4-methyl-1,3-thiazol-5-yl]carbonyl}pyrrolidin-3-amine | 375.18 | 376.25 |
| 455 | | N,N-diethyl-1-{[2-(4-fluoro-2-methylphenyl)-4-methyl-1,3-thiazol-5-yl]carbonyl}piperidin-4-amine | 389.19 | 390.26 |
| 456 | | N,N-diethyl-1-{[2-(4-fluoro-2-methylphenyl)-4-methyl-1,3-thiazol-5-yl]carbonyl}pyrrolidin-3-amine | 375.18 | 376.25 |
| 457 | | N,N-diethyl-1-{[2-(2-ethylphenyl)-4-methyl-1,3-thiazol-5-yl]carbonyl}piperidin-4-amine | 385.22 | 386.29 |

TABLE I-continued

| | Compound | Name | MW | MS |
|---|---|---|---|---|
| 458 | | 1-{[2-(2-ethylphenyl)-4-methyl-1,3-thiazol-5-yl]carbonyl}-N,N-dimethylpyrrolidin-3-amine | 343.17 | 344.24 |
| 459 | | N,N-diethyl-1-{[2-(2-ethylphenyl)-4-methyl-1,3-thiazol-5-yl]carbonyl}pyrrolidin-3-amine | 371.20 | 372.27 |
| 460 | | N,N-diethyl-1-{[4-methyl-2-(2,4,5-trimethylphenyl)-1,3-thiazol-5-yl]carbonyl}piperidin-4-amine | 399.23 | 400.30 |
| 461 | | N,N-diethyl-1-{[4-methyl-2-(2,4,5-trimethylphenyl)-1,3-thiazol-5-yl]carbonyl}pyrrolidin-3-amine | 385.22 | 386.29 |
| 462 | | N,N-diethyl-1-{[2-(2-methoxy-1-naphthyl)-4-methyl-1,3-thiazol-5-yl]carbonyl}piperidin-4-amine | 437.21 | 438.30 |

TABLE I-continued

| Compound | Name | MW | MS |
|---|---|---|---|
| 463 | 1-{[2-(2-methoxy-1-naphthyl)-4-methyl-1,3-thiazol-5-yl]carbonyl}-N,N-dimethylpiperidin-4-amine | 409.18 | 410.26 |
| 464 | 1-{[2-(2-methoxy-1-naphthyl)-4-methyl-1,3-thiazol-5-yl]carbonyl}-N,N-dimethylpyrrolidin-3-amine | 395.17 | 396.24 |
| 465 | N,N-diethyl-1-{[2-(2-methoxy-1-naphthyl)-4-methyl-1,3-thiazol-5-yl]carbonyl}pyrrolidin-3-amine | 423.20 | 424.28 |
| 466 | 1-{[2-(4-chloro-2-methylphenyl)-4-methyl-1,3-thiazol-5-yl]carbonyl}-N,N-diethylpiperidin-4-amine | 405.16 | 406.24 |
| 467 | N,N-diethyl-1-{[4-methyl-2-(4-methyl-1-naphthyl)-1,3-thiazol-5-yl]carbonyl}piperidin-4-amine | 421.22 | 422.29 |

TABLE I-continued
| | Compound | Name | MW | MS |
|---|---|---|---|---|
| 468 | 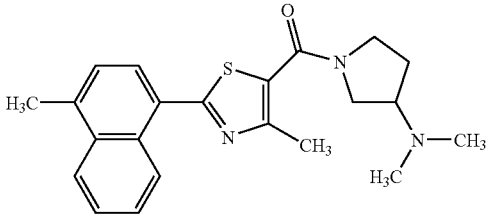 | N,N-dimethyl-1-{[4-methyl-2-(4-methyl-1-naphthyl)-1,3-thiazol-5-yl]carbonyl}pyrrolidin-3-amine | 379.17 | 380.24 |
| 469 | 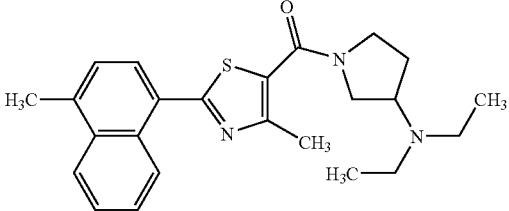 | N,N-diethyl-1-{[4-methyl-2-(4-methyl-1-naphthyl)-1,3-thiazol-5-yl]carbonyl}pyrrolidin-3-amine | 407.20 | 408.28 |
| 470 | 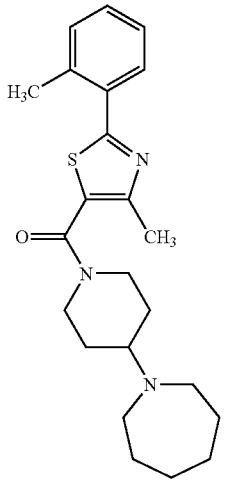 | 1-(1-{[4-methyl-2-(2-methylphenyl)-1,3-thiazol-5-yl]carbonyl}piperidin-4-yl)azepane | 397.22 | 398.29 |
| 471 | 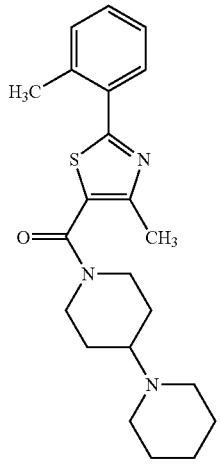 | 1'-{[4-methyl-2-(2-methylphenyl)-1,3-thiazol-5-yl]carbonyl}-1,4'-bipiperidine | 383.20 | 384.27 |

TABLE I-continued
| Compound | | Name | MW | MS |
|---|---|---|---|---|
| 472 | 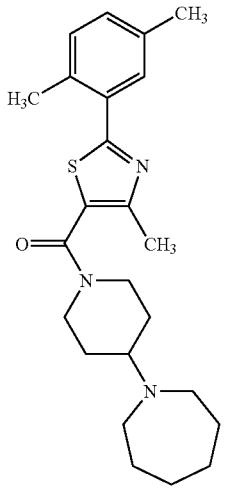 | 1-(1-{[2-(2,5-dimethylphenyl)-4-methyl-1,3-thiazol-5-yl]carbonyl}piperidin-4-yl)azepane | 411.23 | 412.31 |
| 473 | 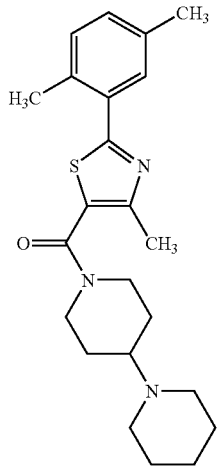 | 1'-{[2-(2,5-dimethylphenyl)-4-methyl-1,3-thiazol-5-yl]carbonyl}-1,4'-bipiperidine | 397.22 | 398.29 |
| 474 | 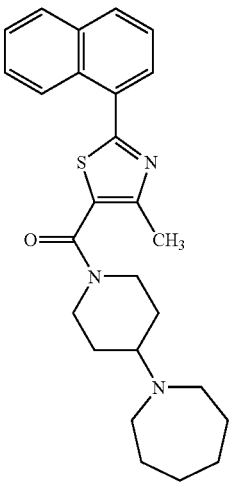 | 1-(1-{[4-methyl-2-(1-naphthyl)-1,3-thiazol-5-yl]carbonyl}piperidin-4-yl)azepane | 433.22 | 434.30 |

TABLE I-continued

| Compound | | Name | MW | MS |
|---|---|---|---|---|
| 475 | | 1'-{[4-methyl-2-(1-naphthyl)-1,3-thiazol-5-yl]carbonyl}-1,4'-bipiperidine | 419.20 | 420.28 |
| 476 | | 1-(1-{[2-(2,3-dimethylphenyl)-4-methyl-1,3-thiazol-5-yl]carbonyl}piperidin-4-yl)azepane | 411.23 | 412.31 |
| 477 | | 1'-{[2-(2,3-dimethylphenyl)-4-methyl-1,3-thiazol-5-yl]carbonyl}-1,4'-bipiperidine | 397.22 | 398.29 |

TABLE I-continued
| | Compound | Name | MW | MS |
|---|---|---|---|---|
| 478 | 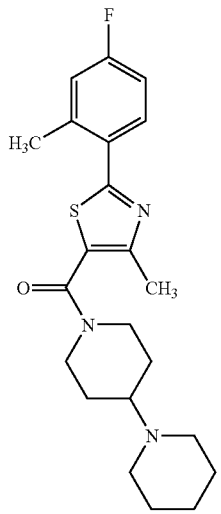 | 1'-{[2-(4-fluoro-2-methylphenyl)-4-methyl-1,3-thiazol-5-yl]carbonyl}-1,4'-bipiperidine | 401.19 | 402.27 |
| 479 | 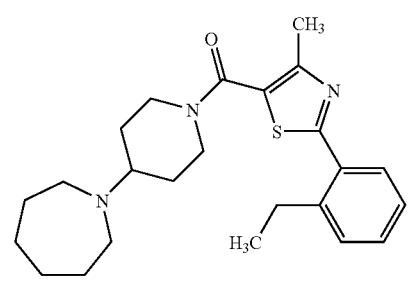 | 1-(1-{[2-(2-ethylphenyl)-4-methyl-1,3-thiazol-5-yl]carbonyl}piperidin-4-yl)azepane | 411.23 | 412.31 |
| 480 | 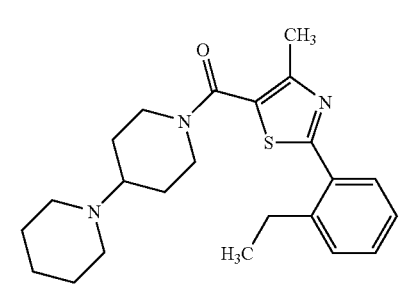 | 1'-{[2-(2-ethylphenyl)-4-methyl-1,3-thiazol-5-yl]carbonyl}-1,4'-bipiperidine | 397.22 | 398.29 |

TABLE I-continued
| Compound | | Name | MW | MS |
|---|---|---|---|---|
| 481 | 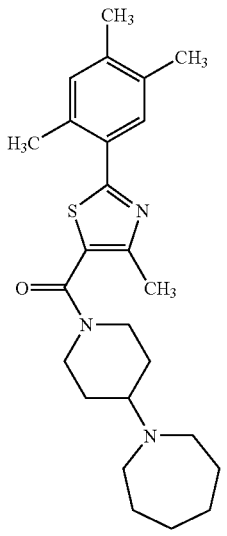 | 1-(1-{[4-methyl-2-(2,4,5-trimethylphenyl)-1,3-thiazol-5-yl]carbonyl}piperidin-4-yl)azepane | | |
| 482 | 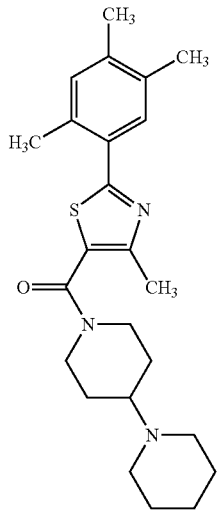 | 1'-{[4-methyl-2-(2,4,5-trimethylphenyl)-1,3-thiazol-5-yl]carbonyl}-1,4'-bipiperidine | 411.23 | 412.31 |
| 483 | 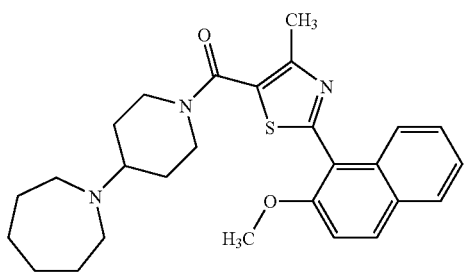 | 1-(1-{[2-(2-methoxy-1-naphthyl)-4-methyl-1,3-thiazol-5-yl]carbonyl}piperidin-4-yl)azepane | 463.23 | 464.31 |

TABLE I-continued

| | Compound | Name | MW | MS |
|---|---|---|---|---|
| 484 | | 1'-{[2-(2-methoxy-1-naphthyl)-4-methyl-1,3-thiazol-5-yl]carbonyl}-1,4'-bipiperidine | 449.21 | 450.30 |
| 485 | | 1-(1-{[2-(4-chloro-2-methylphenyl)-4-methyl-1,3-thiazol-5-yl]carbonyl}piperidin-4-yl)azepane | 431.18 | 432.27 |
| 486 | | 1'-{[2-(4-chloro-2-methylphenyl)-4-methyl-1,3-thiazol-5-yl]carbonyl}-1,4'-bipiperidine | 417.16 | 418.25 |

TABLE I-continued

| Compound | | Name | MW | MS |
|---|---|---|---|---|
| 487 | | 1-(1-{[4-methyl-2-(4-methyl-1-naphthyl)-1,3-thiazol-5-yl]carbonyl}piperidin-4-yl)azepane | 447.23 | 448.32 |
| 488 | | 1'-{[4-methyl-2-(4-methyl-1-naphthyl)-1,3-thiazol-5-yl]carbonyl}-1,4'-bipiperidine | 433.22 | 434.30 |
| 489 | | N-(cyclopropylmethyl)-1-{[4-methyl-2-(2-methylphenyl)-1,3-thiazol-5-yl]carbonyl}-N-propylpiperidin-4-amine | 411.23 | 412.30 |
| 490 | | N-(cyclopropylmethyl)-1-{[2-(2,5-dimethylphenyl)-4-methyl-1,3-thiazol-5-yl]carbonyl}-N-propylpiperidin-4-amine | 425.25 | 426.32 |

TABLE I-continued

| Compound | | Name | MW | MS |
|---|---|---|---|---|
| 491 | (structure) | N-(cyclopropylmethyl)-1-{[4-methyl-2-(1-naphthyl)-1,3-thiazol-5-yl]carbonyl}-N-propylpiperidin-4-amine | 447.23 | 448.31 |
| 492 | (structure) | N-(cyclopropylmethyl)-1-{[2-(2,3-dimethylphenyl)-4-methyl-1,3-thiazol-5-yl]carbonyl}-N-propylpiperidin-4-amine | 425.25 | 426.33 |
| 493 | (structure) | N-(cyclopropylmethyl)-1-{[2-(5-fluoro-2-methylphenyl)-4-methyl-1,3-thiazol-5-yl]carbonyl}-N-propylpiperidin-4-amine | 429.23 | 430.30 |
| 494 | (structure) | N-(cyclopropylmethyl)-1-{[2-(4-fluoro-2-methylphenyl)-4-methyl-1,3-thiazol-5-yl]carbonyl}-N-propylpiperidin-4-amine | 429.23 | 430.30 |
| 495 | (structure) | N-(cyclopropylmethyl)-1-{[4-methyl-2-(2,4,5-trimethylphenyl)-1,3-thiazol-5-yl]carbonyl}-N-propylpiperidin-4-amine | 439.27 | 440.34 |

TABLE I-continued

| Compound | | Name | MW | MS |
|---|---|---|---|---|
| 496 | | N-(cyclopropylmethyl)-1-{[2-(2-methoxy-1-naphthyl)-4-methyl-1,3-thiazol-5-yl]carbonyl}-N-propylpiperidin-4-amine | 477.25 | 478.34 |
| 497 | | N-(cyclopropylmethyl)-1-{[4-methyl-2-(4-methyl-1-naphthyl)-1,3-thiazol-5-yl]carbonyl}-N-propylpiperidin-4-amine | 461.25 | 462.33 |
| 498 | | N-[2-(diethylamino)ethyl]-2-(2,5-dimethylphenyl)-N,4-dimethyl-1,3-thiazole-5-carboxamide | 359.20 | 360.26 |
| 499 | | N-[2-(diethylamino)ethyl]-N,4-dimethyl-2-(1-naphthyl)-1,3-thiazole-5-carboxamide | 381.19 | 382.25 |
| 500 | | N-[2-(diethylamino)ethyl]-N-ethyl-4-methyl-2-(1-naphthyl)-1,3-thiazole-5-carboxamide | 395.20 | 396.26 |

TABLE I-continued

| | Compound | Name | MW | MS |
|---|---|---|---|---|
| 501 | | N-[2-(diethylamino)ethyl]-2-(2,3-dimethylphenyl)-N,4-dimethyl-1,3-thiazole-5-carboxamide | 359.20 | 360.25 |
| 502 | | N-[2-(diethylamino)ethyl]-2-(2,3-dimethylphenyl)-N-ethyl-4-methyl-1,3-thiazole-5-carboxamide | 373.22 | 374.27 |
| 503 | | N-[2-(diethylamino)ethyl]-2-(5-fluoro-2-methylphenyl)-N,4-dimethyl-1,3-thiazole-5-carboxamide | 363.18 | 364.23 |
| 504 | | N-[2-(diethylamino)ethyl]-N-ethyl-2-(5-fluoro-2-methylphenyl)-4-methyl-1,3-thiazole-5-carboxamide | 377.19 | 378.24 |

TABLE I-continued

| Compound | Name | MW | MS |
|---|---|---|---|
| 505 | N-[2-(diethylamino)ethyl]-2-(4-fluoro-2-methylphenyl)-N,4-dimethyl-1,3-thiazole-5-carboxamide | 363.18 | 364.23 |
| 506 | N-[2-(diethylamino)ethyl]-2-(2-ethylphenyl)-N,4-dimethyl-1,3-thiazole-5-carboxamide | 359.20 | 360.26 |
| 507 | N-[2-(diethylamino)ethyl]-N-ethyl-2-(2-ethylphenyl)-4-methyl-1,3-thiazole-5-carboxamide | 373.22 | 374.28 |
| 508 | N-[2-(diethylamino)ethyl]-N,4-dimethyl-2-(2,4,5-trimethylphenyl)-1,3-thiazole-5-carboxamide | 373.22 | 374.27 |

TABLE I-continued
| | Compound | Name | MW | MS |
|---|---|---|---|---|
| 509 | 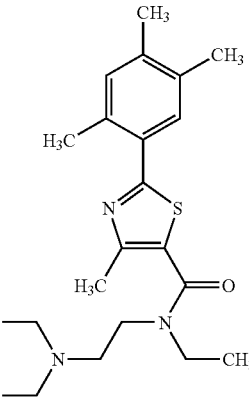 | N-[2-(diethylamino)ethyl]-N-ethyl-4-methyl-2-(2,4,5-trimethylphenyl)-1,3-thiazole-5-carboxamide | 387.23 | 388.29 |
| 510 | 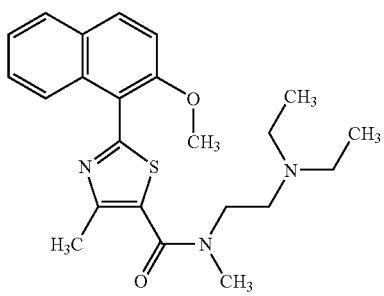 | N-[2-(diethylamino)ethyl]-2-(2-methoxy-1-naphthyl)-N,4-dimethyl-1,3-thiazole-5-carboxamide | 411.20 | 412.27 |
| 511 | 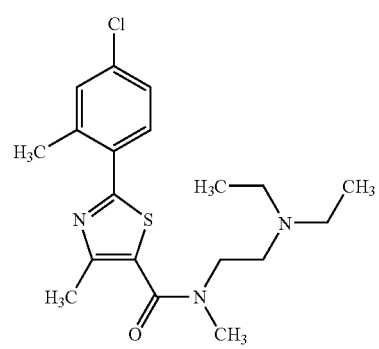 | 2-(4-chloro-2-methylphenyl)-N-[2-(diethylamino)ethyl]-N,4-dimethyl-1,3-thiazole-5-carboxamide | 379.15 | 380.22 |
| 512 | 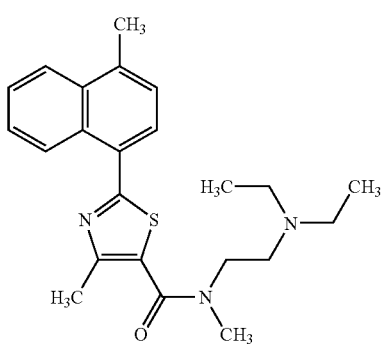 | N-[2-(diethylamino)ethyl]-N,4-dimethyl-2-(4-methyl-1-naphthyl)-1,3-thiazole-5-carboxamide | 395.20 | 396.26 |

TABLE I-continued
| Compound | | Name | MW | MS |
|---|---|---|---|---|
| 513 | 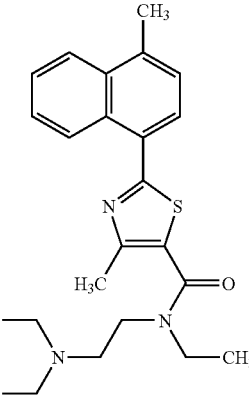 | N-[2-(diethylamino)ethyl]-N-ethyl-4-methyl-2-(4-methyl-1-naphthyl)-1,3-thiazole-5-carboxamide | 409.22 | 410.27 |
| 514 | 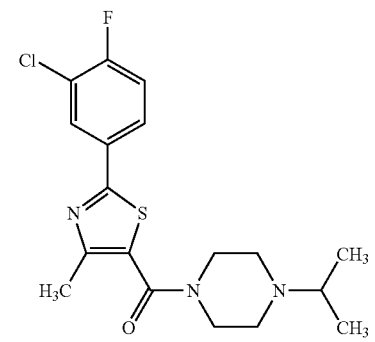 | 1-{[2-(3-chloro-4-fluorophenyl)-4-methyl-1,3-thiazol-5-yl]carbonyl}-4-isopropylpiperazine | 381.11 | 382.24 |
| 515 | 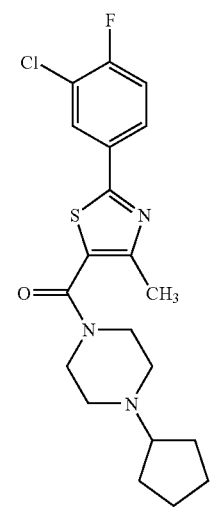 | 1-{[2-(3-chloro-4-fluorophenyl)-4-methyl-1,3-thiazol-5-yl]carbonyl}-4-cyclopentylpiperazine | 407.12 | 408.27 |

TABLE I-continued
| Compound | | Name | MW | MS |
|---|---|---|---|---|
| 516 | 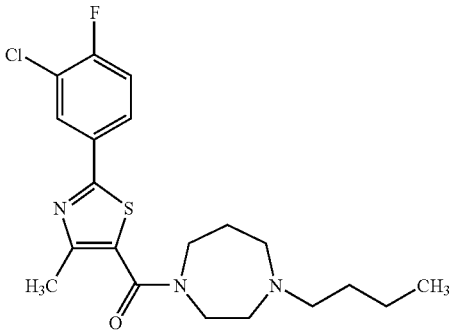 | 1-butyl-4-{[2-(3-chloro-4-fluorophenyl)-4-methyl-1,3-thiazol-5-yl]carbonyl}-1,4-diazepane | 409.14 | 410.29 |
| 517 | 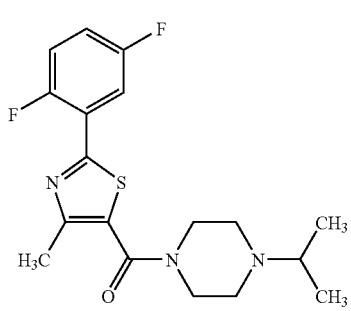 | 1-{[2-(2,5-difluorophenyl)-4-methyl-1,3-thiazol-5-yl]carbonyl}-4-isopropylpiperazine | 365.14 | 366.27 |
| 518 | 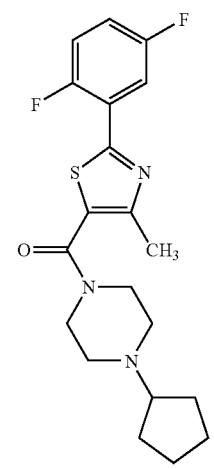 | 1-cyclopentyl-4-{[2-(2,5-difluorophenyl)-4-methyl-1,3-thiazol-5-yl]carbonyl}piperazine | 391.15 | 392.29 |
| 519 | 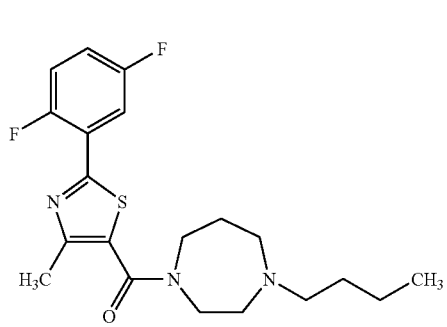 | 1-butyl-4-{[2-(2,5-difluorophenyl)-4-methyl-1,3-thiazol-5-yl]carbonyl}-1,4-diazepane | 393.17 | 394.31 |

TABLE I-continued
| | Compound | Name | MW | MS |
|---|---|---|---|---|
| 520 | 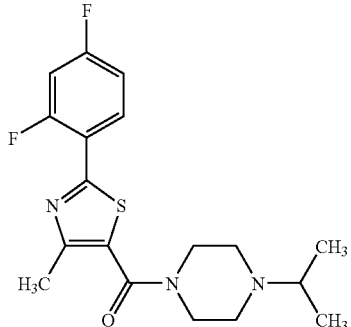 | 1-{[2-(2,4-difluorophenyl)-4-methyl-1,3-thiazol-5-yl]carbonyl}-4-isopropylpiperazine | 365.14 | 366.27 |
| 521 | 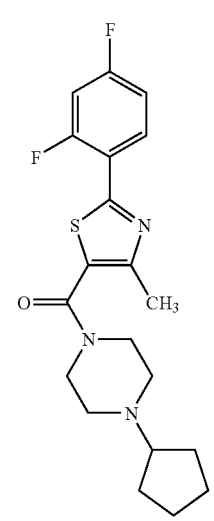 | 1-cyclopentyl-4-{[2-(2,4-difluorophenyl)-4-methyl-1,3-thiazol-5-yl]carbonyl}piperazine | 391.15 | 392.30 |
| 522 | 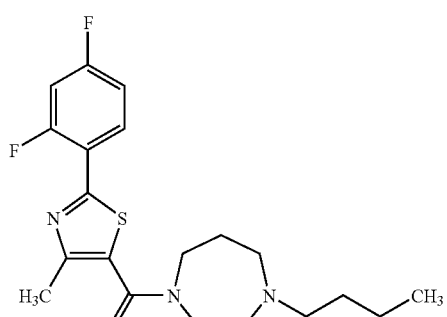 | 1-butyl-4-{[2-(2,4-difluorophenyl)-4-methyl-1,3-thiazol-5-yl]carbonyl}-1,4-diazepane | 393.17 | 394.31 |
| 523 | 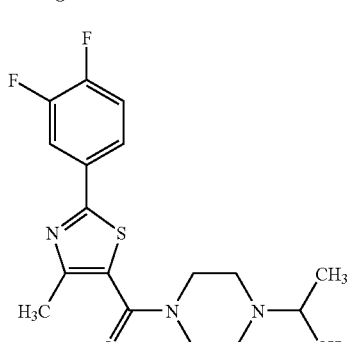 | 1-{[2-(3,4-difluorophenyl)-4-methyl-1,3-thiazol-5-yl]carbonyl}-4-isopropylpiperazine | 365.14 | 366.27 |

TABLE I-continued
| Compound | | Name | MW | MS |
|---|---|---|---|---|
| 524 | 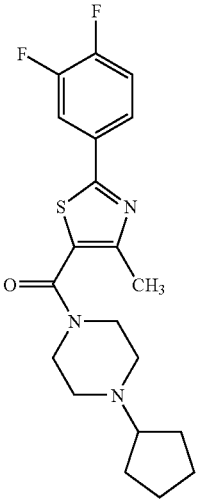 | 1-cyclopentyl-4-{[2-(3,4-difluorophenyl)-4-methyl-1,3-thiazol-5-yl]carbonyl}piperazine | 391.15 | 392.30 |
| 525 | 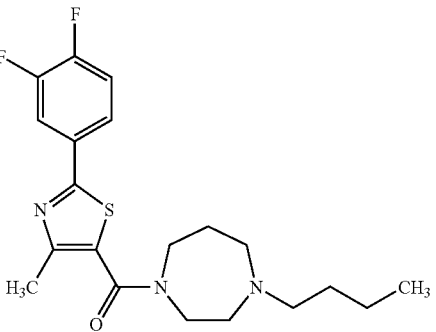 | 1-butyl-4-{[2-(3,4-difluorophenyl)-4-methyl-1,3-thiazol-5-yl]carbonyl}-1,4-diazepane | 393.17 | 394.31 |
| 526 | 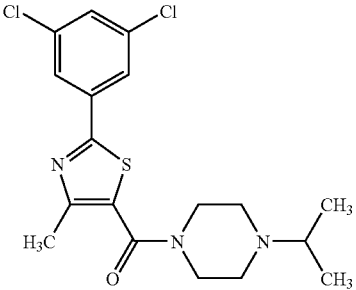 | 1-{[2-(3,5-dichlorophenyl)-4-methyl-1,3-thiazol-5-yl]carbonyl}-4-isopropylpiperazine | 397.08 | 398.22 |

TABLE I-continued

| | Compound | Name | MW | MS |
|---|---|---|---|---|
| 527 | | 1-cyclopentyl-4-{[2-(3,5-dichlorophenyl)-4-methyl-1,3-thiazol-5-yl]carbonyl}piperazine | 423.09 | 424.25 |
| 528 | | 1-butyl-4-{[2-(3,5-dichlorophenyl)-4-methyl-1,3-thiazol-5-yl]carbonyl}-1,4-diazepane | 425.11 | 426.27 |
| 529 | | 1-{[2-(4-chloro-2-fluorophenyl)-4-methyl-1,3-thiazol-5-yl]carbonyl}-4-isopropylpiperazine | 381.11 | 382.25 |
| 530 | | 1-butyl-4-{[2-(4-chloro-2-fluorophenyl)-4-methyl-1,3-thiazol-5-yl]carbonyl}-1,4-diazepane | 409.14 | 410.29 |

TABLE I-continued
| | Compound | Name | MW | MS |
|---|---|---|---|---|
| 531 | 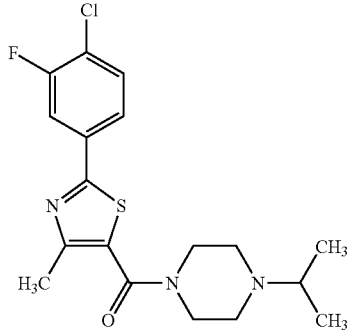 | 1-{[2-(4-chloro-3-fluorophenyl)-4-methyl-1,3-thiazol-5-yl]carbonyl}-4-isopropylpiperazine | 381.11 | 382.25 |
| 532 | 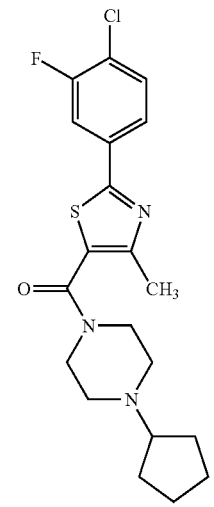 | 1-{[2-(4-chloro-3-fluorophenyl)-4-methyl-1,3-thiazol-5-yl]carbonyl}-4-cyclopentylpiperazine | 407.12 | 408.27 |
| 533 | 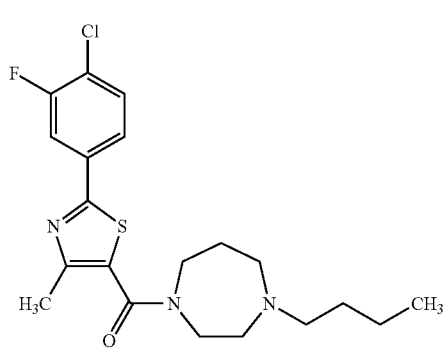 | 1-butyl-4-{[2-(4-chloro-3-fluorophenyl)-4-methyl-1,3-thiazol-5-yl]carbonyl}-1,4-diazepane | 409.14 | 410.29 |
| 534 | 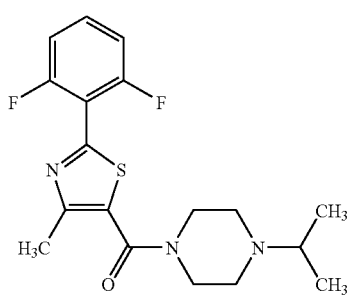 | 1-{[2-(2,6-difluorophenyl)-4-methyl-1,3-thiazol-5-yl]carbonyl}-4-isopropylpiperazine | | |

TABLE I-continued
| Compound | | Name | MW | MS |
|---|---|---|---|---|
| 535 | 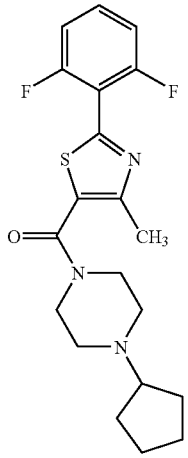 | 1-cyclopentyl-4-{[2-(2,6-difluorophenyl)-4-methyl-1,3-thiazol-5-yl]carbonyl}piperazine | | |
| 536 | 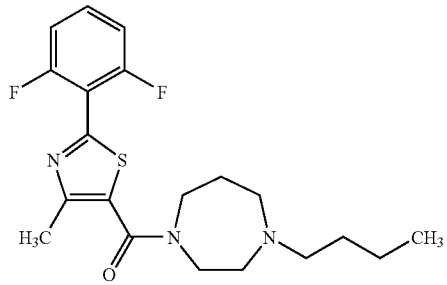 | 1-butyl-4-{[2-(2,6-difluorophenyl)-4-methyl-1,3-thiazol-5-yl]carbonyl}-1,4-diazepane | | |
| 537 | 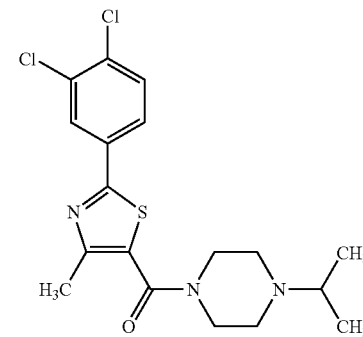 | 1-{[2-(3,4-dichlorophenyl)-4-methyl-1,3-thiazol-5-yl]carbonyl}-4-isopropylpiperazine | 397.08 | 398.23 |

TABLE I-continued
| Compound | | Name | MW | MS |
|---|---|---|---|---|
| 538 | 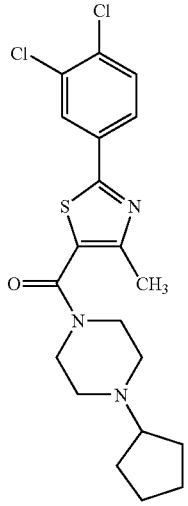 | 1-cyclopentyl-4-{[2-(3,4-dichlorophenyl)-4-methyl-1,3-thiazol-5-yl]carbonyl}piperazine | 423.09 | 424.26 |
| 539 | 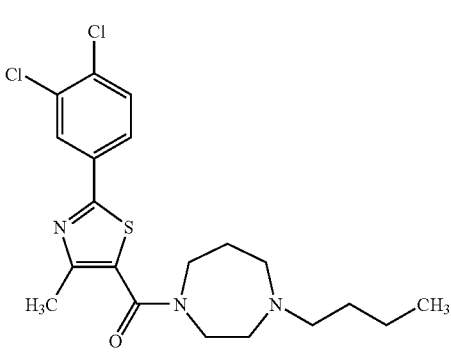 | 1-butyl-4-{[2-(3,4-dichlorophenyl)-4-methyl-1,3-thiazol-5-yl]carbonyl}-1,4-diazepane | 425.11 | 426.27 |
| 540 | 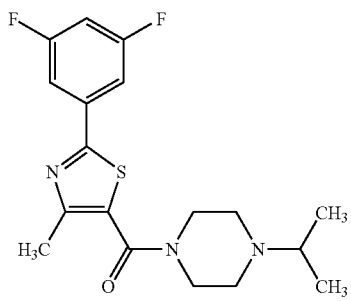 | 1-{[2-(3,5-difluorophenyl)-4-methyl-1,3-thiazol-5-yl]carbonyl}-4-isopropylpiperazine | 365.14 | 366.28 |

TABLE I-continued

| Compound | | Name | MW | MS |
|---|---|---|---|---|
| 541 | | 1-cyclopentyl-4-{[2-(3,5-difluorophenyl)-4-methyl-1,3-thiazol-5-yl]carbonyl}piperazine | 391.15 | 392.30 |
| 542 | | 1-butyl-4-{[2-(3,5-difluorophenyl)-4-methyl-1,3-thiazol-5-yl]carbonyl}-1,4-diazepane | 393.17 | 394.32 |
| 543 | | 1-{[2-(2,3-difluorophenyl)-4-methyl-1,3-thiazol-5-yl]carbonyl}-4-isopropylpiperazine | 365.14 | 366.28 |
| 544 | | 1-cyclopentyl-4-{[2-(2,3-difluorophenyl)-4-methyl-1,3-thiazol-5-yl]carbonyl}piperazine | 391.15 | 392.30 |

TABLE I-continued

| | Compound | Name | MW | MS |
|---|---|---|---|---|
| 545 | | 1-butyl-4-{[2-(2,3-difluorophenyl)-4-methyl-1,3-thiazol-5-yl]carbonyl}-1,4-diazepane | 393.17 | 394.32 |
| 546 | | 1-{[2-(2,4-difluorophenyl)-4-methyl-1,3-thiazol-5-yl]carbonyl}-N,N-diethylpiperidin-4-amine | 393.17 | 394.32 |
| 547 | | 1-{[2-(2,4-difluorophenyl)-4-methyl-1,3-thiazol-5-yl]carbonyl}-N,N-diethylpyrrolidin-3-amine | 379.15 | 380.30 |
| 548 | | 1-{[2-(3,5-dichlorophenyl)-4-methyl-1,3-thiazol-4-yl]carbonyl}-N,N-diethylpiperidin-4-amine | 425.11 | 426.28 |
| 549 | | 1-{[2-(2,6-difluorophenyl)-4-methyl-1,3-thiazol-5-yl]carbonyl}-N,N-diethylpiperidin-4-amine | | |

TABLE I-continued
| Compound | | Name | MW | MS |
|---|---|---|---|---|
| 550 | 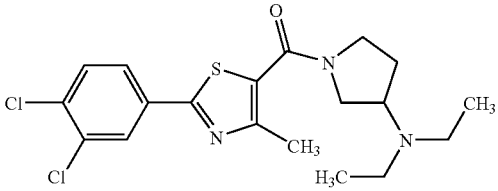 | 1-{[2-(3,4-dichlorophenyl)-4-methyl-1,3-thiazol-5-yl]carbonyl}-N,N-diethylpyrrolidin-3-amine | 411.09 | 412.26 |
| 551 | 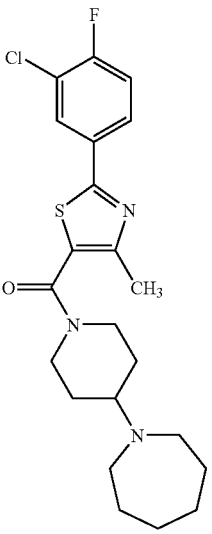 | 1-(1-{[2-(3-chloro-4-fluorophenyl)-4-methyl-1,3-thiazol-5-yl]carbonyl}piperidin-4-yl)azepane | 435.15 | 436.36 |
| 552 | 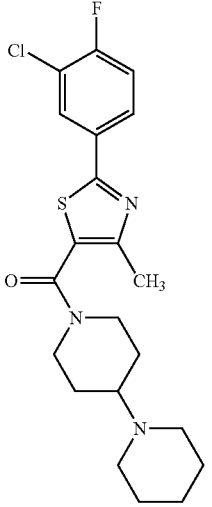 | 1'-{[2-(3-chloro-4-fluorophenyl)-4-methyl-1,3-thiazol-5-yl]carbonyl}-1,4'-bipiperidine | 421.14 | 422.33 |

TABLE I-continued
| | Compound | Name | MW | MS |
|---|---|---|---|---|
| 553 | 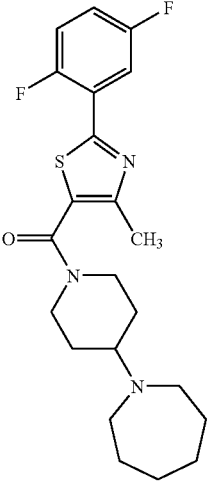 | 1-(1-{[2-(2,5-difluorophenyl)-4-methyl-1,3-thiazol-5-yl]carbonyl}piperidin-4-yl)azepane | 419.18 | 420.38 |
| 554 | 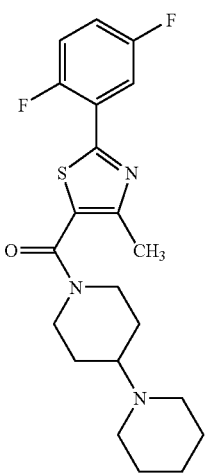 | 1'-{[2-(2,5-difluorophenyl)-4-methyl-1,3-thiazol-5-yl]carbonyl}-1,4'-bipiperidine | 405.17 | 406.36 |
| 555 | 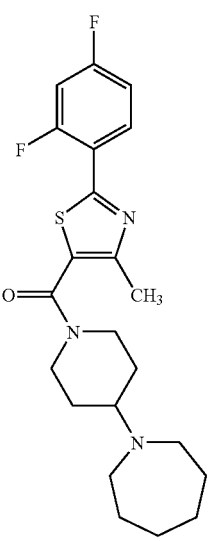 | 1-(1-{[2-(2,4-difluorophenyl)-4-methyl-1,3-thiazol-5-yl]carbonyl}piperidin-4-yl)azepane | 419.18 | 420.38 |

TABLE I-continued
| Compound | | Name | MW | MS |
|---|---|---|---|---|
| 556 | 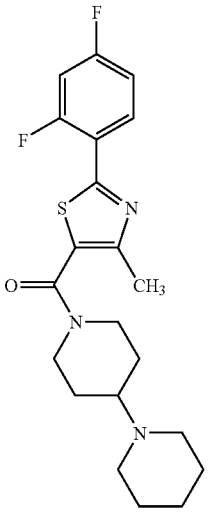 | 1'-{[2-(2,4-difluorophenyl)-4-methyl-1,3-thiazol-5-yl]carbonyl}-1,4'-bipiperidine | 405.17 | 406.36 |
| 557 | 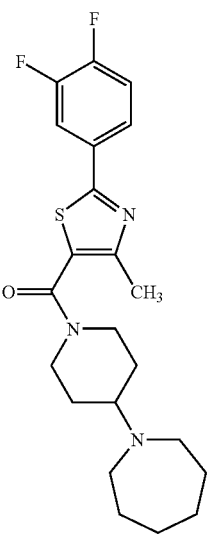 | 1-(1-{[2-(3,4-difluorophenyl)-4-methyl-1,3-thiazol-5-yl]carbonyl}piperidin-4-yl)azepane | 419.18 | 420.38 |
| 558 | 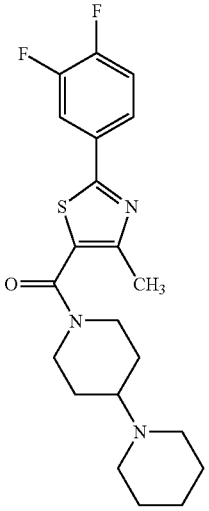 | 1'-{[2-(3,4-difluorophenyl)-4-methyl-1,3-thiazol-5-yl]carbonyl}-1,4'-bipiperidine | 405.17 | 406.36 |

TABLE I-continued
| | Compound | Name | MW | MS |
|---|---|---|---|---|
| 559 | 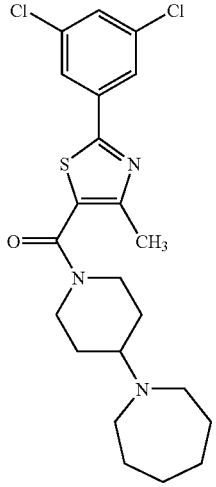 | 1-(1-{[2-(3,5-dichlorophenyl)-4-methyl-1,3-thiazol-5-yl]carbonyl}piperidin-4-yl)azepane | 451.13 | 452.34 |
| 560 | 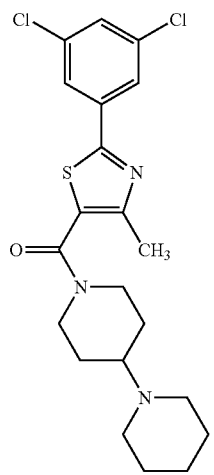 | 1'-{[2-(3,5-dichlorophenyl)-4-methyl-1,3-thiazol-5-yl]carbonyl}-1,4'-bipiperidine | 437.11 | 438.31 |
| 561 | 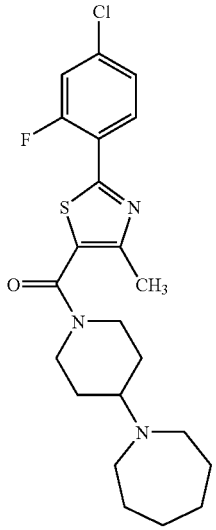 | 1-(1-{[2-(4-chloro-2-fluorophenyl)-4-methyl-1,3-thiazol-5-yl]carbonyl}piperidin-4-yl)azepane | 435.15 | 436.36 |

TABLE I-continued
| Compound | | Name | MW | MS |
|---|---|---|---|---|
| 562 | 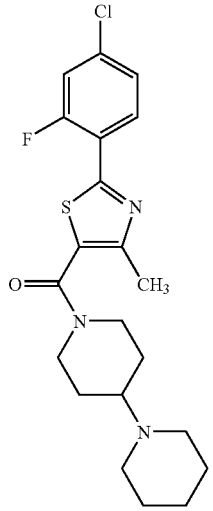 | 1'-{[2-(4-chloro-2-fluorophenyl)-4-methyl-1,3-thiazol-5-yl]carbonyl}-1,4'-bipiperidine | 421.14 | 422.33 |
| 563 | 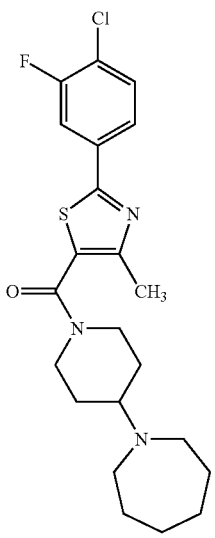 | 1-(1-{[2-(4-chloro-3-fluorophenyl)-4-methyl-1,3-thiazol-5-yl]carbonyl}piperidin-4-yl)azepane | 435.15 | 436.36 |
| 564 | 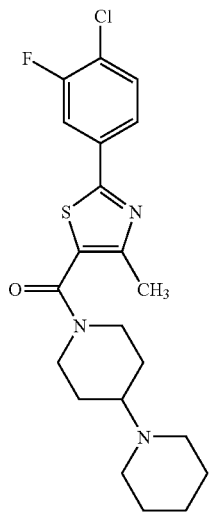 | 1'-{[2-(4-chloro-3-fluorophenyl)-4-methyl-1,3-thiazol-5-yl]carbonyl}-1,4'-bipiperidine | 421.14 | 422.33 |

TABLE I-continued
| | Compound | Name | MW | MS |
|---|---|---|---|---|
| 565 | 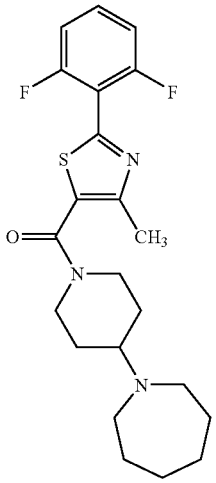 | 1-(1-{[2-(2,6-difluorophenyl)-4-methyl-1,3-thiazol-5-yl]carbonyl}piperidin-4-yl)azepane | | |
| 566 | 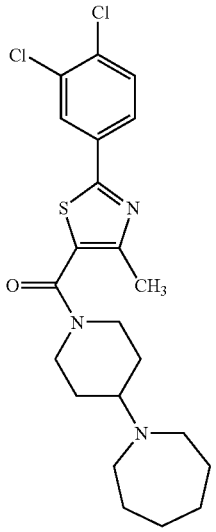 | 1-(1-{[2-(3,4-dichlorophenyl)-4-methyl-1,3-thiazol-5-yl]carbonyl}piperidin-4-yl)azepane | 451.13 | 452.33 |
| 567 | 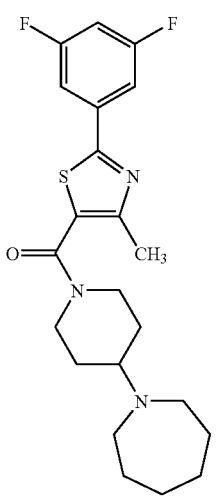 | 1-(1-{[2-(3,5-difluorophenyl)-4-methyl-1,3-thiazol-5-yl]carbonyl}piperidin-4-yl)azepane | 419.18 | 420.38 |

TABLE I-continued
| Compound | | Name | MW | MS |
|---|---|---|---|---|
| 568 | 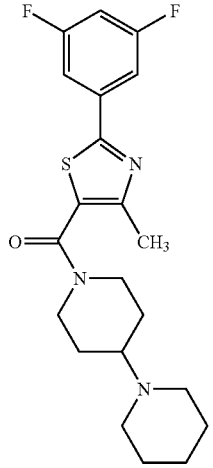 | 1'-{[2-(3,5-difluorophenyl)-4-methyl-1,3-thiazol-5-yl]carbonyl}-1,4'-bipiperidine | 405.17 | 406.36 |
| 569 | 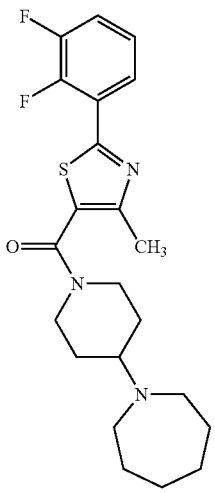 | 1-(1-{[2-(2,3-difluorophenyl)-4-methyl-1,3-thiazol-5-yl]carbonyl}piperidin-4-yl)azepane | 419.18 | 420.38 |
| 570 | 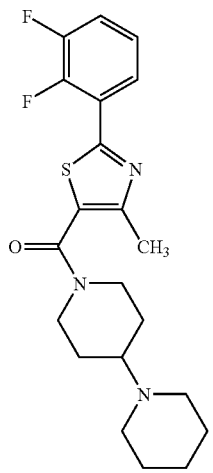 | 1'-{[2-(2,3-difluorophenyl)-4-methyl-1,3-thiazol-5-yl]carbonyl}-1,4'-bipiperidine | 405.17 | 406.36 |

TABLE I-continued
| | Compound | Name | MW | MS |
|---|---|---|---|---|
| 571 | 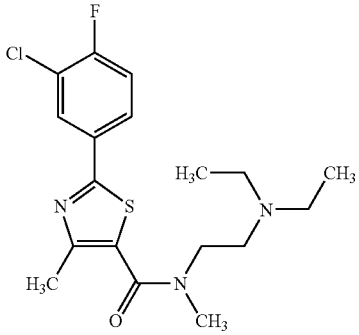 | 2-(3-chloro-4-fluorophenyl)-N-[2-(diethylamino)ethyl]-N,4-dimethyl-1,3-thiazole-5-carboxamide | 383.12 | 384.29 |
| 572 | 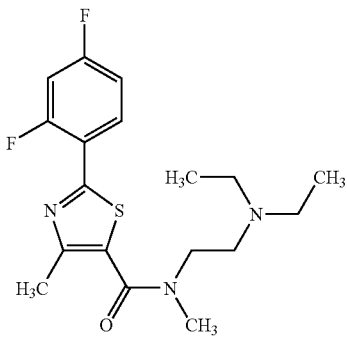 | N-[2-(diethylamino)ethyl]-2-(2,4-difluorophenyl)-N,4-dimethyl-1,3-thiazole-5-carboxamide | 367.15 | 368.31 |
| 573 | 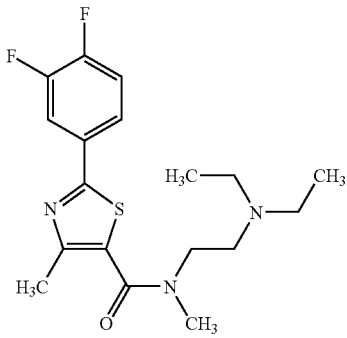 | N-[2-(diethylamino)ethyl]-2-(3,4-difluorophenyl)-N,4-dimethyl-1,3-thiazole-5-carboxamide | 367.15 | 368.31 |
| 574 | 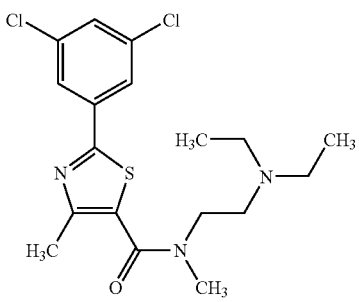 | 2-(3,5-dichlorophenyl)-N-[2-(diethylamino)ethyl]-N,4-dimethyl-1,3-thiazole-5-carboxamide | 399.09 | 400.28 |

TABLE I-continued

| | Compound | Name | MW | MS |
|---|---|---|---|---|
| 575 | 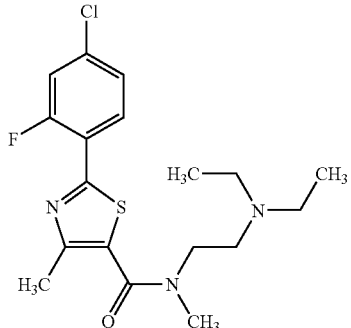 | 2-(4-chloro-2-fluorophenyl)-N-[2-(diethylamino)ethyl]-N,4-dimethyl-1,3-thiazole-5-carboxamide | 383.12 | 384.29 |
| 576 | 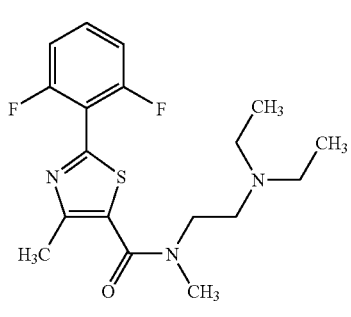 | N-[2-(diethylamino)ethyl]-2-(2,6-difluorophenyl)-N,4-dimethyl-1,3-thiazole-5-carboxamide | | |
| 577 | 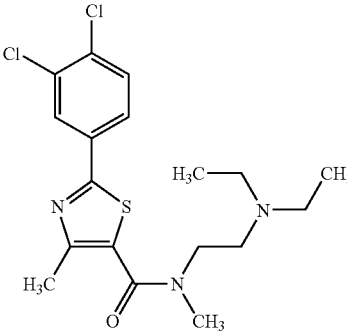 | 2-(3,4-dichlorophenyl)-N-[2-(diethylamino)ethyl]N,4-dimethyl-1,3-thiazole-5-carboxamide | 399.09 | 400.28 |
| 578 | 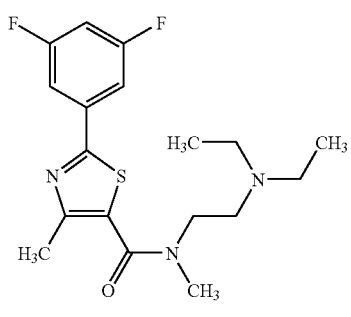 | N-[2-(diethylamino)ethyl]-2-(3,5-difluorophenyl)-N,4-dimethyl-1,3-thiazole-5-carboxamide | 367.15 | 368.32 |
| 579 | 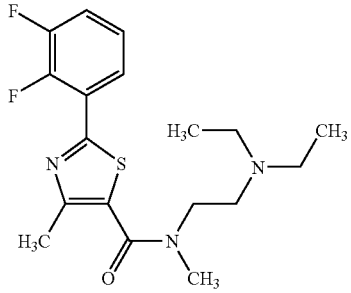 | N-[2-(diethylamino)ethyl]-2-(2,3-difluorophenyl)-N,4-dimethyl-1,3-thiazole-5-carboxamide | 367.15 | 368.32 |

TABLE I-continued

| Compound | | Name | MW | MS |
|---|---|---|---|---|
| 580 | | 2-(2-chlorophenyl)-4-methyl-N-(2-pyrrolidin-1-ylethyl)-1,3-thiazole-5-carboxamide | 349.10 | 350.14 |
| 581 | | 2-(2-chlorophenyl)-4-methyl-N-(2-piperidin-1-ylethyl)-1,3-thiazole-5-carboxamide | 363.12 | 364.16 |
| 582 | | 2-(2,3-dichlorophenyl)-4-methyl-N-(2-pyrrolidin-1-ylethyl)-1,3-thiazole-5-carboxamide | 383.06 | 384.11 |
| 583 | | 2-(2,3-dichlorophenyl)-N-[2-(diethylamino)ethyl]-4-methyl-1,3-thiazole-5-carboxamide | 385.08 | 386.12 |

TABLE I-continued
| Compound | | Name | MW | MS |
|---|---|---|---|---|
| 584 | 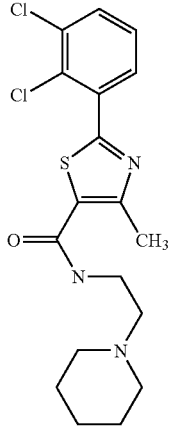 | 2-(2,3-dichlorophenyl)-4-methyl-N-(2-piperidin-1-ylethyl)-1,3-thiazole-5-carboxamide | 397.08 | 398.12 |
| 585 | 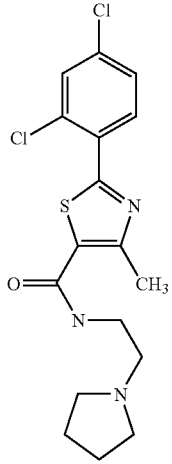 | 2-(2,4-dichlorophenyl)-4-methyl-N-(2-pyrrolidin-1-ylethyl)-1,3-thiazole-5-carboxamide | 383.06 | 384.11 |
| 586 | 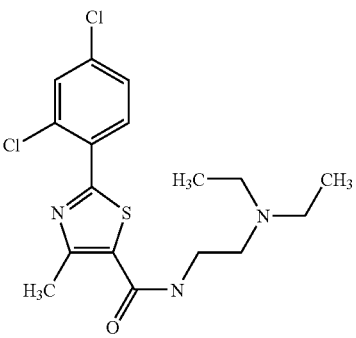 | 2-(2,4-dichlorophenyl)-N-[2-(diethylamino)ethyl]-4-methyl-1,3-thiazole-5-carboxamide | 385.08 | 386.12 |

TABLE I-continued
| | Compound | Name | MW | MS |
|---|---|---|---|---|
| 587 | 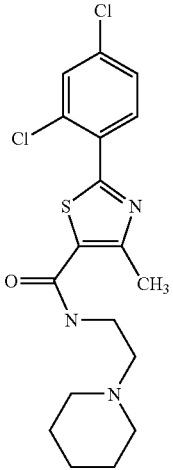 | 2-(2,4-dichlorophenyl)-4-methyl-N-(2-piperidin-1-ylethyl)-1,3-thiazole-5-carboxamide | 397.08 | 398.13 |
| 588 | 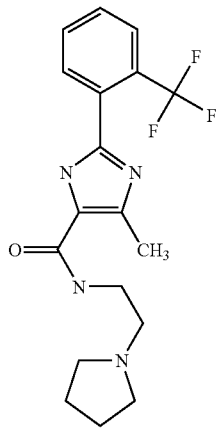 | 4-methyl-N-(2-pyrrolidin-1-ylethyl)-2-[2-(trifluoromethyl)phenyl]-1,3-thiazole-5-carboxamide | 383.13 | 384.17 |
| 589 | 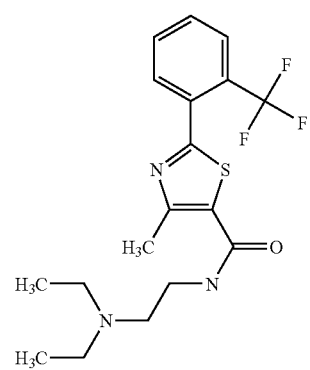 | N-[2-(diethylamino)ethyl]-4-methyl-2-[2-(trifluoromethyl)phenyl]-1,3-thiazole-5-carboxamide | 385.14 | 386.18 |

TABLE I-continued

| Compound | | Name | MW | MS |
|---|---|---|---|---|
| 590 | | 4-methyl-N-(2-piperidin-1-ylethyl)-2-[2-(trifluoromethyl)phenyl]-1,3-thiazole-5-carboxamide | 397.14 | 398.18 |
| 591 | | 2-(2,6-dimethoxyphenyl)-4-methyl-N-(2-pyrrolidin-1-ylethyl)-1,3-thiazole-5-carboxamide | 375.16 | 376.20 |
| 592 | | 2-(2-fluoro-4,6-dimethoxyphenyl)-4-methyl-N-(2-pyrrolidin-1-ylethyl)-1,3-thiazole-5-carboxamide | 393.15 | 394.21 |
| 593 | | 2-(2-fluoro-4,6-dimethoxyphenyl)-4-methyl-N-(2-piperidin-1-ylethyl)-1,3-thiazole-5-carboxamide | 407.17 | 408.23 |
| 594 | | 2-(2-isopropylphenyl)-4-methyl-N-(2-pyrrolidin-1-ylethyl)-1,3-thiazole-5-carboxamide | 357.19 | 358.23 |

TABLE I-continued
| | Compound | Name | MW | MS |
|---|---|---|---|---|
| 595 | 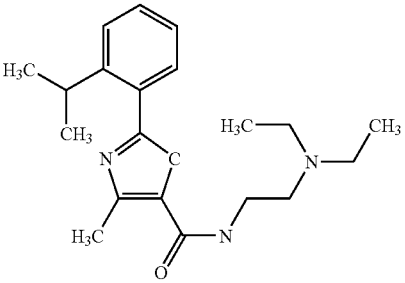 | N-[2-(diethylamino)ethyl]-2-(2-isopropylphenyl)-4-methyl-1,3-thiazole-5-carboxamide | 359.20 | 360.24 |
| 596 | 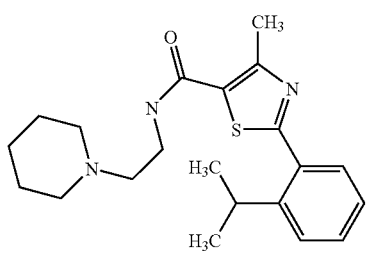 | 2-(2-isopropylphenyl)-4-methyl-N-(2-piperidin-1-ylethyl)-1,3-thiazole-5-carboxamide | 371.20 | 372.24 |
| 597 | 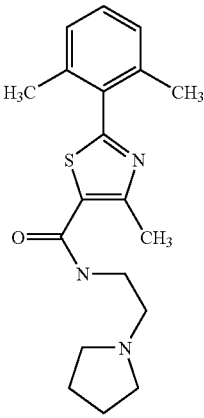 | 2-(2,6-dimethylphenyl)-4-methyl-N-(2-pyrrolidin-1-ylethyl)-1,3-thiazole-5-carboxamide | 343.17 | 344.23 |
| 598 | 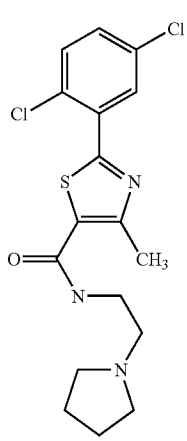 | 2-(2,5-dichlorophenyl)-4-methyl-N-(2-pyrrolidin-1-ylethyl)-1,3-thiazole-5-carboxamide | 383.06 | 384.12 |

TABLE I-continued

| Compound | | Name | MW | MS |
|---|---|---|---|---|
| 599 | | 2-(2,5-dichlorophenyl)-N-[2-(diethylamino)ethyl]-4-methyl-1,3-thiazole-5-carboxamide | 385.08 | 386.13 |
| 600 | | 2-(2,5-dichlorophenyl)-4-methyl-N-(2-piperidin-1-ylethyl)-1,3-thiazole-5-carboxamide | 397.08 | 398.14 |
| 601 | | 2-(2-chloro-6-fluoro-3-methylphenyl)-4-methyl-N-(2-pyrrolidin-1-ylethyl)-1,3-thiazole-5-carboxamide | 381.11 | 382.17 |
| 602 | | 2-(2-chloro-6-fluoro-3-methylphenyl)-N-[2-(diethylamino)ethyl]-4-methyl-1,3-thiazole-5-carboxamide | 383.13 | 384.19 |

TABLE I-continued

| Compound | | Name | MW | MS |
|---|---|---|---|---|
| 603 | | 2-(2-chloro-6-fluoro-3-methylphenyl)-4-methyl-N-(2-piperidin-1-ylethyl)-1,3-thiazole-5-carboxamide | 395.12 | 396.20 |
| 604 | | 2-mesityl-4-methyl-N-(2-piperidin-1-ylethyl)-1,3-thiazole-5-carboxamide | 371.20 | 372.26 |
| 605 | | 2-(2-chlorophenyl)-N-[2-(diisopropylamino)ethyl]-4-methyl-1,3-thiazole-5-carboxamide | 379.15 | 380.20 |
| 606 | | 2-(2,3-dichlorophenyl)-N-[2-(diisopropylamino)ethyl]-4-methyl-1,3-thiazole-5-carboxamide | 413.11 | 414.18 |

TABLE I-continued
| Compound | | Name | MW | MS |
|---|---|---|---|---|
| 607 | 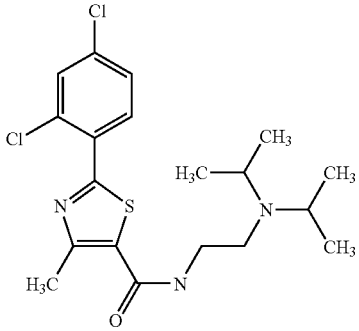 | 2-(2,4-dichlorophenyl)-N-[2-(diisopropylamino)ethyl]-4-methyl-1,3-thiazole-5-carboxamide | 413.11 | 414.17 |
| 608 | 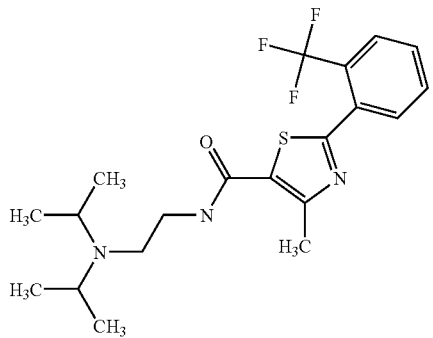 | N-[2-(diisopropylamino)ethyl]-4-methyl-2-[2-(trifluoromethyl)phenyl]-1,3-thiazole-5-carboxamide | 413.17 | 414.22 |
| 609 | 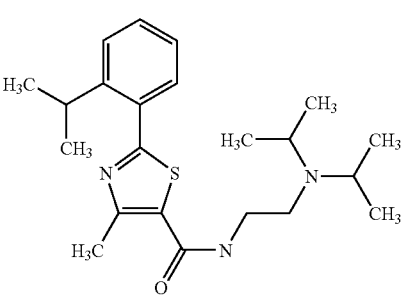 | N-[2-(diisopropylamino)ethyl]-2-(2-isopropylphenyl)-4-methyl-1,3-thiazole-5-carboxamide | 387.23 | 388.28 |
| 610 | 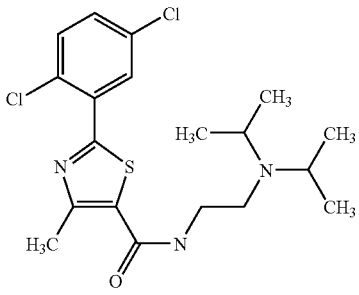 | 2-(2,5-dichlorophenyl)-N-[2-(diisopropylamino)ethyl]-4-methyl-1,3-thiazole-5-carboxamide | 413.11 | 414.18 |

TABLE I-continued
| | Compound | Name | MW | MS |
|---|---|---|---|---|
| 611 | 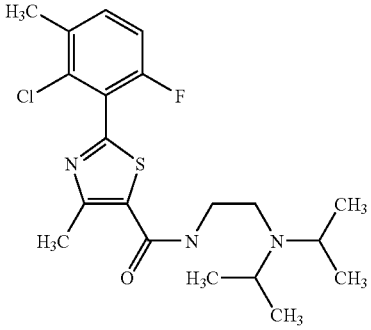 | 2-(2-chloro-6-fluoro-3-methylphenyl)-N-[2-(diisopropylamino)ethyl]-4-methyl-1,3-thiazole-5-carboxamide | 411.15 | 412.37 |
| 612 | 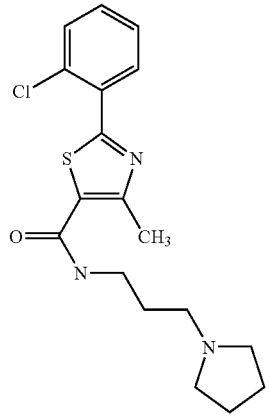 | 2-(2-chlorophenyl)-4-methyl-N-(3-pyrrolidin-1-ylpropyl)-1,3-thiazole-5-carboxamide | 363.12 | 364.18 |
| 613 | 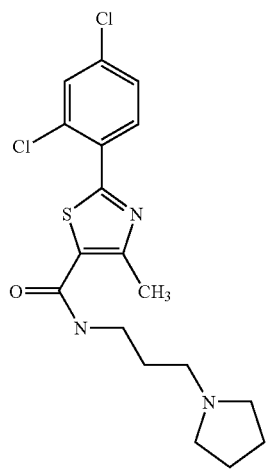 | 2-(2,4-dichlorophenyl)-4-methyl-N-(3-pyrrolidin-1-ylpropyl)-1,3-thiazole-5-carboxamide | 397.08 | 398.15 |

TABLE I-continued
| Compound | | Name | MW | MS |
|---|---|---|---|---|
| 614 | 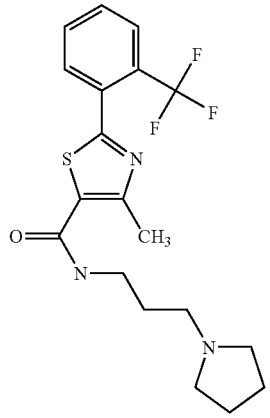 | 4-methyl-N-(3-pyrrolidin-1-ylpropyl)-2-[2-(trifluoromethyl)phenyl]-1,3-thiazole-5-carboxamide | 397.14 | 398.20 |
| 615 | 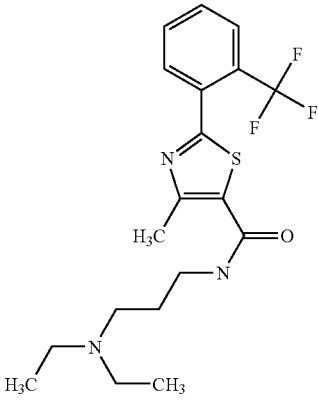 | N-[3-(diethylamino)propyl]-4-methyl-2-[2-(trifluoromethyl)phenyl]-1,3-thiazole-5-carboxamide | 399.16 | 400.21 |
| 616 | 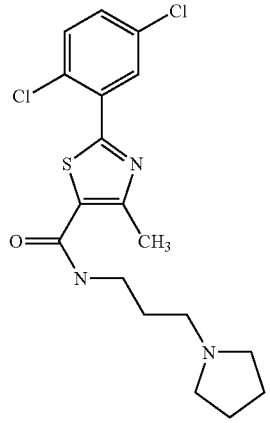 | 2-(2,5-dichlorophenyl)-4-methyl-N-(3-pyrrolidin-1-ylpropyl)-1,3-thiazole-5-carboxamide | 397.08 | 398.15 |

TABLE I-continued
| Compound | | Name | MW | MS |
|---|---|---|---|---|
| 617 | 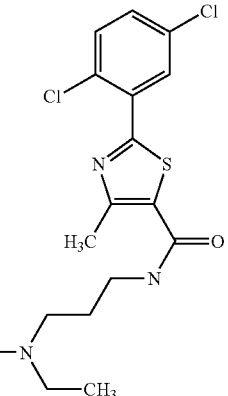 | 2-(2,5-dichlorophenyl)-N-[3-(diethylamino)propyl]-4-methyl-1,3-thiazole-5-carboxamide | 399.09 | 400.16 |
| 618 | 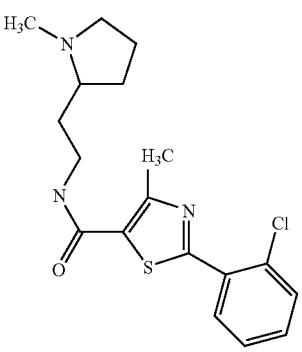 | 2-(2-chlorophenyl)-4-methyl-N-[2-(1-methylpyrrolidin-2-yl)ethyl]-1,3-thiazole-5-carboxamide | 363.12 | 364.18 |
| 619 | 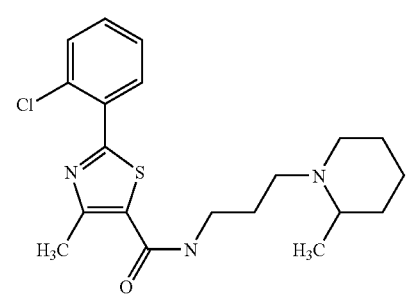 | 2-(2-chlorophenyl)-4-methyl-N-[3-(2-methylpiperidin-1-yl)propyl]-1,3-thiazole-5-carboxamide | 391.15 | 392.21 |
| 620 | 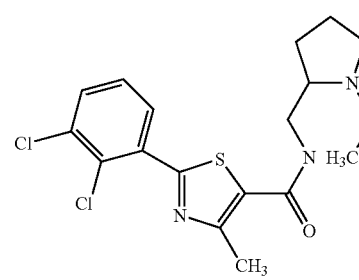 | 2-(2,3-dichlorophenyl)-N-[(1-ethylpyrrolidin-2-yl)methyl]-4-methyl-1,3-thiazole-5-carboxamide | 397.08 | 398.15 |

TABLE I-continued

| | Compound | Name | MW | MS |
|---|---|---|---|---|
| 621 | | 2-(2,3-dichlorophenyl)-4-methyl-N-[2-(1-methylpyrrolidin-2-yl)ethyl]-1,3-thiazole-5-carboxamide | 397.08 | 398.15 |
| 622 | | 2-(2,3-dichlorophenyl)-4-methyl-N-[3-(2-methylpiperidin-1-yl)propyl]-1,3-thiazole-5-carboxamide | 425.11 | 426.18 |
| 623 | | 2-(2,4-dichlorophenyl)-4-methyl-N-[2-(1-methylpyrrolidin-2-yl)ethyl]-1,3-thiazole-5-carboxamide | 397.08 | 398.16 |
| 624 | | 2-(2,4-dichlorophenyl)-4-methyl-N-[3-(2-methylpiperidin-1-yl)propyl]-1,3-thiazole-5-carboxamide | 425.11 | 426.19 |

TABLE I-continued

| Compound | Name | MW | MS |
|---|---|---|---|
| 625 | N-[(1-ethylpyrrolidin-2-yl)methyl]-4-methyl-2-[2-(trifluoromethyl)phenyl]-1,3-thiazole-5-carboxamide | 397.14 | 398.20 |
| 626 | 4-methyl-N-[2-(1-methylpyrrolidin-2-yl)ethyl]-2-[2-(trifluoromethyl)phenyl]-1,3-thiazole-5-carboxamide | 397.14 | 398.21 |
| 627 | 4-methyl-N-[3-(2-methylpiperidin-1-yl)propyl]-2-[2-(trifluoromethyl)phenyl]-1,3-thiazole-5-carboxamide | 425.17 | 426.24 |
| 628 | 2-(2,6-dimethoxyphenyl)-4-methyl-N-[2-(1-methylpyrrolidin-2-yl)ethyl]-1,3-thiazole-5-carboxamide | 389.18 | 390.25 |
| 629 | 2-(2,6-dimethoxyphenyl)-4-methyl-N-[3-(2-methylpiperidin-1-yl)propyl]-1,3-thiazole-5-carboxamide | 417.21 | 418.27 |

TABLE I-continued

| Compound | | Name | MW | MS |
|---|---|---|---|---|
| 630 | | 2-(2-fluoro-4,6-dimethoxyphenyl)-4-methyl-N-[2-(1-methylpyrrolidin-2-yl)ethyl]-1,3-thiazole-5-carboxamide | 407.17 | 408.25 |
| 631 | | 2-(2-fluoro-4,6-dimethoxyphenyl)-4-methyl-N-[3-(2-methylpiperidin-1-yl)propyl]-1,3-thiazole-5-carboxamide | 435.20 | 436.27 |
| 632 | | N-[(1-ethylpyrrolidin-2-yl)methyl]-2-(2-isopropylphenyl)-4-methyl-1,3-thiazole-5-carboxamide | 371.20 | 372.26 |
| 633 | | 2-(2-isopropylphenyl)-4-methyl-N-[2-(1-methylpyrrolidin-2-yl)ethyl]-1,3-thiazole-5-carboxamide | 371.20 | 372.26 |
| 634 | | 2-(2-isopropylphenyl)-4-methyl-N-[3-(2-methylpiperidin-1-yl)propyl]-1,3-thiazole-5-carboxamide | 399.23 | 400.30 |

TABLE I-continued

| Compound | | Name | MW | MS |
|---|---|---|---|---|
| 635 | | 2-(2,6-dimethylphenyl)-4-methyl-N-[2-(1-methylpyrrolidin-2-yl)ethyl]-1,3-thiazole-5-carboxamide | 357.19 | 358.27 |
| 636 | | 2-(2,6-dimethylphenyl)-4-methyl-N-[3-(2-methylpiperidin-1-yl)propyl]-1,3-thiazole-5-carboxamide | 385.22 | 386.30 |
| 637 | | 2-(2,5-dichlorophenyl)-4-methyl-N-[2-(1-methylpyrrolidin-2-yl)ethyl]-1,3-thiazole-5-carboxamide | 397.08 | 398.16 |
| 638 | | 2-(2,5-dichlorophenyl)-4-methyl-N-[3-(2-methylpiperidin-1-yl)propyl]-1,3-thiazole-5-carboxamide | 425.11 | 426.20 |

TABLE I-continued

| | Compound | Name | MW | MS |
|---|---|---|---|---|
| 639 | | 2-(2-chloro-6-fluoro-3-methylphenyl)-4-methyl-N-[2-(1-methylpyrrolidin-2-yl)ethyl]-1,3-thiazole-5-carboxamide | 395.12 | 396.19 |
| 640 | | 2-(2-chloro-6-fluoro-3-methylphenyl)-4-methyl-N-[3-(2-methylpiperidin-1-yl)propyl]-1,3-thiazole-5-carboxamide | 423.15 | 424.22 |
| 641 | | 2-mesityl-4-methyl-N-[2-(1-methylpyrrolidin-2-yl)ethyl]-1,3-thiazole-5-carboxamide | 371.20 | 372.26 |
| 642 | | 2-mesityl-4-methyl-N-[3-(2-methylpiperidin-1-yl)propyl]-1,3-thiazole-5-carboxamide | 399.23 | 400.29 |

TABLE I-continued
| Compound | Name | MW | MS |
|---|---|---|---|
| 643 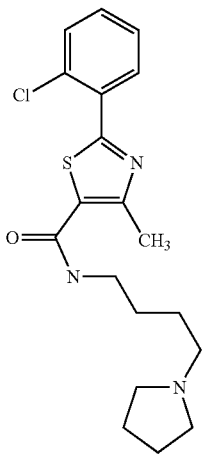 | 2-(2-chlorophenyl)-4-methyl-N-(4-pyrrolidin-1-ylbutyl)-1,3-thiazole-5-carboxamide | 377.13 | 378.19 |
| 644 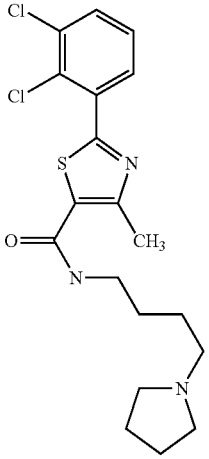 | 2-(2,3-dichlorophenyl)-4-methyl-N-(4-pyrrolidin-1-ylbutyl)-1,3-thiazole-5-carboxamide | 411.09 | 412.15 |
| 645 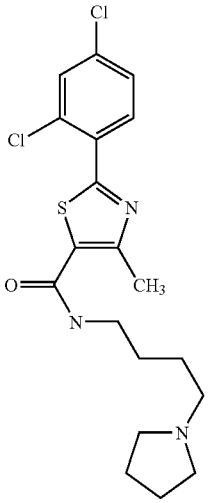 | 2-(2,4-dichlorophenyl)-4-methyl-N-(4-pyrrolidin-1-ylbutyl)-1,3-thiazole-5-carboxamide | 411.09 | 412.15 |

TABLE I-continued

| | Compound | Name | MW | MS |
|---|---|---|---|---|
| 646 | | 4-methyl-N-(4-pyrrolidin-1-ylbutyl)-2-[2-(trifluoromethyl)phenyl]-1,3-thiazole-5-carboxamide | 411.16 | 412.20 |
| 647 | | 2-(2-fluoro-4,6-dimethoxyphenyl)-4-methyl-N-(4-pyrrolidin-1-ylbutyl)-1,3-thiazole-5-carboxamide | 421.18 | 422.23 |
| 648 | | 2-(2-isopropylphenyl)-4-methyl-N-(4-pyrrolidin-1-ylbutyl)-1,3-thiazole-5-carboxamide | 385.22 | 386.26 |
| 649 | | 2-(2,6-dimethylphenyl)-4-methyl-N-(4-pyrrolidin-1-ylbutyl)-1,3-thiazole-5-carboxamide | 371.20 | 372.25 |

TABLE I-continued

| | Compound | Name | MW | MS |
|---|---|---|---|---|
| 650 | | 2-(2,5-dichlorophenyl)-4-methyl-N-(4-pyrrolidin-1-ylbutyl)-1,3-thiazole-5-carboxamide | 411.09 | 412.15 |
| 651 | | 2-mesityl-4-methyl-N-(4-pyrrolidin-1-ylbutyl)-1,3-thiazole-5-carboxamide | 385.22 | 386.27 |
| 652 | | 3-{5-[(4-isopropylpiperazin-1-yl)carbonyl]-4-methyl-1,3-thiazol-2-yl}benzonitrile | 354.15 | 355.29 |
| 653 | | 3-{5-[(4-cyclopentylpiperazin-1-yl)carbonyl]-4-methyl-1,3-thiazole-2-yl}benzonitrile | 380.17 | 381.31 |

TABLE I-continued

| Compound | Name | MW | MS |
|---|---|---|---|
| 654 | 3-{5-[(4-butyl-1,4-diazepan-1-yl)carbonyl]-4-methyl-1,3-thiazol-2-yl}benzonitrile | 382.18 | 383.33 |
| 655 | 4-{5-[(4-isopropylpiperazin-1-yl)carbonyl]-4-methyl-1,3-thiazol-2-yl}benzonitrile | 354.15 | 355.29 |
| 656 | 4-{5-[(4-cyclopentylpiperazin-1-yl)carbonyl]-4-methyl-1,3-thiazol-2-yl}benzonitrile | 380.17 | 381.31 |
| 657 | 1-isopropyl-4-({4-methyl-2-[4-(trifluoromethyl)phenyl]-1,3-thiazol-5-yl}carbonyl)piperazine | 397.14 | 398.30 |

TABLE I-continued
| Compound | | Name | MW | MS |
|---|---|---|---|---|
| 658 | 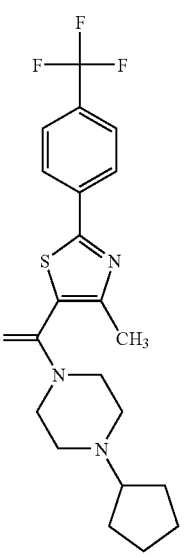 | 1-cyclopentyl-4-({4-methyl-2-[4-(trifluoromethyl)phenyl]-1,3-thiazol-5-yl}carbonyl)piperazine | 423.16 | 424.32 |
| 659 | 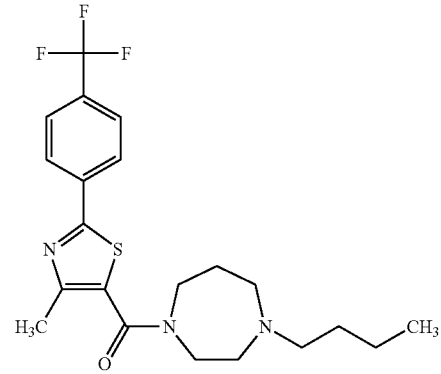 | 1-butyl-4-({4-methyl-2-[4-(trifluoromethyl)phenyl]-1,3-thiazol-5-yl}carbonyl)-1,4-diazepane | 425.17 | 426.33 |
| 660 | 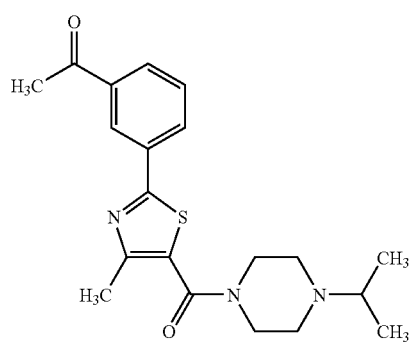 | 1-(3-{5-[(4-isopropylpiperazin-1-yl)carbonyl]-4-methyl-1,3-thiazol-2-yl}phenyl)ethanone | 371.17 | 372.31 |

TABLE I-continued
| | Compound | Name | MW | MS |
|---|---|---|---|---|
| 661 | 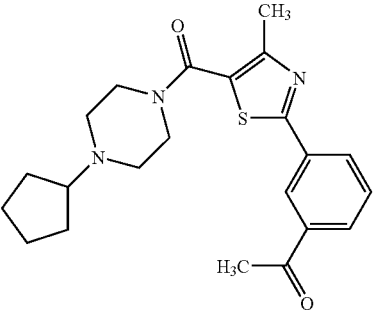 | 1-(3-{5-[(4-cyclopentylpiperazin-1-yl)carbonyl]-4-methyl-1,3-thiazol-2-yl}phenyl)ethanone | 397.18 | 398.34 |
| 662 | 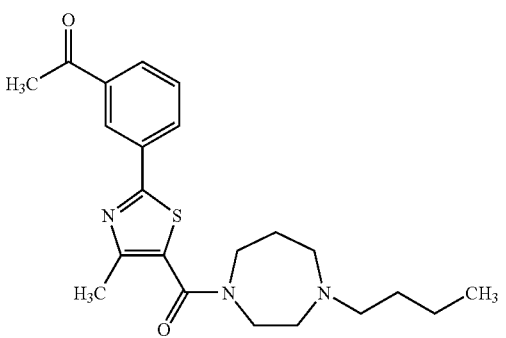 | 1-(3-{5-[(4-butyl-1,4-diazepan-1-yl)carbonyl]-4-methyl-1,3-thiazol-2-yl}phenyl)ethanone | 399.20 | 400.35 |
| 663 | 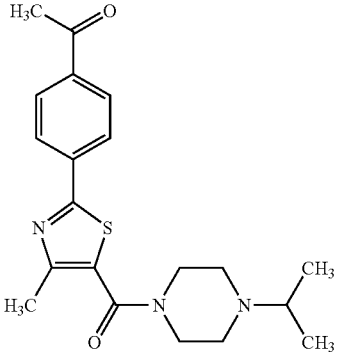 | 1-(4-{5-[(4-isopropylpiperazin-1-yl)carbonyl]-4-methyl-1,3-thiazol-2-yl}phenyl)ethanone | 371.17 | 372.31 |
| 664 | 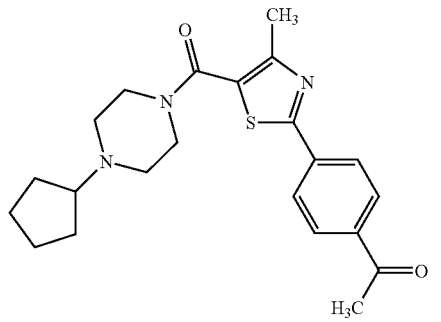 | 1-(4-{5-[(4-cyclopentylpiperazin-1-yl)carbonyl]-4-methyl-1,3-thiazol-2-yl}phenyl)ethanone | 397.18 | 398.34 |

TABLE I-continued
| | Compound | Name | MW | MS |
|---|---|---|---|---|
| 665 | 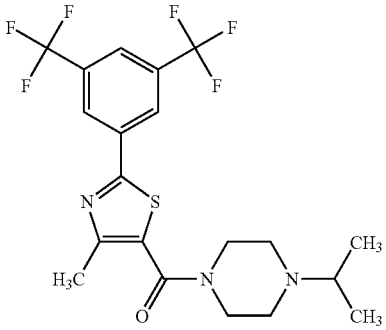 | 1-({2-[3,5-bis(trifluoromethyl)phenyl]-4-methyl-1,3-thiazol-5-yl}carbonyl)-4-isopropylpiperazine | 465.13 | 466.31 |
| 666 | 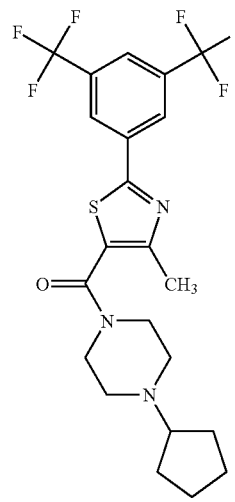 | 1-({2-[3,5-bis(trifluoromethyl)phenyl]-4-methyl-1,3-thiazol-5-yl}carbonyl)-4-cyclopentylpiperazine | 491.15 | 492.34 |
| 667 | 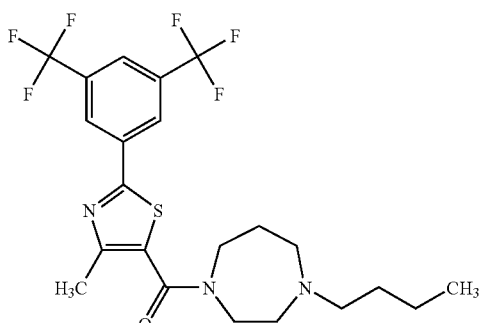 | 1-({2-[3,5-bis(trifluoromethyl)phenyl]-4-methyl-1,3-thiazol-5-yl}carbonyl)-4-butyl-1,4-diazepane | 493.16 | 494.34 |
| 668 | 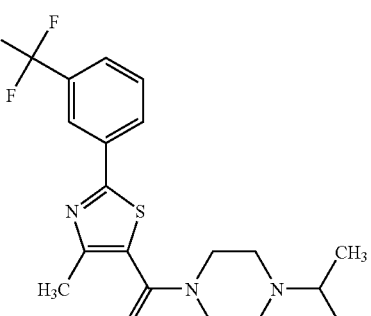 | 1-isopropyl-4-({4-methyl-2-[3-(trifluoromethyl)phenyl]-1,3-thiazol-5-yl}carbonyl)piperazine | 397.14 | 398.30 |

TABLE I-continued
| Compound | Name | MW | MS |
|---|---|---|---|
| 669 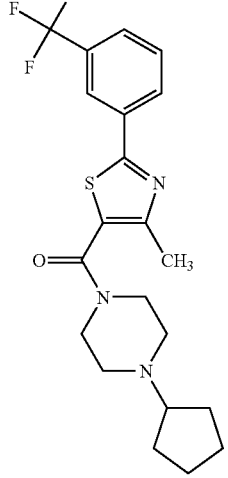 | 1-cyclopentyl-4-({4-methyl-2-[3-(trifluoromethyl)phenyl]-1,3-thiazol-5-yl}carbonyl)piperazine | 423.16 | 424.32 |
| 670 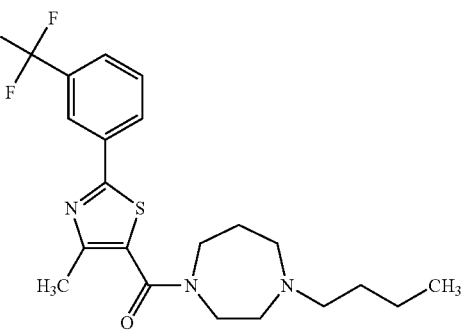 | 1-butyl-4-({4-methyl-2-[3-(trifluoromethyl)phenyl]-1,3-thiazol-5-yl}carbonyl)-1,4-diazepane | 425.17 | 426.33 |
| 671 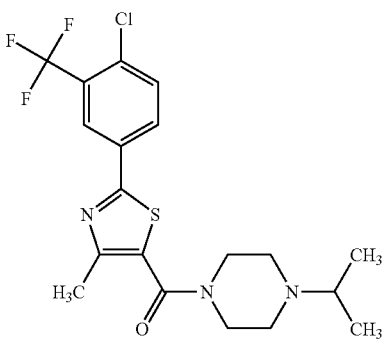 | 1-({2-[4-chloro-3-(trifluoromethyl)phenyl]-4-methyl-1,3-thiazol-5-yl}carbonyl)-4-isopropylpiperazine | 431.10 | 432.27 |

TABLE I-continued
| | Compound | Name | MW | MS |
|---|---|---|---|---|
| 672 | 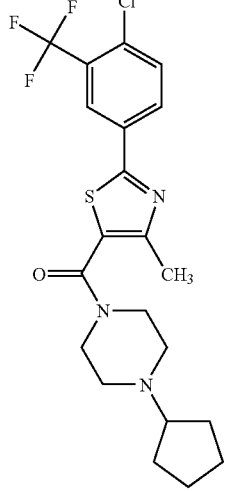 | 1-({2-[4-chloro-3-(trifluoromethyl)phenyl]-4-methyl-1,3-thiazol-5-yl}carbonyl)-4-cyclopentylpiperazine | 457.12 | 458.30 |
| 673 | 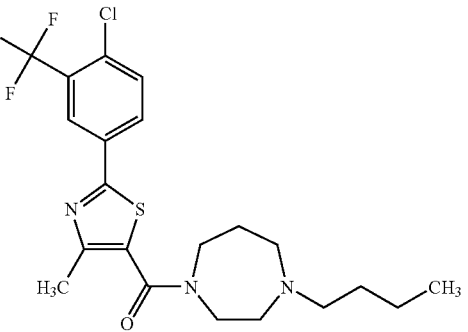 | 1-butyl-4-({2-[4-chloro-3-(trifluoromethyl)phenyl]-4-methyl-1,3-thiazol-5-yl}carbonyl)-1,4-diazepane | 459.14 | 460.31 |
| 674 | 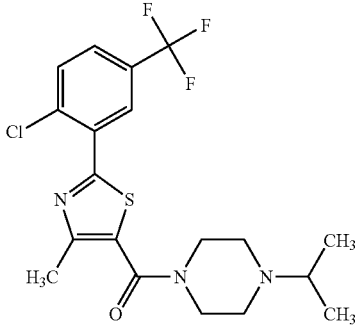 | 1-({2-[2-chloro-5-(trifluoromethyl)phenyl]-4-methyl-1,3-thiazol-5-yl}carbonyl)-4-isopropylpiperazine | 431.10 | 432.27 |

TABLE I-continued

| Compound | Name | MW | MS |
|---|---|---|---|
| 675 | 1-({2-[2-chloro-5-(trifluoromethyl)phenyl]-4-methyl-1,3-thiazol-5-yl}carbonyl)-4-cyclopentylpiperazine | 457.12 | 458.30 |
| 676 | 1-butyl-4-({2-[2-chloro-5-(trifluoromethyl)phenyl]-4-methyl-1,3-thiazol-5-yl}carbonyl)-4-diazepane | 459.14 | 460.31 |
| 677 | ethyl 4-{5-[(4-isopropylpiperazin-1-yl)carbonyl]-4-methyl-1,3-thiazol-2 yl}benzoate | 401.18 | 402.33 |
| 678 | ethyl 4-{5-[(4-cyclopentylpiperazin 1-yl)carbonyl]-4-methyl-1,3-thiazol 2-yl}benzoate | 427.19 | 428.36 |

TABLE I-continued

| Compound | Name | MW | MS |
|---|---|---|---|
| 679 | ethyl 3-{5-[(4-isopropylpiperazin-1-yl)carbonyl]-4-methyl-1,3-thiazol-2-yl}benzoate | 401.18 | 402.33 |
| 680 | ethyl 3-{5-[(4-cyclopentylpiperazin-1-yl)carbonyl]-4-methyl-1,3-thiazol-2-yl}benzoate | 427.19 | 428.36 |
| 681 | 1-({2-[2-chloro-5-(trifluoromethyl)phenyl]-4-methyl-1,3-thiazol-5-yl}carbonyl)-N,N-diethylpiperidin-4-amine | 459.14 | 460.30 |
| 682 | 3-{5-[(4-azepan-1-ylpiperidin-1-yl)carbonyl]-4-methyl-1,3-thiazol-2-yl}benzonitrile | 408.20 | 409.36 |

TABLE I-continued

| Compound | Name | MW | MS |
|---|---|---|---|
| 683 | 4-{5-[(4-azepan-1-ylpiperidin-1-yl)carbonyl]-4-methyl-1,3-thiazol-2-yl}benzonitrile | 408.20 | 409.36 |
| 684 | 4-[5-(1,4'-bipiperidin-1'-ylcarbonyl)-4-methyl-1,3-thiazol-2-yl]benzonitrile | 394.18 | 395.34 |
| 685 | 1-[1-({4-methyl-2-[4-(trifluoromethyl)phenyl]-1,3-thiazol-5-yl}carbonyl)piperidin-4-yl]azepane | 451.19 | 452.36 |
| 686 | 1-(3-{5-[(4-azepan-1-ylpiperidin-1-yl)carbonyl]-4-methyl-1,3-thiazol-2-yl}phenyl)ethanone | 425.21 | 426.38 |
| 687 | 1-{3-[5-(1,4'-bipiperidin-1'-ylcarbonyl)-4-methyl-1,3-thiazol-2-yl]phenyl}ethanone | 411.20 | 412.36 |

TABLE I-continued
| Compound | | Name | MW | MS |
|---|---|---|---|---|
| 688 | 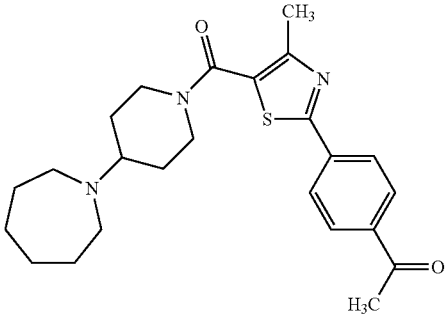 | 1-(4-{5-[(4-azepan-1-ylpiperidin-1-yl)carbonyl]-4-methyl-1,3-thiazol-2-yl}phenyl)ethanone | 425.21 | 426.38 |
| 689 | 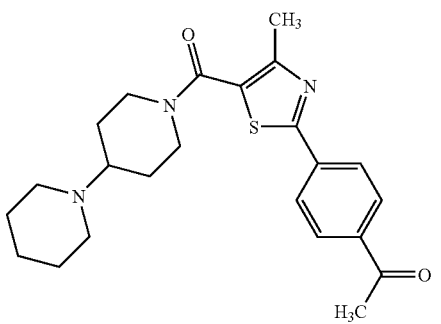 | 1-{4-[5-(1,4'-bipiperidin-1'-ylcarbonyl)-4-methyl-1,3-thiazol-2-yl]phenyl}ethanone | 411.20 | 412.36 |
| 690 | 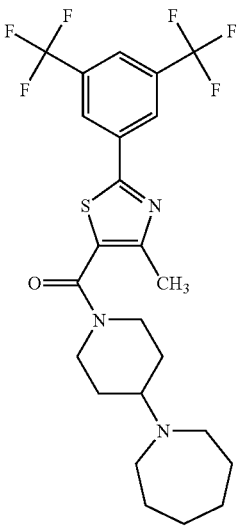 | 1-[1-({2-[3,5-bis(trifluoromethyl)phenyl]-4-methyl-1,3-thiazol-5-yl}carbonyl)piperidin-4-yl]azepane | 519.18 | 520.37 |

TABLE I-continued
| Compound | | Name | MW | MS |
|---|---|---|---|---|
| 691 | 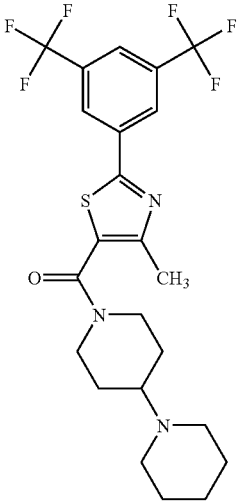 | 1'-({2-[3,5-bis(trifluoromethyl)phenyl]-4-methyl-1,3-thiazol-5-yl}carbonyl)-1,4'-bipiperidine | 505.16 | 506.36 |
| 692 | 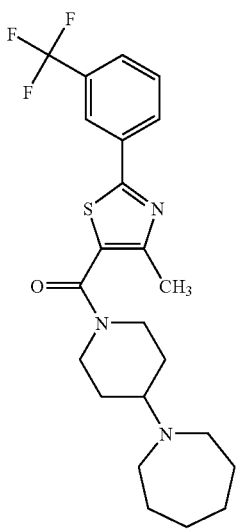 | 1-[1-({4-methyl-2-[3-(trifluoromethyl)phenyl]-1,3-thiazol-5-yl}carbonyl)piperidin-4-yl]azepane | 451.19 | 452.36 |
| 693 | 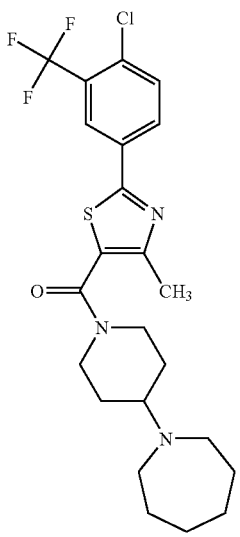 | 1-[1-({2-[4-chloro-3-(trifluoromethyl)phenyl]-4-methyl-1,3-thiazol-5-yl}carbonyl)piperidin-4-yl]azepane | 485.15 | 486.34 |

TABLE I-continued
| Compound | | Name | MW | MS |
|---|---|---|---|---|
| 694 | 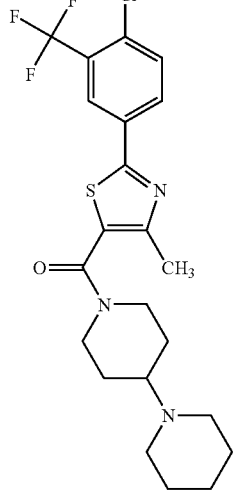 | 1'-({2-[4-chloro-3-(trifluoromethyl)phenyl]-4-methyl-1,3-thiazol-5-yl}carbonyl)-1,4'-bipiperidine | 471.14 | 472.32 |
| 695 | 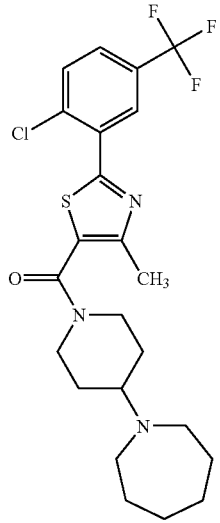 | 1-[1-({2-[2-chloro-5-(trifluoromethyl)phenyl]-4-methyl-1,3-thiazol-5-yl}carbonyl)piperidin-4-yl]azepane | 485.15 | 486.34 |
| 696 | 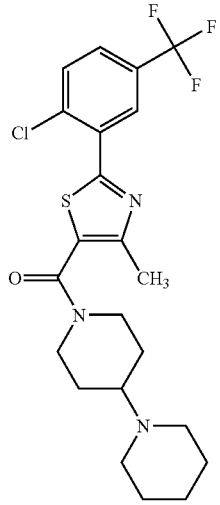 | 1'-([2-[2-chloro-5-(trifluoromethyl)phenyl]-4-methyl-1,3-thiazol-5-yl}carbonyl)-1,4'-bipiperidine | 471.14 | 472.32 |

TABLE I-continued

| Compound | Name | MW | MS |
|---|---|---|---|
| 697 | ethyl 4-{5-[(4-azepan-1-ylpiperidin-1-yl)carbonyl]-4-methyl-1,3-thiazol-2-yl}benzoate | 455.22 | 456.40 |
| 698 | ethyl 4-[5-(1,4'-bipiperidin-1'-ylcarbonyl)-4-methyl-1,3-thiazol-2-yl]benzoate | 441.21 | 442.38 |
| 699 | 1-({2-[2-chloro-5-(trifluoromethyl)phenyl]-4-methyl-1,3-thiazol-5-yl}carbonyl)-N-(cyclopropylmethyl)-N-propylpiperidin-4-amine | 499.17 | 500.36 |
| 700 | 2-(4-cyanophenyl)-N-[2-(diethylamino)ethyl]-N,4-dimethyl-1,3-thiazole-5-carboxamide | 356.17 | 357.30 |

TABLE I-continued
| Compound | | Name | MW | MS |
|---|---|---|---|---|
| 701 | 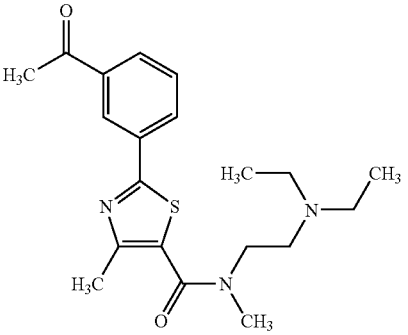 | 2-(3-acetylphenyl)-N-[2-(diethylamino)ethyl]-N,4-dimethyl-1,3-thiazole-5-carboxamide | 373.18 | 374.33 |
| 702 | 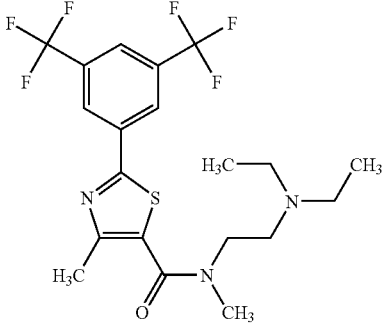 | 2-[3,5-bis(trifluoromethyl)phenyl]-N-[2-(diethylamino)ethyl]-N,4-dimethyl-1,3-thiazole-5-carboxamide | 467.15 | 468.30 |
| 703 | 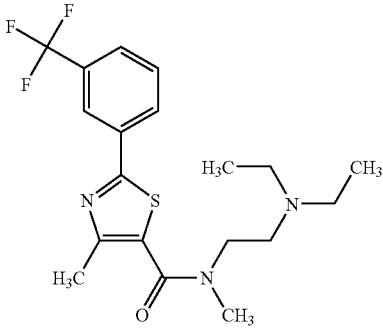 | N-[2-(diethylamino)ethyl]-N,4-dimethyl-2-[3-(trifluoromethyl)phenyl]-1,3-thiazole-5-carboxamide | 399.16 | 400.30 |
| 704 | 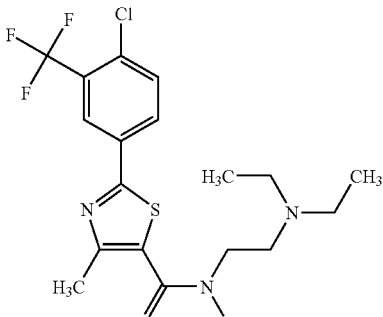 | 2-[4-chloro-3-(trifluoromethyl)phenyl]-N-[2-(diethylamino)ethyl]-N,4-dimethyl-1,3-thiazole-5-carboxamide | 433.12 | 434.28 |

TABLE I-continued

| | Compound | Name | MW | MS |
|---|---|---|---|---|
| 705 | | 2-[2-chloro-5-(trifluoromethyl)phenyl]-N-[2-(diethylamino)ethyl]-N,4-dimethyl-1,3-thiazole-5-carboxamide | 433.12 | 434.28 |
| 706 | | 1-ethyl-4-({4-methyl-2-[2-(trifluoromethyl)phenyl]-1,3-thiazol-5-yl}carbonyl)piperazine | 383.13 | 384.10 |
| 707 | | 1-ethyl-4-{[2-(2-isopropylphenyl)-4-methyl-1,3-thiazol-5-yl]carbonyl}piperazine | 357.19 | 358.16 |
| 708 | | 1-{[2-(2,5-dichlorophenyl)-4-methyl-1,3-thiazol-5-yl]carbonyl}-4-ethylpiperazine | 383.06 | 384.04 |
| 709 | | 1-{[2-(2-chlorophenyl)-4-methyl-1,3-thiazol-5-yl]carbonyl}-4-isopropylpiperazine | 363.12 | 364.10 |

TABLE I-continued

| Compound | | Name | MW | MS |
|---|---|---|---|---|
| 710 | | 1-{[2-(2-chlorophenyl)-4-methyl-1,3-thiazol-5-yl]carbonyl}-4-cyclopentylpiperazine | 389.13 | 390.10 |
| 711 | | 1-butyl-4-{[2-(2-chlorophenyl)-4-methyl-1,3-thiazol-5-yl]carbonyl}-1,4-diazepane | 391.15 | 392.12 |
| 712 | | 1-{[2-(2,3-dichlorophenyl)-4-methyl-1,3-thiazol-5-yl]carbonyl}-4-isopropylpiperazine | 397.08 | 398.06 |
| 713 | | 1-cyclopentyl-4-{[2-(2,3-dichlorophenyl)-4-methyl-1,3-thiazol-5-yl]carbonyl}piperazine | 423.09 | 424.09 |

TABLE I-continued
| | Compound | Name | MW | MS |
|---|---|---|---|---|
| 714 | 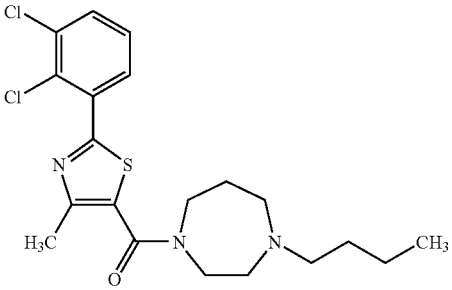 | 1-butyl-4-{[2-(2,3-dichlorophenyl)-4-methyl-1,3-thiazol-5-yl]carbonyl}-1,4-diazepane | 425.11 | 426.09 |
| 715 | 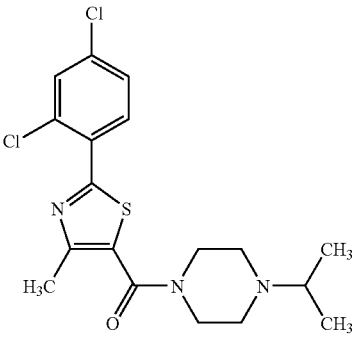 | 1-{[2-(2,4-dichlorophenyl)-4-methyl-1,3-thiazol-5-yl]carbonyl}-4-isopropylpiperazine | 397.08 | 398.05 |
| 716 | 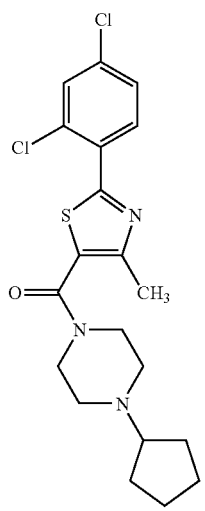 | 1-cyclopentyl-4-{[2-(2,4-dichlorophenyl)-4-methyl-1,3-thiazol-5-yl]carbonyl}piperazine | 423.09 | 424.08 |
| 717 | 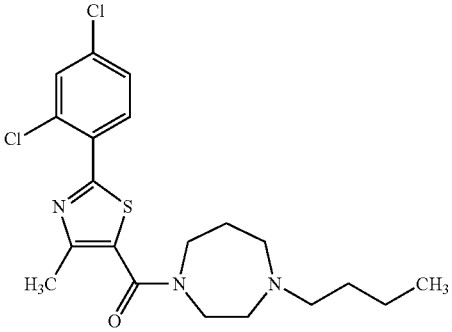 | 1-butyl-4-{[2-(2,4-dichlorophenyl)-4-methyl-1,3-thiazol-5-yl]carbonyl}-1,4-diazepane | 425.11 | 426.09 |

TABLE I-continued

| Compound | Name | MW | MS |
|---|---|---|---|
| 718 | 1-isopropyl-4-({4-methyl-2-[2-(trifluoromethyl)phenyl]-1,3-thiazol-5-yl}carbonyl)piperazine | 397.14 | 398.11 |
| 719 | 1-cyclopentyl-4-({4-methyl-2-[2-(trifluoromethyl)phenyl]-1,3-thiazol-5-yl}carbonyl)piperazine | 423.16 | 424.13 |
| 720 | 1-butyl-4-({4-methyl-2-[2-(trifluoromethyl)phenyl]-1,3-thiazol-5-yl}carbonyl)-1,4-diazepane | 425.17 | 426.14 |
| 721 | 1-{[2-(2,6-dimethoxyphenyl)-4-methyl-1,3-thiazol-5-yl]carbonyl}-4-isopropylpiperazine | 398.18 | 390.15 |
| 722 | 1-cyclopentyl-4-{[2-(2,6-dimethoxyphenyl)-4-methyl-1,3-thiazol-5-yl]carbonyl}piperazine | 415.19 | 416.17 |

TABLE I-continued

| Compound | | Name | MW | MS |
|---|---|---|---|---|
| 723 | | 1-butyl-4-{[2-(2,6-dimethoxyphenyl)-4-methyl-1,3-thiazol-5-yl]carbonyl}-1,4-diazepane | 417.21 | 418.18 |
| 724 | | 1-{[2-(2-fluoro-4,6-dimethoxyphenyl)-4-methyl-1,3-thiazol-5-yl]carbonyl}-1,4-isopropylpiperazine | 407.17 | 408.15 |
| 725 | | 1-cyclopentyl-4-{[2-(2-fluoro-4,6-dimethoxyphenyl)-4-methyl-1,3-thiazol-5-yl]carbonyl}piperazine | 433.18 | 434.17 |
| 726 | | 1-butyl-4-{[2-(2-fluoro-4,6-dimethoxyphenyl)-4-methyl-1,3-thiazol-5-yl]carbonyl}-1,4-diazepane | 435.20 | 436.18 |

TABLE I-continued

| | Compound | Name | MW | MS |
|---|---|---|---|---|
| 727 | | 1-isopropyl-4-{[2-(2-isopropylphenyl)-4-methyl-1,3-thiazol-5-yl]carbonyl}piperazine | 371.20 | 372.17 |
| 728 | | 1-cyclopentyl-4-{[2-(2-isopropylphenyl)-4-methyl-1,3-thiazol-5-yl]carbonyl}piperazine | 397.22 | 398.19 |
| 729 | | 1-butyl-4-{[2-(2-isopropylphenyl)-4-methyl-1,3-thiazol-5-yl]carbonyl}-1,4-diazepane | 399.23 | 400.20 |
| 730 | | 1-{[2-(2,6-dimethylphenyl)-4-methyl-1,3-thiazol-5-yl]carbonyl}-4-isopropylpiperazine | 357.19 | 358.20 |

TABLE I-continued

| | Compound | Name | MW | MS |
|---|---|---|---|---|
| 731 | | 1-cyclopentyl-4-{[2-(2,6-dimethylphenyl)-4-methyl-1,3-thiazol-5-yl]carbonyl}piperazine | | |
| 732 | | 1-butyl-4-{[2-(2,6-dimethylphenyl)-4-methyl-1,3-thiazol-5-yl]carbonyl}-1,4-diazepane | 385.22 | 386.22 |
| 733 | | 1-{[2-(2,5-dichlorophenyl)-4-methyl-1,3-thiazol-5-yl]carbonyl}-4-isopropylpiperazine | 397.08 | 398.05 |
| 734 | | 1-cyclopentyl-4-{[2-(2,5-dichlorophenyl)-4-methyl-1,3-thiazol-5-yl]carbonyl}piperazine | 423.09 | 424.07 |

TABLE I-continued

| | Compound | Name | MW | MS |
|---|---|---|---|---|
| 735 | | 1-butyl-4-{[2-(2,5-dichlorophenyl)-4-methyl-1,3-thiazol-5-yl]carbonyl}-1,4-diazepane | 425.11 | 426.09 |
| 736 | | 1-{[2-(2-chloro-5-fluoro-3-methylphenyl)-4-methyl-1,3-thiazol-5-yl]carbonyl}-4-isopropylpiperazine | 395.12 | 396.13 |
| 737 | | 1-{[2-(2-chloro-5-fluoro-3-methylphenyl)-4-methyl-1,3-thiazol-5-yl]carbonyl}-4-cyclopentylpiperazine | | |
| 738 | | 1-isopropyl-4-[(2-mesityl-4-methyl-1,3-thiazol-5-yl)carbonyl]piperazine | 371.20 | 372.21 |

TABLE I-continued

| Compound | Name | MW | MS |
|---|---|---|---|
| 739 | 1-cyclopentyl-4-[(2-mesityl-4-methyl-1,3-thiazol-5-yl)carbonyl]piperazine | | |
| 740 | 1-{[2-(2-chlorophenyl)-4-methyl-1,3-thiazol-5-yl]carbonyl}-N,N-diethylpiperidin-4-amine | 391.15 | 392.31 |
| 741 | 1-{[2-(2-chlorophenyl)-4-methyl-1,3-thiazol-5-yl]carbonyl}-N,N-diethylpyrrolidin-3-amine | 377.13 | 378.28 |
| 742 | 1-{[2-(2,3-dichlorophenyl)-4-methyl-1,3-thiazol-5-yl]carbonyl}-N,N-diethylpiperidin-4-amine | 425.11 | 426.28 |
| 743 | 1-{[2-(2,3-dichlorophenyl)-4-methyl-1,3-thiazol-5-yl]carbonyl}-N,N-diethylpyrrolidin-3-amine | 411.09 | 412.26 |

TABLE I-continued

| Compound | | Name | MW | MS |
|---|---|---|---|---|
| 744 | | 1-{[2-(2,4-dichlorophenyl)-4-methyl-1,3-thiazol-5-yl]carbonyl}-N,N-diethylpiperidin-4-amine | 425.11 | 426.28 |
| 745 | | 1-{[2-(2,4-dichlorophenyl)-4-methyl-1,3-thiazol-5-yl]carbonyl}-N,N-diethylpyrrolidin-3-amine | 411.09 | 412.27 |
| 746 | | N,N-diethyl-1-({4-methyl-2-[2-(trifluoromethyl)phenyl]-1,3-thiazol-5-yl}carbonyl)piperidin-4-amine | 425.17 | 426.34 |
| 747 | | N,N-dimethyl-1-({4-methyl-2-[2-(trifluoromethyl)phenyl]-1,3-thiazol-5-yl}carbonyl)pyrrolidin-3-amine | 383.13 | 384.28 |
| 748 | | N,N-diethyl-1-({4-methyl-2-[2-(trifluoromethyl)phenyl]-1,3-thiazol-5-yl}carbonyl)pyrrolidin-3-amine | 411.16 | 412.33 |

TABLE I-continued

| | Compound | Name | MW | MS |
|---|---|---|---|---|
| 749 | | N,N-diethyl-1-{[2-(2-fluoro-4,6-dimethoxyphenyl)-4-methyl-1,3-thiazol-5-yl]carbonyl}piperidin-4-amine | 435.20 | 436.37 |
| 750 | | N,N-diethyl-1-{[2-(2-fluoro-4,6-dimethoxyphenyl)-4-methyl-1,3-thiazol-5-yl]carbonyl}pyrrolidin-3-amine | 521.18 | 422.35 |
| 751 | | N,N-diethyl-1-{[2-(2-isopropylphenyl)-4-methyl-1,3-thiazol-5-yl]carbonyl}piperidin-4-amine | 399.23 | 400.39 |
| 752 | | 1-{[2-(2-isopropylphenyl)-4-methyl-1,3-thiazol-5-yl]carbonyl}-N,N-dimethylpyrrolidin-3-amine | 357.19 | 358.33 |
| 753 | | N,N-diethyl-1-{[2-(2-isopropylphenyl)-4-methyl-1,3-thiazol-5-yl]carbonyl}pyrrolidin-3-amine | 385.22 | 386.37 |

TABLE I-continued

| Compound | | Name | MW | MS |
|---|---|---|---|---|
| 754 | (structure) | 1-{[2-(2,6-dimethylphenyl)-4-methyl-1,3-thiazol-5-yl]carbonyl}-N,N-diethylpiperidin-4-amine | 385.22 | 386.38 |
| 755 | (structure) | 1-{[2-(2,5-dichlorophenyl)-4-methyl-1,3-thiazol-5-yl]carbonyl}-N,N-diethylpiperidin-4-amine | 425.11 | 426.28 |
| 756 | (structure) | 1-{[2-(2,5-dichlorophenyl)-4-methyl-1,3-thiazol-5-yl]carbonyl}-N,N-diethylpyrrolidin-3-amine | 411.09 | 412.26 |
| 757 | (structure) | N,N-diethyl-1-[(2-mesityl-4-methyl 1,3-thiazol-5-yl)carbonyl]piperidin-4-amine | 399.23 | 400.40 |

TABLE I-continued
| Compound | | Name | MW | MS |
|---|---|---|---|---|
| 758 | 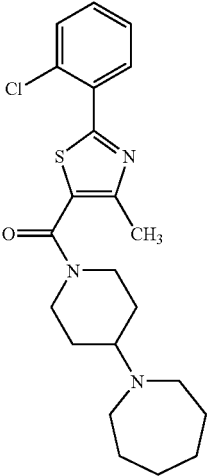 | 1-(1-{[2-(2-chlorophenyl)-4-methyl-1,3-thiazol-5-yl]carbonyl}piperidin-4-yl)azepane | 417.16 | 418.15 |
| 759 | 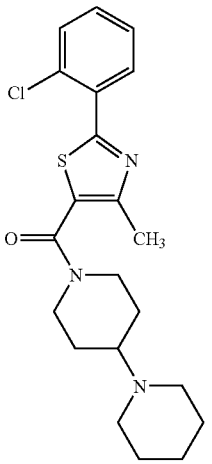 | 1'-{[2-(2-chlorophenyl)-4-methyl-1,3-thiazol-5-yl]carbonyl}-1,4'-bipiperidine | 403.15 | 404.14 |
| 760 | 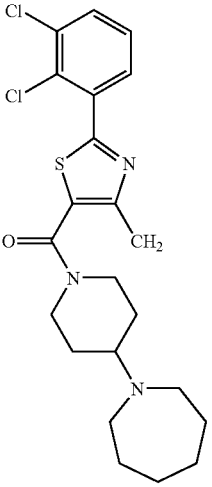 | 1-(1-{[2-(2,3-dichlorophenyl)-4-methyl-1,3-thiazol-5-yl]carbonyl}piperidin-4-yl)azepane | 451.13 | 452.11 |

TABLE I-continued
| Compound | | Name | MW | MS |
|---|---|---|---|---|
| 761 | 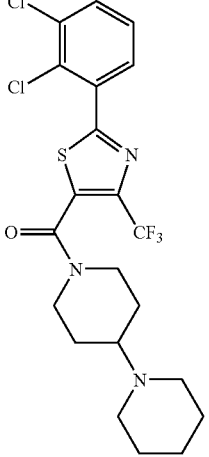 | 1'-{[2-(2,3-dichlorophenyl)-4-methyl-1,3-thiazol-5-yl]carbonyl}-1,4'-bipiperidine | 437.11 | 438.09 |
| 762 | 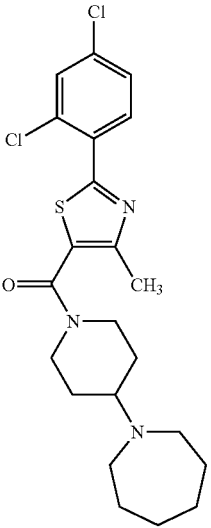 | 1-(1-{[2-(2,4-dichlorophenyl)-4-methyl-1,3-thiazol-5-yl]carbonyl}piperidin-4-yl)azepane | 451.13 | 452.11 |
| 763 | 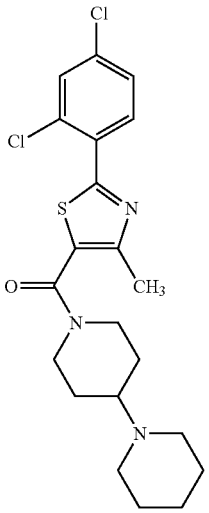 | 1'-{[2-(2,4-dichlorophenyl)-4-methyl-1,3-thiazol-5-yl]carbonyl}-1,4'-bipiperidine | 437.11 | 438.10 |

TABLE I-continued

| | Compound | Name | MW | MS |
|---|---|---|---|---|
| 764 | | 1-[1-({4-methyl-2-[2-(trifluoromethyl)phenyl]-1,3-thiazol-5-yl}carbonyl]piperidin-4-yl]azepane | 451.19 | 452.17 |
| 765 | | 1'-({4-methyl-2-[2-(trifluoromethyl)phenyl]-1,3-thiazol-5-yl}carbonyl)-1,4'-bipiperidine | 437.17 | 438.16 |
| 766 | | 1-(1-{[2-(2,6-dimethoxyphenyl)-4-methyl-1,3-thiazol-5-yl]carbonyl}piperidin-4-yl)azepane | 443.22 | 444.22 |
| 767 | | 1'-{[2-(2,6-dimethoxyphenyl)-4-methyl-1,3-thiazol-5-yl]carbonyl}-1,4'-bipiperidine | 429.21 | 430.21 |

TABLE I-continued

| Compound | Name | MW | MS |
|---|---|---|---|
| 768 | 1'-{[2-(2-fluoro-4,6-dimethoxyphenyl)-4-methyl-1,3-thiazol-5-yl]carbonyl}-1,4'-bipiperidine | 447.20 | 448.22 |
| 769 | 1-(1-{[2-(2-isopropylphenyl)-4-methyl-1,3-thiazol-5-yl]carbonyl}piperidin-4-yl)azepane | 425.25 | 426.23 |
| 770 | 1'-{[2-(2-isopropylphenyl)-4-methyl-1,3-thiazol-5-yl]carbonyl}-1,4'-bipiperidine | 411.23 | 412.21 |
| 771 | 1-(1-{[2-(2,6-dimethylphenyl)-4-methyl-1,3-thiazol-5-yl]carbonyl}piperidin-4-yl)azepane | | |

TABLE I-continued
| Compound | | Name | MW | MS |
|---|---|---|---|---|
| 772 | 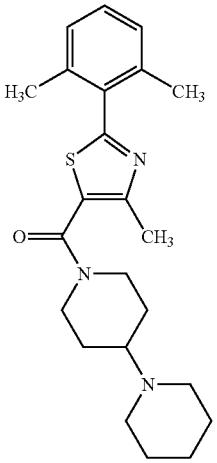 | 1'-{[2-(2,6-dimethylphenyl)-4-methyl-1,3-thiazol-5-yl]carbonyl}-1,4'-bipiperidine | | |
| 773 | 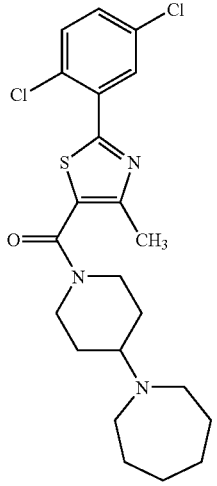 | 1-(1-{2-(2,5-dichlorophenyl)-4-methyl-1,3-thiazol-5-yl]carbonyl}piperidin-4-yl)azepane | 451.13 | 452.11 |
| 774 | 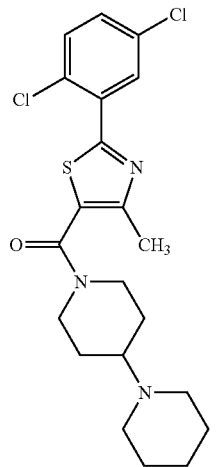 | 1'-{[2-(2,5-dichlorophenyl)-4-methyl-1,3-thiazol-5-yl]carbonyl}-1,4'-bipiperidine | 437.11 | 438.09 |

TABLE I-continued
| Compound | Name | MW | MS |
|---|---|---|---|
| 775 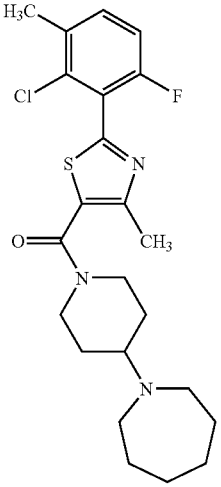 | 1-(1-{[2-(2-chloro-6-fluoro-3-methylphenyl)-4-methyl-1,3-thiazol-5-yl]carbonyl}piperidin-4-yl)azepane | | |
| 776 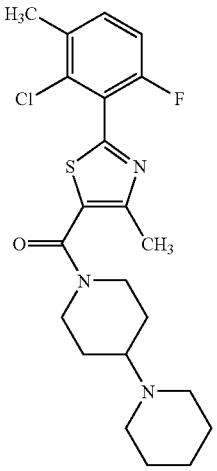 | 1'-{[2-(2-chloro-6-fluoro-3-methylphenyl)-4-methyl-1,3-thiazol-5-yl]carbonyl}-1,4'-bipiperidine | | |
| 777 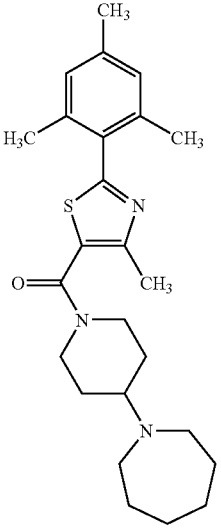 | 1-{1-[(2-mesityl-4-methyl-1,3-thiazol-5-yl)carbonyl]piperidin-4-yl}azepane | | |

TABLE I-continued

| Compound | Name | MW | MS |
|---|---|---|---|
| 778 | 1'-[(2-mesityl-4-methyl-1,3-thiazol-5-yl)carbonyl]-1,4'-bipiperidine | | |
| 779 | 1-{[2-(2-chlorophenyl)-4-methyl-1,3-thiazol-5-yl]carbonyl}-N-(cyclopropylmethyl)-N-propylpiperidin-4-amine | 431.18 | 432.16 |
| 780 | N-(cyclopropylmethyl)-1-{[2-(2,3-dichlorophenyl)-4-methyl-1,3-thiazol-5-yl]carbonyl}-N-propylpiperidin-4-amine | 465.14 | 466.12 |
| 781 | N-cyclopropylmethyl)-1-({4-methyl-2-[2-(trifluoromethyl)phenyl]-1,3-thiazol-5-yl}carbonyl)-N-propylpiperidin-4-amine | 465.21 | 466.17 |

TABLE I-continued

| Compound | | Name | MW | MS |
|---|---|---|---|---|
| 782 | | 1-({4-methyl-2-[2-(trifluoromethyl)phenyl]-1,3-thiazol-5-yl}carbonyl)-N,N-dipropylpiperidin-4-amine | 453.21 | 454.17 |
| 783 | | N-(cyclopropylmethyl)-1-{[2-(2-isopropylphenyl)-4-methyl-1,3-thiazol-5-yl]carbonyl}-N-propylpiperidin-4-amine | 439.27 | 440.23 |
| 784 | | 1-{[2-(2-isopropylphenyl)-4-methyl-1,3-thiazol-5-yl]carbonyl}-N,N-dipropylpiperidin-4-amine | 427.27 | 428.23 |
| 785 | | N-(cyclopropylmethyl)-1-{[2-(2,5-dichlorophenyl)-4-methyl-1,3-thiazol-5-yl]carbonyl}-N-propylpiperidin-4-amine | 465.14 | 466.11 |
| 786 | | 2-(2-chlorophenyl)-N-[2-(diethylamino)ethyl]-N,4-dimethyl-1,3-thiazole-5-carboxamide | 365.13 | 366.10 |

TABLE I-continued

| | Compound | Name | MW | MS |
|---|---|---|---|---|
| 787 | | 2-(2,3-dichlorophenyl)-N-[2-(diethylamino)ethyl]-N,4-dimethyl-1,3-thiazole-5-carboxamide | 399.09 | 400.06 |
| 788 | | 2-(2,3-dichlorophenyl)-N-[2-(diethylamino)ethyl]-N-ethyl-4-methyl-1,3-thiazole-5-carboxamide | 413.11 | 414.07 |
| 789 | | 2-(2,4-dichlorophenyl)-N-[2-(diethylamino)ethyl]-N,4-dimethyl-methyl-1,3-thiazole-5-carboxamide | 399.09 | 400.06 |
| 790 | | N-[2-(diethylamino)ethyl]-N,4-dimethyl-2-[2-(trifluoromethyl)phenyl]-1,3-thiazole-5-carboxamide | 399.16 | 400.13 |

TABLE I-continued
| Compound | | Name | MW | MS |
|---|---|---|---|---|
| 791 | 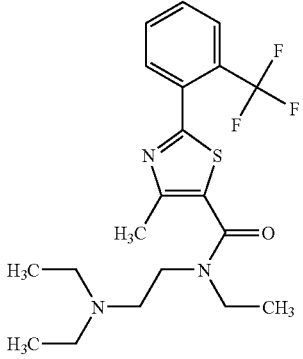 | N-[2-(diethylamino)ethyl]-N-ethyl-4-methyl-2-[2-(trifluoromethyl)phenyl]-1,3-thiazole-5-carboxamide | 413.17 | 414.13 |
| 792 | 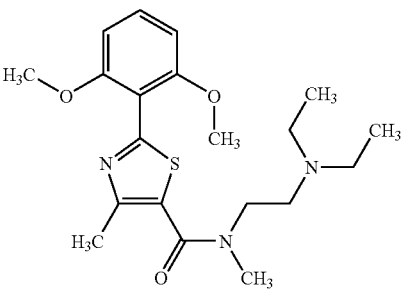 | N-[2-(diethylamino)ethyl]-2-(2,6-dimethoxyphenyl)-N,4-dimethyl-1,3-thiazole-5-carboxamide | 391.19 | 392.17 |
| 793 | 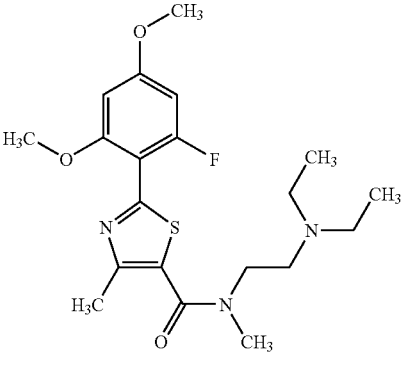 | N-[2-(diethylamino)ethyl]-2-(2-fluoro-4,6-dimethoxyphenyl)-N,4-dimethyl-1,3-thiazole-5-carboxamide | 409.18 | 410.16 |
| 794 | 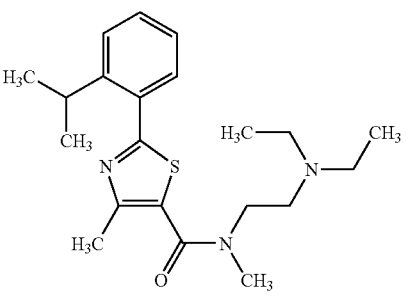 | N-[2-(diethylamino)ethyl]-2-(2-isopropylphenyl)-N,4-dimethyl-1,3-thiazole-5-carboxamide | 373.22 | 374.18 |

TABLE I-continued

| Compound | Name | MW | MS |
|---|---|---|---|
| 795 | N-[2-(diethylamino)ethyl]-N-ethyl-2-(2-isopropylphenyl)-4-methyl-1,3-thiazole-5-carboxamide | 387.23 | 388.20 |
| 796 | N-[2-(diethylamino)ethyl]-2-(2,6-dimethylphenyl-N,4-dimethyl-1,3-thiazole-5-carboxamide | | |
| 797 | 2-(2,5-dichlorophenyl)-N-[2-(diethylamino)ethyl]-N,4-dimethyl-1,3-thiazole-5-carboxamide | 399.09 | 400.06 |
| 798 | 2-(2-chloro-6-fluoro-3-methylphenyl)-N-[2-(diethylamino)ethyl]-N,4-dimethyl-1,3-thiazole-5-carboxamide | | |

TABLE I-continued

| Compound | Name | MW | MS |
|---|---|---|---|
| 799 | N-[2-(diethylamino)ethyl]-2-mesityl-N,4-dimethyl-1,3-thiazole-5-carboxamide | | |
| 800 | 4-methyl-N-(2-pyrrolidin-1-ylethyl)-2-[4-(trifluoromethyl)phenyl]-1,3-thiazole-5-carboxamide | 383.13 | 384.19 |
| 801 | 2-(3-acetylphenyl)-4-methyl-N-(2-pyrrolidin-1-ylethyl)-1,3-thiazole-5-carboxamide | 357.15 | 358.20 |
| 802 | 2-(4-acetylphenyl)-4-methyl-N-(2-pyrrolidin-1-ylethyl)-1,3-thiazole-5-carboxamide | 357.17 | 358.21 |

TABLE I-continued
| | Compound | Name | MW | MS |
|---|---|---|---|---|
| 803 | 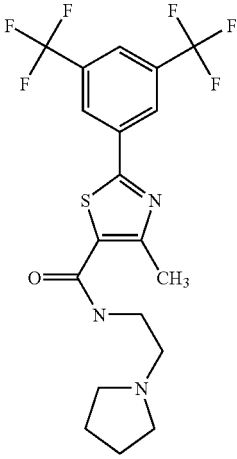 | 2-[3,5-bis(trifluoromethyl)phenyl]-4-methyl-N-(2-pyrrolidin-1-ylethyl)-1,3-thiazole-5-carboxamide | 451.12 | 452.19 |
| 804 | 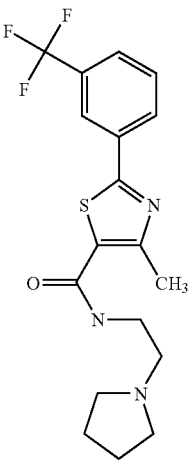 | 4-methyl-N-(2-pyrrolidin-1-ylethyl)-2-[3-(trifluoromethyl)phenyl]-1,3-thiazole-5-carboxamide | 383.13 | 384.18 |
| 805 | 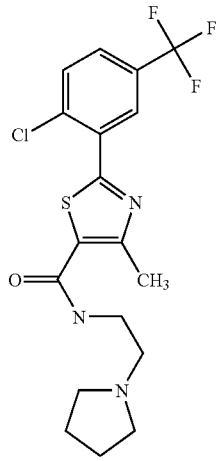 | 2-[2-chloro-5-(trifluoromethyl)phenyl]-4-methyl-N-(2-pyrrolidin-1-ylethyl)-1,3-thiazole-5-carboxamide | 417.09 | 418.15 |

| Compound | Name | MW | MS |
|---|---|---|---|
| 806 | 2-[2-chloro-5-(trifluoromethyl)phenyl]-4-methyl-N-(2-piperidin-1-ylethyl)-1,3-thiazole-5-carboxamide | 431.10 | 432.16 |
| 807 | ethyl 3-(4-methyl-5-{[(2-pyrrolidin-1-ylethyl)amino]carbonyl}-1,3-thiazol-2-yl)benzoate | 387.16 | 388.22 |
| 808 | 2-[2-chloro-5-(trifluoromethyl)phenyl]-4-methyl-N-(3-pyrrolidin-1-ylpropyl)-1,3-thiazole-5-carboxamide | 431.10 | 432.19 |
| 809 | N-[(1-ethylpyrrolidin-2-yl)methyl]-4-methyl-2-[4-(trifluoromethyl)phenyl]-1,3-thiazole-5-carboxamide | 397.14 | 398.22 |

TABLE I-continued

| | Compound | Name | MW | MS |
|---|---|---|---|---|
| 810 | | 4-methyl-N-[2-(1-methylpyrrolidin-2-yl)ethyl]-2-[4-(trifluoromethyl)phenyl]-1,3-thiazole-5-carboxamide | 397.14 | 398.21 |
| 811 | | 4-methyl-N-[3-(2-methylpiperidin-1-yl)propyl]-2-[4-(trifluoromethyl)phenyl]-1,3-thiazole-5-carboxamide | 425.17 | 426.24 |
| 812 | | 2-(3-acetylphenyl)-4-methyl-N-[2-(1-methylpyrrolidin-2-yl)ethyl]-1,3-thiazole-5-carboxamide | 371.17 | 372.25 |
| 813 | | 2-(3-acetylphenyl)-4-methyl-N-[3-(2-methylpiperidin-1-yl)propyl]-1,3-thiazole-5-carboxamide | 399.20 | 400.27 |

TABLE I-continued

| Compound | | Name | MW | MS |
|---|---|---|---|---|
| 814 | | 2-(4-acetylphenyl)-4-methyl-N-[2-(1-methylpyrrolidin-2-yl)ethyl]-1,3-thiazole-5-carboxamide | 371.17 | 372.25 |
| 815 | | 2-[3,5-bis(trifluoromethyl)phenyl]-4-methyl-N-[3-(2-methylpiperidin-1-yl)propyl]-1,3-thiazole-5-carboxamide | 493.16 | 494.23 |
| 816 | | 2-methyl-N-[2-(1-methylpyrrolidin-2-yl)ethyl]-2-[3-(trifluoromethyl)phenyl]-1,3-thiazole-5-carboxamide | 397.14 | 398.22 |
| 817 | | 2-[4-chloro-3-(trifluoromethyl)phenyl]-4-methyl-N-[2-(1-methylpyrrolidin-2-yl)ethyl]-1,3-thiazole-5-carboxamide | 431.10 | 432.19 |

TABLE I-continued
| Compound | | Name | MW | MS |
|---|---|---|---|---|
| 818 | 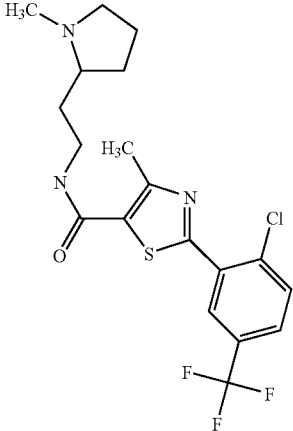 | 2-[2-chloro-5-(trifluoromethyl)phenyl]-4-methyl-N-[2-(1-methylpyrrolidin-2-yl)ethyl]-1,3-thiazole-5-carboxamide | 431.10 | 432.19 |
| 819 | 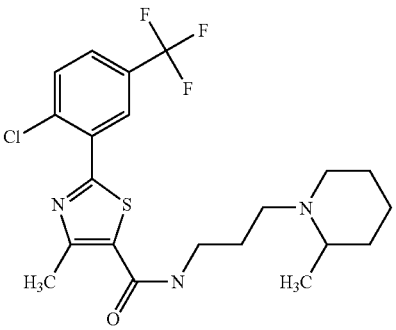 | 2-[2-chloro-5-(trifluoromethyl)phenyl]-4-methyl-N-[3-(2-methylpiperidin-1-yl)propyl]-1,3-thiazole-5-carboxamide | 459.14 | 460.24 |
| 820 | 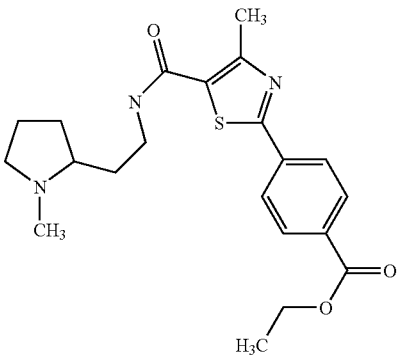 | ethyl 4-[4-methyl-5-({[2-(1-methylpyrrolidin-2-yl)ethyl]amino}carbonyl)-1,3-thiazol-2-yl]benzoate | 401.18 | 402.27 |

| Compound | Name | MW | MS |
|---|---|---|---|
| 821 | ethyl 3-[4-methyl-5-({[2-(1-methylpyrrolidin-2-yl)ethyl]amino}carbonyl)-1,3-thiazol-2-yl]benzoate | 401.18 | 402.27 |
| 822 | 2-(4-acetylphenyl)-4-methyl-N-(4-pyrrolidin-1-ylbutyl)-1,3-thiazole-5-carboxamide | 385.18 | 386.27 |
| 823 | 2-[3,5-bis(trifluoromethyl)phenyl]-4-methyl-N-(4-pyrrolidin-1-ylbutyl)-1,3-thiazole-5-carboxamide | | |

TABLE I-continued
| Compound | | Name | MW | MS |
|---|---|---|---|---|
| 824 | 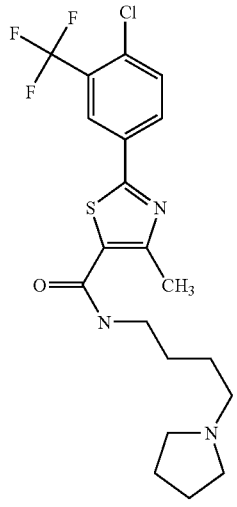 | 2-[4-chloro-3-(trifluoromethyl)phenyl]-4-methyl-N-(4-pyrrolidin-1-ylbutyl)-1,3-thiazole-5-carboxamide | | |
| 825 | 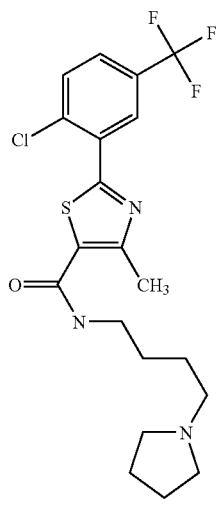 | 2-[2-chloro-5-(trifluoromethyl)phenyl]-4-methyl-N-(4-pyrrolidin-1-ylbutyl)-1,3-thiazole-5-carboxamide | | |

TABLE I-continued
| Compound | | Name | MW | MS |
|---|---|---|---|---|
| 826 | 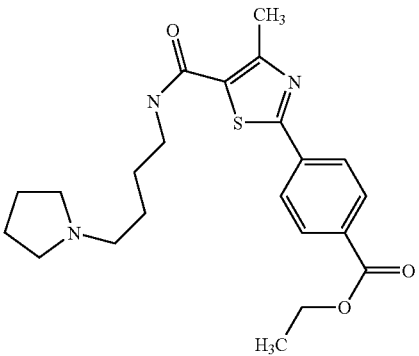 | ethyl 4-(4-methyl-5-{[(4-pyrrolidin-1-ylbutyl)amino]carbonyl}-1,3-thiazol-2-yl)benzoate | 415.19 | 416.31 |
| 827 | 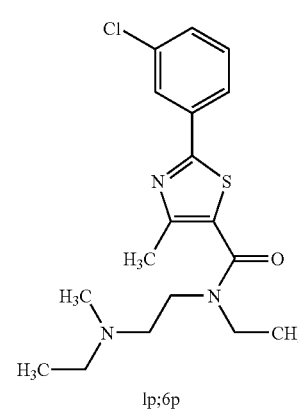  lp;6p | 2-(3-chlorophenyl)-N-ethyl-N-{2-[ethyl(methyl)amino]ethyl}-4-methyl-1,3-thiazole-5-carboxamide | 365.13 | 366.18 |
| 828 | 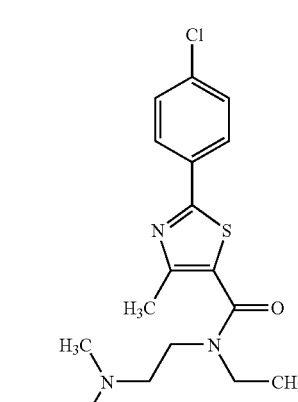 | 2-(4-chlorophenyl)-N-ethyl-N-{2-[ethyl(methyl)amino]ethyl}-4-methyl-1,3-thiazole-5-carboxamide | 365.13 | 366.18 |

TABLE I-continued
| Compound | | Name | MW | MS |
|---|---|---|---|---|
| 829 | 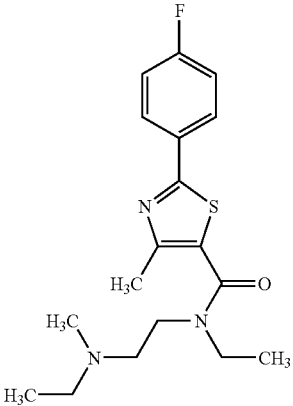 | N-ethyl-N-{2-[ethyl(methyl)amino]ethyl}-2-(4-fluorophenyl)-4-methyl-1,3-thiazole-5-carboxamide | 349.16 | 350.19 |
| 830 | 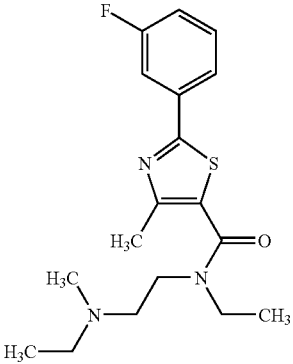 | N-ethyl-N-{2-[ethyl(methyl)amino]ethyl}-2-(3-fluorophenyl)-4-methyl-1,3-thiazole-5-carboxamide | 349.16 | 350.20 |
| 831 | 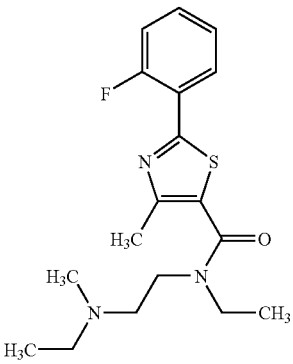 | N-ethyl-N-{2-[ethyl(methyl)amino]ethyl}-2-(2-fluorophenyl)-4-methyl-1,3-thiazole-5-carboxamide | 349.16 | 350.19 |

TABLE I-continued
| Compound | | Name | MW | MS |
|---|---|---|---|---|
| 832 | 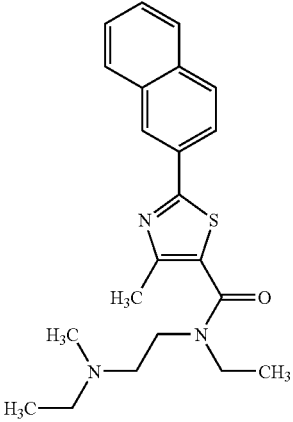 | N-ethyl-N-{2-[ethyl(methyl)amino]ethyl}-4-methyl-2-(2-naphthyl)-1,3-thiazole-5-carboxamide | 381.19 | 382.22 |
| 833 | 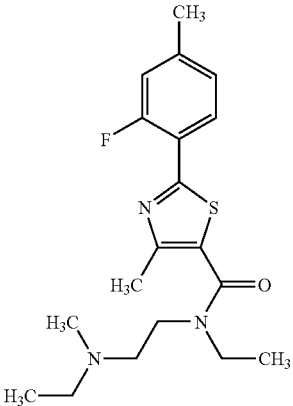 | N-ethyl-N-{2-[ethyl(methyl)amino]ethyl}-4-methyl-1,3-thiazole-5-carboxamide | 363.18 | 364.20 |

TABLE I-continued
| Compound | | Name | MW | MS |
|---|---|---|---|---|
| 834 | 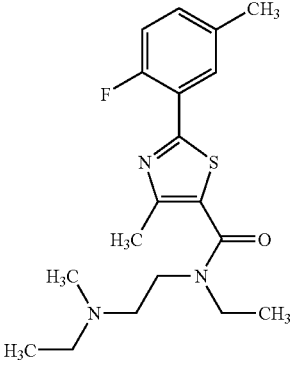 | N-ethyl-N-{2-[ethyl(methyl)amino]ethyl}-2-(2-fluoro-5-methylphenyl)-4-methyl-1,3-thiazole-5-carboxamide | 363.18 | 364.21 |
| 835 | 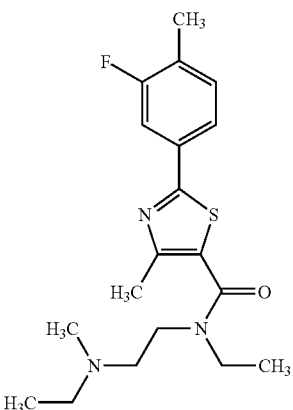 | N-ethyl-N-{2-[ethyl(methyl)amino]ethyl}-2-(3-fluoro-4-methylphenyl)-4-methyl-1,3-thiazole-5-carboxamide | 363.18 | 364.21 |
| 836 | 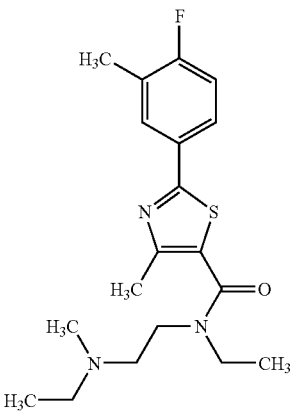 | N-ethyl-N-{2-[ethyl(methyl)amino]ethyl}-2-(4-fluoro-3-methylphenyl)-4-methyl-1,3-thiazole-5-carboxamide | 363.18 | 364.22 |

TABLE I-continued
| Compound | | Name | MW | MS |
|---|---|---|---|---|
| 837 | 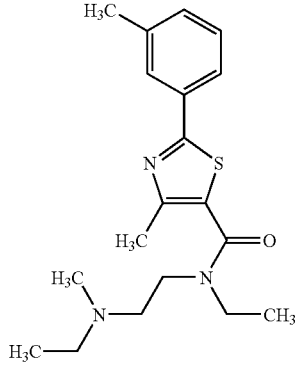 | N-ethyl-N-{2-[ethyl(methyl)amino]ethyl}-4-methyl-2-(3-methylphenyl)-1,3-thiazole-5-carboxamide | 345.19 | 346.23 |
| 838 | 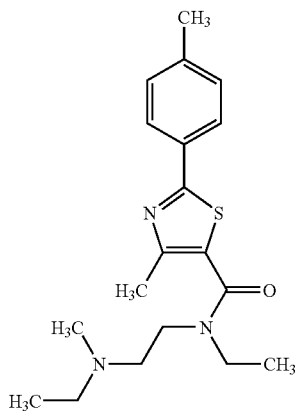 | N-ethyl-N-{2-[ethyl(methyl)amino]ethyl}-4-methyl-2-(4-methylphenyl)-1,3-thiazole-5-carboxamide | 345.19 | 346.23 |
| 839 | 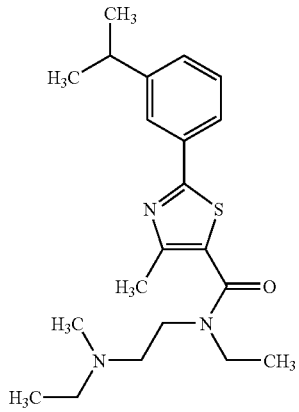 | N-ethyl-N-{2-[ethyl(methyl)amino]ethyl}-2-(3-isopropylphenyl)-4-methyl-1,3-thiazole-5-carboxamide | 373.22 | 374.26 |

TABLE I-continued
| | Compound | Name | MW | MS |
|---|---|---|---|---|
| 840 | 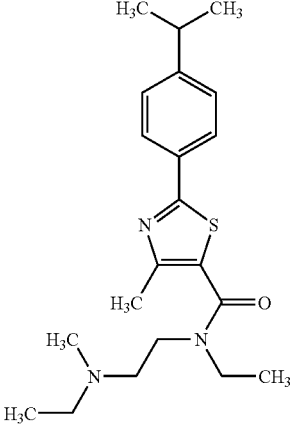 | N-ethyl-N-{2-[ethyl(methyl)amino]ethyl}-2-(4-isopropylphenyl)-4-methyl-1,3-thiazole-5-carboxamide | 373.22 | 374.27 |
| 841 | 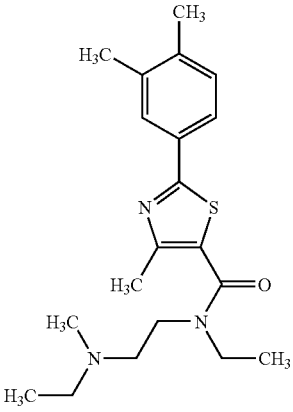 | 2-(3,4-dimethylphenyl)-N-ethyl-N-{2-[ethyl(methyl)amino]ethyl}-4-methyl-1,3-thiazole-5-carboxamide | 359.20 | 360.25 |
| 842 | 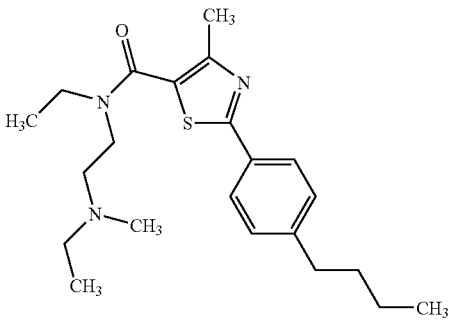 | 2-(4-butylphenyl)-N-ethyl-N-{2-[ethyl(methyl)amino]ethyl}-4-methyl-1,3-thiazole-5-carboxamide | 387.23 | 388.27 |
| 843 | 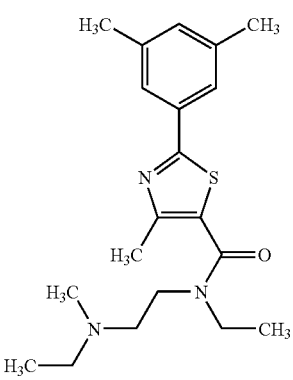 | 2-(3,5-dimethylphenyl)-N-ethyl-N-{2-[ethyl(methyl)amino]ethyl}-4-methyl-1,3-thiazole-5-carboxamide | 359.20 | 360.25 |

TABLE I-continued
| Compound | | Name | MW | MS |
|---|---|---|---|---|
| 844 | 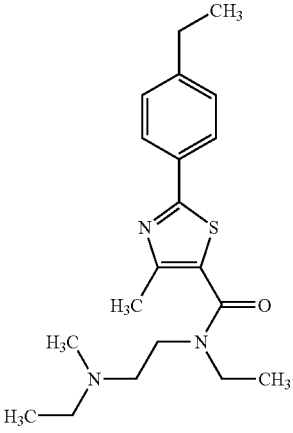 | N-ethyl-N-{2-[ethyl(methyl)amino]ethyl}-2-(4-ethylphenyl)-4-methyl-1,3-thiazole-5-carboxamide | 359.20 | 360.24 |
| 845 | 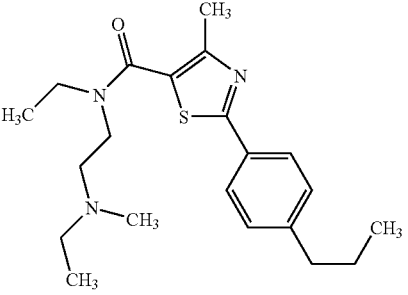 | N-ethyl-N-{2-[ethyl(methyl)amino]ethyl}-4-methyl-2-(4-propylphenyl)-1,3-thiazole-5-carboxamide | 373.22 | 374.26 |
| 846 | 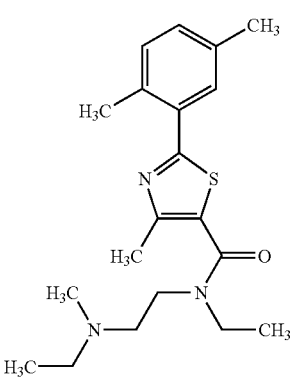 | 2-(2,5-dimethylphenyl)-N-ethyl-N-{2-[ethyl(methyl)amino]ethyl}-4-methyl-1,3-thiazole-5-carboxamide | 359.20 | 360.26 |

TABLE I-continued

| | Compound | Name | MW | MS |
|---|---|---|---|---|
| 847 | | N-ethyl-N-{2-[ethyl(methyl)amino]ethyl}-4-methyl-2-(1-naphthyl)-1,3-thiazole-5-carboxamide | 381.19 | 382.23 |
| 848 | | 2-(2,3-dimethylphenyl)-N-ethyl-N-{2-[ethyl(methyl)amino]ethyl}-4-methyl-1,3-thiazole-5-carboxamide | 359.20 | 360.24 |
| 849 | | N-ethyl-N-{2-[ethyl(methyl)amino]ethyl}-2-(5-fluoro-2-methylphenyl)-5-methyl-1,3-thiazole-5-carboxamide | 363.18 | 364.23 |

TABLE I-continued
| Compound | | Name | MW | MS |
|---|---|---|---|---|
| 850 | 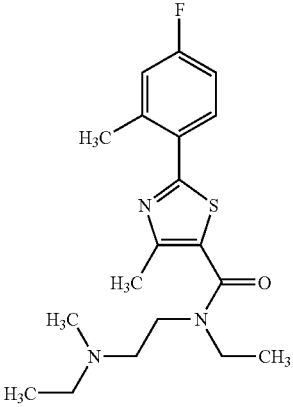 | N-ethyl-N-{2-[ethyl(methyl)amino]ethyl}-2-(4-fluoro-2-methylphenyl)-4-methyl-1,3-thiazole-5-carboxamide | 363.18 | 364.22 |
| 851 | 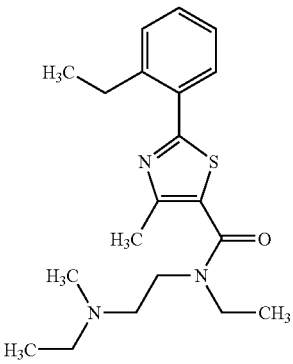 | N-ethyl-N-{2-[ethyl(methyl)amino]ethyl}-2-(2-ethylphenyl)-4-methyl-1,3-thiazole-5-carboxamide | 359.20 | 360.24 |
| 852 | 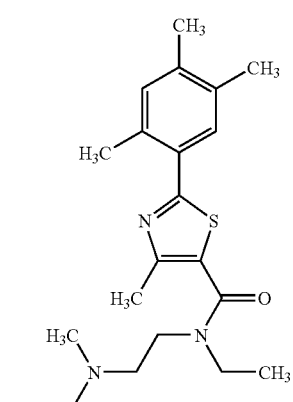 | N-ethyl-N-{2-ethyl(methyl)amino]ethyl}-4-methyl-2-(2,4,5-trimethylphenyl)-1,3-thiazole-5-carboxamide | 373.22 | 374.26 |

TABLE I-continued
| Compound | | Name | MW | MS |
|---|---|---|---|---|
| 853 | 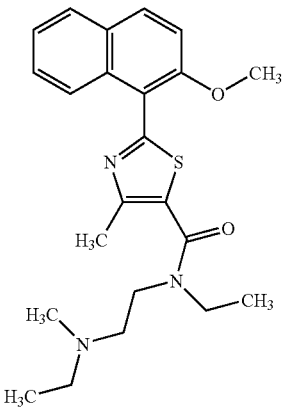 | N-ethyl-N-{2-[ethyl(methyl)amino]ethyl}-2-(2-methoxy-1-naphthyl)-4-methyl-1,3-thiazole-5-carboxamide | 411.20 | 412.25 |
| 854 | 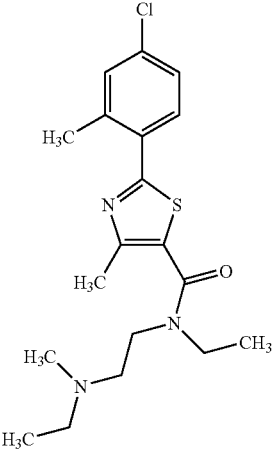 | 2-(4-chloro-2-methylphenyl)-N-ethyl-N-{2-[ethyl(methyl)amino]ethyl}-4-methyl-1,3-thiazole-5-carboxamide | 379.15 | 380.20 |
| 855 | 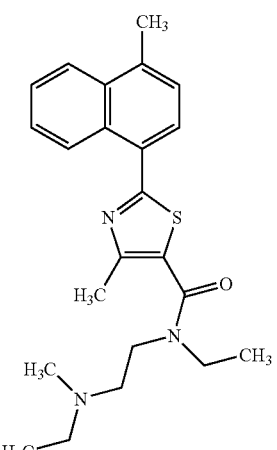 | N-ethyl-N-{2-[ethyl(methyl)amino]ethyl}-4-methyl-2-(4-methyl-1-naphthyl)-1,3-thiazole-5-carboxamide | 395.20 | 396.25 |

TABLE I-continued
| | Compound | Name | MW | MS |
|---|---|---|---|---|
| 856 | 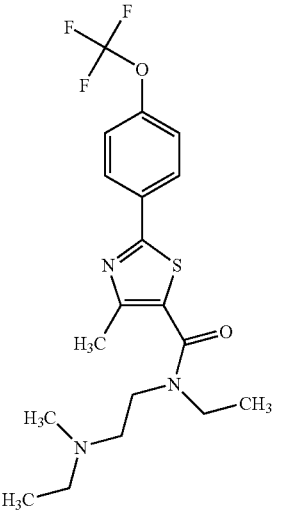 | N-ethyl-N-{2-[ethyl(methyl)amino]ethyl}-4-methyl-2-[4-(trifluoromethoxy)phenyl]-1,3-thiazole-5-carboxamide | 415.15 | 416.20 |
| 857 | 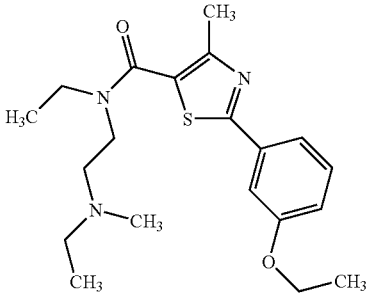 | 2-(3-ethoxyphenyl)-N-ethyl-N-{2-[ethyl(methyl)amino]ethyl}-4-methyl-1,3-thiazole-5-carboxamide | 375.20 | 376.24 |
| 858 | 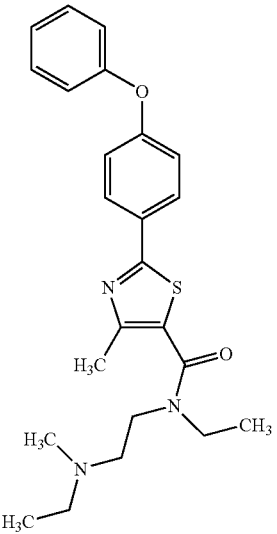 | N-ethyl-N-{2-[ethyl(methyl)amino]ethyl}-4-methyl-2-(4-phenoxyphenyl)-1,3-thiazole-5-carboxamide | 423.20 | 424.25 |

TABLE I-continued
| Compound | | Name | MW | MS |
|---|---|---|---|---|
| 859 | 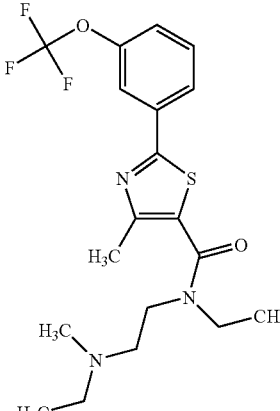 | N-ethyl-N-{2-[ethyl(methyl)amino]ethyl}-4-methyl-2-[3-(trifluoromethoxy)phenyl]-1,3-thiazole-5-carboxamide | 415.15 | 416.20 |
| 860 | 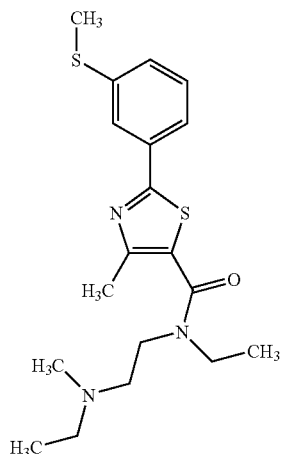 | N-ethyl-N-{2-[ethyl(methyl)amino]ethyl}-4-methyl-2-[3-(methylthio)phenyl]-1,3-thiazole-5-carboxamide | 377.16 | 378.21 |
| 861 | 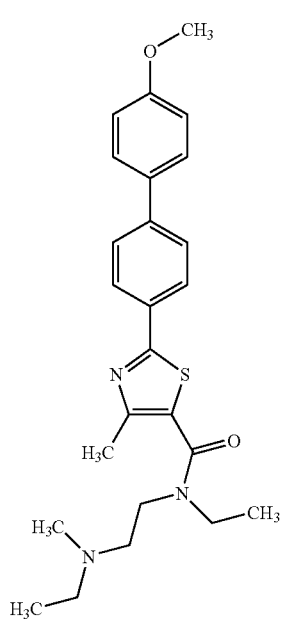 | N-ethyl-N-{2-[ethyl(methyl)amino]ethyl}-2-(4'-methoxybiphenyl-4-yl)-4-methyl-1,3-thiazole-5-carboxamide | 437.21 | 438.27 |

TABLE I-continued

| Compound | Name | MW | MS |
|---|---|---|---|
| 862 | 1-cycloheptyl-4-{[2-(4-methoxy-2-methylphenyl)-4-methyl-1,3-thiazol-5-yl]carbonyl}piperazine | | |
| 863 | 1-cycloheptyl-4-{[2-(2-fluoro-4,6-dimethoxyphenyl)-4-methyl-1,3-thiazol-5-yl]carbonyl}piperazine | | |
| 864 | 1-{[2-(5-chloro-2-methoxyphenyl)-4-methyl-1,3-thiazol-5-yl]carbonyl}-4-ethylpiperazine | 379.11 | 380.15 |
| 865 | 1-ethyl-4-{[2-(2-methoxy-5-methylphenyl)-4-methyl-1,3-thiazol-5-yl]carbonyl}piperazine | 359.17 | 360.20 |

TABLE I-continued

| | Compound | Name | MW | MS |
|---|---|---|---|---|
| 866 | | 1-isopropyl-4-{[2-(2-methoxyphenyl)-4-methyl-1,3-thiazol-5-yl]carbonyl}piperazine | 359.17 | 360.20 |
| 867 | | 1-cyclopentyl-4-{[2-(2-methoxyphenyl)-4-methyl-1,3-thiazol-5-yl]carbonyl}piperazine | 385.18 | 386.22 |
| 868 | | 1-isopropyl-4-{[2-(5-isopropyl-2-methoxyphenyl)-4-methyl-1,3-thiazol-5-yl]carbonyl}piperazine | 401.21 | 402.24 |
| 869 | | 1-cyclopentyl-4-{[2-(5-isopropyl-2-methoxyphenyl)-4-methyl-1,3-thiazol-5-yl]carbonyl}piperazine | 427.23 | 428.27 |
| 870 | | 1-butyl-4-{[2-(5-isopropyl-2-methoxyphenyl)-4-methyl-1,3-thiazol-5-yl]carbonyl}-1,4-diazepane | 429.25 | 430.28 |

TABLE I-continued

| | Compound | Name | MW | MS |
|---|---|---|---|---|
| 871 | | 1-{[2-(5-chloro-2-methoxyphenyl)-4-methyl-1,3-thiazol-5-yl]carbonyl}-4-isopropylpiperazine | 393.13 | 394.16 |
| 872 | | 1-{[2-(5-chloro-2-methoxyphenyl)-4-methyl-1,3-thiazol-5-yl]carbonyl}-4-cyclopentylpiperazine | 419.14 | 420.19 |
| 873 | | 1-butyl-4-{[2-(5-chloro-2-methoxyphenyl)-4-methyl-1,3-thiazol-5-yl]carbonyl}-1,4-diazepane | 421.16 | 422.20 |
| 874 | | 1-cyclopentyl-4-{[2-(2,5-dimethoxyphenyl)-4-methyl-1,3-thiazol-5-yl]carbonyl}piperazine | 415.19 | 416.24 |
| 875 | | 1-butyl-4-{[2-(2,5-dimethoxyphenyl)-4-methyl-1,3-thiazol-4-yl]carbonyl}-1,4-diazepane | 417.21 | 418.24 |

TABLE I-continued

| | Compound | Name | MW | MS |
|---|---|---|---|---|
| 876 | | 1-[(2-dibenzo[b,d]furan-4-yl-4-methyl-1,3-thiazol-5-yl)carbonyl]-4-isopropylpiperazine | 419.17 | 420.20 |
| 877 | | 1-cyclopentyl-4-[(2-dibenzo[b,d]furan-4-yl-4-methyl-1,3-thiazol-5-yl)carbonyl]piperazine | 445.18 | 446.22 |
| 878 | | 1-butyl-4-[(2-dibenzo[b,d]furan-4-yl-4-methyl-1,3-thiazol-5-yl)carbonyl]-1,4-diazepane | 447.20 | 448.23 |
| 879 | | 1-{[2-(5-fluoro-2-methoxyphenyl)-4-methyl-1,3-thiazol-5-yl]carbonyl}-4-isopropylpiperazine | 377.16 | 378.18 |

TABLE I-continued

| | Compound | Name | MW | MS |
|---|---|---|---|---|
| 880 | | 1-cyclopentyl-4-{[2-(5-fluoro-2-methoxyphenyl)-4-methyl-1,3-thiazol-5-yl]carbonyl}piperazine | 403.17 | 404.21 |
| 881 | | 1-butyl-4-{[2-(5-fluoro-2-methoxyphenyl)-4-methyl-1,3-thiazol-5-yl]carbonyl}-1,4-diazepane | 405.19 | 406.22 |
| 882 | | 1-isopropyl-4-{[2-(2-methoxy-5-methylphenyl)-4-methyl-1,3-thiazol-5-yl]carbonyl}piperazine | 373.18 | 374.21 |
| 883 | | 1-cyclopentyl-4-{[2-(2-methoxy-5-methylphenyl)-4-methyl-1,3-thiazol-5-yl]carbonyl}piperazine | 399.20 | 400.23 |
| 884 | | 1-butyl-4-{[2-(2-methoxy-5-methylphenyl)-4-methyl-1,3-thiazol-5-yl]carbonyl}-1,4-diazepane | 401.21 | 402.24 |

TABLE I-continued

| | Compound | Name | MW | MS |
|---|---|---|---|---|
| 885 | | 1-isopropyl-4-{[4-methyl-2-(2-phenoxyphenyl)-1,3-thiazol-5-yl]carbonyl}piperazine | 421.18 | 422.21 |
| 886 | | 1-cyclopentyl-4-{[4-methyl-2-(2-phenoxyphenyl)-1,3-thiazol-5-yl]carbonyl}piperazine | 447.20 | 448.23 |
| 887 | | 1-isopropyl-4-{[4-methyl-2-(2,3,4-trimethoxyphenyl)-1,3-thiazol-5-yl]carbonyl}piperazine | 419.19 | 420.23 |
| 888 | | 1-cyclopentyl-4-{[4-methyl-2-(2,3,4-trimethoxyphenyl)-1,3-thiazol-5-yl]carbonyl}piperazine | 445.20 | 446.25 |

TABLE I-continued

| Compound | Name | MW | MS |
|---|---|---|---|
| 889 | N,N-diethyl-1-{[2-(2-methoxyphenyl)-4-methyl-1,3-thiazol-5-yl]carbonyl}piperidin-4-amine | 387.20 | 388.21 |
| 890 | N,N-diethyl-1-{[2-(5-isopropyl-2-methoxyphenyl)-4-methyl-1,3-thiazol-5-yl]carbonyl}piperidin-4-amine | 429.25 | 430.26 |
| 891 | 1-{[2-(5-isopropyl-2-methoxyphenyl)-4-methyl-1,3-thiazol-5-yl]carbonyl}-N,N-dimethylpiperidin-4-amine | 401.21 | 402.23 |
| 892 | N,N-diethyl-1-{[2-(5-isopropyl-2-methoxyphenyl)-4-methyl-1,3-thiazol-5-yl]carbonyl}pyrrolidin-3-amine | 415.23 | 416.24 |
| 893 | 1-{[2-(5-chloro-2-methoxyphenyl)-4-methyl-1,3-thiazol-5-yl]carbonyl}-N,N-diethylpiperidin-4-amine | 421.16 | 422.17 |

TABLE I-continued

| Compound | | Name | MW | MS |
|---|---|---|---|---|
| 894 | | 1-{[2-(5-chloro-2-methoxyphenyl)-4-methyl-1,3-thiazol-5-yl]carbonyl}-N,N-diethylpyrrolidin-3-amine | 407.14 | 408.16 |
| 895 | | 1-{[2-(2,5-dimethoxyphenyl)-4-methyl-1,3-thiazol-5-yl]carbonyl}-N,N-diethylpiperidin-4-amine | 417.21 | 418.22 |
| 896 | | 1-{[2-(2,5-dimethoxyphenyl)-4-methyl-1,3-thiazol-5-yl]carbonyl}-N,N-dimethylpiperidin-4-amine | 389.18 | 390.19 |
| 897 | | 1-{[2-(2,5-dimethoxyphenyl)-4-methyl-1,3-thiazol-5-yl]carbonyl}-N,N-diethylpyrrolidin-3-amine | 403.19 | 404.21 |
| 898 | | 1-{[2-(2,4-dimethoxyphenyl)-4-methyl-1,3-thiazol-5-yl]carbonyl}-N,N-diethylpyrrolidin-3-amine | 403.19 | 404.21 |

TABLE I-continued

| | Compound | Name | MW | MS |
|---|---|---|---|---|
| 899 | | 1-{[2-(2-ethoxyphenyl)-4-methyl-1,3-thiazol-5-yl]carbonyl}-N,N-diethylpiperidin-4-amine | 401.21 | 402.22 |
| 900 | | 1-{[2-(2-ethoxyphenyl)-4-methyl-1,3-thiazol-5-yl]carbonyl}-N,N-diethylpyrrolidin-3-amine | 387.20 | 388.21 |
| 901 | | 1-[(2-dibenzo[b,d]furan-4-yl-4-methyl-1,3-thiazol-5-yl)carbonyl]-N,N-diethylpiperidin-4-amine | 447.20 | 448.21 |
| 902 | | 1-[(2-dibenzo[b,d]furan-4-yl-4-methyl-1,3-thiazol-5-yl)carbonyl]-N,N-diethylpyrrolidin-3-amine | 433.18 | 434.20 |
| 903 | | N,N-diethyl-1-{[2-(5-fluoro-2-methoxyphenyl)-4-methyl-1,3-thiazol-5-yl]carbonyl}piperidin-4-amine | 405.19 | 406.20 |

TABLE I-continued

| | Compound | Name | MW | MS |
|---|---|---|---|---|
| 904 | | N,N-diethyl-1-{[2-(5-fluoro-2-methoxyphenyl)-4-methyl-1,3-thiazol-5-yl]carbonyl}pyrrolidin-3-amine | 391.17 | 392.18 |
| 905 | | N,N-diethyl-1-{[2-(2-methoxy-5-methylphenyl)-4-methyl-1,3-thiazol-5-yl]carbonyl}piperidin-4-amine | 401.21 | 402.22 |
| 906 | | N,N-diethyl-1-{[2-(2-methoxy-5-methylphenyl)-4-methyl-1,3-thiazol-5-yl]carbonyl}pyrrolidin-3-amine | 387.20 | 388.21 |
| 907 | | N,N-diethyl-1-{[4-methyl-2-(2-phenoxyphenyl)-1,3-thiazol-5-yl]carbonyl}piperidin-4-amine | 449.21 | 450.22 |

TABLE I-continued

| Compound | | Name | MW | MS |
|---|---|---|---|---|
| 908 | | N,N-diethyl-1-{[4-methyl-2-(2-phenoxyphenyl)-1,3-thiazol-5-yl]carbonyl}pyrrolidin-3-amine | 435.20 | 436.21 |
| 909 | | N,N-diethyl-1-{[4-methyl-2-(2,3,4-trimethoxyphenyl)-1,3-thiazol-5-yl]carbonyl}piperidin-4-amine | 447.22 | 448.24 |
| 910 | | N,N-diethyl-1-{[4-methyl-2-(2,3,4-trimethoxyphenyl)-1,3-thiazol-5-yl]carbonyl}pyrrolidin-3-amine | 433.20 | 434.23 |
| 911 | | 1-(1-{[2-(2-methoxyphenyl)-4-methyl-1,3-thiazol-5-yl]carbonyl}piperidin-4-yl)azepane | 413.21 | 414.24 |
| 912 | | 1'-{[2-(2-methoxyphenyl)-4-methyl-1,3-thiazol-5-yl]carbonyl}-1,4'-bipiperidine | 399.20 | 400.22 |

TABLE I-continued

| | Compound | Name | MW | MS |
|---|---|---|---|---|
| 913 | | 1-(1-{[2-(5-isopropyl-2-methoxyphenyl)-4-methyl-1,3-thiazol-5-yl]carbonyl}piperidin-4-yl)azepane | 455.26 | 456.27 |
| 914 | | 1'-{[2-(5-isopropyl-2-methoxyphenyl)-4-methyl-1,3-thiazol-5-yl]carbonyl}-1,4'-bipiperidine | 441.25 | 442.25 |
| 915 | | 1-(1-{[2-(5-chloro-2-methoxyphenyl)-4-methyl-1,3-thiazol-5-yl]carbonyl}piperidin-4-yl)azepane | 447.17 | 448.19 |
| 916 | | 1'-{[2-(5-chloro-2-methoxyphenyl)-4-methyl-1,3-thiazol-5-yl]carbonyl}-1,4'-bipiperidine | 433.16 | 434.18 |
| 917 | | 1-(1-{[2-(2,5-dimethoxyphenyl)-4-methyl-1,3-thiazol-5-yl]carbonyl}piperidin-4-yl)azepane | 443.22 | 444.23 |

TABLE I-continued

| Compound | Name | MW | MS |
|---|---|---|---|
| 918 | 1'-{[2-(2,5-dimethoxyphenyl)-4-methyl-1,3-thiazol-5-yl]carbonyl}-1,4'-bipiperidine | 429.21 | 430.22 |
| 919 | 1-(1-{[2-(2,4-dimethoxyphenyl)-4-methyl-1,3-thiazol-5-yl]carbonyl}-piperidin-4-yl)azepane | 443.22 | 444.25 |
| 920 | 1-(1-{[2-(2-ethoxyphenyl)-4-methyl-1,3-thiazol-5-yl]carbonyl}piperidin-4-yl)azepane | 427.23 | 428.25 |
| 921 | 1'-{[2-(2-ethoxyphenyl)-4-methyl-1,3-thiazol-5-yl]carbonyl}-1,4'-bipiperidine | 413.21 | 414.23 |

TABLE I-continued

| Compound | Name | MW | MS |
|---|---|---|---|
| 922 | 1-{1-[(2-dibenzo[b,d]furan-4-yl-4-methyl-1,3-thiazol-5-yl)carbonyl]piperidin-4-yl}azepane | 473.21 | 474.23 |
| 923 | 1'-[(2-dibenzo[b,d]furan-4-yl-4-methyl-1,3-thiazol-5-yl)carbonyl]-1,4'-bipiperidine | 459.20 | 460.21 |
| 924 | 1-(1-{[2-(5-fluoro-2-methoxyphenyl)-4-methyl-1,3-thiazol-5-yl]carbonyl}piperidin-4-yl)azepane | 431.20 | 432.21 |

TABLE I-continued

| Compound | Name | MW | MS |
|---|---|---|---|
| 925 | 1'-{[2-(5-fluoro-2-methoxyphenyl)-4-methyl-1,3-thiazol-5-yl]carbonyl}-1,4'-bipiperidine | 417.19 | 418.20 |
| 926 | 1-(1-{[2-(2-methoxy-5-methylphenyl)-4-methyl-1,3-thiazol-5-yl]carbonyl}piperidin-4-yl)azepane | 427.23 | 428.24 |
| 927 | 1'-{[2-(2-methoxy-5-methylphenyl)-4-methyl-1,3-thiazol-5-yl]carbonyl}-1,4'-bipiperidine | 413.21 | 414.23 |
| 928 | 1-(1-{[4-methyl-2-(2-phenoxyphenyl)-1,3-thiazol-5-yl]carbonyl}piperidin-4-yl)azepane | 475.23 | 476.24 |

TABLE I-continued

| Compound | Name | MW | MS |
|---|---|---|---|
| 929 | 1'-{[4-methyl-2-(2-phenoxyphenyl)-1,3-thiazol-5-yl]carbonyl}-1,4'-bipiperidine | 461.21 | 462.22 |
| 930 | 1-(1-{[4-methyl-2-(2,3,4-trimethoxyphenyl)-1,3-thiazol-5-yl]carbonyl}piperidin-4-yl)azepane | 473.23 | 474.26 |
| 931 | 1'-{[4-methyl-2-(2,3,4-trimethoxyphenyl)-1,3-thiazol-5-yl]carbonyl}-1,4'-bipiperidine | 459.22 | 460.25 |
| 932 | 2-(5-chloro-2-methoxyphenyl)-4-methyl-N-[3-(2-methylpiperidin-1-yl)propyl]-1,3-thiazole-5-carboxamide | 421.16 | 422.22 |

TABLE I-continued

| | Compound | Name | MW | MS |
|---|---|---|---|---|
| 933 | | 2-(2,5-dimethoxyphenyl)-4-methyl-N-[2-(1-methylpyrrolidin-2-yl)ethyl]-1,3-thiazole-5-carboxamide | 389.18 | 390.23 |
| 934 | | 2-(2,4-dimethoxyphenyl)-4-methyl-N-[2-(1-methylpyrrolidin-2-yl)ethyl]-1,3-thiazole-5-carboxamide | 389.18 | 390.23 |
| 935 | | 2-(2,4-dimethoxyphenyl)-4-methyl-N-[3-(2-methylpiperidin-1-yl)propyl]-1,3-thiazole-5-carboxamide | 417.21 | 418.27 |
| 936 | | 2-(2-ethoxyphenyl)-4-methyl-N-[3-(20methylpiperidin-1-yl)propyl]-1,3-thiazole-5-carboxamide | 401.21 | 402.28 |

TABLE I-continued

| | Compound | Name | MW | MS |
|---|---|---|---|---|
| 937 | | 2-dibenzo[b,d]furan-4-yl-4-methyl-N-[2-(1-methylpyrrolidin-2-yl)ethyl]-1,3-thiazole-5-carboxamide | 419.17 | 420.24 |
| 938 | | 2-(5-fluoro-2-methoxyphenyl)-4-methyl-N-[3-(2-methylpiperidin-1-yl)propyl]-1,3-thiazole-5-carboxamide | 405.19 | 406.25 |
| 939 | | 4-methyl-N-[2-(1-methylpyrrolidin-2-yl)ethyl]-2-(2-phenoxyphenyl)-1,3-thiazole-5-carboxamide | 421.18 | 422.24 |
| 940 | | 4-methyl-N-[2-(1-methylpyrrolidin-2-yl)ethyl]-2-(2,3,4-trimethoxyphenyl)-1,3-thiazole-5-carboxamide | 419.19 | 420.25 |

TABLE I-continued

| | Compound | Name | MW | MS |
|---|---|---|---|---|
| 941 | | 4-methyl-N-[3-(2-methylpiperidin-1-yl)propyl]-2-(2,3,4-trimethoxyphenyl)-1,3-thiazole-5-carboxamide | 447.22 | 448.29 |
| 942 | | 2-(2-methoxyphenyl)-4-methyl-N-(4-pyrrolidin-1-ylbutyl)-1,3-thiazole-5-carboxamide | 373.18 | 374.24 |
| 943 | | 2-(5-isopropyl-2-methoxyphenyl)-4-methyl-N-(4-pyrrolidin-1-ylbutyl)-1,3-thiazole-5-carboxamide | 415.23 | 416.29 |
| 944 | | 2-(5-chloro-2-methoxyphenyl)-4-methyl-N-(4-pyrrolidin-1-ylbutyl)-1,3-thiazole-5-carboxamide | 407.14 | 408.21 |
| 945 | | 2-(2,5-dimethoxyphenyl)-4-methyl-N-(4-pyrrolidin-1-ylbutyl)-1,3-thiazole-5-carboxamide | 403.19 | 404.25 |

TABLE I-continued

| Compound | Name | MW | MS |
|---|---|---|---|
| 946 | 2-(2,4-dimethoxyphenyl)-4-methyl-N-(4-pyrrolidin-1-ylbutyl)-1,3-thiazole-5-carboxamide | 403.19 | 404.25 |
| 947 | 2-(2-ethoxyphenyl)-4-methyl-N-(4-pyrrolidin-1-ylbutyl)-1,3-thiazole-5-carboxamide | 387.20 | 388.26 |
| 948 | 2-dibenzo[b,d]furan-4-yl-4-methyl-N-(4-pyrrolidin-1-ylbutyl)-1,3-thiazole-5-carboxamide | 433.18 | 434.25 |
| 949 | 2-(5-fluoro-2-methoxyphenyl)-4-methyl-N-(4-pyrrolidin-1-ylbutyl)-1,3-thiazole-5-carboxamide | 391.17 | 392.23 |

TABLE I-continued
| | Compound | Name | MW | MS |
|---|---|---|---|---|
| 950 | 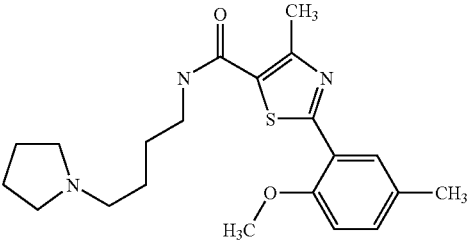 | 2-(2-methoxy-5-methylphenyl)-4-methyl-N-(4-pyrrolidin-1-ylbutyl)-1,3-thiazole-5-carboxamide | 387.20 | 388.25 |
| 951 | 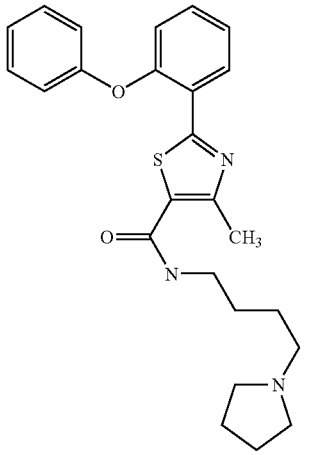 | 4-methyl-2-(2-phenoxyphenyl)-N-(4-pyrrolidin-1-ylbutyl)-1,3-thiazole-5-carboxamide | 435.20 | 436.26 |
| 952 | 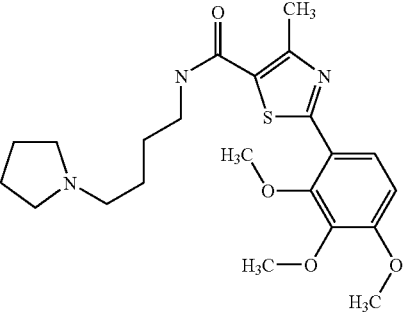 | 4-methyl-N-(4-pyrrolidin-1-ylbutyl)-2-(2,3,4-trimethoxyphenyl)-1,3-thiazole-5-carboxamide | 433.20 | 434.28 |
| 953 | 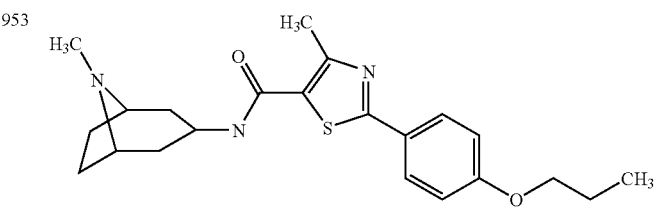 | 4-methyl-N-(8-methyl-8-azabicyclo[3.2.1]oct-3-yl)-2-(4-propoxyphenyl)-1,3-thiazole-5-carboxamide | 399.20 | 400.21 |

TABLE I-continued
| Compound | | Name | MW | MS |
|---|---|---|---|---|
| 954 | 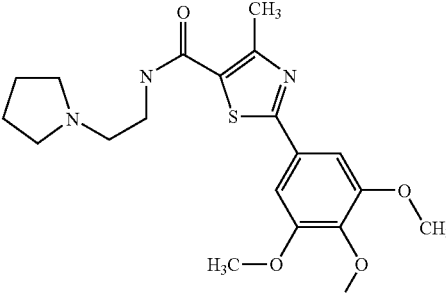 | 4-methyl-N-(2-pyrrolidin-1-ylethyl)-2-(3,4,5-trimethoxyphenyl)-1,3-thiazole-5-carboxamide | 405.17 | 406.16 |
| 955 | 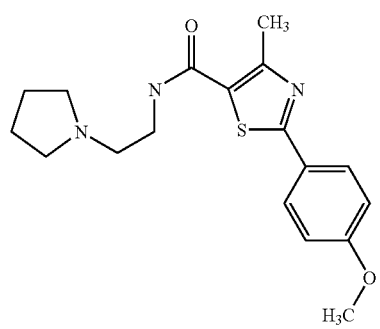 | 2-(4-methoxyphenyl)-4-methyl-N-(2-pyrrolidin-1-ylethyl)-1,3-thiazole-5-carboxamide | 345.15 | 346.14 |
| 956 | 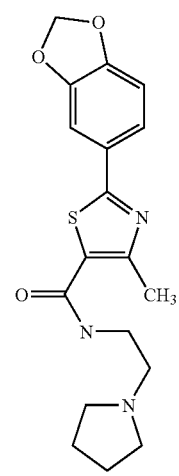 | 2-(1,3-benzodioxol-5-yl)-4-methyl-N-(2-pyrrolidin-1-ylethyl)-1,3-thiazole-5-carboxamide | 359.13 | 360.12 |

TABLE I-continued

| Compound | Name | MW | MS |
|---|---|---|---|
| 957 | 2-(3,4-dimethoxyphenyl)-4-methyl-N-(2-pyrrolidin-1-ylethyl)-1,3-thiazole-5-carboxamide | 375.16 | 376.15 |
| 958 | 2-(4-ethoxyphenyl)-4-methyl-N-(2-pyrrolidin-1-ylethyl)-1,3-thiazole-5-carboxamide | 359.17 | 360.16 |
| 959 | N-[2-(diethylamino)ethyl]-2-(4-ethoxyphenyl)-4-methyl-1,3-thiazole-5-carboxamide | 361.18 | 362.17 |
| 960 | 2-[4-(dimethylamino)phenyl]-4-methyl-N-(2-pyrrolidin-1-ylethyl)-1,3-thiazole-5-carboxamide | 358.18 | 359.19 |

TABLE I-continued

| | Compound | Name | MW | MS |
|---|---|---|---|---|
| 961 | | 2-[4-(dimethylamino)phenyl]-4-methyl-N-(2-piperidin-1-ylethyl)-1,3-thiazole-5-carboxamide | 372.20 | 373.19 |
| 962 | | 2-(2,3-dihydro-1,4-benzodioxin-6-yl)-4-methyl-N-(2-pyrrolidin-1-ylethyl)-1,3-thiazole-5-carboxamide | 373.15 | 374.14 |
| 963 | | 2-(4-methoxy-3-methylphenyl)-4-methyl-N-(2-pyrrolidin-1-ylethyl)-1,3-thiazole-5-carboxamide | 359.17 | 360.16 |
| 964 | | 4-methyl-2-(4-propoxyphenyl)-N-(2-pyrrolidin-1-ylethyl)-1,3-thiazole-5-carboxamide | 373.18 | 374.17 |

TABLE I-continued
| | Compound | Name | MW | MS |
|---|---|---|---|---|
| 965 | 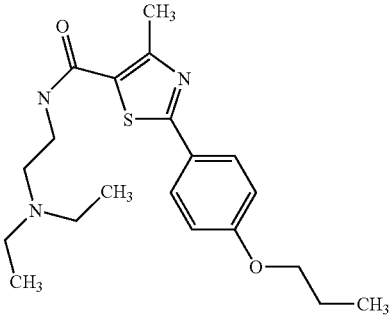 | N-[2-(diethylamino)ethyl]-4-methyl-2-(4-propoxyphenyl)-1,3-thiazole-5-carboxamide | 375.20 | 376.19 |
| 966 | 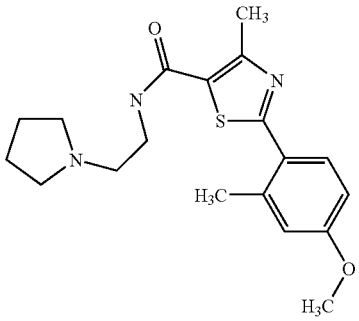 | 2-(4-methoxy-2-methylphenyl)-4-methyl-N-(2-pyrrolidin-1-ylethyl)-1,3-thiazole-5-carboxamide | | |
| 967 | 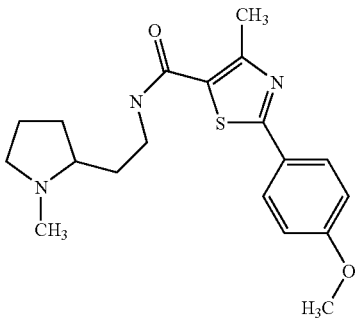 | 2-(4-methoxyphenyl)-4-methyl-N-[2-(1-methylpyrrolidin-2-yl)ethyl]-1,3-thiazole-5-carboxamide | 359.17 | 360.17 |

TABLE I-continued
| | Compound | Name | MW | MS |
|---|---|---|---|---|
| 968 | 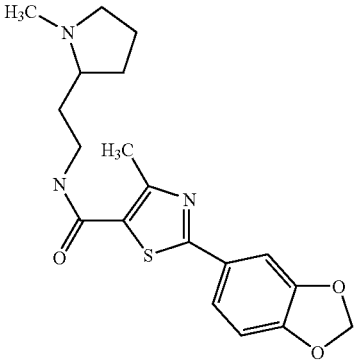 | 2-(1,3-benzodioxol-5-yl)-4-methyl-N-[2-(1-methylpyrrolidin-2-yl)ethyl]-1,3-thiazole-5-carboxamide | 373.15 | 374.15 |
| 969 | 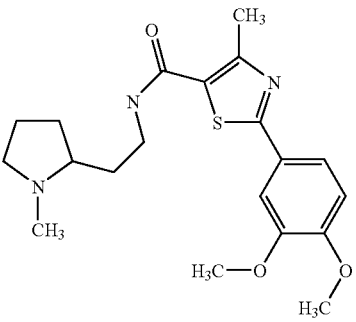 | 2-(3,4-dimethoxyphenyl)-4-methyl-N-[2-(1-methylpyrrolidin-2-yl)ethyl]-1,3-thiazole-5-carboxamide | 389.18 | 390.18 |
| 970 | 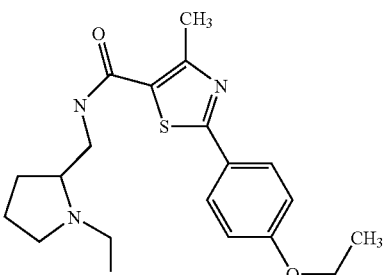 | 2-(4-ethoxyphenyl)-N-[(1-ethylpyrrolidin-2-yl)methyl]-4-methyl-1,3-thiazole-5-carboxamide | 373.18 | 374.19 |

TABLE I-continued

| | Compound | Name | MW | MS |
|---|---|---|---|---|
| 971 | | 2-(4-ethoxyphenyl)-4-methyl-N-[2-(1-methylpyrrolidin-2-yl)ethyl]-1,3-thiazole-5-carboxamide | 373.18 | 374.19 |
| 972 | | 2-[4-(dimethylamino)phenyl]-4-methyl-N-[2-(1-methylpyrrolidin-2-yl)ethyl]-1,3-thiazole-5-carboxamide | 372.20 | 373.21 |
| 973 | | 2-(2,3-dihydro-1,4-benzodioxin-6-yl)-4-methyl-N-[2-(1-methylpyrrolidin-2-yl)ethyl]-1,3-thiazole-5-carboxamide | 387.16 | 388.17 |
| 974 | | 2-[3-(dimethylamino)phenyl]-4-methyl-N-[2-(1-methylpyrrolidin-2-yl)ethyl]-1,3-thiazole-5-carboxamide | 372.20 | 373.23 |

TABLE I-continued

| Compound | Name | MW | MS |
|---|---|---|---|
| 975 | 2-(4-methoxy-3-methylphenyl)-4-methyl-N-[2-(1-methylpyrrolidin-2-yl)ethyl]-1,3-thiazole-5-carboxamide | 373.18 | 374.19 |
| 976 | 2-(4-methoxy-3-methylphenyl)-4-methyl-N-[3-(2-methylpiperidin-1-yl)propyl]-1,3-thiazole-5-carboxamide | | |
| 977 | 4-methyl-N-[2-(1-methylpyrrolidin-2-yl)ethyl]2-2(4-propoxyphenyl)-1,3-thiazole-5-carboxamide | 387.20 | 388.21 |
| 978 | 4-methyl-N-[3-(2-methylpiperidin-1-yl)propyl]-2-(4-propoxyphenyl)-1,3-thiazole-5-carboxamide | | |

TABLE I-continued
| Compound | | Name | MW | MS |
|---|---|---|---|---|
| 979 | 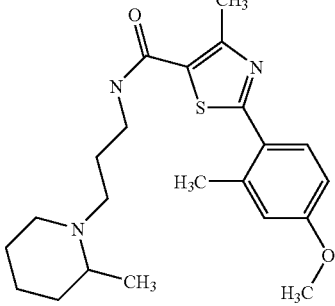 | 2-(4-methoxy-2-methylphenyl)-4-methyl-N-[3-(2-methylpiperidin-1-yl)propyl]-1,3-thiazole-5-carboxamide | | |
| 980 | 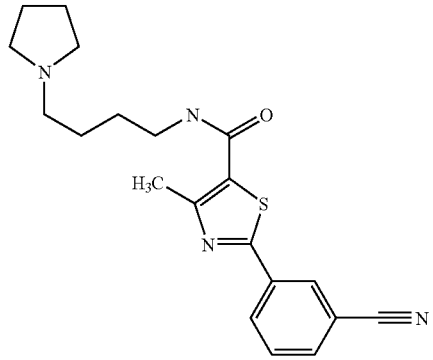 | 2-(3-cyanophenyl)-4-methyl-N-(4-pyrrolidin-1-ylbutyl)-1,3-thiazole-5-carboxamide | 368.17 | 369.21 |
| 981 | 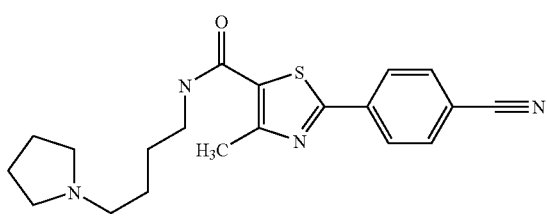 | 2-(4-cyanophenyl)-4-methyl-N-(4-pyrrolidin-1-ylbutyl)-1,3-thiazole-5-carboxamide | 368.17 | 369.21 |

TABLE I-continued
| | Compound | Name | MW | MS |
|---|---|---|---|---|
| 982 | 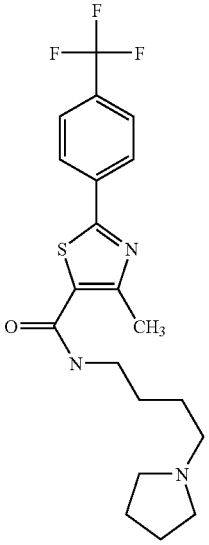 | 4-methyl-N-(4-pyrrolidin-1-ylbutyl)-2-[4-(trifluoromethyl)phenyl]-1,3-thiazole-5-carboxamide | 411.16 | 412.19 |
| 983 | 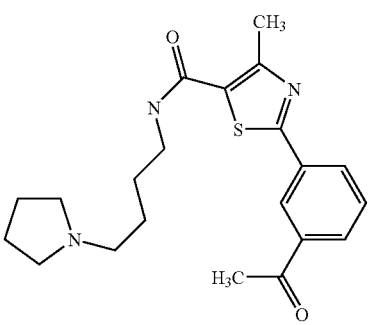 | 2-(3-acetylphenyl)-4-methyl-N-(4-pyrrolidin-1-ylbutyl)-1,3-thiazole-5-carboxamide | 385.18 | 386.23 |
| 984 | 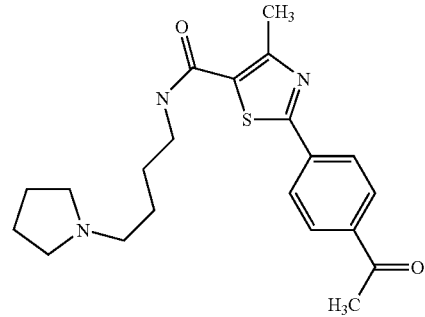 | 2-(4-acetylphenyl)-4-methyl-N-(4-pyrrolidin-1-ylbutyl)-1,3-thiazole-5-carboxamide | 385.18 | 386.25 |

TABLE I-continued
| | Compound | Name | MW | MS |
|---|---|---|---|---|
| 985 | 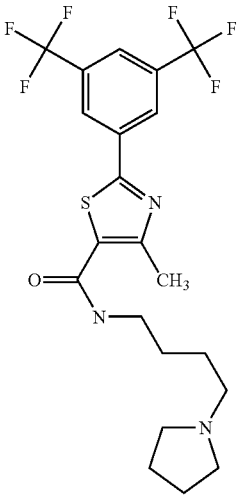 | 2-[3,5-bis(trifluoromethyl)phenyl]-4-methyl-N-(4-pyrrolidin-1-ylbutyl)-1,3-thiazole-5-carboxamide | 479.15 | 480.20 |
| 986 | 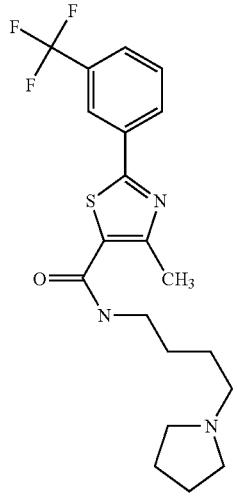 | 4-methyl-N-(4-pyrrolidin-1-ylbutyl)-2-[3-(trifluoromethyl)phenyl]-1,3-thiazole-5-carboxamide | 411.16 | 412.21 |
| 987 | 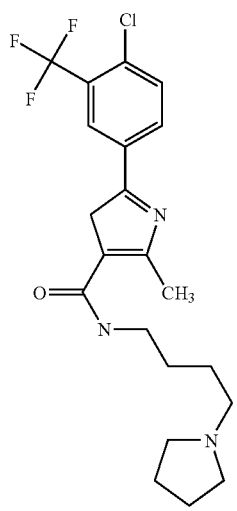 | 2-[4-chloro-3-(trifluoromethyl)phenyl]-4-methyl-N-(4-pyrrolidin-1-ylbutyl)-1,3-thiazole-5-carboxamide | 445.12 | 446.15 |

TABLE I-continued

| Compound | Name | MW | MS |
|---|---|---|---|
| 988 | 2-[2-chloro-5-(trifluoromethyl)phenyl]-4-methyl-N-(4-pyrrolidin-1-ylbutyl)-1,3-thiazole-5-carboxamide | 445.12 | 446.14 |
| 989 | ethyl 4-(4-methyl-5-{[(4-pyrrolidin-1-ylbutyl)amino]carbonyl}-1,3-thiazole-2-yl)benzoate | 415.19 | 416.24 |
| 990 | ethyl 3-(4-methyl-5-{[(4-pyrrolidin-1-ylbutyl)amino]carbonyl}-1,3-thiazol-2-yl)benzoate | 415.19 | 416.24 |
| 991 | 2-(4-cyanophenyl)-4-methyl-N-(1-methylpiperidin-4-yl)-1,3-thiazole-5-carboxamide | 340.14 | 341.16 |

TABLE I-continued
| | Compound | Name | MW | MS |
|---|---|---|---|---|
| 992 | 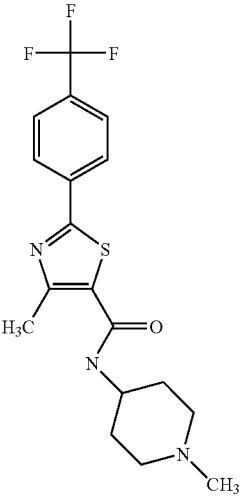 | 4-methyl-N-(1-methylpiperidin-4-yl)-2-[4-(trifluoromethyl)phenyl]-1,3-thiazole-5-carboxamide | 383.13 | 384.14 |
| 993 | 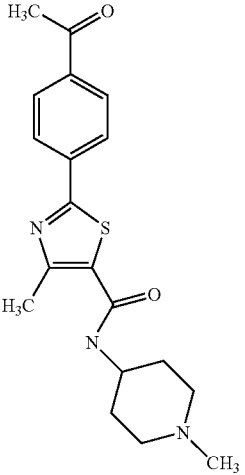 | 2-(4-acetylphenyl)-4-methyl-N-(1-methylpiperidin-4-yl)-1,3-thiazole-5-carboxamide | 357.15 | 358.17 |
| 994 | 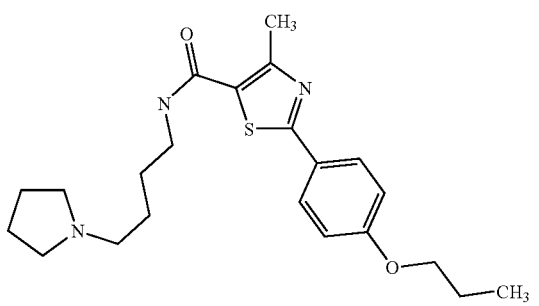 | 4-methyl-2-(4-propoxyphenyl)-N-(4-pyrrolidin-1-ylbutyl)-1,3-thiazole-5-carboxamide | 401.21 | 402.21 |
| 995 | 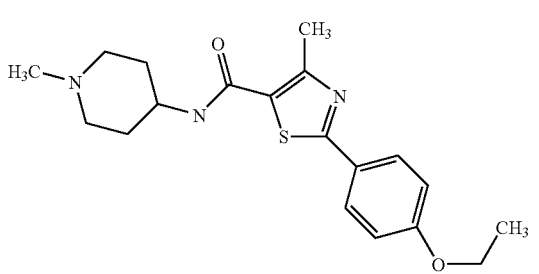 | 2-(4-ethoxyphenyl)-4-methyl-N-(1-methylpiperidin-4-yl)-1,3-thiazole-5-carboxamide | 359.17 | 360.16 |

TABLE I-continued

| Compound | Name | MW | MS |
|---|---|---|---|
| 996 | 2-[4-(dimethylamino)phenyl]-4-methyl-N-(1-methylpiperidin-4-yl)-1,3-thiazole-5-carboxamide | 358.18 | 359.20 |
| 997 | 4-methyl-N-(1-methylpiperidin-4-yl)-2-(4-propoxyphenyl)-1,3-thiazole-5-carboxamide | 373.18 | 374.17 |
| 998 | 2-(4-chlorophenyl)-N-[2-(diisopropylamino)ethyl]-4-methyl-1,3-thiazole-5-carboxamide | 379.15 | 380.16 |
| 999 | N-[2-(diisopropylamino)ethyl]-2-(4-fluorophenyl)-4-methyl-1,3-thiazole-5-carboxamide | 363.18 | 364.18 |

TABLE I-continued

| | Compound | Name | MW | MS |
|---|---|---|---|---|
| 1000 | | N-[2-(diisopropylamino)ethyl]-2-(2-fluoro-4-methylphenyl)-4-methyl-1,3-thiazole-5-carboxamide | 377.19 | 378.20 |
| 1001 | | 4-methyl-N-(1-methylpiperidin-4-yl)-2-(2-naphthyl)-1,3-thiazole-5-carboxamide | 365.16 | 366.17 |
| 1002 | | 2-(4-fluoro-2-methylphenyl)-4-methyl-N-[3-(2-methylpiperidin-1-yl)propyl]-1,3-thiazole-5-carboxamide | 389.2 | 390.1 |
| 1003 | | 1-isopropyl-4-{[4-methyl-2-(1-naphthyl)-1,3-thiazol-5-yl]methyl}-1,4-diazepane | 379.6 | 380.6 |
| 1004 | | 1-cyclopentyl-4-{[1-(2,3-dimethylphenyl)-3,5-dimethyl-1H-pyrazol-4-yl]carbonyl}piperazine | 380.3 | 381.1 |

TABLE I-continued

| Compound | | Name | MW | MS |
|---|---|---|---|---|
| 1005 | | 1-{[1-(2,3-dimethyl)-3,5-dimethyl-1H-pyrazol-5-yl]carbonyl}-N,N-diethylpiperidin-4-amine | 382.3 | 383.2 |
| 1006 | | 1'-{[1-(2,3-dimethylphenyl)-3,5-dimethyl-1H-pyrazol-4-yl]carbonyl}-1,4'-bipiperidine | 394.3 | 395.4 |
| 1007 | | 1-{[1-(4-chloro-2-methylphenyl)-3,5-dimethyl-1H-pyrazol-4-yl]carbonyl}-4-cyclopentylpiperazine | 400.2 | 401.1 |
| 1008 | | 1-cyclopentyl-4-{[3,5-dimethyl-1-(2-methylphenyl)-1H-pyrazol-4-yl]carbonyl}piperazine | 366.2 | 367.2 |
| 1009 | | 1-(1-{[1-(4-chloro-2-methylphenyl)-3,5-dimethyl-1H-pyrazol-4-yl]carbonyl}piperidin-4-yl)azepane | 428.2 | 429.2 |

TABLE I-continued

| Compound | | Name | MW | MS |
|---|---|---|---|---|
| 1010 | | 1-{[1-(2,3-dimethylphenyl)-3,5-dimethyl-1H-pyrazol-4-yl]carbonyl}-4-isopropylpiperazine | 354.2 | 355.2 |
| 1011 | | 1-cyclopentyl-4-[(3,5-dimethyl-1-phenyl-1H-pyrazol-4-yl)carbonyl]piperazine | 352.2 | 353.2 |
| 1012 | | 1'-{[1-(4-chloro-2-methylphenyl)-3,5-dimethyl-1H-pyrazol-4-yl]carbonyl}-1,4'-bipiperidine | 414.2 | 415.2 |
| 1013 | | 1-{[1-(4-chloro-2-methylphenyl)-3,5-dimethyl-1H-pyrazol-4-yl]carbonyl}-4-isopropylpiperazine | 374.2 | 375.1 |
| 1014 | | 1-(4-chloro-2-methylphenyl)-3,5-dimethyl-N-(4-pyrrolidin-1-ylbutyl)-1H-pyrazole-4-carboxamide | 388.2 | 389.1 |
| 1015 | | 1-isopropyl-4-{[1-methyl-2-(1-naphthyl)-1H-imidazol-5-yl]methyl}piperazine | 348.49 | 349.25 |

TABLE I-continued

| Compound | Name | MW | MS |
|---|---|---|---|
| 1016 | 1-isopropyl-4-{[1-methyl-2-(1-naphthyl)-1H-imidazol-4-yl]methyl}piperazine | 348.49 | 349.29 |
| 1017 | 1-cyclobutyl-4-{[2-(1-naphthyl)-1H-imidazol-5-yl]methyl}piperazine | 346.47 | 347.28 |
| 1018 | 2-{[2-(1-naphthyl)-1H-imidazol-5-yl]methyl}octahydro-2H-pyrido[1,2-a]pyrazine | 346.47 | 347.28 |
| 1019 | N,N-diethyl-1-{[2-(1-naphthyl)-1H-imidazol-5-yl]methyl}pyrrolidin-3-amine | 348.49 | 349.27 |
| 1020 | 1-cyclobutyl-4-{[4-methyl-2-(1-naphthyl)-1H-imidazol-5-yl]methyl}piperazine | 360.5 | 361.27 |
| 1021 | 1-cyclopentyl-4-{[2-(1-naphthyl)-1H-imidazol-5-yl]methyl}piperazine | 360.5 | 361.30 |
| 1022 | 1-cyclobutyl-4-{[4-methyl-2-(1-naphthyl)-1H-imidazol-5-yl]carbonyl}piperazine | 374.48 | 375.27 |

TABLE I-continued

| Compound | | Name | MW | MS |
|---|---|---|---|---|
| 1023 | | 1-isopropyl-4-{[4-methyl-2-(1-naphthyl)-1H-imidazol-5-yl]methyl}piperazine | 348.49 | 349.28 |
| 1024 | | 1-cyclopentyl-4-{[4-methyl-2-(1-naphthyl)-1H-imidazol-5-yl]methyl}piperazine | 374.53 | 375.29 |
| 1025 | | 1'-{[2-(1-naphthyl)-1H-imidazol-5-yl]methyl}-1,4'-bipiperidine | 374.53 | 375.29 |
| 1026 | | 1-cyclopentyl-4-{[4-methyl-2-(1-naphthyl)-1H-imidazol-5-yl]carbonyl}piperazine | 388.51 | 389.27 |
| 1027 | | 1-cyclobutyl-4-{[1-ethyl-2-(1-naphthyl)-1H-imidazol-5-yl]methyl}piperazine | 374.53 | 375.28 |
| 1028 | | 1-cyclobutyl-4-{[1-ethyl-2-(1-naphthyl)-1H-imidazol-4-yl]methyl}piperazine | 374.53 | 375.34 |
| 1029 | | 1-cyclobutyl-4-{[1-ethyl-5-methyl-2-(1-naphthyl)-1H-imidazol-4-yl]carbonyl}piperazine | 402.54 | 403.37 |

TABLE I-continued

| Compound | Name | MW | MS |
|---|---|---|---|
| 1030 | 1-isopropyl-4-{[2-(4-methyl-1-naphthyl)-1H-imidazol-5-yl]methyl}piperazine | 348.49 | 349.36 |
| 1031 | 1-cyclobutyl-4-{[2-(4-methyl-1-naphthyl)-1H-imidazol-5-yl]methyl}piperazine | 360.5 | 361.37 |
| 1032 | 1-cyclobutyl-4-{[1-ethyl-5-methyl-2-(1-naphthyl)-1H-imidazol-4-yl]methyl}piperazine | 388.55 | 389.40 |
| 1033 | 1-cyclobutyl-4-{[1-ethyl-4-methyl-2-(1-naphthyl)-1H-imidazol-5-yl]carbonyl}piperazine | 402.54 | 403.39 |
| 1034 | 1-cyclobutyl-4-{[1-ethyl-4-methyl-2-(1-naphthyl)-1H-imidazol-5-yl]methyl}piperazine | 388.55 | 389.42 |
| 1035 | 1-cyclopentyl-4-{[2-(4-methyl-1-naphthyl)-1H-imidazol-5-yl]methyl}piperazine | 374.53 | 375.38 |

TABLE I-continued

| | Compound | Name | MW | MS |
|---|---|---|---|---|
| 1036 | | 1-cyclopentyl-4-{[1-ethyl-2-(1-naphthyl)-1H-imidazol-4-yl]methyl}piperazine | 388.55 | 389.32 |
| 1037 | | 1-{[2-(1-naphthyl)-1H-imidazol-5-yl]methyl}piperazine | 292.38 | 293.23 |
| 1038 | | 1-{[2-(2-ethoxy-1-naphthyl)-1H-imidazol-5-yl]methyl}-4-isopropylpiperazine | 378.52 | 379.32 |
| 1039 | | 2-{[2-(1-naphthyl)-1H-imidazol-5-yl]methyl}octahydropyrrolo[1,2-a]pyrazine | 332.45 | 333.26 |
| 1040 | | 1-cyclobutyl-4-{[2-(2-ethoxy-1-naphthyl)-1H-imidazol-5-yl]methyl}piperazine | 390.53 | 391.31 |

TABLE I-continued

| Compound | | Name | MW | MS |
|---|---|---|---|---|
| 1041 | | 1-cyclopentyl-4-{[2-(ethoxy-1-naphthyl)-1H-imidazol-5-yl]methyl}piperazine | 404.55 | 405.31 |
| 1042 | | [4-bromo-1-(ethoxymethyl)-2-(1-naphthyl)-1H-imidazol-5-yl](1-cyclobutylpiperidin-4-yl)methanol | 498.46 | 498.25 |
| 1043 | | 1-allyl-4-{[1-ethyl-2-(1-naphthyl)-1H-imidazol-4-yl]methyl}piperazine | 360.5 | 361.49 |
| 1044 | | 1-{[1-ethyl-2-(1-naphthyl)-1H-imidazol-4-yl]methyl}-4-isopropylpiperazine | 362.52 | 363.51 |

TABLE I-continued

| Compound | Name | MW | MS |
|---|---|---|---|
| 1045 | 1-ethyl-4-{[1-ethyl-2-(1-naphthyl)-1H-imidazol-4-yl]methyl}piperazine | 348.49 | 349.49 |
| 1046 | 1-butyl-4-{[1-ethyl-2-(1-naphthyl)-1H-imidazol-4-yl]methyl}-1,4-diazepane | 390.57 | 391.56 |
| 1047 | 1-butyl-4-{[1-ethyl-2-(1-naphthyl)-1H-imidazol-4-yl]methyl}piperazine | 376.54 | 377.54 |

TABLE I-continued
| Compound | | Name | MW | MS |
|---|---|---|---|---|
| 1048 | 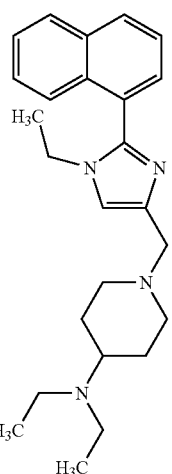 | N,N-diethyl-1-{[1-ethyl-2-(1-naphthyl)-1H-imidazol-4-yl]methyl}piperidin-4-amine | 390.57 | 391.57 |
| 1049 | 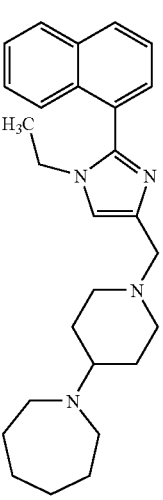 | 1-(1-{[1-ethyl-2-(1-naphthyl)-1H-imidazol-4-yl]methyl}piperidin-4-yl)azepane | 416.61 | 417.60 |
| 1050 | 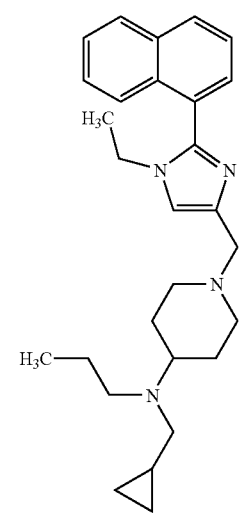 | N-(cyclopropylmethyl)-1-{[1-ethyl-2-(1-naphthyl)-1H-imidazol-4-yl]methyl}-N-propylpiperidin-4-amine | 430.64 | 431.63 |

TABLE I-continued

| | Compound | Name | MW | MS |
|---|---|---|---|---|
| 1051 | | 1-{[1-ethyl-2-(1-naphthyl)-1H-imidazol-4-yl]methyl}-4-pyrrolidin-1-ylpiperidine | 388.55 | 389.55 |
| 1052 | | 1'-{[1-ethyl-2-(1-naphthyl)-1H-imidazol-4-yl]methyl}-1,4'-bipiperidine | 402.58 | 403.58 |
| 1053 | | N,N-diethyl-1-{[1-ethyl-2-(1-naphthyl)-1H-imidazol-4-yl]methyl}pyrrolidin-3-amine | 376.54 | 377.54 |

TABLE I-continued

| Compound | | Name | MW | MS |
|---|---|---|---|---|
| 1054 | | N-{[1-ethyl-2-(1-naphthyl)-1H-imidazol-4-yl]methyl}-N,N',N'-trimethylpropane-1,3-diamine | 350.51 | 351.52 |
| 1055 | | 1-{[1-(ethoxymethyl)-2-(1-naphthyl)-1H-imidazol-4-yl]carbonyl}-4-isopropylpiperazine | 406.53 | 407.38 |
| 1056 | | 1-cyclopentyl-4-{[1-(ethoxymethyl)-2-(1-naphthyl)-1H-imidazol-4-yl]carbonyl}piperazine | 432.56 | 433.41 |
| 1057 | | (1-cyclobutylpiperidin-4-yl)[1-(ethoxymethyl)-2-(1-naphthyl)-1H-imidazol-4-yl]methanol | 419.57 | 420.40 |

TABLE I-continued

| | Compound | Name | MW | MS |
|---|---|---|---|---|
| 1058 | | 1-isopropyl-4-{[2-(1-naphthyl)-1H-imidazol-5-yl]carbonyl}piperazine | 348.45 | 349.33 |
| 1059 | | 1-cyclopentyl-4-{[2-(1-naphthyl)-1H-imidazol-5-yl]carbonyl}piperazine | 374.48 | 375.35 |
| 1060 | | 1-{[1-ethyl-2-(1-naphthyl)-1H-imidazol-4-yl]carbonyl}-4-isopropylpiperazine | 376.5 | 377.33 |
| 1061 | | 1-cyclopentyl-4-{[1-ethyl-2-(1-naphthyl)-1H-imidazol-4-yl]carbonyl}piperazine | 402.54 | 403.39 |
| 1062 | | [1-ethyl-2-(1-naphthyl)-1H-imidazol-4-yl](1-isopropylpiperidin-4-yl)methanol | 377.53 | 378.30 |
| 1063 | | (1-cyclopentylpiperidin-4-yl)[1-ethyl-2-(1-naphthyl)-1H-imidazol-4-yl]methanol | 403.57 | 404.33 |

TABLE I-continued

| | Compound | Name | MW | MS |
|---|---|---|---|---|
| 1064 | | (1-cyclobutylpiperidin-4-yl)[1-ethyl-2-(1-naphthyl)-1H-imidazol-4-yl]methanol | 389.54 | 390.31 |
| 1065 | | 1-cyclobutyl-4-{[4-methyl-2-(1-naphthyl)-1-propyl-1H-imidazol-5-yl]carbonyl}piperazine | 416.57 | 417.33 |
| 1066 | | (1-cyclobutylpiperidin-4-yl)[1-ethyl-2-(1-naphthyl)-1H-imidazol-4-yl]methanol | 387.52 | 388.30 |
| 1067 | | 1-cyclobutyl-4-{[1-ethyl-2-(1-naphthyl)-1H-imidazol-4-yl](methoxy)methyl}piperidine | 430.57 | 404.19 |
| 1068 | | 1-cyclobutyl-4-{[2-(4-fluoro-1-naphthyl)-1H-imidazol-5-yl]methyl}piperazine | 364.46 | 365.28 |
| 1069 | | 1-cyclobutyl-4-{[2-(4-fluoro-1-naphthyl)-1-(methoxymethyl)-1H-imidazol-4-yl]methyl}piperazine | 408.52 | 409.30 |

TABLE I-continued

| Compound | Name | MW | MS |
|---|---|---|---|
| 1070 | 1-sec-butyl-4-{[1-ethyl-2-(1-naphthyl)-1H-imidazol-4-yl]methyl}piperazine | 376.54 | 377.21 |
| 1071 | 1-(1-cyclopropylethyl)-4-{[1-ethyl-2-(1-naphthyl)-1H-imidazol-4-yl]methyl}piperazine | 388.55 | 389.20 |
| 1072 | 1-cyclopentyl-4-{[2-(4-fluoro-1-naphthyl)-1H-imidazol-5-yl]methyl}piperazine | 378.49 | 379.28 |
| 1073 | 1-cyclobutyl-4-{[1-ethyl-2-(1-naphthyl)-1H-imidazol-4-yl]carbonyl}piperazine | 388.51 | 389.29 |

TABLE I-continued
| | Compound | Name | MW | MS |
|---|---|---|---|---|
| 1074 | 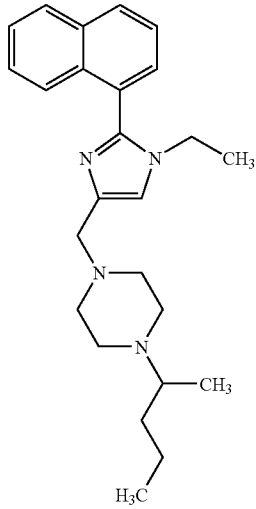 | 1-{[1-ethyl-2-(1-naphthyl)-1H-imidazol-4-yl]methyl}-4-(1-methylbutyl)piperazine | 390.57 | 391.37 |
| 1075 | 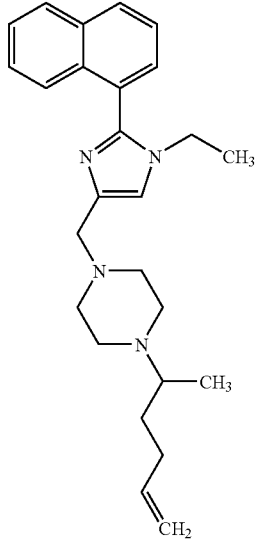 | 1-{[1-ethyl-2-(1-naphthyl)-1H-imidazol-4-yl]methyl}-4-(1-methylpent-4-en-1-yl)piperazine | 402.58 | 403.39 |
| 1076 | 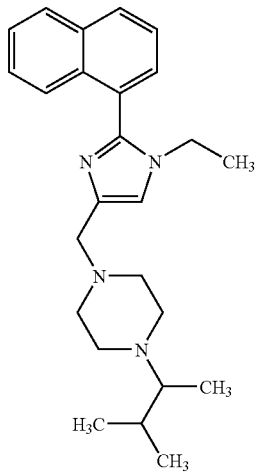 | 1-(1,2-dimethylpropyl)-4-{[1-ethyl-2-(1-naphthyl)-1H-imidazol-4-yl]methyl}piperazine | 390.57 | 391.37 |

TABLE I-continued

| | Compound | Name | MW | MS |
|---|---|---|---|---|
| 1077 | | 1-cyclopentyl-4-{[1-ethyl-5-methyl-2-(1-naphthyl)-1H-imidazol-4-yl]carbonyl}piperazine | 416.57 | 417.32 |
| 1078 | | 1-cyclopentyl-4-{[1-(2-fluoroethyl)-5-methyl-2-(1-naphthyl)-1H-imidazol-4-yl]carbonyl}piperazine | 434.56 | 435.30 |
| 1079 | | 1-cyclopentyl-4-{[1-(2-fluoroethyl)-4-methyl-2-(1-naphthyl)-1H-imidazol-5-yl]carbonyl}piperazine | 434.56 | 435.19 |
| 1080 | | 1-cyclobutyl-4-{[1-(2-fluoroethyl)-4-methyl-2-(1-naphthyl)-1H-imidazol-5-yl]carbonyl}piperazine | 420.53 | 421.29 |
| 1081 | | 2-{5-[(4-cyclobutylpiperazin-1-yl)carbonyl]-4-methyl-2-(1-naphthyl)-1H-imidazol-1-yl}ethanol | 418.54 | 419.29 |

TABLE I-continued

| | Compound | Name | MW | MS |
|---|---|---|---|---|
| 1082 | | 1-cyclobutyl-4-{[1-ethyl-2-(1-naphthyl)-1H-imidazol-5-yl]carbonyl}piperazine | 388.51 | 389.28 |
| 1083 | | 1-{[1-ethyl-2-(1-naphthyl)-1H-imidazol-5-yl]carbonyl}-4-isopropylpiperazine | 376.5 | 377.28 |
| 1084 | | 1-cyclopentyl-4-{[1-ethyl-2-(1-naphthyl)-1H-imidazol-5-yl]carbonyl}piperazine | 402.54 | 403.17 |
| 1085 | | 1-cyclopentyl-4-{[1-ethyl-4-methyl-2-(1-naphthyl)-1H-imidazol-5-yl]carbonyl}piperazine | 416.57 | 417.17 |
| 1086 | | 1-{[1-ethyl-4-methyl-2-(1-naphthyl)-1H-imidazol-5-yl]carbonyl}-4-isopropylpiperazine | 390.53 | 391.36 |

TABLE I-continued

| Compound | | Name | MW | MS |
|---|---|---|---|---|
| 1087 | | 1-ethyl-4-{[1-ethyl-4-methyl-2-(1-naphthyl)-1H-imidazol-5-yl]carbonyl}piperazine | 376.5 | 377.35 |
| 1088 | | N,N-diethyl-1-{[1-ethyl-4-methyl-2-(1-naphthyl)-1H-imidazol-5-yl]carbonyl}piperidin-4-amine | 418.58 | 419.41 |
| 1089 | | 1-(1-{[1-ethyl-4-methyl-2-(1-naphthyl)-1H-imidazol-5-yl]carbonyl}piperidin-4-yl)azepane | 444.62 | 445.42 |

TABLE I-continued

| Compound | Name | MW | MS |
|---|---|---|---|
| 1090 | 1'-{[1-ethyl-4-methyl-2-(1-naphthyl)-1H-imidazol-5-yl]carbonyl}-1,4'-bipiperidine | 430.59 | 431.42 |
| 1091 | N-[2-(diethylamino)ethyl]-1-ethyl-N,4-dimethyl-2-(1-naphthyl)-1H-imidazole-5-carboxamide | 392.54 | 393.36 |
| 1092 | N,1-diethyl-N-{2-[ethyl(methyl)amino]ethyl}-4-methyl-2-(1-naphthyl)-1H-imidazole-5-carboxamide | 392.54 | 393.36 |
| 1093 | N-[2-(diethylamino)ethyl]-N,1-diethyl-4-methyl-2-(1-naphthyl)-1H-imidazole-5-carboxamide | 406.57 | 407.38 |

TABLE I-continued

| | Compound | Name | MW | MS |
|---|---|---|---|---|
| 1094 | | (1-cyclobutylpiperidin-4-yl)[1-ethyl-2-(1-naphthyl)-1H-imidazol-5-yl]methanone | 387.52 | 388.13 |
| 1095 | | 1-cyclobutyl-4-{[1-(2-methoxyethyl)-2-(1-naphthyl)-1H-imidazol-4-yl]methyl}piperazine | 404.55 | 405.17 |
| 1096 | | 1-cyclopentyl-4-{[1-(2-methoxyethyl)-2-(1-naphthyl)-1H-imidazol-4-yl]methyl}piperazine | 418.58 | 419.18 |
| 1097 | | 1-{[4-chloro-1-ethyl-2-(1-naphthyl)-1H-imidazol-5-yl]carbonyl}-4-cyclobutylpiperazine | 422.96 | 423.19 |
| 1098 | | 1-{[4-chloro-1-ethyl-2-(1-naphthyl)-1H-imidazol-5-yl]carbonyl}-4-isopropylpiperazine | 410.95 | 411.19 |

TABLE I-continued

| | Compound | Name | MW | MS |
|---|---|---|---|---|
| 1099 | | 1-{[4-chloro-1-ethyl-2-(1-naphthyl)-1H-imidazol-5-yl]carbonyl}-4-cyclopentylpiperazine | 436.98 | 437.20 |
| 1100 | | 1-cyclobutyl-4-{[1-methyl-2-(1-naphthyl)-1H-imidazol-5-yl]carbonyl}piperazine | 374.48 | 375.21 |
| 1101 | | 1-isopropyl-4-{[1-methyl-2-(1-naphthyl)-1H-imidazol-5-yl]carbonyl}piperazine | 362.47 | 363.25 |
| 1102 | | 1-cyclopentyl-4-{[1-methyl-2-(1-naphthyl)-1H-imidazol-5-yl]carbonyl}piperazine | 388.51 | 389.26 |
| 1103 | | 1-cyclopentyl-4-{[1-(2-methoxyethyl)-2-(1-naphthyl)-1H-imidazol-5-yl]carbonyl}piperazine | 432.56 | 433.25 |

TABLE I-continued

| Compound | | Name | MW | MS |
|---|---|---|---|---|
| 1104 | | 1-cyclobutyl-4-{[1-(2-methoxyethyl)-2-(1-naphthyl)-1H-imidazol-5-yl]carbonyl}piperazine | 418.54 | |
| 1105 | | 1-cyclobutyl-4-{[1-ethyl-2-(1-naphthyl)-4-(trifluoromethyl)-1H-imidazol-5-yl]carbonyl}piperazine | 456.51 | |
| 1106 | | 1-cyclobutyl-4-{[1-ethyl-4-fluoro-2-(1-naphthyl)-1H-imidazol-5-yl]carbonyl}piperazine | 406.5 | |
| 1107 | | 1-cyclopentyl-4-{[1-ethyl-4-fluoro-2-(1-naphthyl)-1H-imidazol-5-yl]carbonyl}piperazine | 420.53 | |

Example 4

Preparation of Chimeric Human H3 Receptor

PCR cloning is used to prepare a chimeric H3 receptor cDNA from human H3 receptor cDNA directly coupled to a rat $G\alpha_{i2}$ cDNA. The final construct is generated from three cDNA fragments: (1) a human H3 receptor cDNA 5' fragment; (2) a human H3 receptor cDNA 3' fragment; and (3) a rat $G\alpha_{i2}$ cDNA fragment, each containing appropriate, overlapping linker sequences.

The human H3 receptor cDNA 5' fragment is generated from a Human Brain cDNA Library (Invitrogen, Carlsbad, Calif.) by PCR using the primers TGAGCCTGCGGGGC-CATGGAG (forward, SEQ ID NO:1) and GAGGAGGTG-CACAGCAGGTAG (reverse, SEQ ID NO:2). PCR is performed using the Advantage-GC cDNA PCR kit (BD Biosciences Clontech, Palo Alto, Calif.) in 25 µl reactions containing: 5 µl GC melt, 5 µl 5×PCR reaction buffer, 0.5 µl dNTP Mix (10 mM each), 10 pmol forward and reverse primers, 0.5 µl Advantage GC cDNA Polymerase Mix and 1 µl undiluted Invitrogen Human Brain Library. Conditions for touchdown PCR thermal cycling are 94° C. for 2 mM then, over 10 cycles: 94° C. for 30 seconds, 60° C. to 55° C. in 0.5° C. intervals for 1 min and 68° C. for 1 min, then over 20 cycles: 94° C. for 30 seconds, 55° C. for 1 min and 68° C. for 1 min. The human H3 receptor cDNA 5' fragment is initially cloned into the vector pcDNA3.1/V5His TOPO TA (Invitrogen).

The human H3 receptor cDNA 3' fragment is generated from a Human Brain Library (Invitrogen) by PCR using the primers CTACCTGCTGTGCACCTCCTC (forward, SEQ ID NO:3) and GCAGTGCTCTAGAGAGCTGTGG (reverse, SEQ ID NO:4) and conditions as described for the human H3 receptor cDNA 5' fragment. The human H3 receptor cDNA 3' fragment is initially cloned into the vector pcDNA3.1/V5His TOPO TA (Invitrogen).

The rat $G\alpha_{i2}$ cDNA fragment is generated from a rat $G\alpha_{i2}$-containing vector (Jones and Reed (1987) *J. Biol. Chem.* 262(29):14241-49) by PCR using the primers CTCTCTA-GAGCACTGCTGGAAGATGGGCTGCACCGTGAGCGC (forward, SEQ ID NO:5) and TCAGAAGAGGCCA-CAGTCCTTCAG (reverse, SEQ ID NO:6) and conditions as described for the human H3 receptor cDNA 5' fragment. The rat $G\alpha_{i2}$ cDNA fragment is initially cloned into the vector pcDNA3.1/V5His TOPO TA (Invitrogen).

Each cDNA fragment is excised from the pcDNA3.1/V5His TOPO TA vector using the restriction enzymes KpnI and NotI. The human H3 receptor cDNA 5' fragment is further treated with the restriction enzyme ApaLI. The human H3 receptor cDNA 3' fragment is further treated with the restriction enzymes ApaLI and XbaI. The rat $G\alpha_{i2}$ cDNA fragment is further treated with the restriction enzyme XbaI. All three individual cDNA fragments are ligated and subcloned together into the KpnI/NotI site of the baculoviral expression vector pBacPAK 9 (BD Biosciences Clontech) to generate the chimeric human H3 receptor-rat $G\alpha_{i2}$ baculoviral expression construct (SEQ ID NO:7).

Example 5

Chimeric Human H3 Receptor Baculovirus Preparation and Infection

The chimeric human H3 receptor-rat $G\alpha_{i2}$ baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City, Kans.) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing $2\times10^6$ Sf9 cells in 5 ml of insect medium. After five days of incubation at 27° C., supernatant medium is harvested from each of the T25 infections for use as passage 1 inoculum.

Two of seven recombinant baculoviral clones are chosen for a second round of amplification, using 1 ml of passage 1 stock to infect $1\times10^8$ cells in 100 ml of insect medium divided into two T175 flasks. Forty-eight hours post infection, passage 2 medium from each 100 ml prep is harvested and plaque assayed to determine virus titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post-infection, the supernatant medium is harvested to yield passage 3 baculoviral stock.

The remaining cell pellet is assayed for affinity binding using the protocol of DeMartino et al. (1994) *J. Biol. Chem.* 269(20):14446-50 (which is incorporated herein by reference for its teaching of binding assays at page 14447), adapted as follows. Radioligand ranges from 0.40-40 nM [$^3$H]—N-(a) methylhistamine (Perkin Elmer, Boston, Mass.) and assay buffer contains 50 mM Tris, 1 mM $CaCl_2$, 5 mM $MgCl_2$, 0.1% BSA, 0.1 mM bacitracin, and 100 KIU/ml aprotinin, pH 7.4. Filtration is carried out using GF/C WHATMAN filters (pre-soaked in 1.0% polyethyeneimine for 2 hr prior to use). Filters are washed three times with 5 ml cold binding buffer without BSA, bacitracin, or aprotinin and air dried for 12-16 hr. Radioactivity retained on filters is measured on a beta scintillation counter.

Titer of the passage 3 baculoviral stock is determined by plaque assay and a multiplicity of infection, incubation time course, binding assay experiment is carried out to determine conditions for optimal receptor expression. A multiplicity of infection of 0.5 and a 72-hr incubation period were the best infection parameters found for chimeric human H3 receptor-rat $G\alpha_{i2}$ expression in up to 1-liter Sf9 cell infection cultures.

Log-phase Sf9 cells (Invitrogen), are infected with one or more stocks of recombinant baculovirus followed by culturing in insect medium at 27° C. Infections are carried out with virus directing the expression of human H3 receptor-rat $G\alpha_{i2}$ in combination with three G-protein subunit-expression virus stocks: 1) rat $G\alpha_{i2}$ G-protein-encoding virus stock (BIOSIGNAL #V5J008), 2) bovine β1 G-protein-encoding virus stock (BIOSIGNAL #V5H012), and 3) human γ2 G-protein-encoding virus stock (BIOSIGNAL #V6B003), which may be obtained from BIOSIGNAL Inc., Montreal.

The infections are conveniently carried out at a multiplicity of infection of 0.5:1.0:0.5:0.5. At 72 hr post-infection, a sample of cell suspension is analyzed for viability by trypan blue dye exclusion, and the remaining Sf9 cells are harvested via centrifugation (3000 rpm/10 min/4° C.).

Example 6

Chimeric Human H3 Receptor Cell Membrane Preparations

Sf9 cell pellets are resuspended in homogenization buffer (10 mM HEPES, 250 mM sucrose, 0.5 μg/ml leupeptin, 2 μg/ml Aprotinin, 200 μM PMSF, and 2.5 mM EDTA, pH 7.4) and homogenized using a POLYTRON homogenizer (setting 5 for 30 seconds). The homogenate is centrifuged (536×g/10 min at 4° C.) to pellet the nuclei and unbroken cells. The supernatant containing the membranes is decanted to a clean centrifuge tube, centrifuged (48,000×g/30 min, 4° C.) and the resulting pellet resuspended in 30 ml homogenization buffer. This centrifugation and resuspension step is repeated twice. The final pellet is resuspended in ice cold Dulbecco's PBS containing 5 mM EDTA and stored in frozen aliquots at −80° C. until used for radioligand binding or functional response assays. The protein concentration of the resulting membrane preparation (hereinafter termed "P2 membranes") is conveniently measured using a Bradford protein assay (Bio-Rad Laboratories, Hercules, Calif.). By this measure, a 1-liter culture of cells typically yields 100-150 mg of total membrane protein.

Example 7

Chimeric Human H3 Receptor GTP Binding Assays

Agonist-stimulated GTP-gamma$^{35}$S binding ("GTP binding") activity can be used to identify antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the chimeric human H3 receptor and three directing the expression of each of the three subunits of a heterotrimeric G-protein) are used to infect a culture of Sf9 cells as described above.

Agonist-stimulated GTP binding on P2 membranes (prepared as described above) is assessed using histamine (Sigma Chemical Co., St. Louis, Mo.) as agonist in order to ascertain that the receptor/G-protein-alpha-beta-gamma combination(s) yield a functional response as measured by GTP binding. P2 membranes are resuspended by Dounce homogenization (tight pestle) in GTP binding assay buffer (50 mM Tris pH 7.0, 120 mM NaCl, 2 mM $MgCl_2$, 2 mM EGTA, 0.1% BSA, 0.1 mM bacitracin, 100 KIU/ml aprotinin, 10 μM GDP) and added to assay tubes at a concentration of 35 μg protein/reaction tube. After adding increasing doses of histamine at concentrations ranging from $10^{-12}$ M to $10^{-5}$ M, reactions are initiated by the addition of 125 μM GTP-gamma$^{35}$S with a final assay volume of 0.20 ml. In competition experiments, non-radiolabeled test compounds are added to separate reactions at concentrations ranging from $10^{-10}$ M to $10^{-6}$ M along with 1 μM histamine to yield a final volume of 0.20 ml.

Neutral antagonists are those test compounds that reduce the histamine-stimulated GTP binding activity towards, but not below, baseline levels. In contrast, in the absence of added histamine, inverse agonists reduce the GTP binding activity of the receptor-containing membranes below baseline. Any test compound that elevates GTP binding activity above baseline in the absence of added histamine in this assay is defined as having agonist activity.

After a 60-min incubation at RT, reactions are terminated by vacuum filtration over GF/C filters (pre-soaked in wash buffer, 0.1% BSA) followed by washing with ice-cold wash buffer (50 mM Tris pH 7.4, 120 mM NaCl). The amount of receptor-bound (and thereby membrane-bound) GTP-gamma$^{35}$S is determined by measuring the bound radioactivity, preferably by liquid scintillation spectrometry of the washed filters. Non-specific binding is determined using 10 uM GTP-gammaS and typically represents less than 5 percent of total binding. Data is expressed as percent above basal (baseline). The results of GTP binding experiments are analyzed using SIGMAPLOT software (SPSS Inc., Chicago, Ill.).

$IC_{50}$ values are calculated by non-linear regression analysis of dose-response curves using Kaleidograph (Synergy Software, Reading, Pa.). Calculated $IC_{50}$ values are converted to $K_i$ values by the Cheng-Prusoff correction (Cheng and Prusoff (1973) *Biochem. Pharmacol.* 22(23):3099-3108). Accordingly, the following equation: $K_i=IC_{50}/(1+[L]/EC_{50})$ is used, where [L] is the histamine concentration in the GTP binding assay, and $EC_{50}$ is the concentration of histamine producing a 50% response, as determined by a dose-response analysis using concentrations of histamine ranging from $10^{-10}$ M to $10^{-6}$ M.

To assess agonist or inverse agonist activity of a test compound, this assay is performed in the absence of added histamine.

Example 8

Microsomal In Vitro Half-Life

This Example illustrates the evaluation of compound half-life values ($t_{1/2}$ values) using a representative liver microsomal half-life assay.

Pooled human liver microsomes are obtained from XenoTech LLC (Kansas City, Kans.). Such liver microsomes may also be obtained from In Vitro Technologies (Baltimore, Md.) or Tissue Transformation Technologies (Edison, N.J.). Six test reactions are prepared, each containing 25 μl microsomes, 5 μl of a 100 μM solution of test compound, and 399 μl 0.1 M phosphate buffer (19 mL 0.1 M $NaH_2PO_4$, 81 mL 0.1 M $Na_2HPO_4$, adjusted to pH 7.4 with $H_3PO_4$). A seventh reaction is prepared as a positive control containing 25 μl microsomes, 399 μl 0.1 M phosphate buffer, and 5 μl of a 100 μM solution of a compound with known metabolic properties (e.g., DIAZEPAM or CLOZAPINE). Reactions are preincubated at 39° C. for 10 min.

CoFactor Mixture is prepared by diluting 16.2 mg NADP and 45.4 mg Glucose-6-phosphate in 4 mL 100 mM $MgCl_2$. Glucose-6-phosphate dehydrogenase solution is prepared by diluting 214.3 μl glucose-6-phosphate dehydrogenase suspension (Roche Molecular Biochemicals; Indianapolis, Ind.) into 1285.7 μl distilled water. 71 μl Starting Reaction Mixture (3 mL CoFactor Mixture; 1.2 mL Glucose-6-phosphate dehydrogenase solution) is added to 5 of the 6 test reactions and to the positive control. 71 μl 100 mM $MgCl_2$ is added to the sixth test reaction, which is used as a negative control. At each time point (0, 1, 3, 5, and 10 min), 75 μl of each reaction mix is pipetted into a well of a 96-well deep-well plate containing 75 μl ice-cold acetonitrile. Samples are vortexed and centrifuged 10 min at 3500 rpm (Sorval. T 6000D centrifuge, H1000B rotor). 75 μl of supernatant from each reaction is transferred to a well of a 96-well plate containing 150 μl of a 0.5 μM solution of a compound with a known LCMS profile (internal standard) per well. LCMS analysis of each sample is carried out and the amount of unmetabolized test compound is measured as AUC, compound concentration vs. time is plotted, and the $t_{1/2}$ value of the test compound is extrapolated.

Preferred compounds provided herein exhibit in vitro $t_{1/2}$ values of greater than 10 min and less than 4 hr, preferably between 30 min and 1 hr, in human liver microsomes.

Example 9

MDCK Toxicity Assay

This Example illustrates the evaluation of compound toxicity using a Madin Darby canine kidney (MDCK) cell cytotoxicity assay.

1 μL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog #30-2003). 100 µL of diluted cells is added to each well, except for five standard curve control wells that contain 100 µL of warm medium without cells. The plate is then incubated at 37° C. under 95% $O_2$, 5% $CO_2$ for 2 hr with constant shaking. After incubation, 50 µL, of mammalian cell lysis solution (from the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 mM.

Compounds causing toxicity will decrease ATP production, relative to untreated cells. The ATP-LITE-M Luminescent ATP detection kit is generally used according to the manufacturer's instructions to measure ATP production in treated and untreated MDCK cells. PACKARD ATP LITE-M reagents are allowed to equilibrate to rt. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 min. A white PACKARD sticker is attached to the bottom of each plate and samples are dark adapted by wrapping plates in foil and placing in the dark for 10 mM. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 µM of a preferred test compound exhibit ATP levels that are at least 80%, preferably at least 90%, of the untreated cells. When a 100 µM concentration of the test compound is used, cells treated with preferred test compounds exhibit ATP levels that are at least 50%, preferably at least 80%, of the ATP levels detected in untreated cells.

What is claimed is:

1. A compound of the formula:

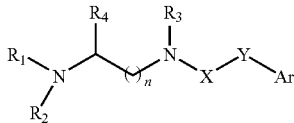

or a pharmaceutically acceptable salt thereof, wherein:

$R_1$ is: (a) $C_1$-$C_8$alkyl, $C_2$-$C_8$alkenyl or ($C_3$-$C_8$cycloalkyl) $C_0$-$C_4$alkyl, each of which is substituted with from 0 to 4 substituents independently chosen from $R_A$; or (b) taken together with $R_2$ or $R_4$ to form a piperazinyl, piperidinyl, or pyrrolidinyl group that is substituted with from 0 to 4 substituents independently chosen from $R_A$;

$R_2$ is $C_1$-$C_8$alkyl, $C_2$-$C_8$alkenyl, ($C_3$-$C_8$cycloalkyl)$C_0$-$C_4$alkyl or taken together with $R_1$, $R_3$ or $R_4$ to form a piperazinyl, piperidinyl, or pyrrolidinyl group that is substituted with from 0 to 4 substituents independently chosen from $R_A$;

$R_3$ is hydrogen, $C_1$-$C_8$alkyl, $C_2$-$C_8$alkenyl, ($C_3$-$C_8$cycloalkyl)$C_0$-$C_4$alkyl or taken together with $R_2$ or $R_4$ to form a piperazinyl, piperidinyl, or pyrrolidinyl group that is substituted with from 0 to 4 substituents independently chosen from $R_A$; or $R_4$ is hydrogen or taken together with $R_1$, $R_2$ or $R_3$ to form a piperazinyl, piperidinyl, or pyrrolidinyl group;

wherein two of $R_1$, $R_2$, $R_3$ and $R_4$ are taken together to form a piperazinyl, piperidinyl, or pyrrolidinyl group;

n is 1, 2 or 3;
X is C=O;
Y is:

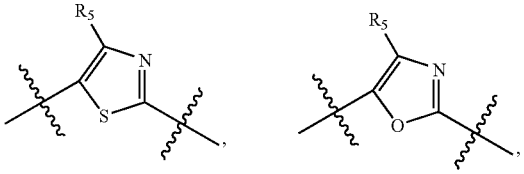

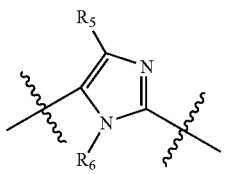

Each $R_5$ is hydrogen, halogen, cyano or $C_1$-$C_8$alkyl that is substituted with from 0 to 4 substituents independently chosen from hydroxy, halogen, amino, cyano and $C_1$-$C_4$alkoxy;

Each $R_6$ is hydrogen or $C_1$-$C_8$alkyl that is substituted with from 0 to 4 substituents independently chosen from hydroxy, halogen, amino, cyano and $C_1$-$C_4$alkoxy;

Ar is phenyl, naphthyl, biphenyl or a 5- to 13-membered heteroaryl, each of which is substituted with from 0 to 4 substituents independently chosen from:

(a) hydroxy, halogen, amino, cyano, nitro, —COOH and aminocarbonyl; and (b) $C_1$-$C_8$alkyl, $C_3$-$C_8$cycloalkyl, $C_2$-$C_8$alkyl ether, $C_1$-$C_8$alkanoyl, $C_3$-$C_8$alkanone, $C_1$-$C_8$alkylsulfonyl, $C_1$-$C_8$alkoxy, $C_1$-$C_8$alkylthio, $C_1$-$C_8$alkoxycarbonyl, $C_2$-$C_8$alkanoyloxy, $C_2$-$C_8$alkanoylamino, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl) aminosulfonyl, $C_1$-$C_6$alkylsulfonylamino, mono- and di-($C_1$-$C_6$alkyl)amino$C_0$-$C_4$alkyl, and 5- to 7-membered heterocycloalkyl, each of which is substituted with from 0 to 4 substituents independently chosen from hydroxy, halogen, amino, cyano, $C_1$-$C_4$alkyl and $C_1$-$C_4$alkoxy; and $R_4$ is independently chosen at each occurrence from:
(a) hydroxy, halogen, amino, cyano, nitro, oxo, —COOH, aminosulfonyl and aminocarbonyl; and
(b) $C_1$-$C_8$alkyl, $C_3$-$C_8$cycloalkyl, $C_2$-$C_8$alkyl ether, $C_1$-$C_8$alkanoyl, $C_3$-$C_8$alkanone, $C_1$-$C_8$alkylsulfonyl, $C_1$-$C_8$alkoxy, $C_1$-$C_8$alkylthio, $C_1$-$C_8$alkoxycarbonyl, $C_2$-$C_8$alkanoyloxy, $C_2$-$C_8$alkanoylamino, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl)aminosulfonyl, $C_1$-$C_6$alkylsulfonylamino, mono- and di-($C_1$-$C_6$alkyl)amino$C_0$-$C_4$alkyl and 5- to 7-membered heterocycloalkyl, each of which is substituted with from 0 to 4 substituents independently chosen from hydroxy, halogen, amino, cyano, $C_1$-$C_4$alkyl and $C_1$-$C_4$alkoxy.

2. A compound of the formula:

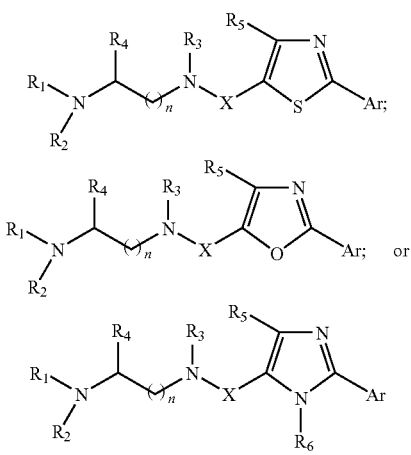

or a pharmaceutically acceptable salt thereof, wherein:
n is 1, 2 or 3;
X is C=O;
$R_1$ is: (a) $C_1$-$C_8$alkyl, $C_2$-$C_8$alkenyl or ($C_3$-$C_8$cycloalkyl)$C_0$-$C_4$alkyl, each of which is substituted with from 0 to 4 substituents independently chosen from $R_4$; or (b) taken together with $R_2$ or $R_4$ to form a piperazinyl, piperidinyl, or pyrrolidinyl group that is substituted with from 0 to 4 substituents independently chosen from $R_4$;
$R_2$ is $C_1$-$C_8$alkyl, $C_2$-$C_8$alkenyl, ($C_3$-$C_8$cycloalkyl)$C_0$-$C_4$alkyl or taken together with $R_1$, $R_3$ or $R_4$ to form a piperazinyl, piperidinyl, or pyrrolidinyl group that is substituted with from 0 to 4 substituents independently chosen from $R_4$;
$R_3$ is hydrogen, $C_1$-$C_8$alkyl, $C_2$-$C_8$alkenyl, ($C_3$-$C_8$cycloalkyl)$C_0$-$C_4$alkyl or taken together with $R_2$ or $R_4$ to form a piperazinyl, piperidinyl, or pyrrolidinyl group that is substituted with from 0 to 4 substituents independently chosen from $R_4$;
$R_4$ is hydrogen or taken together with $R_1$, $R_2$ or $R_3$ to form a piperazinyl, piperidinyl, or pyrrolidinyl group;
wherein two of $R_1$, $R_2$, $R_3$ and $R_4$ are taken together to form a piperazinyl, piperidinyl, or pyrrolidinyl group;
Each $R_5$ is hydrogen, halogen, cyano or $C_1$-$C_8$alkyl that is substituted with from 0 to 4 substituents independently chosen from hydroxy, halogen, amino, cyano and $C_1$-$C_4$alkoxy;
Each $R_6$ is hydrogen or $C_1$-$C_8$alkyl that is substituted with from 0 to 4 substituents independently chosen from hydroxy, halogen, amino, cyano and $C_1$-$C_4$alkoxy;

Ar is phenyl, naphthyl, biphenyl or a 5- to 13-membered heteroaryl, each of which is substituted with from 0 to 4 substituents independently chosen from:
(a) hydroxy, halogen, amino, cyano, nitro, —COOH and aminocarbonyl; and
(b) $C_1$-$C_8$alkyl, $C_3$-$C_8$cycloalkyl, $C_2$-$C_8$alkyl ether, $C_1$-$C_8$alkanoyl, $C_3$-$C_8$alkanone, $C_1$-$C_8$alkylsulfonyl, $C_1$-$C_8$alkoxy, $C_1$-$C_8$alkylthio, $C_1$-$C_8$alkoxycarbonyl, $C_2$-$C_8$alkanoyloxy, $C_2$-$C_8$alkanoylamino, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl)aminosulfonyl, $C_1$-$C_6$alkylsulfonylamino, mono- and di-($C_1$-$C_6$alkyl)amino$C_0$-$C_4$alkyl, and 5- to 7-membered heterocycloalkyl, each of which is substituted with from 0 to 4 substituents independently chosen from hydroxy, halogen, amino, cyano, $C_1$-$C_4$alkyl and $C_1$-$C_4$alkoxy; and $R_4$ is independently chosen at each occurrence from:
(a) hydroxy, halogen, amino, cyano, nitro, oxo, —COOH, aminosulfonyl and aminocarbonyl; and
(b) $C_1$-$C_8$alkyl, $C_3$-$C_8$cycloalkyl, $C_2$-$C_8$alkyl ether, $C_1$-$C_8$alkanoyl, $C_3$-$C_8$alkanone, $C_1$-$C_8$alkylsulfonyl, $C_1$-$C_8$alkoxy, $C_1$-$C_8$alkylthio, $C_1$-$C_8$alkoxycarbonyl, $C_2$-$C_8$alkanoyloxy, $C_2$-$C_8$alkanoylamino, mono- and di-($C_1$-$C_6$alkyl)aminocarbonyl$C_0$-$C_4$alkyl, mono- or di-($C_1$-$C_6$alkyl)aminosulfonyl, mono- and di-($C_1$-$C_6$alkyl)aminosulfonyl, $C_1$-$C_6$alkylsulfonylamino, and mono- and di-($C_1$-$C_6$alkyl)amino$C_0$-$C_4$alkyl, each of which is substituted with from 0 to 4 substituents independently chosen from hydroxy, halogen, amino, cyano, $C_1$-$C_4$alkyl and $C_1$-$C_4$alkoxy.

3. A compound or salt according to claim 2, wherein the compound has the formula:

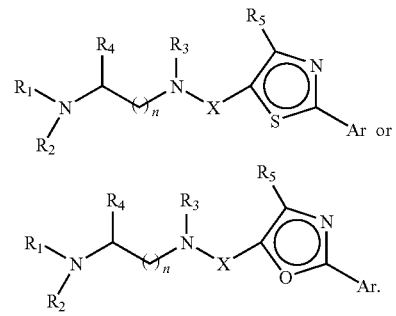

4. A compound or salt according to claim 2, wherein the compound has the formula:

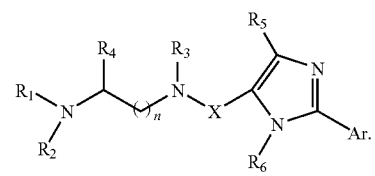

5. A compound or salt according to claim 1, wherein $R_3$ is hydrogen or $C_1$-$C_8$alkyl.

6. A compound or salt according to claim 1, wherein the compound has the formula:

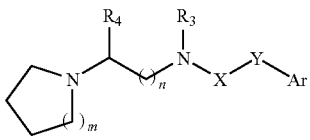

where m is 1 or 2.

7. A compound or salt according to claim 1, wherein the compound has the formula:

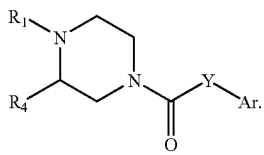

8. A compound or salt according to claim 7, wherein the compound has the formula:

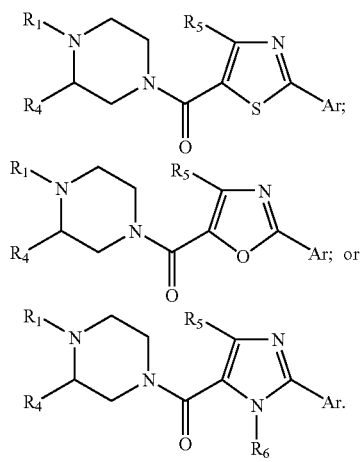

9. A compound or salt according to claim 1, wherein the compound has the formula:

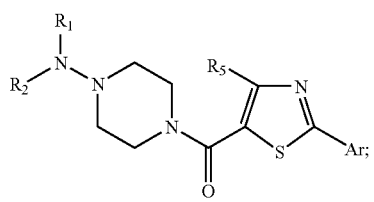

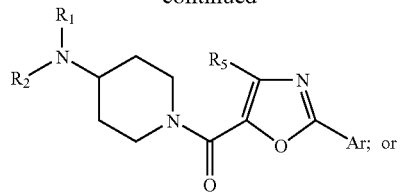

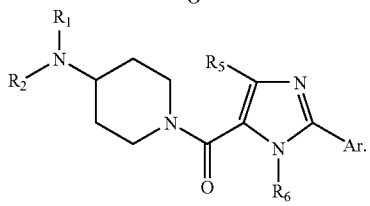

10. A compound or salt according to claim 1, wherein Ar is naphthyl or a 9- or 10-membered heteroaryl, each of which is substituted with form 0 to 3 substituents independently chosen from halogen, cyano, amino, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkanoyl, $C_1$-$C_4$alkoxycarbonyl, $C_2$-$C_4$alkanoyloxy and mono- and di-($C_1$-$C_4$alkyl)amino.

11. A compound or salt according to claim 1, wherein $R_1$ is $C_1$-$C_6$alkyl and $R_4$ is hydrogen.

12. A compound or salt according to claim 1, wherein the compound has a $K_i$ value of 1 micromolar or less, as determined using an assay for H3 receptor GTP binding.

13. A pharmaceutical composition, comprising at least one compound or salt according to claim 1 in combination with a physiologically acceptable carrier or excipient.

14. A pharmaceutical composition according to claim 13 wherein the composition is formulated as an indictable fluid, an aerosol, a cream, a gel, a pill, a capsule, a syrup or a transdermal patch.

15. A method for treating a obesity in a patient, comprising administering to the patient a therapeutically effective amount of a compound or salt according to claim 1, and thereby alleviating the obesity in the patient.

16. A method according to claim 15, wherein the patient is a human.

17. A method for determining the presence or absence of H3 receptor in a sample, comprising the steps of:
   (a) contacting a sample with a compound or salt according to claim 1, under conditions that permit binding of the compound to H3 receptor; and
   (b) detecting a level of the compound bound to H3 receptor, and therefrom determining the presence or absence of H3 receptor in the sample.

18. A packaged pharmaceutical preparation, comprising:
   (a) a pharmaceutical composition according to claim 13 in a container; and
   (b) instructions for using the composition to treat obesity in a patient.

* * * * *